US010175242B2

(12) United States Patent
Koomen

(10) Patent No.: US 10,175,242 B2
(45) Date of Patent: *Jan. 8, 2019

(54) PERSONALIZED MYELOMA DETECTION

(71) Applicant: H. LEE MOFFITT CANCER CENTER AND RESEARCH INSTITUTE, INC., Tampa, FL (US)

(72) Inventor: John Matthew Koomen, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/122,269

(22) PCT Filed: Feb. 28, 2015

(86) PCT No.: PCT/US2015/018212
§ 371 (c)(1),
(2) Date: Aug. 29, 2016

(87) PCT Pub. No.: WO2015/131169
PCT Pub. Date: Sep. 3, 2015

(65) Prior Publication Data
US 2016/0370372 A1    Dec. 22, 2016

Related U.S. Application Data

(60) Provisional application No. 61/946,629, filed on Feb. 28, 2014.

(51) Int. Cl.
*C40B 30/02* (2006.01)
*G01N 33/68* (2006.01)
*G01N 33/574* (2006.01)

(52) U.S. Cl.
CPC ....... *G01N 33/57426* (2013.01); *C40B 30/02* (2013.01); *G01N 33/6848* (2013.01); *G01N 33/6854* (2013.01); *G01N 33/6857* (2013.01)

(58) Field of Classification Search
CPC ......... G01N 33/57426; G01N 33/6848; G01N 33/6854; G01N 33/6857; C40B 30/02
See application file for complete search history.

(56) References Cited

U.S. PATENT DOCUMENTS

| | | | |
|---|---|---|---|
| 7,183,118 B2 * | 2/2007 | Aebersold | C12Q 1/34 436/173 |
| 9,410,967 B2 * | 8/2016 | Koomen | C07K 16/065 |
| 2011/0151494 A1 * | 6/2011 | Koomen | C07K 16/065 435/23 |
| 2013/0260406 A1 * | 10/2013 | Koomen | C07K 16/065 435/23 |
| 2016/0041184 A1 * | 2/2016 | Barnidge | G01N 33/6857 435/24 |

OTHER PUBLICATIONS

The humoral system. http://www.biology.arizona.edu/immunology/tutorials/immunology/humoral.html accessed online on Aug. 22, 2017, 5 pages.*
ExPASy PeptideCutter. http://web.expasy.org/cgi-bin/peptide_cutter/peptidecutter.pl accessed online Aug. 25, 2017, 3 pages.*
Addona TA, Abbatiello SE, Schilling B, Skates SJ, et al. Multi-site assessment of the precision and reproducibility of multiple reaction monitoring-based measurements of proteins in plasma. *Nat Biotechnol* 2009, 27, 633-41.
Agger SA, Marney LC, Hoofnagle AN. Simultaneous quantification of apolipoprotein A-I and apolipoprotein B by liquid-chromatography-multiple-reaction-monitoring mass spectrometry. *Clin Chem*. 2010, 56, 1804-13. PMC3103773.
Alexander Jr. RL. Comparison of radial immunodiffusion and laser Nephelometry for quantitating some serum proteins. *Clin. Chem.* 1980, 26, 314-7.
Anderson L, Hunter CL. Quantitative mass spectrometric multiple reaction monitoring assays for major plasma proteins. *Mol Cell Proteomics* 2006, 5, 573-88.
Barnidge DR, Dratz EA, Martin T, Bonilla LE, Moran LB, Lindall A. Absolute quantification of the G protein-coupled receptor rhodopsin by LC/MS/MS using proteolysis product peptides and synthetic peptide standards. Anal Chem. 2003, 75, 445-51.
Barnidge DR, Goodmanson MK, Klee GG, Muddiman DC. Absolute quantification of the model biomarker prostate-specific antigen in serum by LC-MS/MS using protein cleavage and isotope dilution mass spectrometry. J Proteome Res. 2004, 3, 644-52.
Barnidge, et al., Monitoring M-proteins in patients with multiple myeloma using heavy-chain variable region clonotypic peptides and LC-MS/MS. J Proteome Res ePub Feb. 19, 2014 vol. 13 No. 4, pp. 1905-1910. Especially abstract, p. 1907 col. 1 para 4, p. 1907 fig 1, p. 1908 col. 1 para 2, p. 1908 col. 2 para 3.
Barr JR, Maggio VL, Patterson DG Jr, Cooper GR, Henderson LO, Turner WE, Smith SJ, Hannon WH, Needham LL, Sampson EJ. Isotope dilution—mass spectrometric quantification of specific proteins: model application with apolipoprotein A-I. Clin Chem. 1996, 42, 1676-82.
Berth M, Delanghem J, Langlois M, Buyzere M. Reference values of serum IgA subclasses in caucasian adults by immunonephelometry. Clin. Chem. 1999, 45, 309-10.

(Continued)

*Primary Examiner* — Marcela M Cordero Garcia
(74) *Attorney, Agent, or Firm* — Meunier Carlin & Curfman LLC

(57) ABSTRACT

Disclosed herein is a personalized method for monitoring a condition or disorder associated with antibody production in a subject. The method can involve treating a biological sample comprising immunoglobulin from the subject to enzymatically cleave a target immunoglobulin associated with the PCD into one or more variable domain peptide fragments of the target immunoglobulin, and then measuring the one or more variable domain peptide fragments in the sample by quantitative mass spectrometry to quantify the amount of the target immunoglobulin in the sample.

21 Claims, 7 Drawing Sheets
Specification includes a Sequence Listing.

(56) References Cited

OTHER PUBLICATIONS

Billadeau D, Blackstadt M, Greipp P, Kyle RA, Oken MM, Kay N, Van Ness B. Analysis of B-lymphoid malignancies using allele-specific polymerase chain reaction: a technique for sequential quantitation of residual disease. Blood 1991, 78, 3021-9.

Billadeau D, Quam L, Thomas W, Kay N, Greipp P, Kyle R, Oken MM, Van Ness B. Detection and quantitation of malignant cells in the peripheral blood of multiple myeloma patients. Blood 1992, 80, 1818-24.

Buckley R, Fiscus S. Serum IgD and IgE concentrations in immunodeficiency diseases. J Clin Invest. 1975, 55, 157-65. PMC301727.

Chen K, Jan Y, Chen C, Cheng C, Wu M, Shu K. Multiple myeloma-associated cast nephropathy with crystal structure: Case report and review of the literature. Nephrology 2005, 10, 594-596.

Cheung WC, Beausoleil SA, Zhang X, Sato S, Schieferl SM, Wieler JS, Beaudet JG, Ramenani RK, Popova L, Comb MJ, Rush J, Polakiewicz RD. A proteomics approach for the identification and cloning of monoclonal antibodies from serum. Nat Biotechnol. 2012, 30, 447-52.

Clark R, Katzmann JA, Kyle RA, Fleisher M, Landers JP. Differential diagnosis of gammopathies by capillary electrophoresis and immunosubtraction: analysis of serum samples problematic by agarose gel electrophoresis. Electrophoresis 1998, 19, 2479-84.

Cremer FW, Kiel K, Wallmeier M, Goldschmidt H, Moos M. A quantitative PCR assay for the detection of low amounts of malignant cells in multiple myeloma. Ann Oncol. 1997, 8, 633-6.

Dekker et al. An antibody-based biomarker discovery method by mass spectrometry sequencing of complementarity determining regions. Anal Bioanal Chem Jan. 2011 vol. 399 No. 3 pp. 1081-1091. Especially abstract.

Durie BG, Harousseau JL, Miguel JS, Bladé J, et al. International uniform response criteria for multiple myeloma. Leukemia 2006, 20, 1467-73.

Durie BG, Salmon SE. A clinical staging system for multiple myeloma. Correlation of measured myeloma cell mass with presenting clinical features, response to treatment, and survival. Cancer 1975, 36, 842-854.

Evans VC, Barker G, Heesom KJ, Fan J, Bessant C, Matthews DA. De novo derivation of proteomes from transcriptomes for transcript and protein identification. Nat Methods 2012, 9, 1207-11.

Fenk R, Ak M, Kobbe G, Steidl U, Arnold C, Korthals M, Hünerlitürkoglu A, Rohr UP, Kliszewski S, Bernhardt A, Haas R, Kronenwett R. Levels of minimal residual disease detected by quantitative molecular monitoring herald relapse in patients with multiple myeloma. Haematologica 2004, 89, 557-566.

French MAH, Harrison G. Serum IgG subclass concentrations in healthy adults: a study using monoclonal antisera. Clin Exp Immunol. 1984, 56, 473-5. PMC1536244.

Gerard CJ, Olsson K, Ramanathan R, Reading C, Hanania EG. Improved quantitation of minimal residual disease in multiple myeloma using real-time polymerase chain reaction and plasmid-DNA complementarity determining region III standards. Cancer Res. 1998, 58, 3957-64.

Gerber SA, Rush J, Stemman O, Kirschner MW, Gygi SP. Absolute quantification of proteins and phosphoproteins from cell lysates by tandem MS. Proc Natl Acad Sci USA 2003, 100, 6940-45. PMC165809.

Grabherr MG, Haas BJ, Yassour M, Levin JZ, et al. Full-length transcriptome assembly from RNA-Seq data without a reference genome. Nat Biotechnol. 2011, 29, 644-52.

Greipp PR, San Miguel J, Durie BG, Crowley JJ, et al. International staging system for multiple myeloma. J Clin Oncol 2005, 23, 3412-20.

Guiguet M, Padieu P, Mack G. Laser nephelometric measurement of seven serum proteins compared with radial immunodiffusion. J. Clin. Chem. Biochem. 1983, 21, 217-21.

Hagman et al. Absolute quantification of monoclonal antibodies in biofluids by liquid chromatography-tandem mass spectrometry. Anal Chem Feb. 15, 2008 vol. 80 No. 4 pp. 1290-1296. Especially abstact.

Haraldsson A, Kock-Jansen MJ, Jaminon M, van Eck-Arts PB, de Boo T, Weemaes CM, Bakkeren JA. Determination of kappa and lambda light chains in serum immunoglobulins G, A and M. Ann Clin Biochem. 1991, 28, 461-66.

Holm, S. A simple sequentially rejective multiple test procedure. Scandinavian Journal of Statistics 1979, 6, 65-70.

Hoofnagle AN, Becker JO, Wener MH, Heinecke JW. Quantification of thyroglobulin, a low-abundance serum protein, by immunoaffinity peptide enrichment and tandem mass spectrometry. Clin Chem. 2008, 54, 1796-804. PMC2739673.

Hunder G, Gleich G. Immunoglobulin E (IgE) Levels in serum and synovial fluid in rheumatiod arthritis. Arthritis Rheum. 1974, 17, 955-63.

International Myeloma Working Group. Criteria for the classification of monoclonal gammopathies, multiple myeloma and related disorders: a report of the International Myeloma Working Group. Br J Haematol 2003, 121, 749-57.

International Search Report and Written Opinion issued in International Application No. PCT/US15/18212, dated Jun. 5, 2015.

Jagannath S. Value of serum free light chain testing for the diagnosis and monitoring of monoclonal gammopathies in hematology. Clin Lymphoma Myeloma 2007, 7, 518-23.

Jolliff CR, Blessum CR. Comparison of serum protein electrophoresis by agarose gel and capillary zone electrophoresis in a clinical setting. Electrophoresis 1997, 18, 1781-4.

Katzmann JA, Clark RJ, Abraham RS, Bryant S, et al. Serum reference intervals and diagnostic ranges for free and free immunoglobulin light chains: relative sensitivity for detection on monoclonal light chains. *Clin Chem* 2002, 48, 1437-44.

Keshishian H, Addona T, Burgess M, Kuhn E, Carr SA. Quantitative, multiplexed assays for low abundance proteins in plasma by targeted mass spectrometry and stable isotope dilution. Mol Cell Proteomics 2007, 6, 2212-29. PMC2435059.

Kirsch S, Widart J, Louette J, Focant JF, De Pauw E. Development of an absolute quantification method targeting growth hormone biomarkers using liquid chromatography coupled to isotope dilution mass spectrometry. J Chromatogr A 2007, 1153, 300-6.

Koomen JM, Haura EB, Bepler G, Sutphen R, Remily-Wood ER, Benson K, Hussein M, Hazlehurst LA, Yeatman TJ, Hildreth LT, Sellers TA, Jacobsen PB, Fenstermacher DA, Dalton WS. Proteomic contributions to personalized cancer care. Mol Cell Proteomics 2008, 7, 1780-94. PMC2559938.

Kuhn E, Addona T, Keshishian H, Burgess M, Mani DR, Lee RT, Sabatine MS, Gerszten RE, Carr SA. Developing multiplexed assays for troponin I and interleukin-33 in plasma by peptide immunoaffinity enrichment and targeted mass spectrometry. Clin Chem. 2009, 55, 1108-17. PMC2865473.

Kuhn E, Wu J, Karl J, Liao H, Zolg W, Guild B. Quantification of C-reactive protein in the serum of patients with rheumatoid arthritis using multiple reaction monitoring mass spectrometry and 13C-labeled peptide standards. Proteomics 2004, 4, 1175-86.

Kuzyk MA, Smith D, Yang J, Cross TJ, Jackson AM, Hardie DB, Anderson NL, Borchers CH. Multiple reaction monitoring-based, multiplexed, absolute quantitation of 45 proteins in human plasma. Mol Cell Proteomics 2009, 8, 1860-77. PMC2722777.

Langmead B, Trapnell C, Pop M, Salzberg SL. Ultrafast and memory-efficient alignment of short DNA sequences to the human genome. Genome Biol. 2009, 10, R25. PMC2690996.

Li J, Rix U, Fang B, Bai Y, Edwards A, Colinge J, Bennett KL, Gao J, Song L, Eschrich S, Superti-Furga G, Koomen J, Haura EB. A chemical and phosphoproteomic characterization of dasatinib action in lung cancer. Nat Chem Biol. 2010, 6, 291-9. PMC2842457.

Ma ZQ, Chambers MC, Ham AJ, Cheek KL, Whitwell CW, Aerni HR, Schilling B, Miller AW, Caprioli RM, Tabb DL. ScanRanker: Quality assessment of tandem mass spectra via sequence tagging. J Proteome Res. 2011, 10, 2896-904. PMC3128668.

MacLean B, Tomazela DM, Shulman N, Chambers M, et al. Skyline: an open source document editor for creating and analyzing targeted proteomics experiments. Bioinformatics, 2010, 26, 966-8.

Martin DB, Holzman T, May D, Peterson a, et al. MRMer, an interactive open source and cross-platform system for data extraction and visualization of multiple reaction monitoring experiments. Mol Cell Proteomics 2008, 7, 2270-8.

(56) References Cited

OTHER PUBLICATIONS

Martinez-Lopez J, Martinez-Sanchez P, Garcia-Sanz R, Sarasquete ME, Ayala R, Gonzalez M, Bautista JM, Gonzalez D, San Miguel J, Garcia-Effron G, Lahuerta JJ. Application of self-quenched JH consensus primers for real-time quantitative PCR of IGH gene to minimal residual disease evaluation in multiple myeloma. J Mol Diagn. 2006, 8, 364-70. PMC1867600.
Morita K, Okamoto Y. The discrepancy between electrophoretic and nephelometric determinations of serum gamma globulin level. Clin Lab. 2004, 50, 415-18.
Mussap M, Pietrogrande F, Ponchia S, Stefani PM, Sartori R, Plebani M. Measurement of serum monoclonal components: comparison between densitometry and capillary zone electrophoresis. Clin Chem Lab Med. 2006, 44, 609-11.
O'Connell TX, Horita TJ, Kasravi B. Understanding and interpreting serum protein electrophoresis. *Am Fam Phys.* 2005, 71, 105-112.
Perkins DN, Pappin DJ, Creasy DM, Cottrell JS. Probability-based protein identification by searching sequence databases using mass spectrometry data. Electrophoresis 1999, 20, 3551-67.
Pika T, Minarik J, Schneiderka P, Budikova M, Langova K, Lochman P, Bacovsky J, Farbiakova V, Scudla V. The correlation of serum immunoglobulin free light chain levels and selected biological markers in multiple myeloma. Biomed Pap Med Fac Univ Palacky Olomouc Czech Repub. 2008, 152, 61-4.
Pilarski LM, Lauzon J, Strachan E, Adamia S, Atrazhev A, Belch AR, Backhouse CJ. Sensitive detection using microfluidics technology of single cell PCR products from high and low abundance IgH VDJ templates in multiple myeloma. J Immunol Methods 2005, 305, 94-105.
Prakash A, Rezai T, Krastins B, Sarracino D, Athanas M, Russo P, Zhang H, Tian Y, Li Y, Kulasingam V, Drabovich A, Smith CR, Batruch I, Oran PE, Fredolini C, Luchini A, Liotta L, Petricoin E, Diamandis EP, Chan DW, Nelson R, Lopez MF. Platform for establishing interlaboratory reproducibility of selected reaction monitoring-based mass spectrometry peptide assays. J Proteome Res. 2010, 9, 6678-88.
Puig N, Sarasquete ME, Alcoceba M, Balanzategui A, Chillón MC, Sebastián E, Marin LA, Diaz MG, San Miguel JF, Sanz RG. The use of CD138 positively selected marrow samples increases the applicability of minimal residual disease assessment by PCR in patients with multiple myeloma. Ann Hematol. 2013, 92, 97-100.
Raab MS, Cremer FW, Breitkreutz IN, Gerull S, Luft T, Benner A, Goerner M, Ho AD, Goldschmidt H, Moos M. Molecular monitoring of tumour load kinetics predicts disease progression after non-myeloablative allogeneic stem cell transplantation in multiple myeloma. Ann Oncol. 2005, 16, 611-7.
Reimer CB, Maddison SE. Standardization of human imunoglobulin quantitation: A review of current status and problems. Clin Chem. 1976, 22, 577-82.
Remily-Wood ER, Liu RZ, Xiang Y, Chen Y, Thomas CE, Rajyaguru N, Kaufman LM, Ochoa JE, Hazlehurst L, Pinilla-Ibarz J, Lancet J, Zhang G, Haura E, Shibata D, Yeatman T, Smalley KS, Dalton WS, Huang E, Scott E, Bloom GC, Eschrich SA, Koomen JM. A database of reaction monitoring mass spectrometry assays for elucidating therapeutic response in cancer. Proteomics Clin Appl. 2011, 5, 383-96. PMC3530891.
Schell MJ, Singh B. The reduced monotonic regression method. J Am Stat Assoc. 1997, 92, 128-35.
Schreiber WE, Chiang E, Tse SS. Electrophoresis underestimates the concentration of polyclonal immunoglobulins in serum. Am J Clin Pathol. 1992, 97, 610-13.
Shan L, Chen YA, Davis L, Han G, Zhu W, Molina AD, Arango H, LaPolla JP, Hoffman MS, Sellers T, Kirby T, Nicosia SV, Sutphen R. Measurement of phospholipids may improve diagnostic accuracy in ovarian cancer. Plos One 2012, 7, e46846. PMC3474784.
Shao YE, Hou C-D. Change point determination for a multivariate process using a two-stage hybrid scheme. Applied Soft Computing 2013, 13, 1520-7.
Tate JR, Mollee P, Dimeski G, Carter AC, Gill D. Analytical performance of serum free light-chain assay during monitoring of patients with monoclonal light-chain diseases. Clin Chim Acta 2007, 376, 30-6.
Trapnell C, Pachter L, Salzberg SL. TopHat: discovering splice junctions with RNA-Seq. Bioinformatics 2009, 25, 1105-11. PMC2672628.
Trapnell C, Williams BA, Pertea G, Mortazavi AM, Kwan G, van Baren MJ, Salzberg SL, Wold B, Pachter L. Transcript assembly and quantification by RNA-Seq reveals unannotated transcripts and isoform switching during cell differentiation. Nat Biotech. 2010, 28, 511-5. PMC3146043.
Trepel M, Martens V, Doll C, Rahlff J, Gösch B, Loges S, Binder M. Phenotypic detection of clonotypic B cells in multiple myeloma by specific immunoglobulin ligands reveals their rarity in multiple myeloma. PLoS One 2012, 7, e31998. PMC3285203.
Van de Velde Hj, Liu X, Chen G, Cakana A, Deraedt W, Bayssas M. Complete response correlates with long-term survival and progression-free survival in high-dose therapy in multiple myeloma. Haematologica 2007, 92, 1399-1406.
Yocum AK, Khan AP, Zhao R, Chinnaiyan AM. Development of selected reaction monitoring-MS methodology to measure peptide biomarkers in prostate cancer. Proteomics 2010, 10, 3506-14.
Zhang G, Fang B, Liu RZ, Lin H, et al. Mass spectrometry mapping of epidermal growth factor receptor phosphorylation related to oncogenic mutations and tyrosine kinase inhibitor sensitivity. J Proteome Res. 2011, 10, 305-19.

* cited by examiner

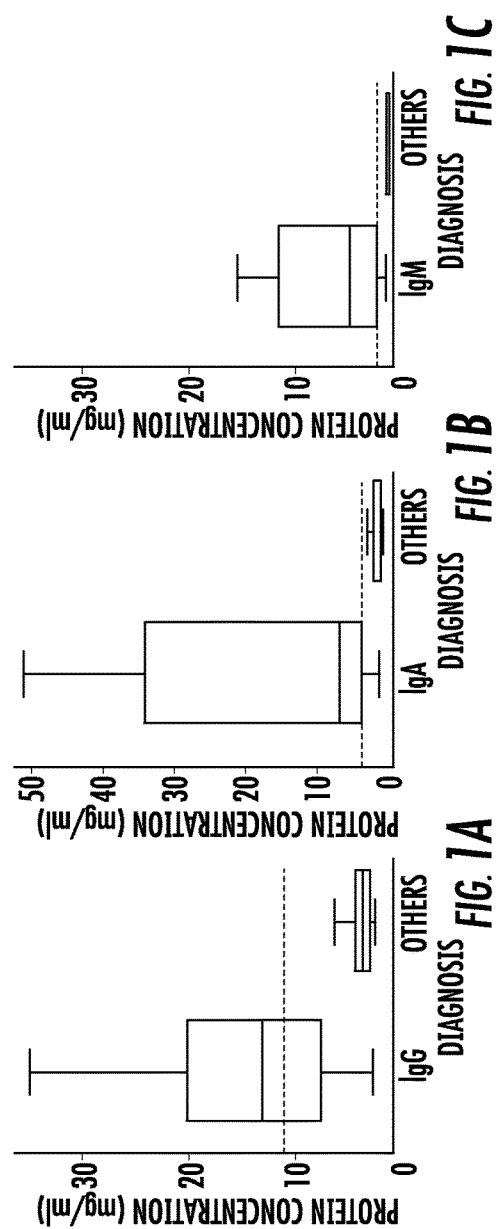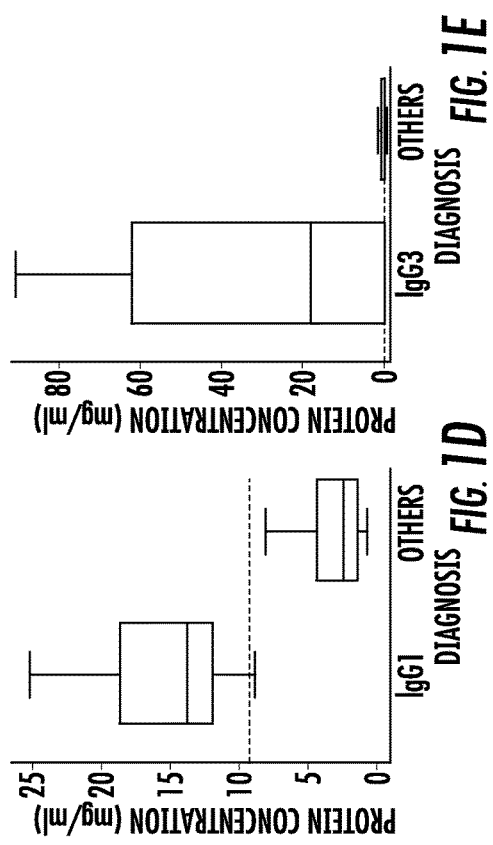

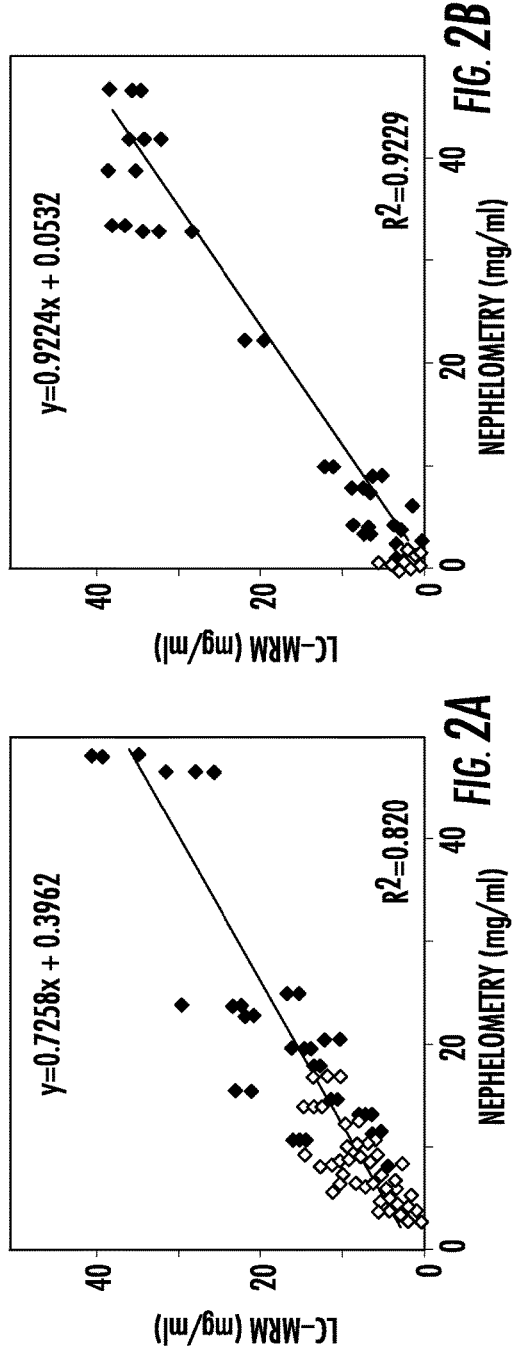
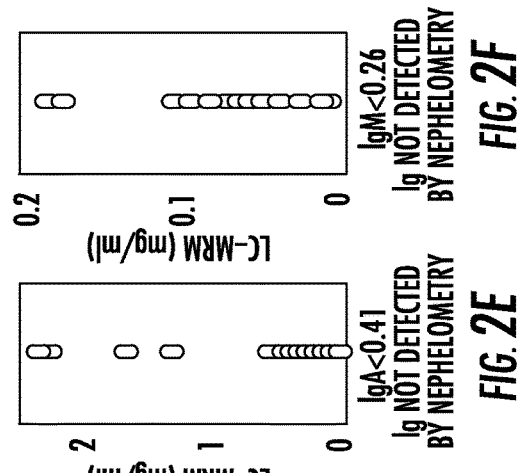
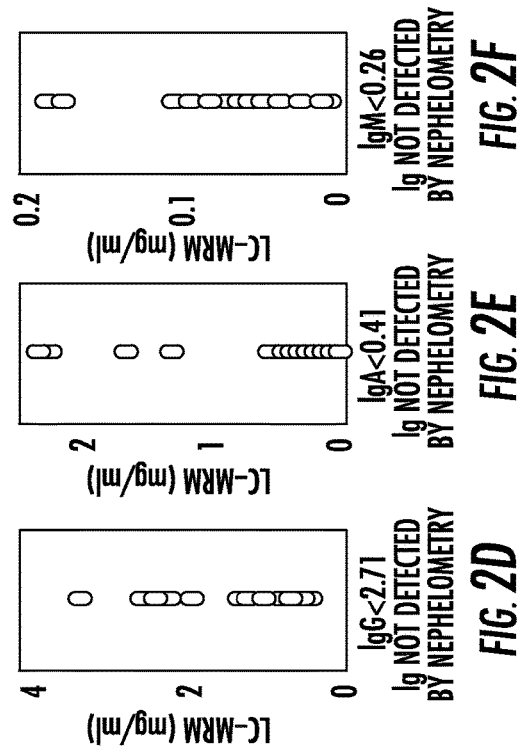
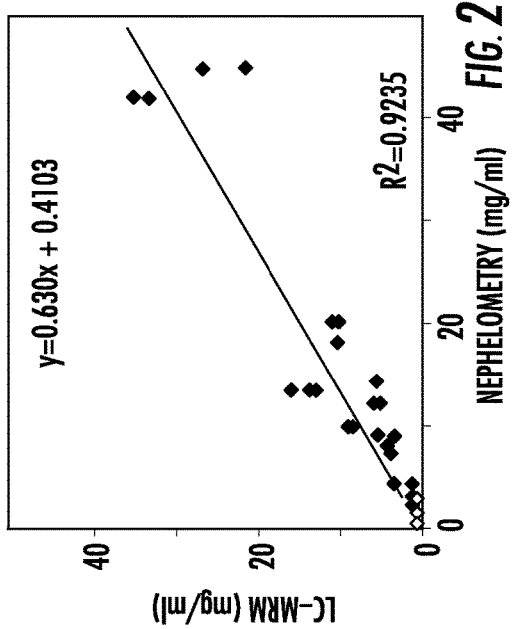

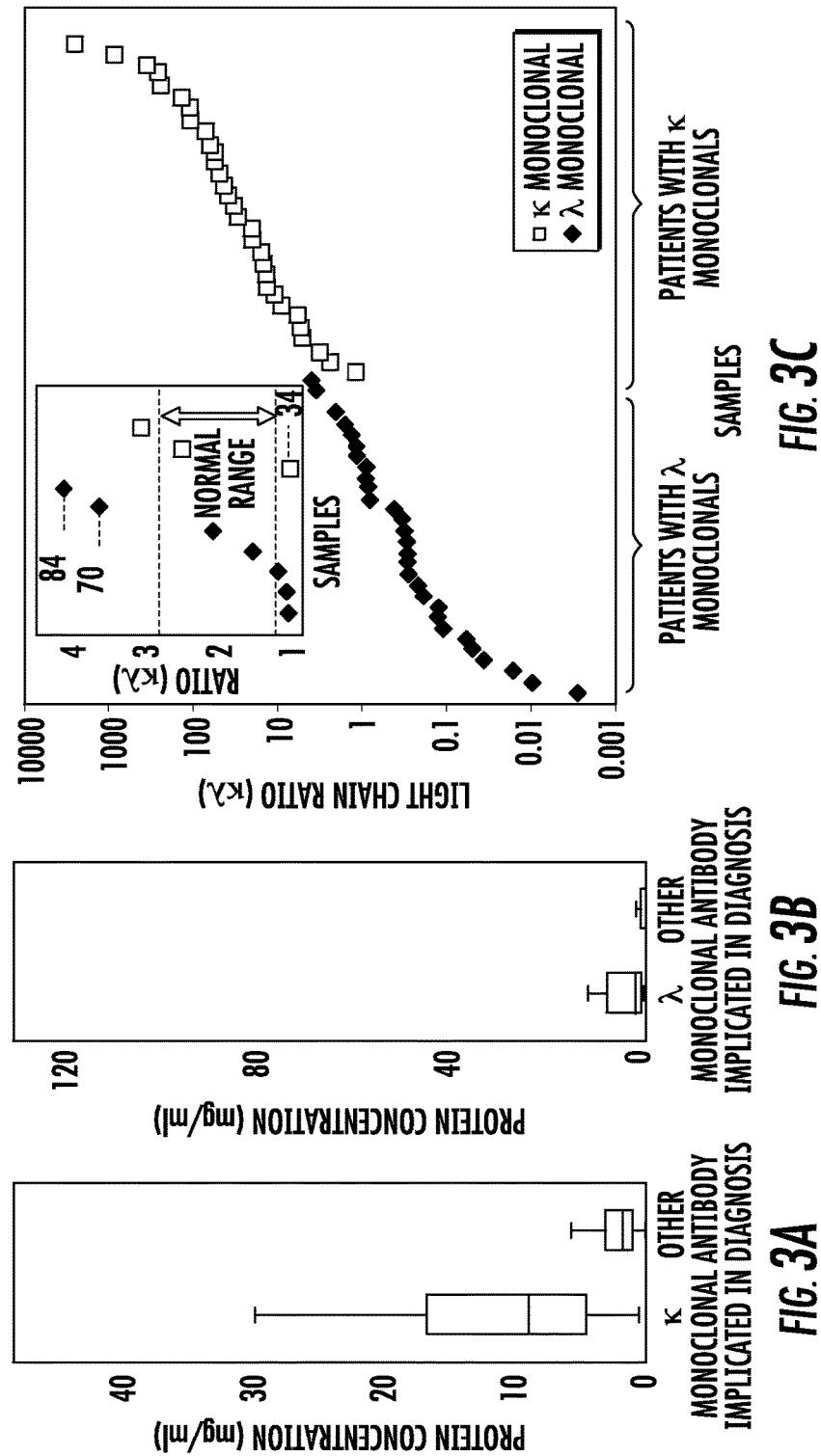

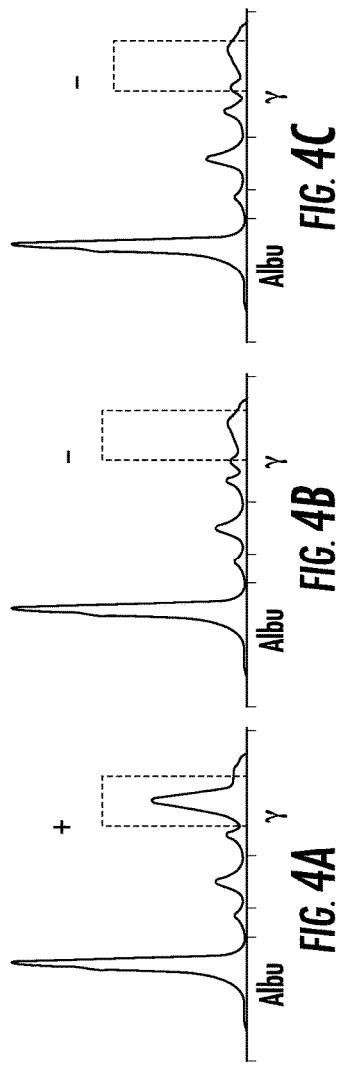
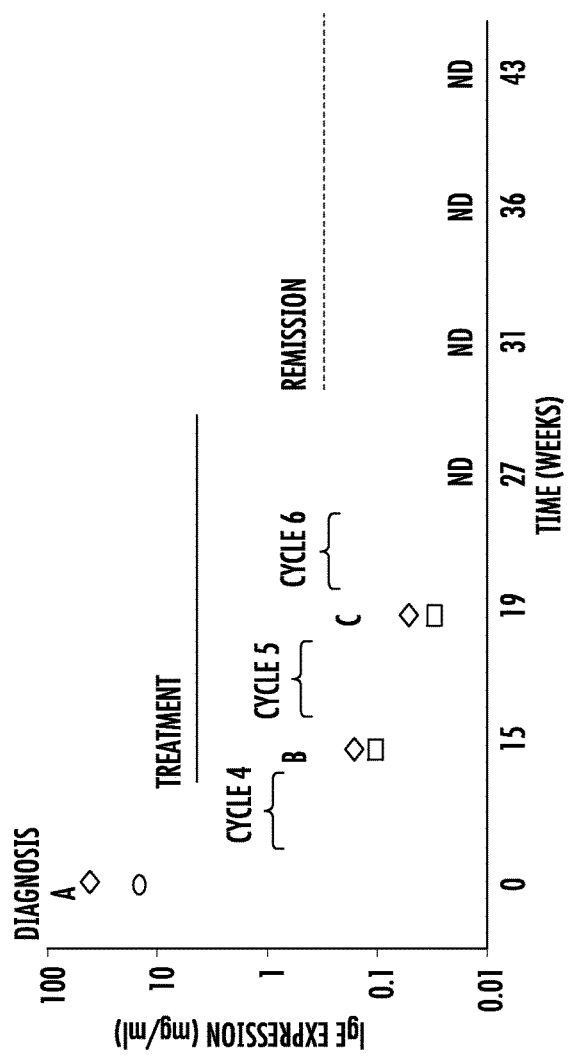

PERSONALIZED MYELOMA DETECTION

CROSS-REFERENCE TO RELATED APPLICATIONS

This application claims benefit of U.S. Provisional Application No. 61/946,629, filed Feb. 28, 2014, which is hereby incorporated herein by reference in its entirety.

BACKGROUND

Multiple myeloma (MM) is a plasma cell cancer characterized by bone marrow clonal plasmacytosis, monoclonal immunoglobulin expression in the serum and/or urine, lytic bone lesions, hypercalcemia, anemia, and renal failure. MM patients initially respond to therapy, but relapse with drug-resistant disease. Therefore, early detection and effective monitoring are critical for management of MM patients. Current clinical assays focus on detection and quantification of the monoclonal immunoglobulin (or M-protein) secreted by the tumor cells, which is essential for diagnosis and monitoring of patients with MM and other plasma cell dyscrasias (PCD). The Durie and Salmon staging system and the International Staging System (ISS) are based on the correlation between the expression of the monoclonal immunoglobulin and the disease burden. The International Myeloma Working Group guidelines also describe the assessment of treatment outcomes based on the changes in expression of the M-protein. Patient monitoring strategies present significant challenges, particularly in the diagnosis of premalignant monoclonal gammopathy of undetermined significance (MGUS), prediction of progression from MGUS to MM, assessment of response to therapy, and detection of relapse.

Evaluation of disease is accomplished by serial measurements of the M-protein in serum and urine using a variety of techniques (Berth M, et al Clin Chem 1999, 45, 309-10; French MAH, et al Clin Exp Immunol 1984, 56, 473-5; Haraldsson A, et al Ann Clin Biochem 1991, 28, 461-66; Chen K, et al Nephrology 2005, 10, 594-596; Buckley R, et al J Clin Invest 1975, 55, 157-65; Hunder G, et al Arthritis Rheum 1974, 17, 955-63). Typically, initial measurements are made using serum protein electrophoresis (SPEP), which is limited in sensitivity to approximately 0.1 gram per deciliter (g/dl) (O'Connell T X, et al Am Fam Phys 2005, 71, 105-112). The monoclonal immunoglobulin produced in high concentration by MM cells can be visualized as a narrow, discrete, dark band usually in the γ region of the gel or electropherogram. SPEP densitometry and total serum protein concentration are used to estimate the amount of the immunoglobulin secreted by the tumor. Patients can be further characterized using immunofixation electrophoresis (IFE). IFE screens test for immunoglobulin G, A, and M heavy chains, as well as kappa (κ) and lambda (λ) light chains. Immunoglobulin D and E myelomas are rare; when suspected, IFE is repeated to detect IgD or IgE. The combination of SPEP and IFE establishes an estimated level in the serum and type of the immunoglobulin that is secreted by the tumor. These traditionally gel-based techniques have recently been replaced by capillary array instruments (Jolliff C R, et al Electrophoresis 1997, 18, 1781-4). For immunoglobulin heavy chains with high expression, SPEP is the current clinical standard for detecting tumor burden, because the disease-specific immunoglobulin is directly monitored.

However, several factors limit SPEP in monitoring tumor burden in patients (Morita K, et al Clin Lab 2004, 50, 415-18; Schreiber W E, et al Am J Clin Pathol 1992, 97, 610-13). Therefore, quantification of the involved immunoglobulin by nephelometry is also used to monitor tumor burden (Clark R, et al Electrophoresis 1998, 19, 2479-84), and it has particular value for immunoglobulins with lower abundances in serum (e.g. IgD and IgE), particularly because the background expression of these immunoglobulins is low. Serum free light chain assays (SFLC) are also implemented using nephelometry to provide an expression ratio between the light chains, which supplements other techniques for the detection of light chain only disease (Jagannath S Clin Lymphoma Myeloma 2007, 7, 518-23; Tate J R, et al Clin Chim Acta 2007, 376, 30-6; Pika T, et al Biomed Pap Med Fac Univ Palacky Olomouc Czech Repub 2008, 152, 61-4). Antibody-based methods for protein quantification are also influenced by the complexity of the immunoglobulin system of the biologically derived antiserum and variation in its reactivity, as well as changes in the levels of proteins in the standard reagents (typically pooled serum) (Reimer C B, et al Clin Chem 1976, 22, 577-82). The presence of immunological subclasses (i.e. IgG1-4 and IgA1-2) also adds to the complexity of the analysis (Reimer C B, et al Clin Chem 1976, 22, 577-82).

Minimal residual disease (MRD) is the name given to small numbers of leukaemic cells that remain in the patient during treatment, or after treatment when the patient is in remission. It is the major cause of relapse in cancer and leukaemia. However, conventional SPEP is not sufficiently effective for detecting MRD.

A quantitative proteomic assay personalized for an individual patient and useful for direct measurement of the disease-specific immunoglobulin would significantly increase the sensitivity of detection over SPEP and allow for detection of MRD so treatment can be altered.

SUMMARY

Disclosed herein is a personalized method for monitoring a condition or disorder associated with antibody production in a subject. In particular, the method can be used to monitor a plasma cell dyscrasia (PCD) in a subject. The method can involve treating a biological sample comprising immunoglobulin from the subject to enzymatically cleave a target immunoglobulin associated with the PCD into one or more variable domain peptide fragments of the target immunoglobulin. The method can further involve measuring the one or more variable domain peptide fragments in the sample by quantitative mass spectrometry to quantify the amount of the target immunoglobulin in the sample. In some embodiments, PCD is monitored in the subject by the amount of the target immunoglobulin in the sample.

The disclosed method is personalized in that variable domain peptide fragments unique to the specific target immunoglobulin associated with PCD in the subject can be used. Therefore, in some embodiments, the method first involves identifying variable domain peptide fragments that can be used to quantify the target immunoglobulin in the subject. This method can involve determining the amino acid sequence of the target immunoglobulin and then identifying in silico one or more variable domain peptide fragments formed by enzymatic digestion of the target immunoglobulin that can be used in the disclosed methods. For example, these peptides preferably contain an amino acid sequences from the variable domain of the target immunoglobulin that is sufficiently unique to distinguish the target immunoglobulin from other immunoglobulin in the biological sample. For example, the one or more variable domain peptides fragments can contain the complementarity defining region (CDR) of the target immunoglobulin. In addition, the variable domain peptides should also be detectable by a mass spectrometer.

The amino acid sequence of the target immunoglobulin can be determined either from the immunoglobulin protein, e.g., isolated from the blood or urine, or from mRNA isolated from isolated plasma cells, e.g., from the bone marrow. In some embodiments, the method involves RNA-sequencing immunoglobulin mRNA from a plasma cell of the subject that is associated with the PCD. This RNA sequence can then be in silico translated into protein to determine the amino acid sequence. In some embodiments, 5' rapid amplification of cDNA ends (RACE) is used to sequence the target immunoglobulin. Primers can be developed against the constant region of the immunoglobulin (toward the C-terminus of the protein) so that the variable region can then be sequenced by reading back to the 5' end of the RNA.

The disclosed method can be used to detect any class of immunoglobulin involved in a PCD. For example, the variable domain peptides can be from a human heavy chain of IgG1-4, IgA1-2, IgM, IgD, or IgE. The variable domain peptides can be from a human kappa light chain or any of the human lambda light chain isoforms. In some cases, the immunoglobulin in the sample is denatured prior to enzymatic cleavage. For example, the immunoglobulin can be denatured by heat, treatment with urea, disulfide reduction, and/or cysteine alkylation.

In some embodiments, the method further involves a treating step to isolate the target immunoglobulin prior to enzymatic cleavage. For example, the treating step can involve one or more of size exclusion chromatography, gel electrophoresis, and/or affinity chromatography.

The immunoglobulin in the sample can be enzymatically cleaved by proteolytic enzyme digestion. Non-limiting examples of proteolytic enzymes include trypsin, pepsin, endoproteinase Lys-C, chymotrypsin, endoproteinase Glu-C, endoproteinase Asp-N, and endoproteinase Arg-C, and any combination thereof.

In some embodiments, the one or more variable peptide fragments are measured by spiking in during the mass spectrometry a known amount of the one or more variable peptides containing a specific label. For example, the specific label can be a heavy isotope label or an amino acid substitution sufficient to create a detectable mass difference. Non-limiting examples of heavy isotope labels include $^{2}H$, $^{13}C$, and $^{15}N$. The amino acid replacements are preferably conservative substitutions, e.g. leucine to valine or aspartic acid to glutamic acid.

Also disclosed herein are methods for quantifying total immunoglobulin in the biological sample by detecting constant domain peptides fragments containing amino acid sequences from a constant domain of the immunoglobulin that are conserved within each class of immunoglobulin. In some embodiments, the method involves determining the ratio of target immunoglobulin (i.e., variable domain peptides) to total immunoglobulin (i.e., constant domain peptides) in the biological sample. This ratio identifies the amount of normal immunoglobulin, which can be used to detect immune paresis.

The mass spectrometry of the disclosed methods preferably involves the use of liquid chromatography coupled to multiple reaction monitoring (LC-MRM). For rapid sample analysis, direct infusion-MRM could also be used. Parallel reaction monitoring and pseudo-MRM could also be used to identify and quantify the peptides using fragment ions observed in tandem mass spectrometry. The mass spectrometry can be conducted on a triple quadrupole mass spectrometer. Ion trap, orbital ion trap, and hybrid quadrupole-time-of-flight mass spectrometers could also be used.

The plasma cell dyscrasia (PCD) can be any plasma cell cancer that results in overproduction of an immunoglobulin. Non-limiting examples of PCDs include multiple myeloma, monoclonal gammopathy of undetermined significance (MGUS), solitary plasmacytoma of bone, extramedullary plasmacytoma, Waldenström's macroglobulinemia (WM), primary amyloidosis, light chain deposition disease and heavy-chain disease. For example, where the PCD is a multiple myeloma, the plasma cells used to sequence the target immunoglobulin can be $CD138^{+}$ cells, e.g., extracted from bone marrow aspirates.

The spectrum of MGUS, solitary plasmacytoma of bone, and asymptomatic and symptomatic multiple myeloma may actually represent a natural progression of the same disease. The disclosed methods may be especially useful to monitor this progression, by precise measurement of the increases in signal/amount of the immunoglobulin secreted by the tumor cells.

The methods may also be used to monitor the efficacy of a treatment regimen on a subject with a PCD, such as multiple myeloma or MGUS, by evaluating the decrease of the signal/amount for the immunoglobulin specific to the disease. This can also be used to detect and eliminate minimal residual disease (MRD) since it can detect antibodies from tumor cells at levels approximately 67 times lower than conventional methods.

In addition, these methods could be used for more sensitive detection of relapse, which would open earlier therapeutic windows and could lead to more effective intervention and better patient outcomes. In some embodiments, the methods involve selecting an alternative therapy if relapse is detected.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1: Box plots Comparing Monoclonal Immunoglobulin Expression in Serum for MM Patients with IgG, IgA, and IgM Diagnoses to Other Patients. Patients with positive diagnosis for specific immunoglobulin types, IgG (A), IgA (B), and IgM (C), are compared with other patients, including both patients not diagnosed with MM and patients diagnosed with MM that express other types of monoclonal immunoglobulins. Data are not included for IgD (n=5) and IgE (n=1), because the separation is clear between those patients and the rest of the population. Current clinical measurements are not able to determine the expression of IgG (or IgA) isoforms, but specific peptides from each sequence can be monitored by LC-MRM to differentiate the isoforms of these heavy chains. Patients with each IgG subtype, IgG1 (D) and IgG3 (E) are compared with all other patients in the study. Data are not included for IgA2 (n=0), IgG2 (n=2), or IgG4 (n=1), because the separation is clear between the patients expressing those isoforms and the rest of the population. In each plot, dashed lines indicate the maximum normal immunoglobulin level.

FIG. 2: Correlation of Immunoglobulin Measurements by Nephelometry and LC-MRM Quantification of Peptides Selected from the Constant Region of Each Immunoglobulin. Data from patients whose MM secrete each immunoglobulin (black diamonds) and from other types of patients (open circles) are plotted for IgG (A), IgA (B), and IgM (C) measurements. Insets show values for LC-MRM quantification for samples that were below the threshold for the nephelometry measurements. LC-MRM could also quantify immunoglobulin expression levels that were not detectable by nephelometry; data are presented for IgG (D), IgA (E), and IgM (F).

FIG. 3: LC-MRM Analysis of Total Light Chain Expression in Serum. Box plots are shown to compare patients expressing kappa light chain in their monoclonal to other patients (A) and those expressing lambda light chain to other patients (B). Average κ:λ ratios determined from triplicate LC-MRM measurements are also shown for each patient (C), with the exception of 5 patients with κ monoclonals that produced detectable, but not quantifiable, amounts of λ light chain. The normal ratio for total expression of light chains in healthy adults (1.3-2.7) is outlined by dotted lines in the inset (C); three patients with low monoclonal immunoglobulin expression had ratios on the opposite side of the normal range from the light chain indicated in their diagnosis.

FIG. 4: LC-MRM and Nephelometry Have Similar Sensitivity for Detection of Treatment Response in an IgE MM Patient. The patient was monitored over time with SPEP (A-C) as well as nephelometry and LC-MRM (D) starting at the time of diagnosis and continuing through the treatment regimen of a clinical trial combining a proteasome inhibitor and an immunomodulator. Both SPEP (circle) and LC-MRM (diamonds) results show IgE elevation at diagnosis (A). During treatment (B and C), the SPEP is negative, but elevated IgE is still detected by nephelometry (squares) and LC-MRM (D, letters A-C indicate quantification from the same serum samples as the SPEP data panels above) are still able to detect elevated IgE. Nephelometry and LC-MRM can observe the decrease in tumor burden after the $5^{th}$ cycle of treatment, and IgE is not detected (ND) in the patient serum by either method after the $6^{th}$ cycle of therapy. Tumor burden is reduced by three orders of magnitude, before the immunoglobulin is no longer detected.

DETAILED DESCRIPTION

Figures 5A, 5B:
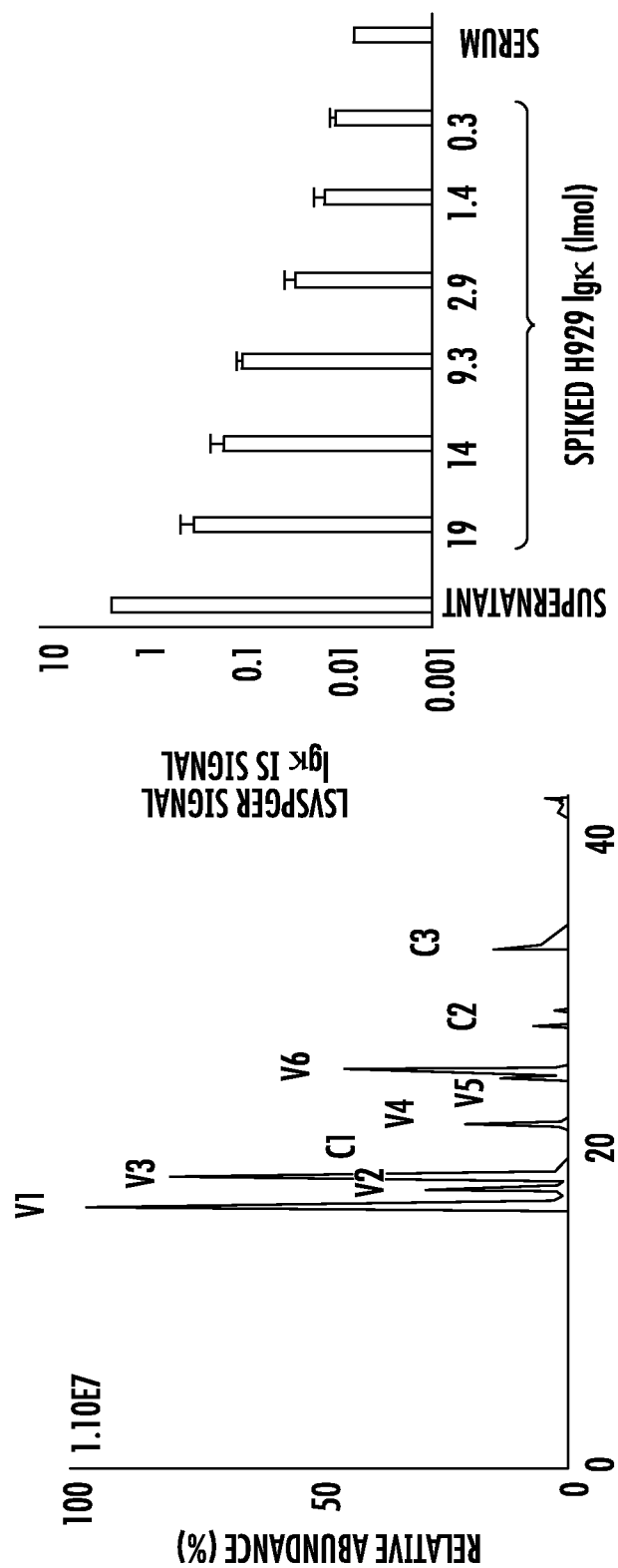
FIG. 5: RNA-Seq, Protein Sequence, and LC-MRM Verification of Constant and Variable Region Peptides for H929 MM Cells. RNA-seq and in silico translation produced a protein sequence, which was verified by LC-MRM detection of constant (C1-C3) and variable region (V1-V6) peptides from digests of conditioned media (A). Spiked H929 Igκ could also be detected in control serum (B).
Figure 6A:
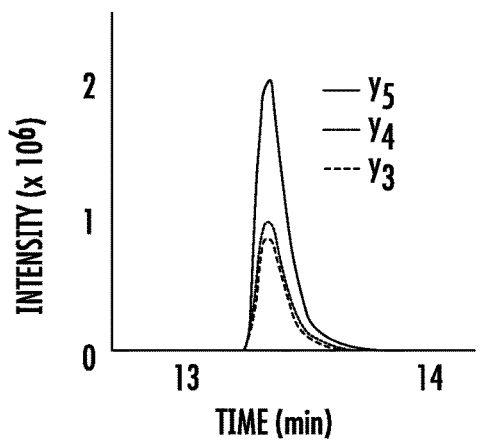
FIG. 6: Detection of Peptides from the Disease-Specific Igκ Light Chain. Three peptides derived from RNA-seq and κ light chain assembly using tumor cells from Patient 1 were observed with LC-MRM in a serum sample with 0.2 g/dl M-protein: VTITCR (SEQ ID NO:23) (FIG. 6A), SLIYAASSLQSGVPSK (SEQ ID NO:24) (FIG. 6C), and ANQDITNSLVWFQQK (SEQ ID NO:25) (FIG. 6D). Data are provided from Patient 2 to illustrate the uniqueness of the three peptides (FIG. 6B, FIG. 6D, and FIG. 6F, respectively).
Figure 6B:
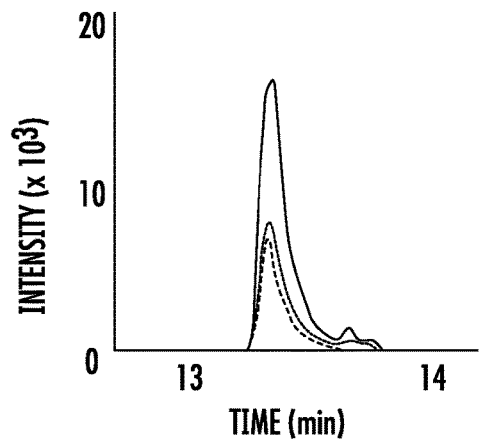
Figure 6C:
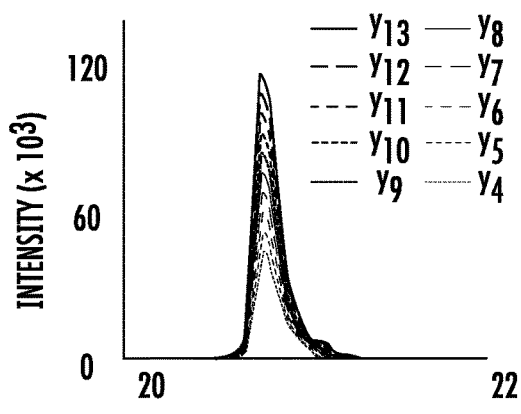
Figure 6D:
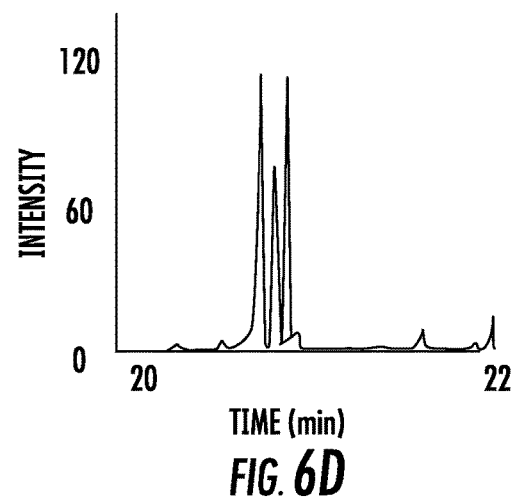
Figure 6E:
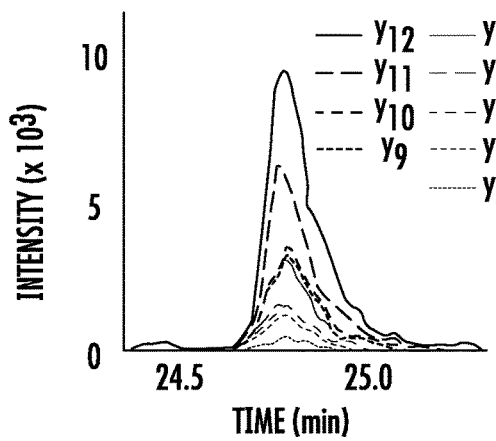
Figure 6F:
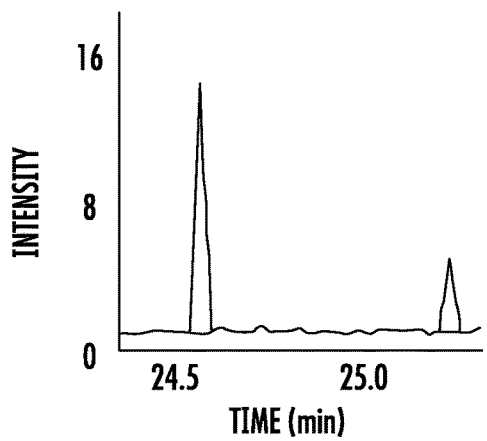
Figure 7A:
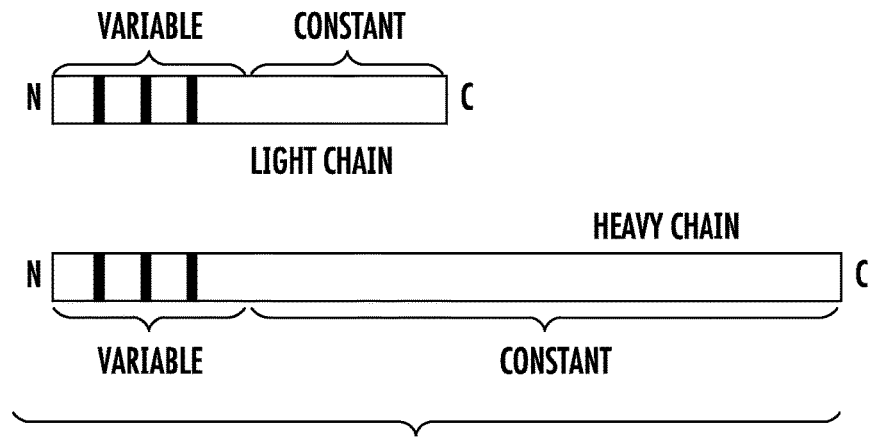
FIG. 7: Exemplary workflow for personalized detection of multiple myeloma tumor burden. Each immunoglobulin (Ig) has unique sequences in the complementarity defining region (black bars), which will be unique to the tumor (A). Two methods are shown for defining the Ig sequence: RNA sequencing and de novo peptide sequencing. Then assays developed for patients are used for longitudinal monitoring of tumor burden.
Figure 7B:
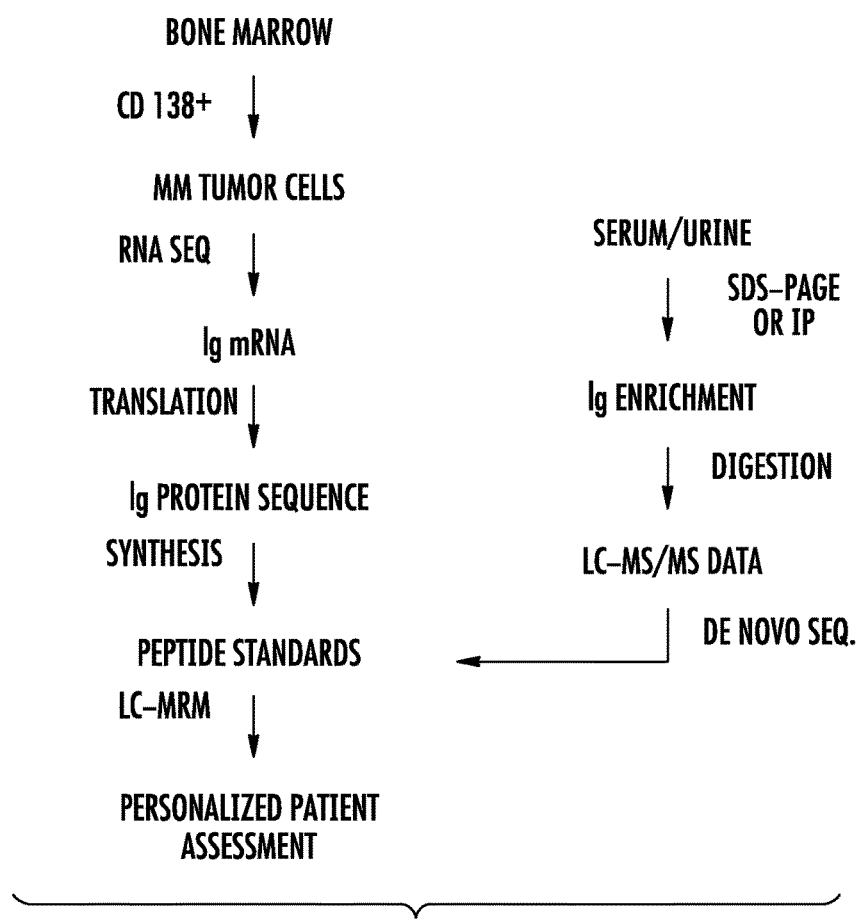

Liquid chromatography-multiple reaction monitoring mass spectrometry (LC-MRM) using stable isotope dilution has enabled the assessment of protein biomarkers (Barr J R, et al Clin Chem 1996, 42, 1676-82; Barnidge D R, et al Anal Chem 2003, 75, 445-51; Gerber S A, et al Proc Natl Acad Sci USA 2003, 100, 6940-45; Anderson L, et al Mol Cell Proteomics 2006, 5, 573-88; Kuzyk M A, et al Mol Cell Proteomics 2009, 8, 1860-77; Keshishian H, et al Mol Cell Proteomics 2007, 6, 2212-29; Kirsch S, et al J Chromatogr A 2007, 1153, 300-6; Kuhn E, et al Proteomics 2004, 4, 1175-86; Barnidge D R, et al J Proteome Res 2004, 3, 644-52; Yocum A K, et al Proteomics 2010, 10, 3506-14). In addition, collaborative groups have standardized LC-MRM assays at multiple sites (Addona T A, et al Nat Biotechnol 2009, 27, 633-41; Prakash A, et al J Proteome Res 2010, 9, 6678-88). Based on these advances, this technology holds great promise for patient assessment, and LC-MRM is being used in translational research programs (Koomen J M, et al Mol Cell Proteomics 2008, 7, 1780-94). This technology has also been used to measure clinically-relevant protein biomarkers, including troponin I and interleukin-33 (Kuhn E, et al Clin Chem 2009, 55, 1108-17), apolipoproteins (Agger S A, et al Clin Chem 2010, 56, 1804-13), and thyroglobulin (Hoofnagle A N, et al Clin Chem 2008, 54, 1796-804).

Quantification of immunoglobulins can be achieved at two levels. Peptides from the constant regions can be quantified to evaluate levels of total immunoglobulin expression. The comparison of LC-MRM of constant region peptides to immunoglobulin quantification with current clinical techniques provides information about the utility, advantages, and disadvantages of the technique. In addition, development of assays for peptides from the variable region enables a measurement of the disease-specific immunoglobulin, similar in specificity to SPEP detection. Using the strategy of informing proteomics with RNA-sequencing (Evans V C, et al Nat Methods 2012, 9, 1207-11), data are provided for personalized detection of myeloma tumor burden using RNA-sequencing and LC-MRM variable region peptide detection for both an in vitro system (i.e. H929 cells) and patients.

Disclosed is a method for detecting and quantifying the tumor burden in patients with a PCD, such as multiple myeloma. RNA sequencing from tumor cells can be used to define the sequence of the immunoglobulin protein that they secrete. This protein can be measured in blood or urine to assess the patient. The disclosed methods increase sensitivity for determining the tumor burden in patients with a PCD, such as multiple myeloma. These measurements can better define the response to therapy and detect relapse earlier.

In current clinical practice, the presence of monoclonal immunoglobulin is detected or quantified by serum protein electrophoresis (SPEP) and the total amount of the immunoglobulin is quantified by nephelometry. In reaction monitoring mass spectrometry, specific structural fragments are isolated from specific peptide precursors and quantified by the integration of their peak area. Each precursor and fragment pair is termed a transition. Several transitions detected at the same time provide confidence in the quantification of the molecule.

A level of antibody can, for example, be determined by comparing to a reference standard of known values. A person of skill in the art is capable of preparing a reference standard of known values. The reference standard can be prepared at the same time, prior to, or after determination of the level of antibody. For MRM mass spectrometry, these standards are typically stable-labeled peptides but peptides that are structurally analogous to the sequence of interest can also be used if stable-labeled peptides are not available. The signals for the endogenous (biological) peptide are compared to the same set of signals from the standard peptide to enable quantification.

As used herein a control can comprise a known value or reference sample. A known value refers to a value from a diseased sample or a group of diseased samples, which can represent, a sample from a subject diagnosed with cancer or a disease associated with antibody production. Optionally, the reference sample is from a diseased subject of similar size, weight, height and gender, as the subject being tested or a pooled sample from multiple healthy controls.

Optionally, the antibody comprises a heavy chain selected from the group consisting of IgG1-4, IgA1-2, IgM, IgD, and IgE. Optionally, the antibody comprises a light chain selected from a kappa light chain or a lambda light chain.

Constant Region Peptides

Exemplary peptides for LC-MRM quantification of total immunoglobulin or specific isoforms are provided below. These measurements can be paired with the detection of specific sequences from the disease-specific monoclonal immunoglobulin to understand disease burden and assist in detecting relapse if another tumor cell secreting a different immunoglobulin grows out after treatment. All peptides listed below can include possible alkylation of cysteine with iodoacetamide (or comparable reagents) and methionine oxidation. In addition, peptides with missed cleavages could be detected, which would be made of combinations of the sequences below.

```
IgG1 Peptides from Constant Region
Trypsin:
                                    (SEQ ID NO: 26)
GFYPSDIAVEWESNGQPENNYK, (SEQ ID NO: 27)
TPEVTCVVVDVSHEDPEVK, (SEQ ID NO: 28)
TTPPVLDSDGSFFLYSK, (SEQ ID NO: 29)
VVSVLTVLHQDWLNGK, (SEQ ID NO: 30)
FNWYVDGVEVHNAK, (SEQ ID NO: 31)
EPQVYTLPPSR, (SEQ ID NO: 32)
STSGGTAALGCLVK, (SEQ ID NO: 33)
EEQYNSTYR, (SEQ ID NO: 1)
GPSVFPLAPSSK, (SEQ ID NO: 34)
NQVSLTCLVK, (SEQ ID NO: 35)
ALPAPIEK, (SEQ ID NO: 36)
DTLMISR, (SEQ ID NO: 37)
SLSLSPGK;

Lys-C:
                                    (SEQ ID NO: 38)
GFYPSDIAVEWESNGQPENNYK, (SEQ ID NO: 39)
THTCPPCPAPELLGGPSVFLFPPK, (SEQ ID NO: 40)
GQPREPQVYTLPPSRDELTK, (SEQ ID NO: 41)
TTPPVLDSDGSFFLYSK, (SEQ ID NO: 42)
FNWYVDGVEVHNAK, (SEQ ID NO: 43)
STSGGTAALGCLVK, (SEQ ID NO: 44)
GPSVFPLAPSSK, (SEQ ID NO: 45)
NQVSLTCLVK, (SEQ ID NO: 46)
ALPAPIEK, (SEQ ID NO: 47)
SLSLSPGK;

Arg-C:
                                    (SEQ ID NO: 48)
EPQVYTLPPSR, (SEQ ID NO: 49)
EEQYNSTYR;

Chymotrypsin:
                                    (SEQ ID NO: 50)
ISRTPEVTCVVVDVSHEDPEVKF, (SEQ ID NO: 51)
VDGVEVHNAKTKPREEQY, (SEQ ID NO: 52)
APSSKSTSGGTAAL, (SEQ ID NO: 53)
ESNGQPENNY, (SEQ ID NO: 54)
TSGVHTFPAVL, (SEQ ID NO: 55)
ASTKGPSVFPL, (SEQ ID NO: 56)
YPSDIAVEW, (SEQ ID NO: 57)
SSVVTVPSSSL, (SEQ ID NO: 58)
FPEPVTVSW, (SEQ ID NO: 59)
FPPKPKDTL, (SEQ ID NO: 60)
TLPPSRDEL, (SEQ ID NO: 61)
TVDKSRW, (SEQ ID NO: 62)
TKNQVSL, (SEQ ID NO: 63)
KTTPPVL;

Glu-C (phosphate buffer):
                                    (SEQ ID NO: 64)
QYNSTYRVVSVLTVLHQD,
```

LTKNQVSLTCLVKGFYPSD, (SEQ ID NO: 65)

KSRWQQGNVFSCSVMHE, (SEQ ID NO: 66)

ALHNHYTQKSLSLSPGK, (SEQ ID NO: 67)

LLGGPSVFLFPPKPKD, (SEQ ID NO: 68)

YKCKVSNKALPAPIE, (SEQ ID NO: 69)

GSFFLYSKLTVD, (SEQ ID NO: 70)

VHNAKTKPREE, (SEQ ID NO: 71)

KTHTCPPCPAPE, (SEQ ID NO: 72)

NNYKTTPPVLD, (SEQ ID NO: 73)

VKFNWYVD, (SEQ ID NO: 74)

TLMISRTPE, (SEQ ID NO: 75)

KKVEPKSCD, (SEQ ID NO: 76)

WLNGKE; (SEQ ID NO: 77)

Glu-C (bicarbonate buffer):
LTKNQVSLTCLVKGFYPSDIAVE, (SEQ ID NO: 78)

ALHNHYTQKSLSLSPGK, (SEQ ID NO: 79)

YKCKVSNKALPAPIE, (SEQ ID NO: 80)

VKFNWYVDGVE, (SEQ ID NO: 81)

VHNAKTKPREE, (SEQ ID NO: 82)

VTCVVVDVSHE, (SEQ ID NO: 83)

SNGQPE; (SEQ ID NO: 84)

Asp-N:
DIAVEWESNGQPENNYKTTPPVL, (SEQ ID NO: 85)

DELTKNQVSLTCLVKGFYPS, (SEQ ID NO: 86)

DTLMISRTPEVTCVVV, (SEQ ID NO: 87)

DGSFFLYSKLTV, (SEQ ID NO: 88)

DPEVKFNWYV, (SEQ ID NO: 89)

DKKVEPKSC; (SEQ ID NO: 90)

IgG2 Peptides from Constant Region
Trypsin:
GFYPSDISVEWESNGQPENNYK, (SEQ ID NO: 91)

TTPPMLDSDGSFFLYSK, (SEQ ID NO: 92)

VVSVLTVVHQDWLNGK, (SEQ ID NO: 93)

STSESTAALGCLVK, (SEQ ID NO: 94)

EPQVYTLPPSR, (SEQ ID NO: 95)

GPSVFPLAPCSR, (SEQ ID NO: 96)

EEQFNSTFR, (SEQ ID NO: 97)

NQVSLTCLVK, (SEQ ID NO: 98)

DTLMISR, (SEQ ID NO: 99)

GLPAPIEK, (SEQ ID NO: 2)

SLSLSPGK; (SEQ ID NO: 100)

Lys-C:
GPSVFPLAPCSRSTSESTAALGCLVK, (SEQ ID NO: 101)

GFYPSDISVEWESNGQPENNYK, (SEQ ID NO: 102)

CCVECPPCPAPPVAGPSVFLFPPK, (SEQ ID NO: 103)

GQPREPQVYTLPPSREEMTK, (SEQ ID NO: 104)

TTPPMLDSDGSFFLYSK, (SEQ ID NO: 105)

NQVSLTCLVK, (SEQ ID NO: 106)

GLPAPIEK, (SEQ ID NO: 107)

SLSLSPGK; (SEQ ID NO: 108)

Arg-C:
ASTKGPSVFPLAPCSR, (SEQ ID NO: 109)

EPQVYTLPPSR, (SEQ ID NO: 110)

EEQFNSTFR; (SEQ ID NO: 111)

Chymotrypsin:
ISRTPEVTCVVVDVSHEDPEVQF, (SEQ ID NO: 112)

VDGVEVHNAKTKPREEQF, (SEQ ID NO: 113)

APCSRSTSESTAAL, (SEQ ID NO: 114)

ESNGQPENNY, (SEQ ID NO: 115)

TSGVHTFPAVL, (SEQ ID NO: 116)

SSVVTVPSSNF, (SEQ ID NO: 117)

ASTKGPSVFPL, (SEQ ID NO: 118)

YPSDISVEW, (SEQ ID NO: 119)

FPEPVTVSW, (SEQ ID NO: 120)

TLPPSREEM, (SEQ ID NO: 121)

FPPKPKDTL, (SEQ ID NO: 122)

TVDKSRW, (SEQ ID NO: 123)

TVVHQDW, (SEQ ID NO: 124)

TKNQVSL; (SEQ ID NO: 125)

Glu-C (phosphate buffer):

CPPCPAPPVAGPSVFLFPPK PKD, (SEQ ID NO: 126)

MTKNQVSLTCLVKGFYPSD, (SEQ ID NO: 127)

QFNSTFRVVSVLTVVHQD, (SEQ ID NO: 128)

KSRWQQGNVFSCSVMHE, (SEQ ID NO: 129)

ASTKGPSVFPLAPCSRSTSE, (SEQ ID NO: 130)

ALHNHYTQKSLSLSPGK, (SEQ ID NO: 131)

YKCKVSNKGLPAPIE, (SEQ ID NO: 132)

GSFFLYSKLTVD, (SEQ ID NO: 133)

VHNAKTKPREE, (SEQ ID NO: 134)

NNYKTTPPMLD, (SEQ ID NO: 135)

STAALGCLVKD, (SEQ ID NO: 136)

VQFNWYVD, (SEQ ID NO: 137)

TLMISRTPE, (SEQ ID NO: 138)

HKPSNTKVD, (SEQ ID NO: 139)

WLNGKE, (SEQ ID NO: 140)

RKCCVE, (SEQ ID NO: 141)

VTCVVVD; (SEQ ID NO: 142)

Glu-C (bicarbonate buffer):

MTKNQVSLTCLVKGFYPSDISVE, (SEQ ID NO: 143)

ASTKGPSVFPLAPCSRSTSE, (SEQ ID NO: 144)

ALHNHYTQKSLSLSPGK, (SEQ ID NO: 145)

YKCKVSNKGLPAPIE, (SEQ ID NO: 146)

VQFNWYVDGVE, (SEQ ID NO: 147)

VHNAKTKPREE, (SEQ ID NO: 148)

VTCVVVDVSHE, (SEQ ID NO: 149)

RKCCVE; (SEQ ID NO: 150)

Asp-N:

DISVEWESNGQPENNYKTTPPML, (SEQ ID NO: 151)

DTLMISRTPEVTCVVV, (SEQ ID NO: 152)

DGSFFLYSKLTV, (SEQ ID NO: 153)

DPEVQFNWYV, (SEQ ID NO: 154)

DHKPSNTKV; (SEQ ID NO: 155)

IgG3 Peptides from Constant Region
Trypsin:

TPEVTCVVVDVSHEDPEVQFK, (SEQ ID NO: 156)

WQQGNIFSCSVMHEALHNR, (SEQ ID NO: 157)

CPAPELLGGPSVFLFPPKPK, (SEQ ID NO: 158)

VVSVLTVLHQDWLNGK, (SEQ ID NO: 159)

WYVDGVEVHNAK, (SEQ ID NO: 3)

TPLGDTTHTCPR, (SEQ ID NO: 160)

EPQVYTLPPSR, (SEQ ID NO: 161)

STSGGTAALGCLVK, (SEQ ID NO: 162)

GPSVFPLAPCSR, (SEQ ID NO: 163)

EEQYNSTFR, (SEQ ID NO: 164)

NQVSLTCLVK, (SEQ ID NO: 165)

-continued

SCDTPPPCPR, (SEQ ID NO: 166)

ALPAPIEK, (SEQ ID NO: 167)

DTLMISR, (SEQ ID NO: 168)

SLSLSPGK; (SEQ ID NO: 169)

Lys-C:
GPSVFPLAPCSRSTSGGTAALGCLVK, (SEQ ID NO: 170)

GQPREPQVYTLPPSREEMTK, (SEQ ID NO: 171)

TPLGDTTHTCPRCPEPK, (SEQ ID NO: 172)

SCDTPPPCPRCPEPK, (SEQ ID NO: 173)

WYVDGVEVHNAK, (SEQ ID NO: 174)

NQVSLTCLVK, (SEQ ID NO: 175)

ALPAPIEK, (SEQ ID NO: 176)

SLSLSPGK; (SEQ ID NO: 177)

Arg-C:
WQQGNIFSCSVMHEALHNR, (SEQ ID NO: 178)

VELKTPLGDTTHTCPR, (SEQ ID NO: 179)

CPEPKSCDTPPPCPR, (SEQ ID NO: 180)

ASTKGPSVFPLAPCSR, (SEQ ID NO: 181)

FTQKSLSLSPGK, (SEQ ID NO: 182)

EPQVYTLPPSR, (SEQ ID NO: 183)

EEQYNSTFR; (SEQ ID NO: 184)

Chymotrypsin:
ISRTPEVTCVVVDVSHEDPEVQF, (SEQ ID NO: 185)

TCNVNHKPSNTKVDKRVEL, (SEQ ID NO: 186)

VDGVEVHNAKTKPREEQY, (SEQ ID NO: 187)

APCSRSTSGGTAAL, (SEQ ID NO: 188)

TSGVHTFPAVL, (SEQ ID NO: 189)

ESSGQPENNY, (SEQ ID NO: 190)

ASTKGPSVFPL, (SEQ ID NO: 191)

YPSDIAVEW, (SEQ ID NO: 192)

SSVVTVPSSSL, (SEQ ID NO: 193)

FPEPVTVSW, (SEQ ID NO: 194)

TLPPSREEM, (SEQ ID NO: 195)

FPPKPKDTL, (SEQ ID NO: 196)

TVDKSRW, (SEQ ID NO: 197)

TKNQVSL; (SEQ ID NO: 198)

Glu-C (phosphate buffer):
MTKNQVSLTCLVKGFYPSD, (SEQ ID NO: 199)

QYNSTFRVVSVLTVLHQD, (SEQ ID NO: 200)

KSRWQQGNIFSCSVMHE, (SEQ ID NO: 201)

ALHNRFTQKSLSLSPGK, (SEQ ID NO: 202)

LLGGPSVFLFPPKPKD, (SEQ ID NO: 203)

TTHTCPRCPEPKSCD, (SEQ ID NO: 204)

YKCKVSNKALPAPIE, (SEQ ID NO: 205)

TPPPCPRCPEPKSCD, (SEQ ID NO: 206)

GSFFLYSKLTVD, (SEQ ID NO: 207)

VHNAKTKPREE, (SEQ ID NO: 208)

NNYNTTPPMLD, (SEQ ID NO: 209)

TPPPCPRCPAPE, (SEQ ID NO: 210)

VQFKWYVD, (SEQ ID NO: 211)

TLMISRTPE, (SEQ ID NO: 212)

WLNGKE, (SEQ ID NO: 213)

LKTPLGD, (SEQ ID NO: 214)

VTCVVVD; (SEQ ID NO: 215)

Glu-C (bicarbonate buffer):
MTKNQVSLTCLVKGFYPSDIAVE, (SEQ ID NO: 216)

ALHNRFTQKSLSLSPGK, (SEQ ID NO: 217)

-continued

YKCKVSNKALPAPIE, (SEQ ID NO: 218)

VQFKWYVDGVE, (SEQ ID NO: 219)

VHNAKTKPREE, (SEQ ID NO: 220)

VTCVVVDVSHE; (SEQ ID NO: 221)

Asp-N:

DIAVEWESSGQPENNYNTTPPML, (SEQ ID NO: 222)

DTLMISRTPEVTCVVV, (SEQ ID NO: 223)

DTTHTCPRCPEPKSC, (SEQ ID NO: 224)

DTPPPCPRCPEPKSC, (SEQ ID NO: 225)

DGSFFLYSKLTV, (SEQ ID NO: 226)

DPEVQFKWYV, (SEQ ID NO: 227)

DKRVELKTPLG; (SEQ ID NO: 228)

IgG4 Peptides from Constant Region

Trypsin:

GFYPSDIAVEWESNGQPENNYK, (SEQ ID NO: 229)

TTPPVLDSDGSFFLYSR, (SEQ ID NO: 4)

EPQVYTLPPSQEEMTK, (SEQ ID NO: 230)

VVSVLTVLHQDWLNGK, (SEQ ID NO: 231)

TYTCNVDHKPSNTK, (SEQ ID NO: 232)

STSESTAALGCLVK, (SEQ ID NO: 233)

GPSVFPLAPCSR, (SEQ ID NO: 234)

EEQFNSTYR, (SEQ ID NO: 235)

NQVSLTCLVK, (SEQ ID NO: 236)

DTLMISR, (SEQ ID NO: 237)

GLPSSIEK, (SEQ ID NO: 238)

SLSLSLGK; (SEQ ID NO: 239)

Lys-C:

GPSVFPLAPCSRSTSESTAALGCLVK, (SEQ ID NO: 240)

GFYPSDIAVEWESNGQPENNYK, (SEQ ID NO: 241)

TTPPVLDSDGSFFLYSRLTVDK, (SEQ ID NO: 242)

GQPREPQVYTLPPSQEEMTK, (SEQ ID NO: 243)

NQVSLTCLVK, (SEQ ID NO: 244)

TYTCNVDHK, (SEQ ID NO: 245)

GLPSSIEK, (SEQ ID NO: 246)

SLSLSLGK; (SEQ ID NO: 247)

Arg-C:

ASTKGPSVFPLAPCSR, (SEQ ID NO: 248)

EEQFNSTYR, (SEQ ID NO: 249)

LTVDKSR; (SEQ ID NO: 250)

Chymotrypsin:

ISRTPEVTCVVVDVSQEDPEVQF, (SEQ ID NO: 251)

TCNVDHKPSNTKVDKRVESKY, (SEQ ID NO: 252)

VDGVEVHNAKTKPREEQF, (SEQ ID NO: 253)

APCSRSTSESTAAL, (SEQ ID NO: 254)

GPPCPSCPAPEF, (SEQ ID NO: 255)

ESNGQPENNY, (SEQ ID NO: 256)

TSGVHTFPAVL, (SEQ ID NO: 257)

ASTKGPSVFPL, (SEQ ID NO: 258)

YPSDIAVEW, (SEQ ID NO: 259)

SSVVTVPSSSL, (SEQ ID NO: 260)

FPEPVTVSW, (SEQ ID NO: 261)

FPPKPKDTL, (SEQ ID NO: 262)

TLPPSQEEM, (SEQ ID NO: 263)

TVDKSRW, (SEQ ID NO: 264)

TKNQVSL, (SEQ ID NO: 265)

KTTPPVL; (SEQ ID NO: 266)

Glu-C (phosphate buffer):

MTKNQVSLTCLVKGFYPSD, (SEQ ID NO: 267)

QFNSTYRVVSVLTVLHQD, (SEQ ID NO: 268)

-continued

ASTKGPSVFPLAPCSRSTSE, (SEQ ID NO: 269)

ALHNHYTQKSLSLSLGK, (SEQ ID NO: 270)

FLGGPSVFLFPPKPKD, (SEQ ID NO: 271)

YKCKVSNKGLPSSIE, (SEQ ID NO: 272)

SKYGPPCPSCPAPE, (SEQ ID NO: 273)

GSFFLYSRLTVD, (SEQ ID NO: 274)

VHNAKTKPREE, (SEQ ID NO: 275)

NNYKTTPPVLD, (SEQ ID NO: 276)

GNVFSCSVMHE, (SEQ ID NO: 277)

STAALGCLVKD, (SEQ ID NO: 278)

VQFNWYVD, (SEQ ID NO: 279)

TLMISRTPE, (SEQ ID NO: 280)

HKPSNTKVD, (SEQ ID NO: 281)

KSRWQE, (SEQ ID NO: 282)

WLNGKE, (SEQ ID NO: 283)

VTCVVVD; (SEQ ID NO: 284)

Glu-C (bicarbonate buffer):
MTKNQVSLTCLVKGFYPSDIAVE, (SEQ ID NO: 285)

ASTKGPSVFPLAPCSRSTSE, (SEQ ID NO: 286)

ALHNHYTQKSLSLSLGK, (SEQ ID NO: 287)

YKCKVSNKGLPSSIE, (SEQ ID NO: 288)

SKYGPPCPSCPAPE, (SEQ ID NO: 289)

VQFNWYVDGVE, (SEQ ID NO: 290)

VHNAKTKPREE, (SEQ ID NO: 291)

GNVFSCSVMHE, (SEQ ID NO: 292)

VTCVVVDVSQE; (SEQ ID NO: 293)

Asp-N:
DIAVEWESNGQPENNYKTTPPVL, (SEQ ID NO: 294)

DTLMISRTPEVTCVVV, (SEQ ID NO: 295)

DGSFFLYSRLTV, (SEQ ID NO: 296)

DPEVQFNWYV, (SEQ ID NO: 297)

DHKPSNTKV; (SEQ ID NO: 298)

IgA1 Peptides from Constant Region
Trypsin:
DLCGCYSVSSVLPGCAEPWNHGK, (SEQ ID NO: 299)

LAGKPTHVNVSVVMAEVDGTCY, (SEQ ID NO: 300)

GDTFSCMVGHEALPLAFTQK, (SEQ ID NO: 301)

QEPSQGTTTFAVTSILR, (SEQ ID NO: 302)

DASGVTFTWTPSSGK, (SEQ ID NO: 303)

TFTCTAAYPESK, (SEQ ID NO: 304)

WLQGSQELPR, (SEQ ID NO: 305)

SAVQGPPER, (SEQ ID NO: 306)

TPLTATLSK, (SEQ ID NO: 5)

YLTWASR, (SEQ ID NO: 307)

VAAEDWK, (SEQ ID NO: 308)

SVTCHVK, (SEQ ID NO: 309)

ASPTSPK; (SEQ ID NO: 310)

Lys-C:
GDTFSCMVGHEALPLAFTQK, (SEQ ID NO: 311)

DVLVRWLQGSQELPREK, (SEQ ID NO: 312)

PTHVNVSVVMAEVDGTCY, (SEQ ID NO: 313)

TFTCTAAYPESK, (SEQ ID NO: 314)

TPLTATLSK, (SEQ ID NO: 315)

TIDRLAGK, (SEQ ID NO: 316)

SVTCHVK; (SEQ ID NO: 317)

Arg-C:
DASGVTFTWTPSSGKSAVQGPPER, (SEQ ID NO: 318)

LAGKPTHVNVSVVMAEVDGTCY, (SEQ ID NO: 319)

-continued

QEPSQGTTTFAVTSILR, (SEQ ID NO: 320)

WLQGSQELPR, (SEQ ID NO: 321)

EKYLTWASR, (SEQ ID NO: 322)

GFSPKDVLVR; (SEQ ID NO: 323)

Chymotrypsin:

SESGQGVTARNFPPSQDASGDL, (SEQ ID NO: 324)

TPSSGKSAVQGPPERDL, (SEQ ID NO: 325)

CSTQPDGNVVIACL, (SEQ ID NO: 326)

ASRQEPSQGTTTF, (SEQ ID NO: 327)

TCTAAYPESKTPL, (SEQ ID NO: 328)

AGKPTHVNVSVVM, (SEQ ID NO: 329)

QGSQELPREKY, (SEQ ID NO: 330)

SVSSVLPGCAEPW, (SEQ ID NO: 331)

AGKSVTCHVKHY, (SEQ ID NO: 332)

ASPTSPKVFPL, (SEQ ID NO: 333)

TQKTIDRL, (SEQ ID NO: 334)

LPPPSEEL, (SEQ ID NO: 335)

AEVDGTCY, (SEQ ID NO: 336)

RDASGVTF, (SEQ ID NO: 337)

TLPATQCL, (SEQ ID NO: 338)

RVAAEDW, (SEQ ID NO: 339)

VGHEALPL, (SEQ ID NO: 340)

RPEVHL, (SEQ ID NO: 341)

SKSGNTF, (SEQ ID NO: 342)

FPQEPL; (SEQ ID NO: 343)

Glu-C (phosphate buffer):

GNVVIACLVQGFFPQEPLSVTWSE, (SEQ ID NO: 344)

ASGVTFTWTPSSGKSAVQGPPE, (SEQ ID NO: 345)

SKTPLTATLSKSGNTFRPE, (SEQ ID NO: 346)

ASPTSPKVFPLSLCSTQPD, (SEQ ID NO: 347)

RLAGKPTHVNVSVVMAE, (SEQ ID NO: 348)

LVTLTCLARGFSPKD, (SEQ ID NO: 349)

SGQGVTARNFPPSQD, (SEQ ID NO: 350)

ALPLAFTQKTID, (SEQ ID NO: 351)

VLVRWLQGSQE, (SEQ ID NO: 352)

ANLTCTLTGLRD, (SEQ ID NO: 353)

VHLLPPPSEE, (SEQ ID NO: 354)

TFSCMVGHE;; (SEQ ID NO: 903)

Glu-C (bicarbonate buffer):

SKTPLTATLSKSGNTFRPE, (SEQ ID NO: 355)

DWKKGDTFSCMVGHE, (SEQ ID NO: 356)

VHLLPPPSEE, (SEQ ID NO: 357)

DLLLGSE; (SEQ ID NO: 358)

Asp-N:

DASGVTFTWTPSSGKSAVQGPPER, (SEQ ID NO: 359)

DTFSCMVGHEALPLAFTQKTI, (SEQ ID NO: 360)

DRLAGKPTHVNVSVVMAEV, (SEQ ID NO: 361)

DLLLGSEANLTCTLTGLR, (SEQ ID NO: 362)

ASPTSPKVFPLSLCSTQP; (SEQ ID NO: 363)

IgA2 Peptides from Constant Region

Trypsin:

MAGKPTHVNVSVVMAEVDGTCY, (SEQ ID NO: 364)

GDTFSCMVGHEALPLAFTQK, (SEQ ID NO: 365)

QEPSQGTTTFAVTSILR, (SEQ ID NO: 366)

DASGATFTWTPSSGK, (SEQ ID NO: 6)

WLQGSQELPR, (SEQ ID NO: 367)

TPLTANITK, (SEQ ID NO: 368)

SAVQGPPER, (SEQ ID NO: 369)

YLTWASR, (SEQ ID NO: 370)

VAAEDWK, (SEQ ID NO: 371)

SVTCHVK; (SEQ ID NO: 372)

Lys-C:
GDTFSCMVGHEALPLAFTQK, (SEQ ID NO: 373)

DVLVRWLQGSQELPREK, (SEQ ID NO: 374)

PTHVNVSVVMAEVDGTCY, (SEQ ID NO: 375)

TPLTANITK, (SEQ ID NO: 376)

TIDRMAGK, (SEQ ID NO: 377)

SVTCHVK; (SEQ ID NO: 378)

Arg-C:
DASGATFTWTPSSGKSAVQGPPER, (SEQ ID NO: 379)

MAGKPTHVNVSVVMAEVDGTCY, (SEQ ID NO: 380)

QEPSQGTTTFAVTSILR, (SEQ ID NO: 381)

WLQGSQELPR, (SEQ ID NO: 382)

EKYLTWASR, (SEQ ID NO: 383)

GFSPKDVLVR, (SEQ ID NO: 384)

Chymotrypsin:
TNPSQDVTVPCPVPPPPPCCHPRL, (SEQ ID NO: 385)

SESGQNVTARNFPPSQDASGDL, (SEQ ID NO: 386)

TLPATQCPDGKSVTCHVKHY, (SEQ ID NO: 387)

TPSSGKSAVQGPPERDL, (SEQ ID NO: 388)

DSTPQDGNVVVACL, (SEQ ID NO: 389)

ASRQEPSQGTTTF, (SEQ ID NO: 390)

AGKPTHVNVSVVM, (SEQ ID NO: 391)

QGSQELPREKY, (SEQ ID NO: 392)

SVSSVLPGCAQPW, (SEQ ID NO: 393)

TANITKSGNTF, (SEQ ID NO: 394)

TQKTIDRM, (SEQ ID NO: 395)

TCTAAHPEL, (SEQ ID NO: 396)

LPPPSEEL, (SEQ ID NO: 397)

AEVDGTCY, (SEQ ID NO: 398)

RVAAEDW, (SEQ ID NO: 399)

VGHEALPL, (SEQ ID NO: 400)

RDASGATF, (SEQ ID NO: 401)

RPEVHL, (SEQ ID NO: 402)

FPQEPL; (SEQ ID NO: 403)

Glu-C (phosphate buffer):
LCGCYSVSSVLPGCAQPWNHGE, (SEQ ID NO: 404)

ASGATFTWTPSSGKSAVQGPPE, (SEQ ID NO: 405)

LKTPLTANITKSGNTFRPE, (SEQ ID NO: 406)

GKSVTCHVKHYTNPSQD, (SEQ ID NO: 407)

LYTTSSQLTLPATQCPD, (SEQ ID NO: 408)

RMAGKPTHVNVSVVMAE, (SEQ ID NO: 409)

LVTLTCLARGFSPKD, (SEQ ID NO: 410)

SGQNVTARNFPPSQD, (SEQ ID NO: 411)

ALPLAFTQKTID, (SEQ ID NO: 412)

VLVRWLQGSQE, (SEQ ID NO: 413)

ANLTCTLTGLRD, (SEQ ID NO: 414)

VHLLPPPSEE, (SEQ ID NO: 415)

TFTCTAAHPE, (SEQ ID NO: 416)

TFSCMVGHE; (SEQ ID NO: 417)

Glu-C (bicarbonate buffer):
RDLCGCYSVSSVLPGCAQPWNHGE, (SEQ ID NO: 418)

LKTPLTANITKSGNTFRPE, (SEQ ID NO: 419)

DWKKGDTFSCMVGHE, (SEQ ID NO: 420)

VHLLPPPSEE, (SEQ ID NO: 421)

TFTCTAAHPE, (SEQ ID NO: 422)

DLLLGSE; (SEQ ID NO: 423)

Asp-N:

DASGATFTWTPSSGKSAVQG PPER, (SEQ ID NO: 424)

DTFSCMVGHEALPLAFTQKT I, (SEQ ID NO: 425)

DRMAGKPTHVNVSVVMAEV, (SEQ ID NO: 426)

DGKSVTCHVKHYTNPSQ, (SEQ ID NO: 427)

DLLLGSEANLTCTLTGLR, (SEQ ID NO: 428)

DLYTTSSQLTLPATQCP; (SEQ ID NO: 429)

IgIVI Peptides from Constant Region
Trypsin:

STGKPTLYNVSLVMSDTAGTCY, (SEQ ID NO: 430)

LTCLVTDLTTYDSVTISWTR, (SEQ ID NO: 431)

GLTFQQNASSMCVPDQDTAIR, (SEQ ID NO: 432)

GVALHRPDVYLLPPAR, (SEQ ID NO: 433)

FTCTVTHTDLPSPLK, (SEQ ID NO: 434)

VFAIPPSFASIFLTK, (SEQ ID NO: 435)

QVGSGVTTDQVQAEAK, (SEQ ID NO: 436)

YVTSAPMPEPQAPGR, (SEQ ID NO: 437)

ESDWLGQSMFTCR, (SEQ ID NO: 438)

DVMQGTDEHVVCK, (SEQ ID NO: 439)

NVPLPVIAELPPK, (SEQ ID NO: 440)

YAATSQVLLPSK, (SEQ ID NO: 441)

LICQATGFSPR, (SEQ ID NO: 442)

QIQVSWLR, (SEQ ID NO: 443)

NNSDISSTR, (SEQ ID NO: 444)

DGFFGNPR, (SEQ ID NO: 8)

VSVFVPPR, (SEQ ID NO: 445)

VQHPNGNK, (SEQ ID NO: 446)

ESGPTTYK, (SEQ ID NO: 447)

VTSTLTIK, (SEQ ID NO: 448)

GQPLSPEK, (SEQ ID NO: 449)

QTISRPK, (SEQ ID NO: 450)

GFPSVLR, (SEQ ID NO: 451)

EQLNLR, (SEQ ID NO: 452)

QNGEAVK; (SEQ ID NO: 453)

Lys-C:

LICQATGFSPRQIQVSWLREGK, (SEQ ID NO: 454)

NNSDISSTRGFPSVLRGGK, (SEQ ID NO: 455)

PTLYNVSLVMSDTAGTCY, (SEQ ID NO: 456)

VSVFVPPRDGFFGNPRK, (SEQ ID NO: 457)

QVGSGVTTDQVQAEAK, (SEQ ID NO: 458)

DVMQGTDEHVVCK, (SEQ ID NO: 459)

NVPLPVIAELPPK, (SEQ ID NO: 460)

YAATSQVLLPSK, (SEQ ID NO: 461)

VQHPNGNK, (SEQ ID NO: 462)

ESGPTTYK, (SEQ ID NO: 463)

VTSTLTIK, (SEQ ID NO: 464)

QTISRPK; (SEQ ID NO: 465)

Arg-C:

GQPLSPEKYVTSAPMPEPQAPGR, (SEQ ID NO: 466)

GLTFQQNASSMCVPDQDTAIR, (SEQ ID NO: 467)

KSKLICQATGFSPR, (SEQ ID NO: 468)

QIQVSWLR, (SEQ ID NO: 469)

DGFFGNPR, (SEQ ID NO: 470)

GFPSVLR, (SEQ ID NO: 471)

EQLNLR; (SEQ ID NO: 472)

Chymotrypsin:

TRQNGEAVKTHTNISESHPNATF, (SEQ ID NO: 473)

VSCENSPSDTSSVAVGCL, (SEQ ID NO: 474)

KNNSDISSTRGFPSVL, (SEQ ID NO: 475)

VTSAPMPEPQAPGRY, (SEQ ID NO: 476)

TCTVTHTDLPSPL, (SEQ ID NO: 477)

SAVGEASICEDDW, (SEQ ID NO: 478)

CVPDQDTAIRVF, (SEQ ID NO: 479)

KQTISRPKGVAL, (SEQ ID NO: 480)

SPRQIQVSW, (SEQ ID NO: 481)

TCRVDHRGL, (SEQ ID NO: 482)

RESATITCL, (SEQ ID NO: 483)

LPPAREQL, (SEQ ID NO: 484)

GNPRKSKL, (SEQ ID NO: 485)

TVSEEEW, (SEQ ID NO: 486)

TIKESDW, (SEQ ID NO: 487)

SDTAGTCY, (SEQ ID NO: 488)

DSVTISW, (SEQ ID NO: 489)

LPSKDVM, (SEQ ID NO: 490)

VPPRDGF, (SEQ ID NO: 491)

HRPDVY, (SEQ ID NO: 492)

QQNASSM, (SEQ ID NO: 493)

LPDSITL, (SEQ ID NO: 494)

ICQATGF, (SEQ ID NO: 495)

NSGERF; (SEQ ID NO: 496)

Glu-C (phosphate buffer):

LPSPLKQTISRPKGVALHRPD, (SEQ ID NO: 497)

HRGLTFQQNASSMCVPD, (SEQ ID NO: 498)

KSTGKPTLYNVSLVMSD, (SEQ ID NO: 499)

VFVQWMQRGQPLSPE, (SEQ ID NO: 500)

SGPTTYKVTSTLTIKE, (SEQ ID NO: 501)

HVVCKVQHPNGNKE, (SEQ ID NO: 502)

SITLSWKYKNNSD, (SEQ ID NO: 503)

SATITCLVTGFSPAD, (SEQ ID NO: 504)

LPPKVSVFVPPRD, (SEQ ID NO: 505)

WLGQSMFTCRVD, (SEQ ID NO: 506)

SVTISWTRQNGE, (SEQ ID NO: 507)

SHPNATFSAVGE, (SEQ ID NO: 508)

RFTCTVTHTD, (SEQ ID NO: 509)

TSSVAVGCLAQD, (SEQ ID NO: 510)

AVKTHTNISE, (SEQ ID NO: 511)

KNVPLPVIAE, (SEQ ID NO: 512)

VYLLPPARE, (SEQ ID NO: 513)

GKQVGSGVTTD, (SEQ ID NO: 514)

TYTCVAHE, (SEQ ID NO: 515)

ALPNRVTE, (SEQ ID NO: 516)

VMQGTDE, (SEQ ID NO: 517)

QLNLRE; (SEQ ID NO: 518)

Glu-C (bicarbonate buffer):

SGPTTYKVTSTLTIKE, (SEQ ID NO: 519)

GKQVGSGVTTDQVQAE, (SEQ ID NO: 520)

HVVCKVQHPNGNKE, (SEQ ID NO: 521)

GSASAPTLFPLVSCE, (SEQ ID NO: 522)

SHPNATFSAVGE, (SEQ ID NO: 523)

AVKTHTNISE, (SEQ ID NO: 524)

KNVPLPVIAE, (SEQ ID NO: 525)

TYTCVAHE,                   (SEQ ID NO: 526)

ALPNRVTE,                   (SEQ ID NO: 527)

DDWNSGE,                    (SEQ ID NO: 528)

QLNLRE;                     (SEQ ID NO: 529)

Asp-N:

DLPSPLKQTISRPKGVALHR P,     (SEQ ID NO: 530)

DHRGLTFQQNASSMCVP,          (SEQ ID NO: 531)

DKSTGKPTLYNVSLVMS,          (SEQ ID NO: 532)

DWNSGERFTCTVTHT,            (SEQ ID NO: 533)

DSITLSWKYKNNS,              (SEQ ID NO: 534)

DWLGQSMFTCRV,               (SEQ ID NO: 535)

DTSSVAVGCLAQ,               (SEQ ID NO: 536)

DTAGTCY;                    (SEQ ID NO: 537)

IgD Peptides from Constant Region
Trypsin:

SLWNAGTSVTCTLNHPSLPPQR,     (SEQ ID NO: 538)

VPAPPSPQPATYTCVVSHEDSR,     (SEQ ID NO: 539)

DSYYMTSSQLSTPLQQWR,         (SEQ ID NO: 540)

AQASSVPTAQPQAEGSLAK,        (SEQ ID NO: 541)

SLEVSYVTDHGPMK,             (SEQ ID NO: 542)

ATFTCFVVGSDLK,              (SEQ ID NO: 543)

VPTGGVEEGLLER,              (SEQ ID NO: 544)

APDVFPIISGCR,               (SEQ ID NO: 545)

DAHLTWEVAGK,                (SEQ ID NO: 546)

HSNGSQSQHSR,                (SEQ ID NO: 547)

CVVQHTASK,                  (SEQ ID NO: 548)

EPAAQAPVK,                  (SEQ ID NO: 11)

TFPEIQR,                    (SEQ ID NO: 549)

ATTAPATTR,                  (SEQ ID NO: 550)

EEQEER,                     (SEQ ID NO: 551)

TLLNASR,                    (SEQ ID NO: 552)

WPESPK;                     (SEQ ID NO: 553)

Lys-C:

AQASSVPTAQPQAEGSLAK,        (SEQ ID NO: 554)

ATTAPATTRNTGRGGEEK,         (SEQ ID NO: 555)

APDVFPIISGCRHPK,            (SEQ ID NO: 556)

ATFTCFVVGSDLK,              (SEQ ID NO: 557)

EIFRWPESPK,                 (SEQ ID NO: 558)

DAHLTWEVAGK,                (SEQ ID NO: 559)

EEQEERETK,                  (SEQ ID NO: 560)

CVVQHTASK;                  (SEQ ID NO: 561)

Arg-C:

QGEYKCVVQHTASKSKKEIFR,      (SEQ ID NO: 562)

SLWNAGTSVTCTLNHPSLPPQR,     (SEQ ID NO: 563)

VPAPPSPQPATYTCVVSHED SR,    (SEQ ID NO: 564)

DSYYMTSSQLSTPLQQWR,         (SEQ ID NO: 565)

GGEEKKKEKEKEEQEER,          (SEQ ID NO: 566)

SLEVSYVTDHGPMK,             (SEQ ID NO: 567)

HSNGSQSQHSR,                (SEQ ID NO: 568)

TFPEIQR,                    (SEQ ID NO: 569)

TLLNASR;                    (SEQ ID NO: 570)

Chymotrypsin:

RWPESPKAQASSVPTAQPQAEGSL,   (SEQ ID NO: 571)

GTQSQPQRTFPEIQRRDSY,        (SEQ ID NO: 572)

KCVVQHTASKSKKEIF,           (SEQ ID NO: 573)

ERHSNGSQSQHSRL,             (SEQ ID NO: 574)

EVAGKVPTGGVEEGL,            (SEQ ID NO: 575)

APARPPPQPGSTTF,             (SEQ ID NO: 576)

-continued

RVPAPPSPQPATY, (SEQ ID NO: 577)

TCVVSHEDSRTL, (SEQ ID NO: 578)

EDQREVNTSGF, (SEQ ID NO: 579)

REPAAQAPVKL, (SEQ ID NO: 580)

NHPSLPPQRL, (SEQ ID NO: 581)

ASSDPPEAASW, (SEQ ID NO: 582)

HPTSVTVTW, (SEQ ID NO: 583)

NAGTSVTCTL, (SEQ ID NO: 584)

VTDHGPM, (SEQ ID NO: 585)

TPAVQDL, (SEQ ID NO: 586)

RDKATF; (SEQ ID NO: 587)

Glu-C (phosphate buffer):
SYYMTSSQLSTPLQQWRQGE, (SEQ ID NO: 588)

GSLAKATTAPATTRNTGRGGEE, (SEQ ID NO: 589)

CPSHTQPLGVYLLTPAVQD, (SEQ ID NO: 590)

YKCVVQHTASKSKKE, (SEQ ID NO: 591)

VSGFSPPNILLMWLE, (SEQ ID NO: 592)

SPKAQASSVPTAQPQAE, (SEQ ID NO: 593)

VFPIISGCRHPKD, (SEQ ID NO: 594)

SRTLLNASRSLE, (SEQ ID NO: 595)

KATFTCFVVGSD, (SEQ ID NO: 596)

VAGKVPTGGVEE, (SEQ ID NO: 597)

AASWLLCE, (SEQ ID NO: 598)

IFRWPE, (SEQ ID NO: 599)

AHLTWE; (SEQ ID NO: 600)

Glu-C (bicarbonate buffer):
GSLAKATTAPATTRNTGRGGEE, (SEQ ID NO: 601)

YKCVVQHTASKSKKE, (SEQ ID NO: 602)

VSGFSPPNILLMWLE, (SEQ ID NO: 603)

SPKAQASSVPTAQPQAE, (SEQ ID NO: 604)

DSRTLLNASRSLE, (SEQ ID NO: 605)

VSYVTDHGPMK, (SEQ ID NO: 606)

VAGKVPTGGVEE, (SEQ ID NO: 607)

AASWLLCE; (SEQ ID NO: 608)

Asp-N:
DSRTLLNASRSLEVSYVT, (SEQ ID NO: 609)

DVFPIISGCRHPK, (SEQ ID NO: 610)

DKATFTCFVVGS; (SEQ ID NO: 611)

IgE Peptides from Constant Region
Trypsin:
TYTCQVTYQGHTFEDSTK, (SEQ ID NO: 612)

GVSAYLSRPSPFDLFIR, (SEQ ID NO: 613)

AAPEVYAFATPEWPGSR, (SEQ ID NO: 614)

VAHTPSSTDWVDNK, (SEQ ID NO: 615)

SPTITCLVVDLAPSK, (SEQ ID NO: 616)

NGTLTVTSTLPVGTR, (SEQ ID NO: 617)

AVHEAASPSQTVQR, (SEQ ID NO: 618)

DWIEGETYQCR, (SEQ ID NO: 619)

ASGKPVNHSTR, (SEQ ID NO: 620)

GTVNLTWSR, (SEQ ID NO: 621)

GSGFFVFSR, (SEQ ID NO: 12)

VTHPHLPR, (SEQ ID NO: 622)

DFTPPTVK, (SEQ ID NO: 623)

HSTTQPR, (SEQ ID NO: 624)

HWLSDR, (SEQ ID NO: 625)

TFSVCSR, (SEQ ID NO: 626)

AEWEQK, (SEQ ID NO: 627)

QMFTCR, (SEQ ID NO: 628)

DEFICR, (SEQ ID NO: 629)

AVSVNPGK, (SEQ ID NO: 630)

CADSNPR; (SEQ ID NO: 631)

Lys-C:
TSGPRAAPEVYAFATPEWPGSRDK, (SEQ ID NO: 632)

GSGFFVFSRLEVTRAEWEQK, (SEQ ID NO: 633)

QMFTCRVAHTPSSTDWVDNK, (SEQ ID NO: 634)

TFSVCSRDFTPPTVK, (SEQ ID NO: 635)

SPTITCLVVDLAPSK, (SEQ ID NO: 636)

GTVNLTWSRASGK, (SEQ ID NO: 637)

PVNHSTRK (SEQ ID NO: 638)

Arg-C:
VAHTPSSTDWVDNKTFSVCSR, (SEQ ID NO: 639)

GVSAYLSRPSPFDLFIR, (SEQ ID NO: 640)

AAPEVYAFATPEWPGSR, (SEQ ID NO: 641)

AEWEQKDEFICR, (SEQ ID NO: 642)

NGTLTVTSTLPVGTR, (SEQ ID NO: 643)

AVHEAASPSQTVQR, (SEQ ID NO: 644)

DWIEGETYQCR, (SEQ ID NO: 645)

KTKGSGFFVFSR, (SEQ ID NO: 646)

ASGKPVNHSTR, (SEQ ID NO: 647)

VTHPHLPR, (SEQ ID NO: 648)

STTKTSGPR, (SEQ ID NO: 649)

HSTTQPR, (SEQ ID NO: 650)

KEEKQR, (SEQ ID NO: 651)

AVSVNPGK (SEQ ID NO: 652)

Chymotrypsin:
ICRAVHEAASPSQTVQRAVSVNPGK, (SEQ ID NO: 653)

SRASGKPVNHSTRKEEKQRNGTL, (SEQ ID NO: 654)

EDSTKKCADSNPRGVSAY, (SEQ ID NO: 655)

RSTTKTSGPRAAPEVY, (SEQ ID NO: 656)

TRCCKNIPSNATSVTL, (SEQ ID NO: 657)

QSSCDGGGHFPPTIQL, (SEQ ID NO: 658)

ATPEWPGSRDKRTL, (SEQ ID NO: 659)

QCRVTHPHLPRAL, (SEQ ID NO: 660)

TCRVAHTPSSTDW, (SEQ ID NO: 661)

TVTSTLPVGTRDW, (SEQ ID NO: 662)

IRKSPTITCL, (SEQ ID NO: 663)

STASTTQEGEL, (SEQ ID NO: 664)

MPEDISVQW, (SEQ ID NO: 665)

TPGTINITW, (SEQ ID NO: 666)

EVTRAEW, (SEQ ID NO: 667)

APSKGTVNL, (SEQ ID NO: 668)

TPPTVKIL, (SEQ ID NO: 669)

SVCSRDF, (SEQ ID NO: 670)

EQKDEF, (SEQ ID NO: 671)

ASTQSEL, (SEQ ID NO: 672)

VDNKTF; (SEQ ID NO: 673)

Glu-C (phosphate buffer):
ARHSTTQPRKTKGSGFFVFSRLE, (SEQ ID NO: 674)

KQRNGTLTVTSTLPVGTRD, (SEQ ID NO: 675)

SNPRGVSAYLSRPSPFD, (SEQ ID NO: 676)

RTYTCQVTYQGHTFE, (SEQ ID NO: 677)

AASPSQTVQRAVSVNPGK, (SEQ ID NO: 678)

LFIRKSPTITCLVVD, (SEQ ID NO: 679)

KRTLACLIQNFMPE, (SEQ ID NO: 680)

```
                                      (SEQ ID NO: 681)
FTPPTVKILQSSCD, (SEQ ID NO: 682)
LTLSQKHWLSD, (SEQ ID NO: 683)
NKTFSVCSRD, (SEQ ID NO: 684)
ISVQWLHNE, (SEQ ID NO: 685)
FICRAVHE, (SEQ ID NO: 686)
LSTASTTQE, (SEQ ID NO: 687)
VYAFATPE, (SEQ ID NO: 688)
STKKCAD, (SEQ ID NO: 689)
LASTQSE, (SEQ ID NO: 690)
WPGSRD;

Glu-C (bicarbonate buffer):
                                      (SEQ ID NO: 691)
KQRNGTLTVTSTLPVGTRDWIE, (SEQ ID NO: 692)
WPGSRDKRTLACLIQNFMPE, (SEQ ID NO: 693)
AASPSQTVQRAVSVNPGK, (SEQ ID NO: 694)
DGQVMDVDLSTASTTQE, (SEQ ID NO: 695)
DISVQWLHNE, (SEQ ID NO: 696)
FICRAVHE, (SEQ ID NO: 697)
VYAFATPE, (SEQ ID NO: 698)
LASTQSE;

Asp-N:
                                      (SEQ ID NO: 699)
DRTYTCQVTYQGHTFE, (SEQ ID NO: 700)
DSNPRGVSAYLSRPSPF, (SEQ ID NO: 701)
DKRTLACLIQNFMPE, (SEQ ID NO: 702)
DLFIRKSPTITCLVV, (SEQ ID NO: 703)
DISVQWLHNEVQLP, (SEQ ID NO: 704)
DFTPPTVKILQSSC, (SEQ ID NO: 705)
DNKTFSVCSR, (SEQ ID NO: 706)
DSTKKCA;

Igκ Peptides from Constant Region
Trypsin:
                                      (SEQ ID NO: 707)
VDNALQSGNSQESVTEQDSK, (SEQ ID NO: 9)
TVAAPSVFIFPPSDEQLK, (SEQ ID NO: 708)
VYACEVTHQGLSSPVTK, (SEQ ID NO: 709)
SGTASVVCLLNNFYPR, (SEQ ID NO: 710)
DSTYSLSSTLTLSK;

Lys-C:
                                      (SEQ ID NO: 711)
VDNALQSGNSQESVTEQDSK, (SEQ ID NO: 712)
SGTASVVCLLNNFYPREAK, (SEQ ID NO: 713)
TVAAPSVFIFPPSDEQLK, (SEQ ID NO: 714)
VYACEVTHQGLSSPVTK, (SEQ ID NO: 715)
DSTYSLSSTLTLSK, (SEQ ID NO: 716)
SFNRGEC;

Chymotrypsin:
                                      (SEQ ID NO: 717)
QSGNSQESVTEQDSKDSTY, (SEQ ID NO: 718)
YPREAKVQW, (SEQ ID NO: 719)
IFPPSDEQL, (SEQ ID NO: 720)
KSGTASVVCL, (SEQ ID NO: 721)
ACEVTHQGL, (SEQ ID NO: 722)
SSPVTKSF, (SEQ ID NO: 723)
EKHKVY, (SEQ ID NO: 724)
TVAAPSVF;

Glu-C (phosphate buffer):
                                      (SEQ ID NO: 725)
QLKSGTASVVCLLNNFYPRE, (SEQ ID NO: 726)
VTHQGLSSPVTKSFNRGE, (SEQ ID NO: 727)
TVAAPSVFIFPPSDE, (SEQ ID NO: 728)
STYSLSSTLTLSKAD, (SEQ ID NO: 729)
NALQSGNSQE, (SEQ ID NO: 730)
KHKVYACE,
```

-continued

AKVQWKVD; (SEQ ID NO: 731)

Glu-C (bicarbonate buffer):
QDSKDSTYSLSSTLTLSKADYE, (SEQ ID NO: 732)

QLKSGTASVVCLLNNFYPRE, (SEQ ID NO: 733)

AKVQWKVDNALQSGNSQE, (SEQ ID NO: 734)

VTHQGLSSPVTKSFNRGE, (SEQ ID NO: 735)

TVAAPSVFIFPPSDE, (SEQ ID NO: 736)

KHKVYACE; (SEQ ID NO: 737)

Asp-N:
NALQSGNSQESVTEQ, (SEQ ID NO: 738)

DSTYSLSSTLTLSKA, (SEQ ID NO: 739)

TVAAPSVFIFPPS; (SEQ ID NO: 740)

Igλ1 Peptides from Constant Region
Trypsin:
ATLVCLISDFYPGAVTVAWK, (SEQ ID NO: 741)

ANPTVTLFPPSSEELQANK, (SEQ ID NO: 742)

YAASSYLSLTPEQWK, (SEQ ID NO: 743)

SYSCQVTHEGSTVEK, (SEQ ID NO: 744)

AGVETTKPSK, (SEQ ID NO: 745)

TVAPTECS; (SEQ ID NO: 746)

Lys-C:
ATLVCLISDFYPGAVTVAWK, (SEQ ID NO: 747)

ANPTVTLFPPSSEELQANK, (SEQ ID NO: 748)

SHRSYSCQVTHEGSTVEK, (SEQ ID NO: 749)

YAASSYLSLTPEQWK, (SEQ ID NO: 750)

TVAPTECS, (SEQ ID NO: 751)

AGVETTK, (SEQ ID NO: 752)

ADGSPVK; (SEQ ID NO: 753)

Arg-C:
SYSCQVTHEGSTVEKTVAPTECS; (SEQ ID NO: 754)

Chymotrypsin:
KADGSPVKAGVETTKPSKQSNNKY, (SEQ ID NO: 755)

SCQVTHEGSTVEKTVAPTECS, (SEQ ID NO: 756)

GQPKANPTVTL, (SEQ ID NO: 757)

YPGAVTVAW, (SEQ ID NO: 758)

FPPSSEEL, (SEQ ID NO: 759)

KSHRSY, (SEQ ID NO: 760)

QANKATL; (SEQ ID NO: 761)

Glu-C (phosphate buffer):
TTKPSKQSNNKYAASSYLSLTPE, (SEQ ID NO: 762)

GQPKANPTVTLFPPSSEE, (SEQ ID NO: 763)

QWKSHRSYSCQVTHE, (SEQ ID NO: 764)

LQANKATLVCLISD, (SEQ ID NO: 765)

FYPGAVTVAWKAD, (SEQ ID NO: 766)

GSPVKAGVE, (SEQ ID NO: 904)

KTVAPTE; (SEQ ID NO: 767)

Glu-C (bicarbonate buffer):
TTKPSKQSNNKYAASSYLSLTPE, (SEQ ID NO: 768)

GQPKANPTVTLFPPSSEE, (SEQ ID NO: 769)

QWKSHRSYSCQVTHE, (SEQ ID NO: 770)

KTVAPTE; (SEQ ID NO: 771)

Asp-N:
DFYPGAVTVAWKA; (SEQ ID NO: 772)

Igλ2 Peptides from Constant Region
Trypsin:
ATLVCLISDFYPGAVTVAWK, (SEQ ID NO: 773)

AAPSVTLFPPSSEELQANK, (SEQ ID NO: 774)

YAASSYLSLTPEQWK, (SEQ ID NO: 775)

SYSCQVTHEGSTVEK, (SEQ ID NO: 776)

AGVETTTPSK, (SEQ ID NO: 10)

TVAPTECS, (SEQ ID NO: 777)

ADSSPVK; (SEQ ID NO: 778)

Lys-C:
ATLVCLISDFYPGAVTVAWK, (SEQ ID NO: 779)
SHRSYSCQVTHEGSTVEK, (SEQ ID NO: 780)
AAPSVTLFPPSSEELQANK, (SEQ ID NO: 781)
YAASSYLSLTPEQWK, (SEQ ID NO: 782)
AGVETTTPSK, (SEQ ID NO: 783)
TVAPTECS, (SEQ ID NO: 784)
ADSSPVK; (SEQ ID NO: 785)

Arg-C:
SYSCQVTHEGSTVEKTVAPTECS; (SEQ ID NO: 786)

Chymotrypsin:
KADSSPVKAGVETTTPSKQSNNKY, (SEQ ID NO: 787)
SCQVTHEGSTVEKTVAPTECS, (SEQ ID NO: 788)
GQPKAAPSVTL, (SEQ ID NO: 789)
YPGAVTVAW, (SEQ ID NO: 790)
FPPSSEEL, (SEQ ID NO: 791)
KSHRSY, (SEQ ID NO: 792)
QANKATL; (SEQ ID NO: 793)

Glu-C (phosphate buffer):
TTTPSKQSNNKYAASSYLSLTPE, (SEQ ID NO: 794)
QWKSHRSYSCQVTHE, (SEQ ID NO: 795)
GQPKAAPSVTLFPPSSEE, (SEQ ID NO: 796)
LQANKATLVCLISD, (SEQ ID NO: 797)
FYPGAVTVAWKAD, (SEQ ID NO: 798)
SSPVKAGVE, (SEQ ID NO: 799)
KTVAPTE; (SEQ ID NO: 800)

Glu-C (bicarbonate buffer):
TTTPSKQSNNKYAASSYLSLTPE, (SEQ ID NO: 801)
QWKSHRSYSCQVTHE, (SEQ ID NO: 802)
GQPKAAPSVTLFPPSSEE, (SEQ ID NO: 803)
KTVAPTE; (SEQ ID NO: 804)

Asp-N:
DFYPGAVTVAWKA; (SEQ ID NO: 805)

Igλ3 Peptides from Constant Region
Trypsin:
ATLVCLISDFYPGAVTVAWK, (SEQ ID NO: 806)
AAPSVTLFPPSSEELQANK, (SEQ ID NO: 807)
YAASSYLSLTPEQWK, (SEQ ID NO: 808)
SYSCQVTHEGSTVEK, (SEQ ID NO: 809)
AGVETTTPSK, (SEQ ID NO: 810)
TVAPTECS; (SEQ ID NO: 811)

Lys-C:
ATLVCLISDFYPGAVTVAWK, (SEQ ID NO: 812)
AAPSVTLFPPSSEELQANK, (SEQ ID NO: 813)
YAASSYLSLTPEQWK, (SEQ ID NO: 814)
SYSCQVTHEGSTVEK, (SEQ ID NO: 815)
AGVETTTPSK, (SEQ ID NO: 816)
TVAPTECS, (SEQ ID NO: 817)
ADSSPAK; (SEQ ID NO: 818)

Chymotrypsin:
KADSSPAKAGVETTTPSKQSNNKY, (SEQ ID NO: 819)
SCQVTHEGSTVEKTVAPTECS, (SEQ ID NO: 820)
GQPKAAPSVTL, (SEQ ID NO: 821)
YPGAVTVAW, (SEQ ID NO: 822)
FPPSSEEL, (SEQ ID NO: 823)
KSHKSY, (SEQ ID NO: 824)
QANKATL; (SEQ ID NO: 825)

Glu-C (phosphate buffer):
TTTPSKQSNNKYAASSYLSLTPE, (SEQ ID NO: 826)
QWKSHKSYSCQVTHE, (SEQ ID NO: 827)
GQPKAAPSVTLFPPSSEE, (SEQ ID NO: 828)

LQANKATLVCLISD, (SEQ ID NO: 829)

FYPGAVTVAWKAD, (SEQ ID NO: 830)

SSPAKAGVE, (SEQ ID NO: 831)

KTVAPTE; (SEQ ID NO: 832)

Glu-C (bicarbonate buffer):
TTTPSKQSNNKYAASSYLSLTPE, (SEQ ID NO: 833)

QWKSHKSYSCQVTHE, (SEQ ID NO: 834)

GQPKAAPSVTLFPPSSEE, (SEQ ID NO: 835)

KTVAPTE; (SEQ ID NO: 836)

Asp-N:
DFYPGAVTVAWKA; (SEQ ID NO: 837)

Igλ6 Peptides from Constant Region
Trypsin:
AAPSVTLFPPSSEELQANK, (SEQ ID NO: 838)

YAASSYLSLTPEQWK, (SEQ ID NO: 839)

ATLVCLISDFYPGAVK, (SEQ ID NO: 840)

ADGSPVNTGVETTTPSK, (SEQ ID NO: 841)

SYSCQVTHEGSTVEK, (SEQ ID NO: 842)

TVAPAECS; (SEQ ID NO: 843)

Lys-C:
SHRSYSCQVTHEGSTVEK, (SEQ ID NO: 844)

AAPSVTLFPPSSEELQANK, (SEQ ID NO: 845)

YAASSYLSLTPEQWK, (SEQ ID NO: 846)

ATLVCLISDFYPGAVK, (SEQ ID NO: 847)

ADGSPVNTGVETTTPSK, (SEQ ID NO: 848)

TVAPAECS; (SEQ ID NO: 849)

Arg-C:
SYSCQVTHEGSTVEKTVAPAECS; (SEQ ID NO: 850)

Chymotrypsin:
KADGSPVNTGVETTTPSKQSNNKY, (SEQ ID NO: 851)

SCQVTHEGSTVEKTVAPAECS, (SEQ ID NO: 852)

GQPKAAPSVTL, (SEQ ID NO: 853)

YPGAVKVAW, (SEQ ID NO: 854)

FPPSSEEL, (SEQ ID NO: 855)

KSHRSY, (SEQ ID NO: 856)

QANKATL; (SEQ ID NO: 857)

Glu-C (phosphate buffer):
TTTPSKQSNNKYAASSYLSLTPE, (SEQ ID NO: 858)

QWKSHRSYSCQVTHE, (SEQ ID NO: 859)

GQPKAAPSVTLFPPSSEE, (SEQ ID NO: 860)

LQANKATLVCLISD, (SEQ ID NO: 861)

FYPGAVKVAWKAD, (SEQ ID NO: 862)

GSPVNTGVE, (SEQ ID NO: 863)

KTVAPAE; (SEQ ID NO: 864)

Glu-C (bicarbonate buffer):
TTTPSKQSNNKYAASSYLSLTPE, (SEQ ID NO: 865)

QWKSHRSYSCQVTHE, (SEQ ID NO: 866)

GQPKAAPSVTLFPPSSEE, (SEQ ID NO: 867)

KTVAPAE; (SEQ ID NO: 868)

Asp-N:
DFYPGAVKVAWKA; (SEQ ID NO: 869)

Igλ7 Peptides from Constant Region
Trypsin:
ATLVCLVSDFYPGAVTVAWK, (SEQ ID NO: 870)

AAPSVTLFPPSSEELQANK, (SEQ ID NO: 871)

YAASSYLSLTPEQWK, (SEQ ID NO: 872)

VTHEGSTVEK, (SEQ ID NO: 873)

VGVETTKPSK, (SEQ ID NO: 874)

TVAPAECS; (SEQ ID NO: 875)

Lys-C:
ATLVCLVSDFYPGAVTVAWK, (SEQ ID NO: 876)

SHRSYSCRVTHEGSTVEK, (SEQ ID NO: 877)

AAPSVTLFPPSSEELQANK, (SEQ ID NO: 878)

-continued

YAASSYLSLTPEQWK, (SEQ ID NO: 879)

TVAPAECS, (SEQ ID NO: 880)

VGVETTK, (SEQ ID NO: 881)

ADGSPVK; (SEQ ID NO: 882)

Arg-C:

VTHEGSTVEKTVAPAECS; (SEQ ID NO: 883)

Chymotrypsin:

KADGSPVKVGVETTKPSKQSNNKY, (SEQ ID NO: 884)

SCRVTHEGSTVEKTVAPAECS, (SEQ ID NO: 885)

GQPKAAPSVTL, (SEQ ID NO: 886)

YPGAVTVAW, (SEQ ID NO: 887)

FPPSSEEL, (SEQ ID NO: 888)

KSHRSY, (SEQ ID NO: 889)

QANKATL; (SEQ ID NO: 890)

Glu-C (phosphate buffer):

TTKPSKQSNNKYAASSYLSLTPE, (SEQ ID NO: 891)

QWKSHRSYSCRVTHE, (SEQ ID NO: 892)

GQPKAAPSVTLFPPSSEE, (SEQ ID NO: 893)

LQANKATLVCLVSD, (SEQ ID NO: 894)

FYPGAVTVAWKAD, (SEQ ID NO: 895)

GSPVKVGVE, (SEQ ID NO: 896)

KTVAPAE; (SEQ ID NO: 897)

Glu-C (bicarbonate buffer):

TTKPSKQSNNKYAASSYLSLTPE, (SEQ ID NO: 898)

QWKSHRSYSCRVTHE, (SEQ ID NO: 899)

GQPKAAPSVTLFPPSSEE, (SEQ ID NO: 900)

KTVAPAE; (SEQ ID NO: 901)
and

Asp-N:

DFYPGAVTVAWKA. (SEQ ID NO: 902)

Definitions

The term "subject" refers to any individual who is the target of administration or treatment. The subject can be a vertebrate, for example, a mammal Thus, the subject can be a human or veterinary patient. The term "patient" refers to a subject under the treatment of a clinician, e.g., physician.

The term "biological sample" refers to any sample from a subject that may contain immunoglobulin secreted from plasma cells. Non-limiting examples include blood, urine, plasma, and serum.

The terms "peptide," "protein," and "polypeptide" are used interchangeably to refer to a natural or synthetic molecule comprising two or more amino acids linked by the carboxyl group of one amino acid to the alpha amino group of another.

As used herein, the term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Quantification of Peptides from Immunoglobulin Constant and Variable Regions by Liquid Chromatography-Multiple Reaction Monitoring Mass Spectrometry for Assessment of Multiple Myeloma Patients Materials and Methods Chemicals and reagents were acquired from Sigma-Aldrich (Milwaukee, Wis.); HPLC solvents were purchased from Burdick and Jackson (Honeywell, Muskegon, Mich.). Standard peptides were synthesized, HPLC-purified, characterized with MALDI MS, QqQ MS, and amino acid analysis, as previously described (Remily-Wood E R, et al Proteomics Clin Appl 2011, 5, 383-96).

Sample Collection and Summary of Patient Data

De-identified serum was collected from patients in accordance with protocols approved by the University of South Florida Institutional Review Board. Blood was collected in serum separator tubes (BD, Franklin Lakes, N.J.), clotted for 30 minutes, spun down at 3,600 rpm for 10 minutes (5702, Eppendorf), and refrigerated until analysis (t<3 weeks). Samples (n=83) were collected. The study population contained 46 males and 37 females between ages 34 and 87 (median age 63) with diagnoses including MM (45), smoldering MM (3), light chain only MM (1), non-secretory MM (1) MGUS (6), plasmacytoma (5), plasma cell leukemia (2), Waldenstrom's macroglobinemia (8), Non-Hodgkin's Lymphoma (6), other leukemias or lymphomas (4), amyloidosis (2), and prostate cancer (1). Samples were selected to represent all types of PCDs with varying levels of immunoglobulin expression and age-matched patients with other diseases. Of these patients, 71 had elevated levels of immunoglobulin expression detected by SPEP compared to reference values for healthy controls. Twelve patients had immunoglobulin expression levels comparable to healthy controls and were not detectable by SPEP (SPEP−).

Bone marrow aspirates were collected from 2 patients (not included in the cohort used for the constant region analysis). MM tumor cells were obtained by Ficoll and CD138+ plasma cell selection (Miltenyi, Auburn, Calif.). An aliquot of 0.5 million cells was used for RNA-sequencing.

Clinical Measurements

SPEP was performed using capillary zone electrophoresis (Capillarys, Sebia). Immunoglobulin concentrations were calculated using measurements of total serum protein (Fusion 5.1FS Chemistry Analyzer, Ortho Clinical Diagnostics, NJ). Immunotyping was performed using monospecific antisera for IgG, IgA, and IgM heavy chains as well as κ and λ light chains (Capillarys, Sebia) Immunofixation electrophoresis (SPIFE 3000, Helena Laboratories) was used to confirm serum immunotyping results or to test for IgD and IgE. Nephelometry of the immunoglobulins was performed (Vitros 5.1 FS Chemistry System, Ortho-Clinical Diagnostics) to determine the concentration of IgA, IgG, and IgM using goat antisera as the primary active reagents.

LC-MRM Quantification of Proteins in Serum

Peptide targets were selected from LC-MS/MS data (see FIG. 51). Serum proteins were denatured with 8M urea, reduced with tris(2-carboxyethyl) phosphine, and alkylated with iodoacetamide prior to a ten-fold dilution in aqueous 30 mM ammonium bicarbonate and in-solution tryptic digestion (Promega, Madison, Wis.). Internal standards were spiked into each sample (Table 1) (Berth M, et al Clin Chem 1999, 45, 309-10; French MAH, et al Clin Exp Immunol 1984, 56, 473-5; Haraldsson A, et al Ann Clin Biochem 1991, 28, 461-66; Chen K, et al Nephrology 2005, 10, 594-596; Buckley R, et al J Clin Invest 1975, 55, 157-65; Hunder G, et al Arthritis Rheum 1974, 17, 955-63). The equivalent of 0.5 nanoliters of tryptically digested serum was injected for each LC-MRM analysis.

TABLE 1

Endogenous Peptides and Labeled Standards used for LC-MRM Quantification of Immunoglobulins.

| Protein | Average Expression & Reference Range (mg/ml) | Peptide | IS | Transitions | Median Intra-Assay CV (%) | Median Inter-Assay CV (%) | Outliers |
|---|---|---|---|---|---|---|---|
| IgG1 | 5.91<br>3.19-10.2 | GPSVFPLAPSSK<br>(SEQ ID NO: 1) | 10.2 | $y_8$-$y_{10}$ | 7.5 | 7.2 | 3 |
| IgG2 | 3.04<br>1.23-6.63 | GLPAPIEK<br>(SEQ ID NO: 2) | 6.63 | $y_4$-$y_6$ | 6.0 | 5.9 | 2 |
| IgG3 | 0.61<br>0.16-1.94 | WYVDGVEVHNAK<br>(SEQ ID NO: 3) | 1.94 | $y_6$, $y_8$, $y_9$ | 16 | 18.3 | 12 |
| IgG4 | 0.24<br>0.03-1.33 | TTPPVLDSDGSFFLYSR<br>(SEQ ID NO: 4) | NS | $y_8$, $y_{10}$, $y_{12}$ | — | — | — |
| IgA1 | 1.88<br>1.36-2.5 | TPLTATLSK<br>(SEQ ID NO: 5) | NS | $y_5$-$y_7$ | — | — | — |
| IgA2 | 0.54<br>0.28-0.61 | DASGATFTWTPSSGK*<br>(SEQ ID NO: 6) | 0.6 | $y_7$-$y_{10}$ | 21 | 16 | 5 |
| IgA1-2 | 2.42<br>1.64-3.11 | WLQGSQELPR<br>(SEQ ID NO: 7) | 3.1 | $y_6$-$y_8$ | 6.8 | 9.6 | 2 |
| IgM | 0.70<br>0.4-2.3 | DGFFGNPR<br>(SEQ ID NO: 8) | 2.3 | $y_4$-$y_6$ | 11 | 7.6 | 1 |
| κ LC | 2.31<br>1.55-3.08 | TVAAPSVFIFPPSDEQLK*<br>(SEQ ID NO: 9) | 3.0 | $y_8$, $y_9$, $y_{11}$ | 7.3 | 6.6 | 6 |
| λ LC | 1.54<br>0.83-2.24 | AGVETTTPSK<br>(SEQ ID NO: 10) | 2.24 | $y_5$-$y_7$ | 19 | 9.0 | 16 |
| IgD | 0.0139<br>0.001-0.024 | EPAAQAPVK<br>(SEQ ID NO: 11) | 0.50 | $y_5$-$y_7$ | 0.52 | — | 0 |
| IgE | 0.0001<br>0-0.002 | GSGFFVFSR*<br>(SEQ ID NO: 12) | 0.50 | $y_5$-$y_7$ | 6.7 | — | 0 |
| Albumin | 35<br>30-40 | LVNEVTEFAK*<br>(SEQ ID NO: 13) | 3.5 | $y_5$, $y_7$, $y_8$ | 5.0 | 6.3 | 0 |

Peptides representative for individual proteins and groups of isoforms are quantified. Standard peptides were synthesized with either isotope-labeled amino acids or with a structural analog created by single conservative amino acid replacement (as noted by *) that differs only by a methylene group in the side chain of the underlined residue. The limit of detection based on internal standards is also shown along with other monitored peptides that do not have quantitative assays developed. Eleven additional peptides are monitored to improve confidence in quantification by evaluation of consistency, but SIS peptides have not been synthesized. Reference ranges provided by ARUP Laboratories.

LC-MRM was performed using a nanoLC interfaced with a triple quadrupole mass spectrometer (EasyNanoLC and TSQ Quantum Ultra or Vantage, Thermo, San Jose, Calif.), as previously described (see supplement for additional details) (Remily-Wood E R, et al Proteomics Clin Appl 2011, 5, 383-96). Briefly, peptides were desalted on a reversed phase pre-column prior to reversed phase chromatography using 10 minute gradients (C18 Pepmap100, Thermo, San Jose, Calif.). Peptide precursors were selected with 0.4 Q1 resolution; fragment ions were then selected with 0.7 Q3 resolution. Scan width was 0.002, and transitions were acquired for 5-20 milliseconds. If the peptides were not optimized by manual infusion, collision energy values were calculated using Equation 1 based on the mass-to-charge ratio (m/z) of the doubly protonated peptide precursor (MacLean B, et al Bioinformatics, 2010, 26, 966-8; Zhang G, et al J Proteome Res 2011, 10, 305-19).

$$CE=(0.034*m/z)+3.314 \text{ V} \quad \text{Equation 1:}$$

Batches of ten samples were analyzed on the instrument with a reverse calibration curve of the following three standards: a common serum standard was spiked with stable isotope-labeled standard peptides at the average normal abundance, maximum normal abundance, and maximum normal abundance plus 1 mg/ml. Samples were analyzed one through ten, followed by standard samples, and then this batch was repeated for triplicate measurements.

Data Analysis

Peak areas (PA) were calculated using MRMer implemented in GenePattern. Raw data files were converted into mzxml; LC-MRM peaks were extracted and visualized for transition evaluation. Resulting data were assessed for quality control and compared between patient groups using Post-MRMer. After data review, protein concentrations (in mg/ml) were calculated using the PA ratio of the endogenous peptide to its corresponding standard. The resulting data were evaluated using existing reference ranges for protein-based measurements and compared with nephelometry measurements. Intra-assay CV values were determined using triplicate LC-MRM analysis; inter-assay CV values were calculated from ten LC-MRM analyses of different preparations of the same serum samples (n=3). Median values are reported. Batch-to-batch variation was also examined.

Statistical Analyses

To evaluate assay robustness, the data set was filtered for outliers, when CV>0.5 and at least one value calculated to be above the previously defined range of healthy controls. Samples below the defined normal maximum value were not examined for outliers because the low protein expression level often contributed to increased CV values. In the cases with high CV values, an individual measurement was discarded when its distance from the median was twice (or greater) the distance of the other data point from the median. Out of 249 data points for each peptide, zero to fifteen outliers were removed (see Table 1). Batch effects were also evaluated using the reverse calibration curves and visual inspection of the entire dataset for all 83 patient specimens. From the remaining sample points, the mean, median, and standard deviation were calculated and a two-sided Wilcoxon rank-sum test was used to determine if a statistical difference existed between the expression of each protein in patients diagnosed with each specific type of PCD (as determined by clinical diagnoses for the different immunoglobulins or LC-MRM analysis for specific isoforms of IgA and IgG) and all other patient samples. The Holm-Bonferroni method was used to adjust for multiple hypotheses testing with type I error ($\alpha$), which was set to 0.05.

RNA Sequencing and LC-MRM Detection of Variable Region Peptides

H929 multiple myeloma cells and two patient specimens (all n=0.5×10$^6$ cells) were selected for a proof-of-concept experiment in immunoglobulin variable region sequencing and detection of variable region peptides. mRNA sequencing (RNA-seq) was performed from 100 ng of total RNA using the Encore Complete Library System (NuGEN, San Carlos, Calif.). Strand-specific cDNA generated from this kit was used to prepare a barcoded library appropriate for multiplexed massively parallel sequencing. Paired-end 100 base reads (n~2×10$^7$) were generated using the HiScan SQ sequencer (Illumina, San Diego, Calif.). Demultiplexing and data quality evaluation were performed using CASAVA 1.8.2 (Illumina) RNA-seq reads were aligned to the human hs37d5 reference genome and the Gencode v14 gene model using Tophat2. The expressed transcripts were assembled and evaluated using the de novo assembly software, Trinity. Contiguous sequences are aligned back to the human genome with BLAST, and best hits are manually examined. NCBI ORF identifies potential protein constructs. After generating the protein sequence for the immunoglobulin secreted by the tumor cells, LC-MRM was used to screen for the detection of tryptic peptides from the Igκ constant and variable regions in H929 conditioned culture media, as described above. For patient specimens, both samples were analyzed for LC-MRM detection of variable region peptides from Patient 1 to examine their detection in low levels of disease and against a control background.

Results and Discussion

LC-MRM Quantification of Heavy Chains Using Constant Region Peptides

Triplicate LC-MRM analysis was performed on 83 patient samples. For most standards, spike-in concentrations equivalent to the maximum value for expression in healthy controls to enabled rapid patient evaluation (higher endogenous peptide signal indicates disease burden). Spiked amounts of the internal standards for albumin and those common to multiple IgG isoforms were decreased due to their high abundance in serum. Due to the low abundance of IgD and IgE in healthy controls, their internal standards were spiked at 0.5 mg/ml (or 0.05 g/dl), which is well below the typical limit for starting treatment after disease relapse and half the limit of detection for SPEP. With the exception of peptides monitoring IgA isoforms, median CV values were below 20%.

Comparison of SPEP/IFE results to LC-MRM is useful for verification that the new technique is able to accurately discern involved immunoglobulins for PCD patients. As expected, LC-MRM detection of increased expression of immunoglobulins matched the clinical diagnoses made by serial SPEP/IFE measurements in all cases when the involved immunoglobulin abundance exceeded the reference range for healthy controls. Samples were taken from 19 IgG patients (average SPEP 14.9 mg/ml), 20 IgA patients (average SPEP 14.0 mg/ml), and 17 patients with elevated IgM (average SPEP 10.8 mg/ml). LC-MRM was able to identify increased expression in 18/19 patients with IgG disease. For SPEP+ patients with IgA disease, 18/20 could be detected by LC-MRM of the peptide, WLQGSQELPR (SEQ ID NO:7). The relative quantification of the second peptide from IgA1 detected elevated expression in one of these patients, but the total IgA expression was in the normal range for the other patient. When SPEP detects low levels the monoclonal immunoglobulin but the total immunoglobulin expression level was still in the reference range for healthy controls, both LC-MRM and nephelometry were unable to detect the disease. Longitudinal monitoring of these IgG and IgA patients may still indicate the presence of disease and increases in tumor burden. All 17 SPEP+ IgM cases could be detected. All IgD (n=5) and IgE (n=1) patients were also correctly identified. Seven patients diagnosed with free light chain disease expressed no elevated concentrations of any heavy chain immunoglobulin. LC-MRM measurements of immunoglobulins were in the normal range for all SPEP− samples. Samples from two patients with biclonal MM diagnoses made by SPEP/IFE were analyzed with LC-MRM (one IgG/IgM and one IgA/IgG). Both immunoglobulin chains were detected above the normal range for the IgA/IgG biclonal patient, but only the elevated IgM expression was detected in the IgM/IgG biclonal patient.

The LC-MRM heavy chain measurements correlated well to the values determined by nephelometry, the current clinical standard for quantification. Comparison of IgG measurements using the two methods is shown in FIG. 1A. LC-MRM IgG data was compiled by summing the IgG1, IgG2, and IgG3 values. Because the IgG4 could not be quantified absolutely (due to poor synthesis of the SIS peptide), that value is excluded, and LC-MRM measurements should be slightly less than those from nephelometry (i.e. slope <1). This calculation may also limit the correlation ($R^2=0.82$). Correlation was poorer in patients with high IgG expression levels, perhaps due to LC-MRM saturation from nanoLC column loading limits. Removal of the samples with saturated IgG detection increased the correlation between LC-MRM and nephelometry ($R^2=0.98$). IgA and IgM values were also highly correlated (FIG. 1B and FIG. 1C). In addition, both LC-MRM and nephelometry measurements were compared to SPEP data. As expected, LC-MRM and nephelometry correlate better with each other than with SPEP, due to the fact that they both measure the total immunoglobulin rather than the disease-specific M-protein.

LC-MRM has better sensitivity than nephelometry, but has slightly poorer precision. LC-MRM was able to quantify immunoglobulin concentrations in patients when nephelometry reported that the values were below the stated limits of quantification: 2.71 mg/ml IgG, 0.41 mg/ml IgA, and 0.26 mg/ml IgM. Data are shown for IgG (n=11) in FIG. 1D, IgA (n=29) in FIG. 1E, and IgM (n=34) in FIG. 1F. This improvement in sensitivity may enable better evaluation of immune paresis, reduction of the population of other plasma cells due to the clonal expansion of the tumor cells, which could have a bearing on patient prognosis. Intra-assay and inter-assay CV values are approximately 5% and 10% for nephelometry (Alexander Jr R L Clin Chem 1980, 26, 314-7; Guiguet M, et al J Clin Chem Biochem 1983, 21, 217-21); LC-MRM intra-assay CV values are competitive, but inter-assay CV values are ~2-fold higher due to the additional processing steps (Table 1).

LC-MRM of constant region peptides also enables the quantification of individual immunoglobulin heavy chain isoforms, which builds on existing clinical methods. This additional information could enable more sensitive detection of disease for patients with MM tumors that secrete lower abundance isoforms (e.g. IgG4). In order to assess the value of this additional level of detail provided by LC-MRM, the expression levels of each immunoglobulin were compared between the patients expressing each monoclonal immunoglobulin and those with other types of PCDs. Box plots are used for visualization (FIG. 2), and statistical results are included in Table 2. In FIG. 2A, the IgG patients are compared to other samples (as described above). IgA patients were differentiated using a peptide representing total IgA, WLQGSQELPR (SEQ ID NO:7) (FIG. 2B). IgM levels were detected using the peptide, DGFFGNPR (SEQ ID NO:8) (FIG. 2C). Box plots are not shown for IgD or IgE, because of the low sample size of those patients and limited detection of those endogenous peptides. As expected, statistical significance improves as the normal range of protein expression decreases; in other words, quantification of total immunoglobulin levels is more effective at detecting disease when the background levels of that immunoglobulin are lower. Therefore, LC-MRM detection of isoforms can further separate IgG patients (defined by serial SPEP/IFE measurements) into IgG1 (n=11), IgG2 (n=2), IgG3 (n=4), and IgG4 (n=1) based on the elevation of isoform-specific peptides. Two examples are shown in box plots in FIG. 2; statistical results are included in Table 2 to indicate the increased separation of the groups and subsequently better detection of elevated immunoglobulin levels for IgG isoforms with lower total expression. Patients identified by LC-MRM with IgG1 disease (n=11) had significantly higher IgG1 expression levels than other patients (FIG. 2D). Patients with IgG3 disease (n=4) had significantly higher levels of that isoform than other patients (FIG. 2E). Due to insufficient sample size, data are not plotted for IgG2 and IgG4. IgA patients could be separated by isoforms into IgA1 and IgA2, but no IgA2 patients were detected in this cohort.

TABLE 2

Statistical Evaluation of LC-MRM Performance in Separating Patient Groups.

| Monitored Protein(s) | Corresponding Ig Diagnosis | | | | Other Diagnoses | | | | Statistical Results | |
|---|---|---|---|---|---|---|---|---|---|---|
| | n | Mean | SD | Median | n | Mean | SD | Median | z-value | p-value |
| IgA1, 2 | 21 | 14.83 | 16.53 | 6.20 | 62 | 0.66 | 0.61 | 0.46 | 5.10 | $3.5E^{-7}$ |
| IgA2 | 21 | 0.03 | 0.04 | 0.01 | 62 | 0.08 | 0.18 | 0.03 | −1.36 | 0.17 |
| IgG1, 2, 3 | 21 | 16.59 | 18.57 | 12.40 | 62 | 4.26 | 3.06 | 3.78 | 4.92 | $8.8E^{-7}$ |
| IgG1 | 10 | 15.19 | 5.38 | 13.74 | 73 | 2.40 | 1.91 | 1.81 | 5.09 | $3.7E^{-7}$ |
| IgG3 | 4 | 30.95 | 41.11 | 17.62 | 79 | 0.66 | 0.60 | 0.53 | 2.24 | 0.02 |
| IgM | 18 | 7.26 | 9.05 | 3.69 | 65 | 0.10 | 0.10 | 0.06 | 6.45 | $1.4E^{-10}$ |
| κ KLC | 36 | 11.99 | 11.09 | 8.83 | 47 | 2.37 | 1.72 | 2.04 | 6.16 | $7.2E^{-10}$ |
| λ LC | 36 | 12.00 | 30.00 | 1.75 | 47 | 0.44 | 0.63 | 0.22 | 5.66 | $1.6E^{-8}$ |
| IgD | 5 | 6.57 | 8.37 | 2.30 | 78 | 0.00 | 0.03 | 0.00 | 7.23 | $4.8E^{-13}$ |

Each immunoglobulin measurement is compared between the population of SPEP positive patients and patients with other diagnoses. For isoform-specific measurements, the diagnosis of the involved immunoglobulin is achieved solely by LC-MRM. In each case, the number of patients as well as the mean, standard deviation, and the median of the protein expression are listed. Statistical significance was assessed by the Holm-Bonferroni method; z-values and p-values are listed.

This additional information has the potential to improve patient monitoring, especially in cases of IgG MM where some isoforms are naturally high in abundance (such as IgG1 and IgG2) and others are significantly lower (IgG3 and IgG4). The patient's total IgG concentration may fall within the reference range for healthy controls (4.5-20 mg/ml), but a single isoform can be detected by LC-MRM and shown to be significantly overexpressed. For example, the total IgG was measured to be within normal limits for three patients, but elevated levels of IgG3 were detected with LC-MRM. This additional capability enables more sensitive detection of disease, and it also may implicate involvement of multiple immunoglobulins, which could indicate another clonal tumor population. As an example, 3 patients were found by LC-MRM quantification to have elevated IgG3 levels that were previously undetected (two in IgM patients and one in a patient not presenting with MM).

LC-MRM Quantification of Light Chains using Constant Region Peptides

In addition to monitoring heavy chains and their isoforms, LC-MRM was used to measure constant regions peptides as surrogates for the expression of the light chains, κ and λ, and to calculate a κ:λ ratio. Assays were developed for κ: TVAAPSVFIFPPSDEQLK (SEQ ID NO:9) and λ: AGVETTTPSK (SEQ ID NO:10). These measurements could be used to detect dysregulation of light chain expression not only as overexpression but also by the κ:λ ratio. LC-MRM data was not compared to the results of SFLC assays, because the values are expected to differ (due to the comparison of total light chain by LC-MRM to free light chain by SFLC). However, LC-MRM was effective in detecting light chain-only disease in all cases (4/4). Patients with light chain-only disease that could not be monitored by SFLC were not included in this study, so it is unclear if LC-MRM would have utility there.

To evaluate the separation of patients with κ and λ diagnoses by LC-MRM, box plots are shown in FIG. 3A and FIG. 3B, respectively. Statistical results are listed in Table 2. Protein expression levels in patients diagnosed with elevated κ were significantly higher than in other patients; λ levels were also significantly different in λ patients when compared to other patients. The κ:λ ratio values have been plotted in log-scale (FIG. 3C). Data from non-MM patients and those expressing biclonal light chains (i.e. both κ and λ) were not included, nor were samples (n=5) where only one light chain could be quantified. Out of the 30 K samples, only one patient was found to have a lower than expected κ:λ ratio (the reference range for total κ:λ in healthy controls is 1.3-2.7) (Katzmann J A, et al Clin Chem 2002, 48, 1437-44), and one patient had a ratio within the normal range. Out of the 30λ patients, two samples were found to have κ:λ ratios above the normal range, and two samples fell within the normal limits. Additional discussion on the characteristics of these patients is included in the supplement.

Longitudinal Patient Monitoring

An IgE MM patient was monitored using LC-MRM for comparison with existing protein-based methods (FIG. 4); total IgE quantification is more sensitive for disease detection than SPEP due to the low levels of background IgE expression (at μg/ml levels). Serum samples were acquired at diagnosis and each time the patient received treatment. Initially, LC-MRM and SPEP show a distinct M-protein correlating to IgE myeloma, assigned by IFE to confirm the SPEP diagnosis and by endogenous IgE peptide intensity in LC-MRM (FIG. 4A). However, analyses during the course of treatment illustrate the similarity of nephelometry and LC-MRM for monitoring IgE. SPEP results show no elevated IgE protein in the serum after the fourth and fifth cycles of treatment at 15 and 19 weeks after diagnosis (FIGS. 4B and 4C); nephelometry and LC-MRM were still able to detect elevated IgE levels at those time points (FIG. 4D). Compared with SPEP, nephelometry and LC-MRM can better characterize the disease in this IgE patient, demonstrating another decrease in tumor burden after the fifth cycle of treatment. After the sixth cycle of treatment and during the subsequent follow-up, neither method could detect IgE. Based on the clinical evaluation (and not LC-MRM data), treatment was discontinued after six cycles, and the patient has been in remission.

Detection of Variable Region Peptides for M-Protein Quantification

LC-MRM of constant region peptides has similar performance for detection of disease with similar intra-assay variability but higher inter-assay variability as compared with current immunoglobulin quantification techniques. One way to improve the LC-MRM method is to define the sequence of the variable region, which could lead to detection of the specific monoclonal immunoglobulin, similar to SPEP. De novo assembly was performed from RNA-seq data to determine the Ig sequence secreted by the H929 cell line. Although NCBI ORF Finder identified several potential constructs, a single protein sequence had the expected size and the expected constant region primary amino acid sequence. This amino acid sequence matched that expected from a translation of the IGKC, IGKJ1, and IGKV3-15 regions. Differences at the junctions were detected as can be expected during Ig recombination: proline was inserted between IGKV3-15 and IGKJ1, and arginine was inserted between IGKJ1 and IGKC. For the Igκ secreted by H929 cells, three constant region peptides (C) and 6 variable region peptides (V) could be detected by LC-MRM (FIG. 5). The peptides are: C1: VDNALQSGNSQESVTEQDSK (SEQ ID NO:14), C2: DSTYSLSSTLTLSK (SEQ ID NO:15), C3: TVAAPSVFIFPPSDEQLK (SEQ ID NO:16), V1: ATGIPAR (SEQ ID NO:17), V2: VTLSCR (SEQ ID NO:18), V3: LSVSPGER (SEQ ID NO:19), V4: LL(ox) MYDASTR (SEQ ID NO:20), V5: ASQSVSSHLVWY-QQKPGQAPR (SEQ ID NO:21), and V6: LLMYDASTR (SEQ ID NO:22); the identity of each peptide was verified by comparison of RT and fragmentation with LC-MS/MS and standards. Because the specific amino acid sequences of the variable region peptides from monoclonal immunoglobulin may be contained in other antibodies secreted by different cells, the quantification of the disease-specific VRPs are limited by the amount of the peptide produced from the background of immunoglobulins secreted by normal plasma cells. Detection of the IgK immunoglobulin from H929 cells by LC-MRM of the LSVSPGER (SEQ ID NO:19) sequence in a background of serum from a healthy control could be accomplished over more than two orders of magnitude and down to a spiked level of 0.6 fmol/μl of serum, which corresponds to detection above background for 0.0015 g/dl. This value represents ~67-fold improvement over the SPEP detection limit at 0.1 g/dl.

In addition, RNA-sequencing and in silico translation also provided the protein sequences of two K immunoglobulins from patients. Both patients are currently in remission, but serum samples were collected and analyzed with LC-MRM for variable region peptides. The first patient was IgA/K with a current M-protein measurement by SPEP of 0.2 g/dl, which is below the 0.5-1 g/dl level used to initiate treatment for relapse; the second patient has IgG/K disease with no detectable M-protein at the time the sample was taken. Therefore, three peptides from the κ light chain of Patient 1 were tested in both patients to see the specificity of assays for the variable region peptides (FIG. 6). In all cases, the level of each variable region peptide was at least 1000-fold higher in Patient 1 than in Patient 2. Based on these preliminary data, this approach could generate personalized assays for detection of tumor burden.

CONCLUSIONS

Using reference ranges for current protein-based assays, LC-MRM quantification of immunoglobulins was compared against current clinical methods using a sample size of 83 patients. While the LC-MRM assay is slower to run (overnight versus a few minutes), the therapeutic window for these patients is long, so treatment decisions do not have to be made immediately and the additional time required for this assay is not detrimental to the patients (Koomen J M, et al Mol Cell Proteomics 2008, 7, 1780-94). The ability of LC-MRM to monitor all immunoglobulins (and albumin as well as other proteins) allows for an increase in efficiency, with MM immunoglobulin and isoform quantification accomplished with one experiment (and one instrument). The LC-MRM method may improve analysis of the rarer MM types (IgD, IgE, and light chain only disease) that currently require multiple tests for monitoring. Peptide-based LC-MRM quantification of total immunoglobulin expression levels offers slight improvements in sensitivity over nephelometry, as well as the ability to quantify isoforms, with a trade-off in precision (~2-fold higher CV values). For higher abundance immunoglobins (e.g. IgG1), the precision is the critical variable for detection of disease because of the background level of protein expression, which is a disadvantage for LC-MRM. For lower abundance isoforms and other immunoglobulins (e.g. IgD or IgE), an increase in sensitivity would be critical to detect low levels of tumor burden during treatment and relapse. The increase in sensitivity can also be used to monitor the amount of immune paresis (reduction in other immunoglobulin levels due to reduction of normal plasma cells from the bone marrow by the growth of the tumor), but this parameter is not currently factored into patient treatment decisions.

In this experiment, outliers in triplicate measurements were detected at levels of 6.4% or less; some peptides did not have any outliers detected. Reduction of CV values and elimination of outliers will be critical for clinical implementation without triplicate analysis. Automation of sample preparation may provide improvements in precision, and injection of larger sample amounts for analytical scale chromatography would be expected to improve on the nanoLC analysis here by eliminating saturation effects, improving precision, and eliminating outliers. If technology shifts to mass spectrometry-based methods, this set of assays could be clinically utilized. In order to pursue its implementation, a large cohort of healthy controls would need to be analyzed to define the appropriate reference ranges for peptide-based LC-MRM assays. Furthermore, additional data should be collected for longitudinal patient monitoring to define the levels of natural variation in immunoglobulin abundance in serum and to determine the threshold for increases in immunoglobulin level that should trigger additional treatment.

Finally, the determination of variable region sequences and the resulting tryptic peptides is a promising method for improving patient monitoring with quantitative mass spectrometry. Although this requires an initial RNA-seq experiment to identify the highly expressed rearrangements, these transcripts can be identified with as few as 20 million RNA-seq reads due to the high expression of Ig in multiple myeloma tumor cells. This method allows for a highly specific tracking of the disease-specific monoclonal protein. This personalized approach could offer a better understanding of the unique aspects of an individual patient's disease, but the effectiveness of the assay would vary between patients because of the sequence-specific performance of the variable region peptides and the patient-specific background of other immunoglobulins with the same sequence.

An assay platform that measures both constant region peptides for all immunoglobulins and variable region peptides for the patient's disease-specific immunoglobulin could significantly improve on sensitivity. The detection of the disease-specific biomarker is then paired with the ability to detect changes in the other immunoglobulins, which could indicate immune paresis (describing disease severity) or expansion of another MM clone that secretes a different immunoglobulin (i.e. relapse with a different MM tumor). This platform would be of use in monitoring depth of response to therapy, which has prognostic value, and determining disease progression either from premalignant conditions (e.g. MGUS) or in relapse after treatment. Improvements in the ability to quantify the tumor burden are likely to shape novel clinical approaches to MM treatment.

Example 2: Assay Development Using LC-MS/MS of Serum at the Time of Diagnosis and De Novo Peptide Sequencing to Determine Variable Region Peptides Liquid chromatography-tandem mass spectrometry (LC-MS/MS) peptide sequencing can be used for the detection and identification of variable region peptides (VRPs) in serum samples or enriched Ig fractions. Unlike the sequencing of antibodies with affinity capture using a known antigen, separations methods are used to create fractions of total Ig, and the expression level of the monoclonal Ig specific to disease will need to be sufficiently high to make the VRPs obvious.

Sample Selection for De Novo Peptide Sequencing

In order to test the potential of LC-MS/MS to define VRPs for assay development, serum from 10 of the 30 patients in Example 1 with varying expression levels (1 mg/ml to >20 mg/ml) are blinded and used for testing the effectiveness of VRP detection by LC-MS/MS.

De Novo Immunoglobulin Peptide Sequencing

Because of the wide range of expression levels different methods for identifying variable region peptides from the monoclonal Ig can be employed. When the expression is very high (e.g. >20 mg/ml or 25% of total blood protein), tryptic digests of total serum proteins can be compared to isolate unique peptides in each sample. However, when the expression is lower, the monoclonal Ig will need to be enriched. For that purpose, gel-based SPEP is used with excision of the γ region or SDS-PAGE with excision of heavy (50 kDa) and light chain (25 kDa) bands prior to LC-MS/MS. For IgG, enrichment with immobilized protein A/G (Ultralink, Pierce) is used for enrichment. All samples are denatured (8 M urea), reduced, alkylated, and digested with trypsin. LC-MS/MS is performed with UPLC (RSLC, Dionex, Sunnyvale, Calif.) and high mass accuracy MS and MS/MS in an hybrid linear ion trap-orbital ion trap mass spectrometer (LTQ Orbitrap, Thermo, San Jose, Calif.), as described previously. Peptide sequences are identified by database searches with Sequest (Thermo, San Jose, Calif.) and Mascot against the human entries in the UniProt database containing both forward and reverse protein sequences to enable assessment of false discovery rate (% reverse out of the total). Scaffold will assemble data to define and eliminate the common background.

For the samples with the highest abundance Ig expression, SIEVE is used to compare replicates of one sample against all others to find unique peptides, which are manually sequenced de novo using high resolution and accurate mass MS and MS/MS data. In addition, ScanRanker is used for sequence tagging, identifying peptides using the MS/MS data first. Comparisons of these results between samples indicates the unique peptides in each sample. Finally, conserved amino acids and sequences in the variable region of the immunoglobulins are used to search for patterns in the MS/MS data or for peptides with specific cleavage sites (and therefore specific C-termini) These strategies are applied to raw serum digests and enriched Ig fractions to define the amount of Ig expression required for each method to be effective. VRPs detected by LC-MS/MS are compared to the RNA-seq to determine the ability to develop these assays from serum without the need for bone marrow.

Example 3: Determination of the Sequence of the Immunoglobulin (Ig) Secreted by the Multiple Myeloma Tumor Cells Using RNA-Sequencing (RNA-Seq) Using CD138+ Cells Selected from Bone Marrow Aspirates The example data involved 100 base read lengths (e.g. HiSEq, Illumina), but longer read lengths produced by other instruments (e.g. 300 base reads with MiSeq, Illumina) would be advantageous for data quality. Attempts are made to reconstruct the heavy chain constant regions (IgG1-4, IgA1-2, IgM, IgD, and IgE), the light chain constant regions (Igκ and Igλ), the joining regions, and the variable regions for each immunoglobulin. Successful reads should assemble constant region, joining region, and variable region for the intact immunoglobulin. Both heavy chain and light chain can be important for patient monitoring.

mRNA enrichment can be used to improve the application of sequencing and reduce the total amount of sequencing required for each patient.

5' RACE can also be used for targeted sequencing to increase the number of reads for the immunoglobulins and decrease the overall need for sequencing per patient. Briefly, since the constant regions of the antibody are at the C-terminus, primers to the beginning of the C-terminus of the constant region can be used to read back through the joining region and the variable region. Primers can be designed against the heavy chains and their isoforms as well as the light chains and their isoforms.

Data from the above methods are assembled and translated to protein. The protein sequence is used to define peptide biomarkers that can be measured with quantitative mass spectrometry. The Ig sequence is blasted against existing publically available databases and previous patients to define the most unique parts of the sequence.

The Ig sequence is digested in silico to generate peptides that contain the maximally unique sequence. Multiple enzymes are tested, including but not limited to trypsin, endoproteinase Lys-C, chymotrypsin, endoproteinase Glu-C, Asp-N, Arg-C, etc. The effectiveness of the peptide lies in its uniqueness and its ability to be detected by the mass spectrometer.

Heavy and light chain proteins are isolated by SDS-PAGE and excised for in-gel digestion. Alternatively, the filter-aided sample preparation (FASP) can be used for in-solution digestion, if enzymes perform poorly for in-gel digestion.

Liquid chromatography-multiple reaction monitoring mass spectrometry (LC-MRM) is used to screen for constant region and variable region peptides. Standards are then synthesized for the endogenous peptide using stable isotope-labeled amino acids or single conservative amino acid replacements and characterized by LC-MRM to test assay sensitivity (LOD, LLOQ, ULOQ), linearity, accuracy, precision, and other figures of merit.

For peptides with highly unique sequences but poor response in the mass spectrometer, chemical labeling with tandem mass tags (TMT, Proteome Sciences) or tags for relative and absolute quantification (mTRAQ or iTRAQ, ABSciex) are applied to enhance the signal for those peptides. As needed, enrichment of the immunoglobulin light and heavy chains are achieved by SDS-PAGE, MW fractionation, or affinity pulldown.

Biomarkers are applied to patient samples to measure disease burden. LC-MRM is used to quantify constant region peptides to measure the total class of each immunoglobulin and its isoforms. The exact peptides depend on the enzyme selected. Examples for trypsin are provided on the following pages. LC-MRM is also used to quantify variable region peptides to measure the disease-specific immunoglobulin. Alternatively, LC-MS/MS or pseudo reaction monitoring (PRM) strategies can also be used.

Quantification of the disease-specific peptides can be used to define patients progressing from pre-malignant conditions, measure response to therapy, and detect relapse.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for monitoring a plasma cell dyscrasia in a subject, comprising:
   a) treating a biological sample comprising immunoglobulin from CD138+ plasma cells from bone marrow aspirates from the subject to enzymatically cleave target immunoglobulins, wherein the target immunoglobulins are IgG, IgA, IgD, and IgE heavy chains, into variable domain peptide fragments of the target immunoglobulins; and
   b) measuring the variable domain peptide fragments in the sample by quantitative mass spectrometry to quantify the amount of each of IgG, IgA, IgD, and IgE heavy chains in the sample using multiple reaction monitoring (MRM);
   wherein the plasma cell dyscrasia is monitored by the amount of the target immunoglobulins in the sample.

2. The method of claim 1, wherein the variable domain peptide fragments are first identified by a method comprising:
   a) determining the amino add sequence of the target immunoglobulins; and
   b) identifying in silico variable domain peptide fragments formed by enzymatic digestion of the target immunoglobulins that:

i. contain amino add sequences from the variable domain of the target immunoglobulins that are sufficiently unique to distinguish the target immunoglobulins from other immunoglobulins in the biological sample, and
ii. are capable of being detected by a mass spectrometer.

3. The method of claim 2, wherein the variable domain peptide fragments contain the complementarity defining region (CDR) of the target immunoglobulins.

4. The method of claim 2, wherein the amino acid sequence of the target immunoglobulins is determined by a method comprising:
b. RNA-sequencing immunoglobulin mRNA from a plasma cell of the subject that is associated with the plasma cell dyscrasia; and
c. in silico translating the RNA sequence of the immunoglobulin to protein.

5. The method of claim 1, wherein the plasma cell dyscrasia comprises a multiple myeloma, and wherein the method monitors tumor burden in the subject.

6. The method of claim 1, further comprising measuring in the sample after enzymatic cleavage one or more constant domain peptide fragments containing amino acid sequences from a constant domain of the immunoglobulins to quantify total immunoglobulins in the sample.

7. The method of claim 6, wherein the plasma cell dyscrasia is monitored by the ratio of target immunoglobulins to total immunoglobulins in the biological sample.

8. The method of claim 1, wherein the target immunoglobulins further comprise human kappa light chain or human lambda light chain.

9. The method of claim 1, wherein the plasma cell dyscrasia is multiple myeloma or monoclonal gammopathy of undetermined significance (MGUS).

10. The method of claim 1, wherein the peptide fragments are measured by spiking in during the mass spectrometry a known amount of the one or more peptides containing a specific label.

11. The method of claim 10, wherein the specific label comprises a heavy isotope label or an amino acid substitution sufficient to create a detectable mass difference.

12. The method of claim 11, wherein the heavy isotope label is $^2$H, $^{13}$C, or $^{15}$N.

13. The method of claim 1, wherein the immunoglobulin in the sample is denatured prior to enzymatic cleavage.

14. The method of claim 13, wherein the immunoglobulin is denatured by treatment with urea, disulfide reduction, and/or cysteine alkylation.

15. The method of claim 1, wherein the immunoglobulin in the sample is enzymatically cleaved by proteolytic enzyme digestion.

16. The method of claim 15, wherein the proteolytic enzyme is trypsin.

17. The method of claim 1, further comprising a treating step to isolate the target immunoglobulin prior to enzymatic cleavage, wherein the treating step comprises one or more of size exclusion chromatography, gel electrophoresis, and/or affinity chromatography.

18. The method of claim 1, wherein the mass spectrometry comprises liquid chromatography coupled to multiple reaction monitoring (LC-MRM).

19. The method of claim 18, wherein the mass spectrometry is conducted on a triple quadrupole mass spectrometer.

20. The method of claim 1, wherein the method is used to monitor for progression of monoclonal gammopathy of undetermined significance in the subject to multiple myeloma or relapse of disease after prior treatment.

21. The method of claim 1, wherein the method is used to monitor the efficacy of a treatment regimen on a subject with multiple myeloma or MGUS.

* * * * *

SEQUENCE LISTING

```
<160> NUMBER OF SEQ ID NOS: 904

<210> SEQ ID NO 1
<211> LENGTH: 12
<212> TYPE: PRT
<213> ORGANISM: Homo sapiens

<400> SEQUENCE: 1

Gly Pro Ser Val Phe Pro Leu Ala Pro Ser Ser Lys
1               5                   10
```

<210> SEQ ID NO 2
<211> LENGTH: 8
<212> TYPE: PRT
<213> ORGANISM: Homo sapiens

<400> SEQUENCE: 2

Gly Leu Pro Ala Pro Ile Glu Lys
1               5

<210> SEQ ID NO 3
<211> LENGTH: 12
<212> TYPE: PRT
<213> ORGANISM: Homo sapiens

<400> SEQUENCE: 3

Trp Tyr Val Asp Gly Val Glu Val His Asn Ala Lys
1               5                   10

<210> SEQ ID NO 4
<211> LENGTH: 17
<212> TYPE: PRT
<213> ORGANISM: Homo sapiens

<400> SEQUENCE: 4

Thr Thr Pro Pro Val Leu Asp Ser Asp Gly Ser Phe Phe Leu Tyr Ser
1               5                   10                  15

Arg

<210> SEQ ID NO 5
<211> LENGTH: 9
<212> TYPE: PRT
<213> ORGANISM: Homo sapiens

<400> SEQUENCE: 5

Thr Pro Leu Thr Ala Thr Leu Ser Lys
1               5

<210> SEQ ID NO 6
<211> LENGTH: 15
<212> TYPE: PRT
<213> ORGANISM: Homo sapiens

<400> SEQUENCE: 6

Asp Ala Ser Gly Ala Thr Phe Thr Trp Thr Pro Ser Ser Gly Lys
1               5                   10                  15

<210> SEQ ID NO 7
<211> LENGTH: 10
<212> TYPE: PRT
<213> ORGANISM: Homo sapiens

<400> SEQUENCE: 7

Trp Leu Gln Gly Ser Gln Glu Leu Pro Arg
1               5                   10

<210> SEQ ID NO 8
<211> LENGTH: 8
<212> TYPE: PRT
<213> ORGANISM: Homo sapiens

<400> SEQUENCE: 8

Asp Gly Phe Phe Gly Asn Pro Arg
1               5

<210> SEQ ID NO 9
<211> LENGTH: 18
<212> TYPE: PRT
<213> ORGANISM: Homo sapiens

<400> SEQUENCE: 9

Thr Val Ala Ala Pro Ser Val Phe Ile Phe Pro Pro Ser Asp Glu Gln
1               5                   10                  15

Leu Lys

<210> SEQ ID NO 10
<211> LENGTH: 10
<212> TYPE: PRT
<213> ORGANISM: Homo sapiens

<400> SEQUENCE: 10

Ala Gly Val Glu Thr Thr Thr Pro Ser Lys
1               5                   10

<210> SEQ ID NO 11
<211> LENGTH: 9
<212> TYPE: PRT
<213> ORGANISM: Homo sapiens

<400> SEQUENCE: 11

Glu Pro Ala Ala Gln Ala Pro Val Lys
1               5

<210> SEQ ID NO 12
<211> LENGTH: 9
<212> TYPE: PRT
<213> ORGANISM: Homo sapiens

<400> SEQUENCE: 12

Gly Ser Gly Phe Phe Val Phe Ser Arg
1               5

<210> SEQ ID NO 13
<211> LENGTH: 10
<212> TYPE: PRT
<213> ORGANISM: Homo sapiens

<400> SEQUENCE: 13

Leu Val Asn Glu Val Thr Glu Phe Ala Lys
1               5                   10

<210> SEQ ID NO 14
<211> LENGTH: 20
<212> TYPE: PRT
<213> ORGANISM: Homo sapiens

<400> SEQUENCE: 14

Val Asp Asn Ala Leu Gln Ser Gly Asn Ser Gln Glu Ser Val Thr Glu
1               5                   10                  15

Gln Asp Ser Lys
            20

<210> SEQ ID NO 15
<211> LENGTH: 14
<212> TYPE: PRT
<213> ORGANISM: Homo sapiens

<400> SEQUENCE: 15

Asp Ser Thr Tyr Ser Leu Ser Ser Thr Leu Thr Leu Ser Lys
1               5                   10

<210> SEQ ID NO 16
<211> LENGTH: 18
<212> TYPE: PRT
<213> ORGANISM: Homo sapiens

<400> SEQUENCE: 16

Thr Val Ala Ala Pro Ser Val Phe Ile Phe Pro Pro Ser Asp Glu Gln
1               5                   10                  15

Leu Lys

<210> SEQ ID NO 17
<211> LENGTH: 7
<212> TYPE: PRT
<213> ORGANISM: Homo sapiens

<400> SEQUENCE: 17

Ala Thr Gly Ile Pro Ala Arg
1               5

<210> SEQ ID NO 18
<211> LENGTH: 6
<212> TYPE: PRT
<213> ORGANISM: Homo sapiens

<400> SEQUENCE: 18

Val Thr Leu Ser Cys Arg
1               5

<210> SEQ ID NO 19
<211> LENGTH: 8
<212> TYPE: PRT
<213> ORGANISM: Homo sapiens

<400> SEQUENCE: 19

Leu Ser Val Ser Pro Gly Glu Arg
1               5

<210> SEQ ID NO 20
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X = Oxidized Leucine

<400> SEQUENCE: 20

Leu Xaa Met Tyr Asp Ala Ser Thr Arg
1               5

<210> SEQ ID NO 21
<211> LENGTH: 21
<212> TYPE: PRT
<213> ORGANISM: Homo sapiens

<400> SEQUENCE: 21

Ala Ser Gln Ser Val Ser Ser His Leu Val Trp Tyr Gln Gln Lys Pro
1               5                   10                  15

Gly Gln Ala Pro Arg
            20

```
<210> SEQ ID NO 22
<211> LENGTH: 9
<212> TYPE: PRT
<213> ORGANISM: Homo sapiens

<400> SEQUENCE: 22

Leu Leu Met Tyr Asp Ala Ser Thr Arg
1               5

<210> SEQ ID NO 23
<211> LENGTH: 6
<212> TYPE: PRT
<213> ORGANISM: Homo sapiens

<400> SEQUENCE: 23

Val Thr Ile Thr Cys Arg
1               5

<210> SEQ ID NO 24
<211> LENGTH: 16
<212> TYPE: PRT
<213> ORGANISM: Homo sapiens

<400> SEQUENCE: 24

Ser Leu Ile Tyr Ala Ala Ser Ser Leu Gln Ser Gly Val Pro Ser Lys
1               5                   10                  15

<210> SEQ ID NO 25
<211> LENGTH: 15
<212> TYPE: PRT
<213> ORGANISM: Homo sapiens

<400> SEQUENCE: 25

Ala Asn Gln Asp Ile Thr Asn Ser Leu Val Trp Phe Gln Gln Lys
1               5                   10                  15

<210> SEQ ID NO 26
<211> LENGTH: 22
<212> TYPE: PRT
<213> ORGANISM: Homo sapiens

<400> SEQUENCE: 26

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 27
<211> LENGTH: 19
<212> TYPE: PRT
<213> ORGANISM: Homo sapiens

<400> SEQUENCE: 27

Thr Pro Glu Val Thr Cys Val Val Val Asp Val Ser His Glu Asp Pro
1               5                   10                  15

Glu Val Lys

<210> SEQ ID NO 28
<211> LENGTH: 17
<212> TYPE: PRT
<213> ORGANISM: Homo sapiens

<400> SEQUENCE: 28
```

```
Thr Thr Pro Pro Val Leu Asp Ser Asp Gly Ser Phe Phe Leu Tyr Ser
1               5                   10                  15

Lys

<210> SEQ ID NO 29
<211> LENGTH: 16
<212> TYPE: PRT
<213> ORGANISM: Homo sapiens

<400> SEQUENCE: 29

Val Val Ser Val Leu Thr Val Leu His Gln Asp Trp Leu Asn Gly Lys
1               5                   10                  15

<210> SEQ ID NO 30
<211> LENGTH: 14
<212> TYPE: PRT
<213> ORGANISM: Homo sapiens

<400> SEQUENCE: 30

Phe Asn Trp Tyr Val Asp Gly Val Glu Val His Asn Ala Lys
1               5                   10

<210> SEQ ID NO 31
<211> LENGTH: 11
<212> TYPE: PRT
<213> ORGANISM: Homo sapiens

<400> SEQUENCE: 31

Glu Pro Gln Val Tyr Thr Leu Pro Pro Ser Arg
1               5                   10

<210> SEQ ID NO 32
<211> LENGTH: 14
<212> TYPE: PRT
<213> ORGANISM: Homo sapiens

<400> SEQUENCE: 32

Ser Thr Ser Gly Gly Thr Ala Ala Leu Gly Cys Leu Val Lys
1               5                   10

<210> SEQ ID NO 33
<211> LENGTH: 9
<212> TYPE: PRT
<213> ORGANISM: Homo sapiens

<400> SEQUENCE: 33

Glu Glu Gln Tyr Asn Ser Thr Tyr Arg
1               5

<210> SEQ ID NO 34
<211> LENGTH: 10
<212> TYPE: PRT
<213> ORGANISM: Homo sapiens

<400> SEQUENCE: 34

Asn Gln Val Ser Leu Thr Cys Leu Val Lys
1               5                   10

<210> SEQ ID NO 35
<211> LENGTH: 8
<212> TYPE: PRT
<213> ORGANISM: Homo sapiens

<400> SEQUENCE: 35
```

Ala Leu Pro Ala Pro Ile Glu Lys
1               5

<210> SEQ ID NO 36
<211> LENGTH: 7
<212> TYPE: PRT
<213> ORGANISM: Homo sapiens

<400> SEQUENCE: 36

Asp Thr Leu Met Ile Ser Arg
1               5

<210> SEQ ID NO 37
<211> LENGTH: 8
<212> TYPE: PRT
<213> ORGANISM: Homo sapiens

<400> SEQUENCE: 37

Ser Leu Ser Leu Ser Pro Gly Lys
1               5

<210> SEQ ID NO 38
<211> LENGTH: 22
<212> TYPE: PRT
<213> ORGANISM: Homo sapiens

<400> SEQUENCE: 38

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 39
<211> LENGTH: 24
<212> TYPE: PRT
<213> ORGANISM: Homo sapiens

<400> SEQUENCE: 39

Thr His Thr Cys Pro Pro Cys Pro Ala Pro Glu Leu Leu Gly Gly Pro
1               5                   10                  15

Ser Val Phe Leu Phe Pro Pro Lys
            20

<210> SEQ ID NO 40
<211> LENGTH: 20
<212> TYPE: PRT
<213> ORGANISM: Homo sapiens

<400> SEQUENCE: 40

Gly Gln Pro Arg Glu Pro Gln Val Tyr Thr Leu Pro Pro Ser Arg Asp
1               5                   10                  15

Glu Leu Thr Lys
            20

<210> SEQ ID NO 41
<211> LENGTH: 17
<212> TYPE: PRT
<213> ORGANISM: Homo sapiens

<400> SEQUENCE: 41

Thr Thr Pro Pro Val Leu Asp Ser Asp Gly Ser Phe Phe Leu Tyr Ser
1               5                   10                  15

Lys

<210> SEQ ID NO 42
<211> LENGTH: 14
<212> TYPE: PRT
<213> ORGANISM: Homo sapiens

<400> SEQUENCE: 42

Phe Asn Trp Tyr Val Asp Gly Val Glu Val His Asn Ala Lys
1               5                   10

<210> SEQ ID NO 43
<211> LENGTH: 14
<212> TYPE: PRT
<213> ORGANISM: Homo sapiens

<400> SEQUENCE: 43

Ser Thr Ser Gly Gly Thr Ala Ala Leu Gly Cys Leu Val Lys
1               5                   10

<210> SEQ ID NO 44
<211> LENGTH: 12
<212> TYPE: PRT
<213> ORGANISM: Homo sapiens

<400> SEQUENCE: 44

Gly Pro Ser Val Phe Pro Leu Ala Pro Ser Ser Lys
1               5                   10

<210> SEQ ID NO 45
<211> LENGTH: 10
<212> TYPE: PRT
<213> ORGANISM: Homo sapiens

<400> SEQUENCE: 45

Asn Gln Val Ser Leu Thr Cys Leu Val Lys
1               5                   10

<210> SEQ ID NO 46
<211> LENGTH: 8
<212> TYPE: PRT
<213> ORGANISM: Homo sapiens

<400> SEQUENCE: 46

Ala Leu Pro Ala Pro Ile Glu Lys
1               5

<210> SEQ ID NO 47
<211> LENGTH: 8
<212> TYPE: PRT
<213> ORGANISM: Homo sapiens

<400> SEQUENCE: 47

Ser Leu Ser Leu Ser Pro Gly Lys
1               5

<210> SEQ ID NO 48
<211> LENGTH: 11
<212> TYPE: PRT
<213> ORGANISM: Homo sapiens

<400> SEQUENCE: 48

Glu Pro Gln Val Tyr Thr Leu Pro Pro Ser Arg
1               5                   10

```
<210> SEQ ID NO 49
<211> LENGTH: 9
<212> TYPE: PRT
<213> ORGANISM: Homo sapiens

<400> SEQUENCE: 49

Glu Glu Gln Tyr Asn Ser Thr Tyr Arg
1               5

<210> SEQ ID NO 50
<211> LENGTH: 23
<212> TYPE: PRT
<213> ORGANISM: Homo sapiens

<400> SEQUENCE: 50

Ile Ser Arg Thr Pro Glu Val Thr Cys Val Val Val Asp Val Ser His
1               5                   10                  15

Glu Asp Pro Glu Val Lys Phe
            20

<210> SEQ ID NO 51
<211> LENGTH: 18
<212> TYPE: PRT
<213> ORGANISM: Homo sapiens

<400> SEQUENCE: 51

Val Asp Gly Val Glu Val His Asn Ala Lys Thr Lys Pro Arg Glu Glu
1               5                   10                  15

Gln Tyr

<210> SEQ ID NO 52
<211> LENGTH: 14
<212> TYPE: PRT
<213> ORGANISM: Homo sapiens

<400> SEQUENCE: 52

Ala Pro Ser Ser Lys Ser Thr Ser Gly Gly Thr Ala Ala Leu
1               5                   10

<210> SEQ ID NO 53
<211> LENGTH: 10
<212> TYPE: PRT
<213> ORGANISM: Homo sapiens

<400> SEQUENCE: 53

Glu Ser Asn Gly Gln Pro Glu Asn Asn Tyr
1               5                   10

<210> SEQ ID NO 54
<211> LENGTH: 11
<212> TYPE: PRT
<213> ORGANISM: Homo sapiens

<400> SEQUENCE: 54

Thr Ser Gly Val His Thr Phe Pro Ala Val Leu
1               5                   10

<210> SEQ ID NO 55
<211> LENGTH: 11
<212> TYPE: PRT
<213> ORGANISM: Homo sapiens

<400> SEQUENCE: 55

Ala Ser Thr Lys Gly Pro Ser Val Phe Pro Leu
```

<210> SEQ ID NO 56
<211> LENGTH: 9
<212> TYPE: PRT
<213> ORGANISM: Homo sapiens

<400> SEQUENCE: 56

Tyr Pro Ser Asp Ile Ala Val Glu Trp
1               5

<210> SEQ ID NO 57
<211> LENGTH: 11
<212> TYPE: PRT
<213> ORGANISM: Homo sapiens

<400> SEQUENCE: 57

Ser Ser Val Val Thr Val Pro Ser Ser Ser Leu
1               5                   10

<210> SEQ ID NO 58
<211> LENGTH: 9
<212> TYPE: PRT
<213> ORGANISM: Homo sapiens

<400> SEQUENCE: 58

Phe Pro Glu Pro Val Thr Val Ser Trp
1               5

<210> SEQ ID NO 59
<211> LENGTH: 9
<212> TYPE: PRT
<213> ORGANISM: Homo sapiens

<400> SEQUENCE: 59

Phe Pro Pro Lys Pro Lys Asp Thr Leu
1               5

<210> SEQ ID NO 60
<211> LENGTH: 9
<212> TYPE: PRT
<213> ORGANISM: Homo sapiens

<400> SEQUENCE: 60

Thr Leu Pro Pro Ser Arg Asp Glu Leu
1               5

<210> SEQ ID NO 61
<211> LENGTH: 7
<212> TYPE: PRT
<213> ORGANISM: Homo sapiens

<400> SEQUENCE: 61

Thr Val Asp Lys Ser Arg Trp
1               5

<210> SEQ ID NO 62
<211> LENGTH: 7
<212> TYPE: PRT
<213> ORGANISM: Homo sapiens

<400> SEQUENCE: 62

Thr Lys Asn Gln Val Ser Leu
1               5

<210> SEQ ID NO 63
<211> LENGTH: 7
<212> TYPE: PRT
<213> ORGANISM: Homo sapiens

<400> SEQUENCE: 63

Lys Thr Thr Pro Pro Val Leu
1               5

<210> SEQ ID NO 64
<211> LENGTH: 18
<212> TYPE: PRT
<213> ORGANISM: Homo sapiens

<400> SEQUENCE: 64

Gln Tyr Asn Ser Thr Tyr Arg Val Val Ser Val Leu Thr Val Leu His
1               5                   10                  15

Gln Asp

<210> SEQ ID NO 65
<211> LENGTH: 19
<212> TYPE: PRT
<213> ORGANISM: Homo sapiens

<400> SEQUENCE: 65

Leu Thr Lys Asn Gln Val Ser Leu Thr Cys Leu Val Lys Gly Phe Tyr
1               5                   10                  15

Pro Ser Asp

<210> SEQ ID NO 66
<211> LENGTH: 17
<212> TYPE: PRT
<213> ORGANISM: Homo sapiens

<400> SEQUENCE: 66

Lys Ser Arg Trp Gln Gln Gly Asn Val Phe Ser Cys Ser Val Met His
1               5                   10                  15

Glu

<210> SEQ ID NO 67
<211> LENGTH: 17
<212> TYPE: PRT
<213> ORGANISM: Homo sapiens

<400> SEQUENCE: 67

Ala Leu His Asn His Tyr Thr Gln Lys Ser Leu Ser Leu Ser Pro Gly
1               5                   10                  15

Lys

<210> SEQ ID NO 68
<211> LENGTH: 16
<212> TYPE: PRT
<213> ORGANISM: Homo sapiens

<400> SEQUENCE: 68

Leu Leu Gly Gly Pro Ser Val Phe Leu Phe Pro Pro Lys Pro Lys Asp
1               5                   10                  15

<210> SEQ ID NO 69
<211> LENGTH: 15
<212> TYPE: PRT
<213> ORGANISM: Homo sapiens

```
<400> SEQUENCE: 69

Tyr Lys Cys Lys Val Ser Asn Lys Ala Leu Pro Ala Pro Ile Glu
1               5                   10                  15

<210> SEQ ID NO 70
<211> LENGTH: 12
<212> TYPE: PRT
<213> ORGANISM: Homo sapiens

<400> SEQUENCE: 70

Gly Ser Phe Phe Leu Tyr Ser Lys Leu Thr Val Asp
1               5                   10

<210> SEQ ID NO 71
<211> LENGTH: 11
<212> TYPE: PRT
<213> ORGANISM: Homo sapiens

<400> SEQUENCE: 71

Val His Asn Ala Lys Thr Lys Pro Arg Glu Glu
1               5                   10

<210> SEQ ID NO 72
<211> LENGTH: 12
<212> TYPE: PRT
<213> ORGANISM: Homo sapiens

<400> SEQUENCE: 72

Lys Thr His Thr Cys Pro Pro Cys Pro Ala Pro Glu
1               5                   10

<210> SEQ ID NO 73
<211> LENGTH: 11
<212> TYPE: PRT
<213> ORGANISM: Homo sapiens

<400> SEQUENCE: 73

Asn Asn Tyr Lys Thr Thr Pro Pro Val Leu Asp
1               5                   10

<210> SEQ ID NO 74
<211> LENGTH: 8
<212> TYPE: PRT
<213> ORGANISM: Homo sapiens

<400> SEQUENCE: 74

Val Lys Phe Asn Trp Tyr Val Asp
1               5

<210> SEQ ID NO 75
<211> LENGTH: 9
<212> TYPE: PRT
<213> ORGANISM: Homo sapiens

<400> SEQUENCE: 75

Thr Leu Met Ile Ser Arg Thr Pro Glu
1               5

<210> SEQ ID NO 76
<211> LENGTH: 9
<212> TYPE: PRT
<213> ORGANISM: Homo sapiens

<400> SEQUENCE: 76
```

```
Lys Lys Val Glu Pro Lys Ser Cys Asp
1               5
```

<210> SEQ ID NO 77
<211> LENGTH: 6
<212> TYPE: PRT
<213> ORGANISM: Homo sapiens

<400> SEQUENCE: 77

```
Trp Leu Asn Gly Lys Glu
1               5
```

<210> SEQ ID NO 78
<211> LENGTH: 23
<212> TYPE: PRT
<213> ORGANISM: Homo sapiens

<400> SEQUENCE: 78

```
Leu Thr Lys Asn Gln Val Ser Leu Thr Cys Leu Val Lys Gly Phe Tyr
1               5                   10                  15

Pro Ser Asp Ile Ala Val Glu
            20
```

<210> SEQ ID NO 79
<211> LENGTH: 17
<212> TYPE: PRT
<213> ORGANISM: Homo sapiens

<400> SEQUENCE: 79

```
Ala Leu His Asn His Tyr Thr Gln Lys Ser Leu Ser Leu Ser Pro Gly
1               5                   10                  15

Lys
```

<210> SEQ ID NO 80
<211> LENGTH: 15
<212> TYPE: PRT
<213> ORGANISM: Homo sapiens

<400> SEQUENCE: 80

```
Tyr Lys Cys Lys Val Ser Asn Lys Ala Leu Pro Ala Pro Ile Glu
1               5                   10                  15
```

<210> SEQ ID NO 81
<211> LENGTH: 11
<212> TYPE: PRT
<213> ORGANISM: Homo sapiens

<400> SEQUENCE: 81

```
Val Lys Phe Asn Trp Tyr Val Asp Gly Val Glu
1               5                   10
```

<210> SEQ ID NO 82
<211> LENGTH: 11
<212> TYPE: PRT
<213> ORGANISM: Homo sapiens

<400> SEQUENCE: 82

```
Val His Asn Ala Lys Thr Lys Pro Arg Glu Glu
1               5                   10
```

<210> SEQ ID NO 83
<211> LENGTH: 11
<212> TYPE: PRT

<213> ORGANISM: Homo sapiens

<400> SEQUENCE: 83

Val Thr Cys Val Val Asp Val Ser His Glu
1               5                   10

<210> SEQ ID NO 84
<211> LENGTH: 6
<212> TYPE: PRT
<213> ORGANISM: Homo sapiens

<400> SEQUENCE: 84

Ser Asn Gly Gln Pro Glu
1               5

<210> SEQ ID NO 85
<211> LENGTH: 23
<212> TYPE: PRT
<213> ORGANISM: Homo sapiens

<400> SEQUENCE: 85

Asp Ile Ala Val Glu Trp Glu Ser Asn Gly Gln Pro Glu Asn Asn Tyr
1               5                   10                  15

Lys Thr Thr Pro Pro Val Leu
            20

<210> SEQ ID NO 86
<211> LENGTH: 20
<212> TYPE: PRT
<213> ORGANISM: Homo sapiens

<400> SEQUENCE: 86

Asp Glu Leu Thr Lys Asn Gln Val Ser Leu Thr Cys Leu Val Lys Gly
1               5                   10                  15

Phe Tyr Pro Ser
            20

<210> SEQ ID NO 87
<211> LENGTH: 16
<212> TYPE: PRT
<213> ORGANISM: Homo sapiens

<400> SEQUENCE: 87

Asp Thr Leu Met Ile Ser Arg Thr Pro Glu Val Thr Cys Val Val Val
1               5                   10                  15

<210> SEQ ID NO 88
<211> LENGTH: 12
<212> TYPE: PRT
<213> ORGANISM: Homo sapiens

<400> SEQUENCE: 88

Asp Gly Ser Phe Phe Leu Tyr Ser Lys Leu Thr Val
1               5                   10

<210> SEQ ID NO 89
<211> LENGTH: 10
<212> TYPE: PRT
<213> ORGANISM: Homo sapiens

<400> SEQUENCE: 89

Asp Pro Glu Val Lys Phe Asn Trp Tyr Val
1               5                   10

```
<210> SEQ ID NO 90
<211> LENGTH: 9
<212> TYPE: PRT
<213> ORGANISM: Homo sapiens

<400> SEQUENCE: 90

Asp Lys Lys Val Glu Pro Lys Ser Cys
1               5

<210> SEQ ID NO 91
<211> LENGTH: 22
<212> TYPE: PRT
<213> ORGANISM: Homo sapiens

<400> SEQUENCE: 91

Gly Phe Tyr Pro Ser Asp Ile Ser Val Glu Trp Glu Ser Asn Gly Gln
1               5                   10                  15

Pro Glu Asn Asn Tyr Lys
            20

<210> SEQ ID NO 92
<211> LENGTH: 17
<212> TYPE: PRT
<213> ORGANISM: Homo sapiens

<400> SEQUENCE: 92

Thr Thr Pro Pro Met Leu Asp Ser Asp Gly Ser Phe Phe Leu Tyr Ser
1               5                   10                  15

Lys

<210> SEQ ID NO 93
<211> LENGTH: 16
<212> TYPE: PRT
<213> ORGANISM: Homo sapiens

<400> SEQUENCE: 93

Val Val Ser Val Leu Thr Val Val His Gln Asp Trp Leu Asn Gly Lys
1               5                   10                  15

<210> SEQ ID NO 94
<211> LENGTH: 14
<212> TYPE: PRT
<213> ORGANISM: Homo sapiens

<400> SEQUENCE: 94

Ser Thr Ser Glu Ser Thr Ala Ala Leu Gly Cys Leu Val Lys
1               5                   10

<210> SEQ ID NO 95
<211> LENGTH: 11
<212> TYPE: PRT
<213> ORGANISM: Homo sapiens

<400> SEQUENCE: 95

Glu Pro Gln Val Tyr Thr Leu Pro Pro Ser Arg
1               5                   10

<210> SEQ ID NO 96
<211> LENGTH: 12
<212> TYPE: PRT
<213> ORGANISM: Homo sapiens

<400> SEQUENCE: 96
```

Gly Pro Ser Val Phe Pro Leu Ala Pro Cys Ser Arg
1               5                   10

<210> SEQ ID NO 97
<211> LENGTH: 9
<212> TYPE: PRT
<213> ORGANISM: Homo sapiens

<400> SEQUENCE: 97

Glu Glu Gln Phe Asn Ser Thr Phe Arg
1               5

<210> SEQ ID NO 98
<211> LENGTH: 10
<212> TYPE: PRT
<213> ORGANISM: Homo sapiens

<400> SEQUENCE: 98

Asn Gln Val Ser Leu Thr Cys Leu Val Lys
1               5                   10

<210> SEQ ID NO 99
<211> LENGTH: 7
<212> TYPE: PRT
<213> ORGANISM: Homo sapiens

<400> SEQUENCE: 99

Asp Thr Leu Met Ile Ser Arg
1               5

<210> SEQ ID NO 100
<211> LENGTH: 8
<212> TYPE: PRT
<213> ORGANISM: Homo sapiens

<400> SEQUENCE: 100

Ser Leu Ser Leu Ser Pro Gly Lys
1               5

<210> SEQ ID NO 101
<211> LENGTH: 26
<212> TYPE: PRT
<213> ORGANISM: Homo sapiens

<400> SEQUENCE: 101

Gly Pro Ser Val Phe Pro Leu Ala Pro Cys Ser Arg Ser Thr Ser Glu
1               5                   10                  15

Ser Thr Ala Ala Leu Gly Cys Leu Val Lys
            20                  25

<210> SEQ ID NO 102
<211> LENGTH: 22
<212> TYPE: PRT
<213> ORGANISM: Homo sapiens

<400> SEQUENCE: 102

Gly Phe Tyr Pro Ser Asp Ile Ser Val Glu Trp Glu Ser Asn Gly Gln
1               5                   10                  15

Pro Glu Asn Asn Tyr Lys
            20

<210> SEQ ID NO 103
<211> LENGTH: 24
<212> TYPE: PRT

<213> ORGANISM: Homo sapiens

<400> SEQUENCE: 103

Cys Cys Val Glu Cys Pro Pro Cys Pro Ala Pro Val Ala Gly Pro
1               5                   10                  15

Ser Val Phe Leu Phe Pro Pro Lys
            20

<210> SEQ ID NO 104
<211> LENGTH: 20
<212> TYPE: PRT
<213> ORGANISM: Homo sapiens

<400> SEQUENCE: 104

Gly Gln Pro Arg Glu Pro Gln Val Tyr Thr Leu Pro Pro Ser Arg Glu
1               5                   10                  15

Glu Met Thr Lys
            20

<210> SEQ ID NO 105
<211> LENGTH: 17
<212> TYPE: PRT
<213> ORGANISM: Homo sapiens

<400> SEQUENCE: 105

Thr Thr Pro Pro Met Leu Asp Ser Asp Gly Ser Phe Phe Leu Tyr Ser
1               5                   10                  15

Lys

<210> SEQ ID NO 106
<211> LENGTH: 10
<212> TYPE: PRT
<213> ORGANISM: Homo sapiens

<400> SEQUENCE: 106

Asn Gln Val Ser Leu Thr Cys Leu Val Lys
1               5                   10

<210> SEQ ID NO 107
<211> LENGTH: 8
<212> TYPE: PRT
<213> ORGANISM: Homo sapiens

<400> SEQUENCE: 107

Gly Leu Pro Ala Pro Ile Glu Lys
1               5

<210> SEQ ID NO 108
<211> LENGTH: 8
<212> TYPE: PRT
<213> ORGANISM: Homo sapiens

<400> SEQUENCE: 108

Ser Leu Ser Leu Ser Pro Gly Lys
1               5

<210> SEQ ID NO 109
<211> LENGTH: 16
<212> TYPE: PRT
<213> ORGANISM: Homo sapiens

<400> SEQUENCE: 109

Ala Ser Thr Lys Gly Pro Ser Val Phe Pro Leu Ala Pro Cys Ser Arg

<210> SEQ ID NO 110
<211> LENGTH: 11
<212> TYPE: PRT
<213> ORGANISM: Homo sapiens

<400> SEQUENCE: 110

Glu Pro Gln Val Tyr Thr Leu Pro Pro Ser Arg
1               5                   10

<210> SEQ ID NO 111
<211> LENGTH: 9
<212> TYPE: PRT
<213> ORGANISM: Homo sapiens

<400> SEQUENCE: 111

Glu Glu Gln Phe Asn Ser Thr Phe Arg
1               5

<210> SEQ ID NO 112
<211> LENGTH: 23
<212> TYPE: PRT
<213> ORGANISM: Homo sapiens

<400> SEQUENCE: 112

Ile Ser Arg Thr Pro Glu Val Thr Cys Val Val Val Asp Val Ser His
1               5                   10                  15

Glu Asp Pro Glu Val Gln Phe
            20

<210> SEQ ID NO 113
<211> LENGTH: 18
<212> TYPE: PRT
<213> ORGANISM: Homo sapiens

<400> SEQUENCE: 113

Val Asp Gly Val Glu Val His Asn Ala Lys Thr Lys Pro Arg Glu Glu
1               5                   10                  15

Gln Phe

<210> SEQ ID NO 114
<211> LENGTH: 14
<212> TYPE: PRT
<213> ORGANISM: Homo sapiens

<400> SEQUENCE: 114

Ala Pro Cys Ser Arg Ser Thr Ser Glu Ser Thr Ala Ala Leu
1               5                   10

<210> SEQ ID NO 115
<211> LENGTH: 10
<212> TYPE: PRT
<213> ORGANISM: Homo sapiens

<400> SEQUENCE: 115

Glu Ser Asn Gly Gln Pro Glu Asn Asn Tyr
1               5                   10

<210> SEQ ID NO 116
<211> LENGTH: 11
<212> TYPE: PRT
<213> ORGANISM: Homo sapiens

```
<400> SEQUENCE: 116

Thr Ser Gly Val His Thr Phe Pro Ala Val Leu
1               5                   10

<210> SEQ ID NO 117
<211> LENGTH: 11
<212> TYPE: PRT
<213> ORGANISM: Homo sapiens

<400> SEQUENCE: 117

Ser Ser Val Val Thr Val Pro Ser Ser Asn Phe
1               5                   10

<210> SEQ ID NO 118
<211> LENGTH: 11
<212> TYPE: PRT
<213> ORGANISM: Homo sapiens

<400> SEQUENCE: 118

Ala Ser Thr Lys Gly Pro Ser Val Phe Pro Leu
1               5                   10

<210> SEQ ID NO 119
<211> LENGTH: 9
<212> TYPE: PRT
<213> ORGANISM: Homo sapiens

<400> SEQUENCE: 119

Tyr Pro Ser Asp Ile Ser Val Glu Trp
1               5

<210> SEQ ID NO 120
<211> LENGTH: 9
<212> TYPE: PRT
<213> ORGANISM: Homo sapiens

<400> SEQUENCE: 120

Phe Pro Glu Pro Val Thr Val Ser Trp
1               5

<210> SEQ ID NO 121
<211> LENGTH: 9
<212> TYPE: PRT
<213> ORGANISM: Homo sapiens

<400> SEQUENCE: 121

Thr Leu Pro Pro Ser Arg Glu Glu Met
1               5

<210> SEQ ID NO 122
<211> LENGTH: 9
<212> TYPE: PRT
<213> ORGANISM: Homo sapiens

<400> SEQUENCE: 122

Phe Pro Pro Lys Pro Lys Asp Thr Leu
1               5

<210> SEQ ID NO 123
<211> LENGTH: 7
<212> TYPE: PRT
<213> ORGANISM: Homo sapiens

<400> SEQUENCE: 123
```

Thr Val Asp Lys Ser Arg Trp
1               5

<210> SEQ ID NO 124
<211> LENGTH: 7
<212> TYPE: PRT
<213> ORGANISM: Homo sapiens

<400> SEQUENCE: 124

Thr Val Val His Gln Asp Trp
1               5

<210> SEQ ID NO 125
<211> LENGTH: 7
<212> TYPE: PRT
<213> ORGANISM: Homo sapiens

<400> SEQUENCE: 125

Thr Lys Asn Gln Val Ser Leu
1               5

<210> SEQ ID NO 126
<211> LENGTH: 23
<212> TYPE: PRT
<213> ORGANISM: Homo sapiens

<400> SEQUENCE: 126

Cys Pro Pro Cys Pro Ala Pro Pro Val Ala Gly Pro Ser Val Phe Leu
1               5                   10                  15

Phe Pro Pro Lys Pro Lys Asp
            20

<210> SEQ ID NO 127
<211> LENGTH: 19
<212> TYPE: PRT
<213> ORGANISM: Homo sapiens

<400> SEQUENCE: 127

Met Thr Lys Asn Gln Val Ser Leu Thr Cys Leu Val Lys Gly Phe Tyr
1               5                   10                  15

Pro Ser Asp

<210> SEQ ID NO 128
<211> LENGTH: 18
<212> TYPE: PRT
<213> ORGANISM: Homo sapiens

<400> SEQUENCE: 128

Gln Phe Asn Ser Thr Phe Arg Val Val Ser Val Leu Thr Val Val His
1               5                   10                  15

Gln Asp

<210> SEQ ID NO 129
<211> LENGTH: 17
<212> TYPE: PRT
<213> ORGANISM: Homo sapiens

<400> SEQUENCE: 129

Lys Ser Arg Trp Gln Gln Gly Asn Val Phe Ser Cys Ser Val Met His
1               5                   10                  15

Glu

```
<210> SEQ ID NO 130
<211> LENGTH: 20
<212> TYPE: PRT
<213> ORGANISM: Homo sapiens

<400> SEQUENCE: 130

Ala Ser Thr Lys Gly Pro Ser Val Phe Pro Leu Ala Pro Cys Ser Arg
1               5                   10                  15

Ser Thr Ser Glu
            20

<210> SEQ ID NO 131
<211> LENGTH: 17
<212> TYPE: PRT
<213> ORGANISM: Homo sapiens

<400> SEQUENCE: 131

Ala Leu His Asn His Tyr Thr Gln Lys Ser Leu Ser Leu Ser Pro Gly
1               5                   10                  15

Lys

<210> SEQ ID NO 132
<211> LENGTH: 15
<212> TYPE: PRT
<213> ORGANISM: Homo sapiens

<400> SEQUENCE: 132

Tyr Lys Cys Lys Val Ser Asn Lys Gly Leu Pro Ala Pro Ile Glu
1               5                   10                  15

<210> SEQ ID NO 133
<211> LENGTH: 12
<212> TYPE: PRT
<213> ORGANISM: Homo sapiens

<400> SEQUENCE: 133

Gly Ser Phe Phe Leu Tyr Ser Lys Leu Thr Val Asp
1               5                   10

<210> SEQ ID NO 134
<211> LENGTH: 11
<212> TYPE: PRT
<213> ORGANISM: Homo sapiens

<400> SEQUENCE: 134

Val His Asn Ala Lys Thr Lys Pro Arg Glu Glu
1               5                   10

<210> SEQ ID NO 135
<211> LENGTH: 11
<212> TYPE: PRT
<213> ORGANISM: Homo sapiens

<400> SEQUENCE: 135

Asn Asn Tyr Lys Thr Thr Pro Pro Met Leu Asp
1               5                   10

<210> SEQ ID NO 136
<211> LENGTH: 11
<212> TYPE: PRT
<213> ORGANISM: Homo sapiens

<400> SEQUENCE: 136

Ser Thr Ala Ala Leu Gly Cys Leu Val Lys Asp
```

```
1               5                   10
```

<210> SEQ ID NO 137
<211> LENGTH: 8
<212> TYPE: PRT
<213> ORGANISM: Homo sapiens

<400> SEQUENCE: 137

Val Gln Phe Asn Trp Tyr Val Asp
1               5

<210> SEQ ID NO 138
<211> LENGTH: 9
<212> TYPE: PRT
<213> ORGANISM: Homo sapiens

<400> SEQUENCE: 138

Thr Leu Met Ile Ser Arg Thr Pro Glu
1               5

<210> SEQ ID NO 139
<211> LENGTH: 9
<212> TYPE: PRT
<213> ORGANISM: Homo sapiens

<400> SEQUENCE: 139

His Lys Pro Ser Asn Thr Lys Val Asp
1               5

<210> SEQ ID NO 140
<211> LENGTH: 6
<212> TYPE: PRT
<213> ORGANISM: Homo sapiens

<400> SEQUENCE: 140

Trp Leu Asn Gly Lys Glu
1               5

<210> SEQ ID NO 141
<211> LENGTH: 6
<212> TYPE: PRT
<213> ORGANISM: Homo sapiens

<400> SEQUENCE: 141

Arg Lys Cys Cys Val Glu
1               5

<210> SEQ ID NO 142
<211> LENGTH: 7
<212> TYPE: PRT
<213> ORGANISM: Homo sapiens

<400> SEQUENCE: 142

Val Thr Cys Val Val Val Asp
1               5

<210> SEQ ID NO 143
<211> LENGTH: 23
<212> TYPE: PRT
<213> ORGANISM: Homo sapiens

<400> SEQUENCE: 143

Met Thr Lys Asn Gln Val Ser Leu Thr Cys Leu Val Lys Gly Phe Tyr
1               5                   10                  15

```
Pro Ser Asp Ile Ser Val Glu
            20

<210> SEQ ID NO 144
<211> LENGTH: 20
<212> TYPE: PRT
<213> ORGANISM: Homo sapiens

<400> SEQUENCE: 144

Ala Ser Thr Lys Gly Pro Ser Val Phe Pro Leu Ala Pro Cys Ser Arg
1               5                   10                  15

Ser Thr Ser Glu
            20

<210> SEQ ID NO 145
<211> LENGTH: 17
<212> TYPE: PRT
<213> ORGANISM: Homo sapiens

<400> SEQUENCE: 145

Ala Leu His Asn His Tyr Thr Gln Lys Ser Leu Ser Leu Ser Pro Gly
1               5                   10                  15

Lys

<210> SEQ ID NO 146
<211> LENGTH: 15
<212> TYPE: PRT
<213> ORGANISM: Homo sapiens

<400> SEQUENCE: 146

Tyr Lys Cys Lys Val Ser Asn Lys Gly Leu Pro Ala Pro Ile Glu
1               5                   10                  15

<210> SEQ ID NO 147
<211> LENGTH: 11
<212> TYPE: PRT
<213> ORGANISM: Homo sapiens

<400> SEQUENCE: 147

Val Gln Phe Asn Trp Tyr Val Asp Gly Val Glu
1               5                   10

<210> SEQ ID NO 148
<211> LENGTH: 11
<212> TYPE: PRT
<213> ORGANISM: Homo sapiens

<400> SEQUENCE: 148

Val His Asn Ala Lys Thr Lys Pro Arg Glu Glu
1               5                   10

<210> SEQ ID NO 149
<211> LENGTH: 11
<212> TYPE: PRT
<213> ORGANISM: Homo sapiens

<400> SEQUENCE: 149

Val Thr Cys Val Val Val Asp Val Ser His Glu
1               5                   10

<210> SEQ ID NO 150
<211> LENGTH: 6
<212> TYPE: PRT
<213> ORGANISM: Homo sapiens
```

<400> SEQUENCE: 150

Arg Lys Cys Cys Val Glu
1               5

<210> SEQ ID NO 151
<211> LENGTH: 23
<212> TYPE: PRT
<213> ORGANISM: Homo sapiens

<400> SEQUENCE: 151

Asp Ile Ser Val Glu Trp Glu Ser Asn Gly Gln Pro Glu Asn Asn Tyr
1               5                   10                  15

Lys Thr Thr Pro Pro Met Leu
            20

<210> SEQ ID NO 152
<211> LENGTH: 16
<212> TYPE: PRT
<213> ORGANISM: Homo sapiens

<400> SEQUENCE: 152

Asp Thr Leu Met Ile Ser Arg Thr Pro Glu Val Thr Cys Val Val Val
1               5                   10                  15

<210> SEQ ID NO 153
<211> LENGTH: 12
<212> TYPE: PRT
<213> ORGANISM: Homo sapiens

<400> SEQUENCE: 153

Asp Gly Ser Phe Phe Leu Tyr Ser Lys Leu Thr Val
1               5                   10

<210> SEQ ID NO 154
<211> LENGTH: 10
<212> TYPE: PRT
<213> ORGANISM: Homo sapiens

<400> SEQUENCE: 154

Asp Pro Glu Val Gln Phe Asn Trp Tyr Val
1               5                   10

<210> SEQ ID NO 155
<211> LENGTH: 9
<212> TYPE: PRT
<213> ORGANISM: Homo sapiens

<400> SEQUENCE: 155

Asp His Lys Pro Ser Asn Thr Lys Val
1               5

<210> SEQ ID NO 156
<211> LENGTH: 21
<212> TYPE: PRT
<213> ORGANISM: Homo sapiens

<400> SEQUENCE: 156

Thr Pro Glu Val Thr Cys Val Val Val Asp Val Ser His Glu Asp Pro
1               5                   10                  15

Glu Val Gln Phe Lys
            20

```
<210> SEQ ID NO 157
<211> LENGTH: 19
<212> TYPE: PRT
<213> ORGANISM: Homo sapiens

<400> SEQUENCE: 157

Trp Gln Gln Gly Asn Ile Phe Ser Cys Ser Val Met His Glu Ala Leu
1               5                   10                  15

His Asn Arg

<210> SEQ ID NO 158
<211> LENGTH: 20
<212> TYPE: PRT
<213> ORGANISM: Homo sapiens

<400> SEQUENCE: 158

Cys Pro Ala Pro Glu Leu Leu Gly Gly Pro Ser Val Phe Leu Phe Pro
1               5                   10                  15

Pro Lys Pro Lys
            20

<210> SEQ ID NO 159
<211> LENGTH: 16
<212> TYPE: PRT
<213> ORGANISM: Homo sapiens

<400> SEQUENCE: 159

Val Val Ser Val Leu Thr Val Leu His Gln Asp Trp Leu Asn Gly Lys
1               5                   10                  15

<210> SEQ ID NO 160
<211> LENGTH: 12
<212> TYPE: PRT
<213> ORGANISM: Homo sapiens

<400> SEQUENCE: 160

Thr Pro Leu Gly Asp Thr Thr His Thr Cys Pro Arg
1               5                   10

<210> SEQ ID NO 161
<211> LENGTH: 11
<212> TYPE: PRT
<213> ORGANISM: Homo sapiens

<400> SEQUENCE: 161

Glu Pro Gln Val Tyr Thr Leu Pro Pro Ser Arg
1               5                   10

<210> SEQ ID NO 162
<211> LENGTH: 14
<212> TYPE: PRT
<213> ORGANISM: Homo sapiens

<400> SEQUENCE: 162

Ser Thr Ser Gly Gly Thr Ala Ala Leu Gly Cys Leu Val Lys
1               5                   10

<210> SEQ ID NO 163
<211> LENGTH: 12
<212> TYPE: PRT
<213> ORGANISM: Homo sapiens

<400> SEQUENCE: 163

Gly Pro Ser Val Phe Pro Leu Ala Pro Cys Ser Arg
```

```
                      1               5                    10
```

<210> SEQ ID NO 164
<211> LENGTH: 9
<212> TYPE: PRT
<213> ORGANISM: Homo sapiens

<400> SEQUENCE: 164

```
Glu Glu Gln Tyr Asn Ser Thr Phe Arg
1               5
```

<210> SEQ ID NO 165
<211> LENGTH: 10
<212> TYPE: PRT
<213> ORGANISM: Homo sapiens

<400> SEQUENCE: 165

```
Asn Gln Val Ser Leu Thr Cys Leu Val Lys
1               5                   10
```

<210> SEQ ID NO 166
<211> LENGTH: 10
<212> TYPE: PRT
<213> ORGANISM: Homo sapiens

<400> SEQUENCE: 166

```
Ser Cys Asp Thr Pro Pro Cys Pro Arg
1               5                   10
```

<210> SEQ ID NO 167
<211> LENGTH: 8
<212> TYPE: PRT
<213> ORGANISM: Homo sapiens

<400> SEQUENCE: 167

```
Ala Leu Pro Ala Pro Ile Glu Lys
1               5
```

<210> SEQ ID NO 168
<211> LENGTH: 7
<212> TYPE: PRT
<213> ORGANISM: Homo sapiens

<400> SEQUENCE: 168

```
Asp Thr Leu Met Ile Ser Arg
1               5
```

<210> SEQ ID NO 169
<211> LENGTH: 8
<212> TYPE: PRT
<213> ORGANISM: Homo sapiens

<400> SEQUENCE: 169

```
Ser Leu Ser Leu Ser Pro Gly Lys
1               5
```

<210> SEQ ID NO 170
<211> LENGTH: 26
<212> TYPE: PRT
<213> ORGANISM: Homo sapiens

<400> SEQUENCE: 170

```
Gly Pro Ser Val Phe Pro Leu Ala Pro Cys Ser Arg Ser Thr Ser Gly
1               5                   10                  15
```

```
Gly Thr Ala Ala Leu Gly Cys Leu Val Lys
            20                  25

<210> SEQ ID NO 171
<211> LENGTH: 20
<212> TYPE: PRT
<213> ORGANISM: Homo sapiens

<400> SEQUENCE: 171

Gly Gln Pro Arg Glu Pro Gln Val Tyr Thr Leu Pro Pro Ser Arg Glu
1               5                   10                  15

Glu Met Thr Lys
            20

<210> SEQ ID NO 172
<211> LENGTH: 17
<212> TYPE: PRT
<213> ORGANISM: Homo sapiens

<400> SEQUENCE: 172

Thr Pro Leu Gly Asp Thr Thr His Thr Cys Pro Arg Cys Pro Glu Pro
1               5                   10                  15

Lys

<210> SEQ ID NO 173
<211> LENGTH: 15
<212> TYPE: PRT
<213> ORGANISM: Homo sapiens

<400> SEQUENCE: 173

Ser Cys Asp Thr Pro Pro Pro Cys Pro Arg Cys Pro Glu Pro Lys
1               5                   10                  15

<210> SEQ ID NO 174
<211> LENGTH: 12
<212> TYPE: PRT
<213> ORGANISM: Homo sapiens

<400> SEQUENCE: 174

Trp Tyr Val Asp Gly Val Glu Val His Asn Ala Lys
1               5                   10

<210> SEQ ID NO 175
<211> LENGTH: 10
<212> TYPE: PRT
<213> ORGANISM: Homo sapiens

<400> SEQUENCE: 175

Asn Gln Val Ser Leu Thr Cys Leu Val Lys
1               5                   10

<210> SEQ ID NO 176
<211> LENGTH: 8
<212> TYPE: PRT
<213> ORGANISM: Homo sapiens

<400> SEQUENCE: 176

Ala Leu Pro Ala Pro Ile Glu Lys
1               5

<210> SEQ ID NO 177
<211> LENGTH: 8
<212> TYPE: PRT
```

```
<400> SEQUENCE: 177

Ser Leu Ser Leu Ser Pro Gly Lys
1               5

<210> SEQ ID NO 178
<211> LENGTH: 19
<212> TYPE: PRT
<213> ORGANISM: Homo sapiens

<400> SEQUENCE: 178

Trp Gln Gln Gly Asn Ile Phe Ser Cys Ser Val Met His Glu Ala Leu
1               5                   10                  15

His Asn Arg

<210> SEQ ID NO 179
<211> LENGTH: 16
<212> TYPE: PRT
<213> ORGANISM: Homo sapiens

<400> SEQUENCE: 179

Val Glu Leu Lys Thr Pro Leu Gly Asp Thr Thr His Thr Cys Pro Arg
1               5                   10                  15

<210> SEQ ID NO 180
<211> LENGTH: 15
<212> TYPE: PRT
<213> ORGANISM: Homo sapiens

<400> SEQUENCE: 180

Cys Pro Glu Pro Lys Ser Cys Asp Thr Pro Pro Pro Cys Pro Arg
1               5                   10                  15

<210> SEQ ID NO 181
<211> LENGTH: 16
<212> TYPE: PRT
<213> ORGANISM: Homo sapiens

<400> SEQUENCE: 181

Ala Ser Thr Lys Gly Pro Ser Val Phe Pro Leu Ala Pro Cys Ser Arg
1               5                   10                  15

<210> SEQ ID NO 182
<211> LENGTH: 12
<212> TYPE: PRT
<213> ORGANISM: Homo sapiens

<400> SEQUENCE: 182

Phe Thr Gln Lys Ser Leu Ser Leu Ser Pro Gly Lys
1               5                   10

<210> SEQ ID NO 183
<211> LENGTH: 11
<212> TYPE: PRT
<213> ORGANISM: Homo sapiens

<400> SEQUENCE: 183

Glu Pro Gln Val Tyr Thr Leu Pro Pro Ser Arg
1               5                   10

<210> SEQ ID NO 184
<211> LENGTH: 9
<212> TYPE: PRT
<213> ORGANISM: Homo sapiens
```

<400> SEQUENCE: 184

Glu Glu Gln Tyr Asn Ser Thr Phe Arg
1               5

<210> SEQ ID NO 185
<211> LENGTH: 23
<212> TYPE: PRT
<213> ORGANISM: Homo sapiens

<400> SEQUENCE: 185

Ile Ser Arg Thr Pro Glu Val Thr Cys Val Val Val Asp Val Ser His
1               5                   10                  15

Glu Asp Pro Glu Val Gln Phe
            20

<210> SEQ ID NO 186
<211> LENGTH: 19
<212> TYPE: PRT
<213> ORGANISM: Homo sapiens

<400> SEQUENCE: 186

Thr Cys Asn Val Asn His Lys Pro Ser Asn Thr Lys Val Asp Lys Arg
1               5                   10                  15

Val Glu Leu

<210> SEQ ID NO 187
<211> LENGTH: 18
<212> TYPE: PRT
<213> ORGANISM: Homo sapiens

<400> SEQUENCE: 187

Val Asp Gly Val Glu Val His Asn Ala Lys Thr Lys Pro Arg Glu Glu
1               5                   10                  15

Gln Tyr

<210> SEQ ID NO 188
<211> LENGTH: 14
<212> TYPE: PRT
<213> ORGANISM: Homo sapiens

<400> SEQUENCE: 188

Ala Pro Cys Ser Arg Ser Thr Ser Gly Gly Thr Ala Ala Leu
1               5                   10

<210> SEQ ID NO 189
<211> LENGTH: 11
<212> TYPE: PRT
<213> ORGANISM: Homo sapiens

<400> SEQUENCE: 189

Thr Ser Gly Val His Thr Phe Pro Ala Val Leu
1               5                   10

<210> SEQ ID NO 190
<211> LENGTH: 10
<212> TYPE: PRT
<213> ORGANISM: Homo sapiens

<400> SEQUENCE: 190

Glu Ser Ser Gly Gln Pro Glu Asn Asn Tyr
1               5                   10

<210> SEQ ID NO 191
<211> LENGTH: 11
<212> TYPE: PRT
<213> ORGANISM: Homo sapiens

<400> SEQUENCE: 191

Ala Ser Thr Lys Gly Pro Ser Val Phe Pro Leu
1               5                   10

<210> SEQ ID NO 192
<211> LENGTH: 9
<212> TYPE: PRT
<213> ORGANISM: Homo sapiens

<400> SEQUENCE: 192

Tyr Pro Ser Asp Ile Ala Val Glu Trp
1               5

<210> SEQ ID NO 193
<211> LENGTH: 11
<212> TYPE: PRT
<213> ORGANISM: Homo sapiens

<400> SEQUENCE: 193

Ser Ser Val Val Thr Val Pro Ser Ser Ser Leu
1               5                   10

<210> SEQ ID NO 194
<211> LENGTH: 9
<212> TYPE: PRT
<213> ORGANISM: Homo sapiens

<400> SEQUENCE: 194

Phe Pro Glu Pro Val Thr Val Ser Trp
1               5

<210> SEQ ID NO 195
<211> LENGTH: 9
<212> TYPE: PRT
<213> ORGANISM: Homo sapiens

<400> SEQUENCE: 195

Thr Leu Pro Pro Ser Arg Glu Glu Met
1               5

<210> SEQ ID NO 196
<211> LENGTH: 9
<212> TYPE: PRT
<213> ORGANISM: Homo sapiens

<400> SEQUENCE: 196

Phe Pro Pro Lys Pro Lys Asp Thr Leu
1               5

<210> SEQ ID NO 197
<211> LENGTH: 7
<212> TYPE: PRT
<213> ORGANISM: Homo sapiens

<400> SEQUENCE: 197

Thr Val Asp Lys Ser Arg Trp
1               5

<210> SEQ ID NO 198

```
<211> LENGTH: 7
<212> TYPE: PRT
<213> ORGANISM: Homo sapiens

<400> SEQUENCE: 198

Thr Lys Asn Gln Val Ser Leu
1               5

<210> SEQ ID NO 199
<211> LENGTH: 19
<212> TYPE: PRT
<213> ORGANISM: Homo sapiens

<400> SEQUENCE: 199

Met Thr Lys Asn Gln Val Ser Leu Thr Cys Leu Val Lys Gly Phe Tyr
1               5                   10                  15

Pro Ser Asp

<210> SEQ ID NO 200
<211> LENGTH: 18
<212> TYPE: PRT
<213> ORGANISM: Homo sapiens

<400> SEQUENCE: 200

Gln Tyr Asn Ser Thr Phe Arg Val Val Ser Val Leu Thr Val Leu His
1               5                   10                  15

Gln Asp

<210> SEQ ID NO 201
<211> LENGTH: 17
<212> TYPE: PRT
<213> ORGANISM: Homo sapiens

<400> SEQUENCE: 201

Lys Ser Arg Trp Gln Gln Gly Asn Ile Phe Ser Cys Ser Val Met His
1               5                   10                  15

Glu

<210> SEQ ID NO 202
<211> LENGTH: 17
<212> TYPE: PRT
<213> ORGANISM: Homo sapiens

<400> SEQUENCE: 202

Ala Leu His Asn Arg Phe Thr Gln Lys Ser Leu Ser Leu Ser Pro Gly
1               5                   10                  15

Lys

<210> SEQ ID NO 203
<211> LENGTH: 16
<212> TYPE: PRT
<213> ORGANISM: Homo sapiens

<400> SEQUENCE: 203

Leu Leu Gly Gly Pro Ser Val Phe Leu Phe Pro Pro Lys Pro Lys Asp
1               5                   10                  15

<210> SEQ ID NO 204
<211> LENGTH: 15
<212> TYPE: PRT
<213> ORGANISM: Homo sapiens

<400> SEQUENCE: 204
```

Thr Thr His Thr Cys Pro Arg Cys Pro Glu Pro Lys Ser Cys Asp
1               5                   10                  15

<210> SEQ ID NO 205
<211> LENGTH: 15
<212> TYPE: PRT
<213> ORGANISM: Homo sapiens

<400> SEQUENCE: 205

Tyr Lys Cys Lys Val Ser Asn Lys Ala Leu Pro Ala Pro Ile Glu
1               5                   10                  15

<210> SEQ ID NO 206
<211> LENGTH: 15
<212> TYPE: PRT
<213> ORGANISM: Homo sapiens

<400> SEQUENCE: 206

Thr Pro Pro Pro Cys Pro Arg Cys Pro Glu Pro Lys Ser Cys Asp
1               5                   10                  15

<210> SEQ ID NO 207
<211> LENGTH: 12
<212> TYPE: PRT
<213> ORGANISM: Homo sapiens

<400> SEQUENCE: 207

Gly Ser Phe Phe Leu Tyr Ser Lys Leu Thr Val Asp
1               5                   10

<210> SEQ ID NO 208
<211> LENGTH: 11
<212> TYPE: PRT
<213> ORGANISM: Homo sapiens

<400> SEQUENCE: 208

Val His Asn Ala Lys Thr Lys Pro Arg Glu Glu
1               5                   10

<210> SEQ ID NO 209
<211> LENGTH: 11
<212> TYPE: PRT
<213> ORGANISM: Homo sapiens

<400> SEQUENCE: 209

Asn Asn Tyr Asn Thr Thr Pro Pro Met Leu Asp
1               5                   10

<210> SEQ ID NO 210
<211> LENGTH: 12
<212> TYPE: PRT
<213> ORGANISM: Homo sapiens

<400> SEQUENCE: 210

Thr Pro Pro Pro Cys Pro Arg Cys Pro Ala Pro Glu
1               5                   10

<210> SEQ ID NO 211
<211> LENGTH: 8
<212> TYPE: PRT
<213> ORGANISM: Homo sapiens

<400> SEQUENCE: 211

Val Gln Phe Lys Trp Tyr Val Asp

```
<210> SEQ ID NO 212
<211> LENGTH: 9
<212> TYPE: PRT
<213> ORGANISM: Homo sapiens

<400> SEQUENCE: 212

Thr Leu Met Ile Ser Arg Thr Pro Glu
1               5

<210> SEQ ID NO 213
<211> LENGTH: 6
<212> TYPE: PRT
<213> ORGANISM: Homo sapiens

<400> SEQUENCE: 213

Trp Leu Asn Gly Lys Glu
1               5

<210> SEQ ID NO 214
<211> LENGTH: 7
<212> TYPE: PRT
<213> ORGANISM: Homo sapiens

<400> SEQUENCE: 214

Leu Lys Thr Pro Leu Gly Asp
1               5

<210> SEQ ID NO 215
<211> LENGTH: 7
<212> TYPE: PRT
<213> ORGANISM: Homo sapiens

<400> SEQUENCE: 215

Val Thr Cys Val Val Val Asp
1               5

<210> SEQ ID NO 216
<211> LENGTH: 23
<212> TYPE: PRT
<213> ORGANISM: Homo sapiens

<400> SEQUENCE: 216

Met Thr Lys Asn Gln Val Ser Leu Thr Cys Leu Val Lys Gly Phe Tyr
1               5                   10                  15

Pro Ser Asp Ile Ala Val Glu
            20

<210> SEQ ID NO 217
<211> LENGTH: 17
<212> TYPE: PRT
<213> ORGANISM: Homo sapiens

<400> SEQUENCE: 217

Ala Leu His Asn Arg Phe Thr Gln Lys Ser Leu Ser Leu Ser Pro Gly
1               5                   10                  15

Lys

<210> SEQ ID NO 218
<211> LENGTH: 15
<212> TYPE: PRT
<213> ORGANISM: Homo sapiens
```

<400> SEQUENCE: 218

Tyr Lys Cys Lys Val Ser Asn Lys Ala Leu Pro Ala Pro Ile Glu
1               5                   10                  15

<210> SEQ ID NO 219
<211> LENGTH: 11
<212> TYPE: PRT
<213> ORGANISM: Homo sapiens

<400> SEQUENCE: 219

Val Gln Phe Lys Trp Tyr Val Asp Gly Val Glu
1               5                   10

<210> SEQ ID NO 220
<211> LENGTH: 11
<212> TYPE: PRT
<213> ORGANISM: Homo sapiens

<400> SEQUENCE: 220

Val His Asn Ala Lys Thr Lys Pro Arg Glu Glu
1               5                   10

<210> SEQ ID NO 221
<211> LENGTH: 11
<212> TYPE: PRT
<213> ORGANISM: Homo sapiens

<400> SEQUENCE: 221

Val Thr Cys Val Val Val Asp Val Ser His Glu
1               5                   10

<210> SEQ ID NO 222
<211> LENGTH: 23
<212> TYPE: PRT
<213> ORGANISM: Homo sapiens

<400> SEQUENCE: 222

Asp Ile Ala Val Glu Trp Glu Ser Ser Gly Gln Pro Glu Asn Asn Tyr
1               5                   10                  15

Asn Thr Thr Pro Pro Met Leu
            20

<210> SEQ ID NO 223
<211> LENGTH: 16
<212> TYPE: PRT
<213> ORGANISM: Homo sapiens

<400> SEQUENCE: 223

Asp Thr Leu Met Ile Ser Arg Thr Pro Glu Val Thr Cys Val Val Val
1               5                   10                  15

<210> SEQ ID NO 224
<211> LENGTH: 15
<212> TYPE: PRT
<213> ORGANISM: Homo sapiens

<400> SEQUENCE: 224

Asp Thr Thr His Thr Cys Pro Arg Cys Pro Glu Pro Lys Ser Cys
1               5                   10                  15

<210> SEQ ID NO 225
<211> LENGTH: 15
<212> TYPE: PRT
<213> ORGANISM: Homo sapiens

<400> SEQUENCE: 225

Asp Thr Pro Pro Pro Cys Pro Arg Cys Pro Glu Pro Lys Ser Cys
1               5                   10                  15

<210> SEQ ID NO 226
<211> LENGTH: 12
<212> TYPE: PRT
<213> ORGANISM: Homo sapiens

<400> SEQUENCE: 226

Asp Gly Ser Phe Phe Leu Tyr Ser Lys Leu Thr Val
1               5                   10

<210> SEQ ID NO 227
<211> LENGTH: 10
<212> TYPE: PRT
<213> ORGANISM: Homo sapiens

<400> SEQUENCE: 227

Asp Pro Glu Val Gln Phe Lys Trp Tyr Val
1               5                   10

<210> SEQ ID NO 228
<211> LENGTH: 11
<212> TYPE: PRT
<213> ORGANISM: Homo sapiens

<400> SEQUENCE: 228

Asp Lys Arg Val Glu Leu Lys Thr Pro Leu Gly
1               5                   10

<210> SEQ ID NO 229
<211> LENGTH: 22
<212> TYPE: PRT
<213> ORGANISM: Homo sapiens

<400> SEQUENCE: 229

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 230
<211> LENGTH: 16
<212> TYPE: PRT
<213> ORGANISM: Homo sapiens

<400> SEQUENCE: 230

Glu Pro Gln Val Tyr Thr Leu Pro Pro Ser Gln Glu Glu Met Thr Lys
1               5                   10                  15

<210> SEQ ID NO 231
<211> LENGTH: 16
<212> TYPE: PRT
<213> ORGANISM: Homo sapiens

<400> SEQUENCE: 231

Val Val Ser Val Leu Thr Val Leu His Gln Asp Trp Leu Asn Gly Lys
1               5                   10                  15

<210> SEQ ID NO 232
<211> LENGTH: 14
<212> TYPE: PRT

<213> ORGANISM: Homo sapiens

<400> SEQUENCE: 232

Thr Tyr Thr Cys Asn Val Asp His Lys Pro Ser Asn Thr Lys
1               5                   10

<210> SEQ ID NO 233
<211> LENGTH: 14
<212> TYPE: PRT
<213> ORGANISM: Homo sapiens

<400> SEQUENCE: 233

Ser Thr Ser Glu Ser Thr Ala Ala Leu Gly Cys Leu Val Lys
1               5                   10

<210> SEQ ID NO 234
<211> LENGTH: 12
<212> TYPE: PRT
<213> ORGANISM: Homo sapiens

<400> SEQUENCE: 234

Gly Pro Ser Val Phe Pro Leu Ala Pro Cys Ser Arg
1               5                   10

<210> SEQ ID NO 235
<211> LENGTH: 9
<212> TYPE: PRT
<213> ORGANISM: Homo sapiens

<400> SEQUENCE: 235

Glu Glu Gln Phe Asn Ser Thr Tyr Arg
1               5

<210> SEQ ID NO 236
<211> LENGTH: 10
<212> TYPE: PRT
<213> ORGANISM: Homo sapiens

<400> SEQUENCE: 236

Asn Gln Val Ser Leu Thr Cys Leu Val Lys
1               5                   10

<210> SEQ ID NO 237
<211> LENGTH: 7
<212> TYPE: PRT
<213> ORGANISM: Homo sapiens

<400> SEQUENCE: 237

Asp Thr Leu Met Ile Ser Arg
1               5

<210> SEQ ID NO 238
<211> LENGTH: 8
<212> TYPE: PRT
<213> ORGANISM: Homo sapiens

<400> SEQUENCE: 238

Gly Leu Pro Ser Ser Ile Glu Lys
1               5

<210> SEQ ID NO 239
<211> LENGTH: 8
<212> TYPE: PRT
<213> ORGANISM: Homo sapiens

<400> SEQUENCE: 239

Ser Leu Ser Leu Ser Leu Gly Lys
1               5

<210> SEQ ID NO 240
<211> LENGTH: 26
<212> TYPE: PRT
<213> ORGANISM: Homo sapiens

<400> SEQUENCE: 240

Gly Pro Ser Val Phe Pro Leu Ala Pro Cys Ser Arg Ser Thr Ser Glu
1               5                   10                  15

Ser Thr Ala Ala Leu Gly Cys Leu Val Lys
            20                  25

<210> SEQ ID NO 241
<211> LENGTH: 22
<212> TYPE: PRT
<213> ORGANISM: Homo sapiens

<400> SEQUENCE: 241

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 242
<211> LENGTH: 22
<212> TYPE: PRT
<213> ORGANISM: Homo sapiens

<400> SEQUENCE: 242

Thr Thr Pro Pro Val Leu Asp Ser Asp Gly Ser Phe Phe Leu Tyr Ser
1               5                   10                  15

Arg Leu Thr Val Asp Lys
            20

<210> SEQ ID NO 243
<211> LENGTH: 20
<212> TYPE: PRT
<213> ORGANISM: Homo sapiens

<400> SEQUENCE: 243

Gly Gln Pro Arg Glu Pro Gln Val Tyr Thr Leu Pro Pro Ser Gln Glu
1               5                   10                  15

Glu Met Thr Lys
            20

<210> SEQ ID NO 244
<211> LENGTH: 10
<212> TYPE: PRT
<213> ORGANISM: Homo sapiens

<400> SEQUENCE: 244

Asn Gln Val Ser Leu Thr Cys Leu Val Lys
1               5                   10

<210> SEQ ID NO 245
<211> LENGTH: 9
<212> TYPE: PRT
<213> ORGANISM: Homo sapiens

<400> SEQUENCE: 245

Thr Tyr Thr Cys Asn Val Asp His Lys
1               5

<210> SEQ ID NO 246
<211> LENGTH: 8
<212> TYPE: PRT
<213> ORGANISM: Homo sapiens

<400> SEQUENCE: 246

Gly Leu Pro Ser Ser Ile Glu Lys
1               5

<210> SEQ ID NO 247
<211> LENGTH: 8
<212> TYPE: PRT
<213> ORGANISM: Homo sapiens

<400> SEQUENCE: 247

Ser Leu Ser Leu Ser Leu Gly Lys
1               5

<210> SEQ ID NO 248
<211> LENGTH: 16
<212> TYPE: PRT
<213> ORGANISM: Homo sapiens

<400> SEQUENCE: 248

Ala Ser Thr Lys Gly Pro Ser Val Phe Pro Leu Ala Pro Cys Ser Arg
1               5                   10                  15

<210> SEQ ID NO 249
<211> LENGTH: 9
<212> TYPE: PRT
<213> ORGANISM: Homo sapiens

<400> SEQUENCE: 249

Glu Glu Gln Phe Asn Ser Thr Tyr Arg
1               5

<210> SEQ ID NO 250
<211> LENGTH: 7
<212> TYPE: PRT
<213> ORGANISM: Homo sapiens

<400> SEQUENCE: 250

Leu Thr Val Asp Lys Ser Arg
1               5

<210> SEQ ID NO 251
<211> LENGTH: 23
<212> TYPE: PRT
<213> ORGANISM: Homo sapiens

<400> SEQUENCE: 251

Ile Ser Arg Thr Pro Glu Val Thr Cys Val Val Val Asp Val Ser Gln
1               5                   10                  15

Glu Asp Pro Glu Val Gln Phe
            20

<210> SEQ ID NO 252
<211> LENGTH: 21
<212> TYPE: PRT
<213> ORGANISM: Homo sapiens

```
<400> SEQUENCE: 252

Thr Cys Asn Val Asp His Lys Pro Ser Asn Thr Lys Val Asp Lys Arg
1               5                   10                  15

Val Glu Ser Lys Tyr
            20

<210> SEQ ID NO 253
<211> LENGTH: 18
<212> TYPE: PRT
<213> ORGANISM: Homo sapiens

<400> SEQUENCE: 253

Val Asp Gly Val Glu Val His Asn Ala Lys Thr Lys Pro Arg Glu Glu
1               5                   10                  15

Gln Phe

<210> SEQ ID NO 254
<211> LENGTH: 14
<212> TYPE: PRT
<213> ORGANISM: Homo sapiens

<400> SEQUENCE: 254

Ala Pro Cys Ser Arg Ser Thr Ser Glu Ser Thr Ala Ala Leu
1               5                   10

<210> SEQ ID NO 255
<211> LENGTH: 12
<212> TYPE: PRT
<213> ORGANISM: Homo sapiens

<400> SEQUENCE: 255

Gly Pro Pro Cys Pro Ser Cys Pro Ala Pro Glu Phe
1               5                   10

<210> SEQ ID NO 256
<211> LENGTH: 10
<212> TYPE: PRT
<213> ORGANISM: Homo sapiens

<400> SEQUENCE: 256

Glu Ser Asn Gly Gln Pro Glu Asn Asn Tyr
1               5                   10

<210> SEQ ID NO 257
<211> LENGTH: 11
<212> TYPE: PRT
<213> ORGANISM: Homo sapiens

<400> SEQUENCE: 257

Thr Ser Gly Val His Thr Phe Pro Ala Val Leu
1               5                   10

<210> SEQ ID NO 258
<211> LENGTH: 11
<212> TYPE: PRT
<213> ORGANISM: Homo sapiens

<400> SEQUENCE: 258

Ala Ser Thr Lys Gly Pro Ser Val Phe Pro Leu
1               5                   10

<210> SEQ ID NO 259
<211> LENGTH: 9
```

```
<212> TYPE: PRT
<213> ORGANISM: Homo sapiens

<400> SEQUENCE: 259

Tyr Pro Ser Asp Ile Ala Val Glu Trp
1               5

<210> SEQ ID NO 260
<211> LENGTH: 11
<212> TYPE: PRT
<213> ORGANISM: Homo sapiens

<400> SEQUENCE: 260

Ser Ser Val Val Thr Val Pro Ser Ser Ser Leu
1               5                   10

<210> SEQ ID NO 261
<211> LENGTH: 9
<212> TYPE: PRT
<213> ORGANISM: Homo sapiens

<400> SEQUENCE: 261

Phe Pro Glu Pro Val Thr Val Ser Trp
1               5

<210> SEQ ID NO 262
<211> LENGTH: 9
<212> TYPE: PRT
<213> ORGANISM: Homo sapiens

<400> SEQUENCE: 262

Phe Pro Pro Lys Pro Lys Asp Thr Leu
1               5

<210> SEQ ID NO 263
<211> LENGTH: 9
<212> TYPE: PRT
<213> ORGANISM: Homo sapiens

<400> SEQUENCE: 263

Thr Leu Pro Pro Ser Gln Glu Glu Met
1               5

<210> SEQ ID NO 264
<211> LENGTH: 7
<212> TYPE: PRT
<213> ORGANISM: Homo sapiens

<400> SEQUENCE: 264

Thr Val Asp Lys Ser Arg Trp
1               5

<210> SEQ ID NO 265
<211> LENGTH: 7
<212> TYPE: PRT
<213> ORGANISM: Homo sapiens

<400> SEQUENCE: 265

Thr Lys Asn Gln Val Ser Leu
1               5

<210> SEQ ID NO 266
<211> LENGTH: 7
<212> TYPE: PRT
<213> ORGANISM: Homo sapiens
```

<400> SEQUENCE: 266

Lys Thr Thr Pro Pro Val Leu
1               5

<210> SEQ ID NO 267
<211> LENGTH: 19
<212> TYPE: PRT
<213> ORGANISM: Homo sapiens

<400> SEQUENCE: 267

Met Thr Lys Asn Gln Val Ser Leu Thr Cys Leu Val Lys Gly Phe Tyr
1               5                   10                  15

Pro Ser Asp

<210> SEQ ID NO 268
<211> LENGTH: 18
<212> TYPE: PRT
<213> ORGANISM: Homo sapiens

<400> SEQUENCE: 268

Gln Phe Asn Ser Thr Tyr Arg Val Val Ser Val Leu Thr Val Leu His
1               5                   10                  15

Gln Asp

<210> SEQ ID NO 269
<211> LENGTH: 20
<212> TYPE: PRT
<213> ORGANISM: Homo sapiens

<400> SEQUENCE: 269

Ala Ser Thr Lys Gly Pro Ser Val Phe Pro Leu Ala Pro Cys Ser Arg
1               5                   10                  15

Ser Thr Ser Glu
            20

<210> SEQ ID NO 270
<211> LENGTH: 17
<212> TYPE: PRT
<213> ORGANISM: Homo sapiens

<400> SEQUENCE: 270

Ala Leu His Asn His Tyr Thr Gln Lys Ser Leu Ser Leu Ser Leu Gly
1               5                   10                  15

Lys

<210> SEQ ID NO 271
<211> LENGTH: 16
<212> TYPE: PRT
<213> ORGANISM: Homo sapiens

<400> SEQUENCE: 271

Phe Leu Gly Gly Pro Ser Val Phe Leu Phe Pro Pro Lys Pro Lys Asp
1               5                   10                  15

<210> SEQ ID NO 272
<211> LENGTH: 15
<212> TYPE: PRT
<213> ORGANISM: Homo sapiens

<400> SEQUENCE: 272

Tyr Lys Cys Lys Val Ser Asn Lys Gly Leu Pro Ser Ser Ile Glu

```
                1               5                  10                  15

<210> SEQ ID NO 273
<211> LENGTH: 14
<212> TYPE: PRT
<213> ORGANISM: Homo sapiens

<400> SEQUENCE: 273

Ser Lys Tyr Gly Pro Pro Cys Pro Ser Cys Pro Ala Pro Glu
1               5                  10

<210> SEQ ID NO 274
<211> LENGTH: 12
<212> TYPE: PRT
<213> ORGANISM: Homo sapiens

<400> SEQUENCE: 274

Gly Ser Phe Phe Leu Tyr Ser Arg Leu Thr Val Asp
1               5                  10

<210> SEQ ID NO 275
<211> LENGTH: 11
<212> TYPE: PRT
<213> ORGANISM: Homo sapiens

<400> SEQUENCE: 275

Val His Asn Ala Lys Thr Lys Pro Arg Glu Glu
1               5                  10

<210> SEQ ID NO 276
<211> LENGTH: 11
<212> TYPE: PRT
<213> ORGANISM: Homo sapiens

<400> SEQUENCE: 276

Asn Asn Tyr Lys Thr Thr Pro Pro Val Leu Asp
1               5                  10

<210> SEQ ID NO 277
<211> LENGTH: 11
<212> TYPE: PRT
<213> ORGANISM: Homo sapiens

<400> SEQUENCE: 277

Gly Asn Val Phe Ser Cys Ser Val Met His Glu
1               5                  10

<210> SEQ ID NO 278
<211> LENGTH: 11
<212> TYPE: PRT
<213> ORGANISM: Homo sapiens

<400> SEQUENCE: 278

Ser Thr Ala Ala Leu Gly Cys Leu Val Lys Asp
1               5                  10

<210> SEQ ID NO 279
<211> LENGTH: 8
<212> TYPE: PRT
<213> ORGANISM: Homo sapiens

<400> SEQUENCE: 279

Val Gln Phe Asn Trp Tyr Val Asp
1               5
```

```
<210> SEQ ID NO 280
<211> LENGTH: 9
<212> TYPE: PRT
<213> ORGANISM: Homo sapiens

<400> SEQUENCE: 280

Thr Leu Met Ile Ser Arg Thr Pro Glu
1               5

<210> SEQ ID NO 281
<211> LENGTH: 9
<212> TYPE: PRT
<213> ORGANISM: Homo sapiens

<400> SEQUENCE: 281

His Lys Pro Ser Asn Thr Lys Val Asp
1               5

<210> SEQ ID NO 282
<211> LENGTH: 6
<212> TYPE: PRT
<213> ORGANISM: Homo sapiens

<400> SEQUENCE: 282

Lys Ser Arg Trp Gln Glu
1               5

<210> SEQ ID NO 283
<211> LENGTH: 6
<212> TYPE: PRT
<213> ORGANISM: Homo sapiens

<400> SEQUENCE: 283

Trp Leu Asn Gly Lys Glu
1               5

<210> SEQ ID NO 284
<211> LENGTH: 7
<212> TYPE: PRT
<213> ORGANISM: Homo sapiens

<400> SEQUENCE: 284

Val Thr Cys Val Val Val Asp
1               5

<210> SEQ ID NO 285
<211> LENGTH: 23
<212> TYPE: PRT
<213> ORGANISM: Homo sapiens

<400> SEQUENCE: 285

Met Thr Lys Asn Gln Val Ser Leu Thr Cys Leu Val Lys Gly Phe Tyr
1               5                   10                  15

Pro Ser Asp Ile Ala Val Glu
            20

<210> SEQ ID NO 286
<211> LENGTH: 20
<212> TYPE: PRT
<213> ORGANISM: Homo sapiens

<400> SEQUENCE: 286

Ala Ser Thr Lys Gly Pro Ser Val Phe Pro Leu Ala Pro Cys Ser Arg
1               5                   10                  15
```

Ser Thr Ser Glu
            20

<210> SEQ ID NO 287
<211> LENGTH: 17
<212> TYPE: PRT
<213> ORGANISM: Homo sapiens

<400> SEQUENCE: 287

Ala Leu His Asn His Tyr Thr Gln Lys Ser Leu Ser Leu Ser Leu Gly
1               5                   10                  15

Lys

<210> SEQ ID NO 288
<211> LENGTH: 15
<212> TYPE: PRT
<213> ORGANISM: Homo sapiens

<400> SEQUENCE: 288

Tyr Lys Cys Lys Val Ser Asn Lys Gly Leu Pro Ser Ser Ile Glu
1               5                   10                  15

<210> SEQ ID NO 289
<211> LENGTH: 14
<212> TYPE: PRT
<213> ORGANISM: Homo sapiens

<400> SEQUENCE: 289

Ser Lys Tyr Gly Pro Pro Cys Pro Ser Cys Pro Ala Pro Glu
1               5                   10

<210> SEQ ID NO 290
<211> LENGTH: 11
<212> TYPE: PRT
<213> ORGANISM: Homo sapiens

<400> SEQUENCE: 290

Val Gln Phe Asn Trp Tyr Val Asp Gly Val Glu
1               5                   10

<210> SEQ ID NO 291
<211> LENGTH: 11
<212> TYPE: PRT
<213> ORGANISM: Homo sapiens

<400> SEQUENCE: 291

Val His Asn Ala Lys Thr Lys Pro Arg Glu Glu
1               5                   10

<210> SEQ ID NO 292
<211> LENGTH: 11
<212> TYPE: PRT
<213> ORGANISM: Homo sapiens

<400> SEQUENCE: 292

Gly Asn Val Phe Ser Cys Ser Val Met His Glu
1               5                   10

<210> SEQ ID NO 293
<211> LENGTH: 11
<212> TYPE: PRT
<213> ORGANISM: Homo sapiens

<400> SEQUENCE: 293

Val Thr Cys Val Val Asp Val Ser Gln Glu
1               5                   10

<210> SEQ ID NO 294
<211> LENGTH: 23
<212> TYPE: PRT
<213> ORGANISM: Homo sapiens

<400> SEQUENCE: 294

Asp Ile Ala Val Glu Trp Glu Ser Asn Gly Gln Pro Glu Asn Asn Tyr
1               5                   10                  15

Lys Thr Thr Pro Pro Val Leu
            20

<210> SEQ ID NO 295
<211> LENGTH: 16
<212> TYPE: PRT
<213> ORGANISM: Homo sapiens

<400> SEQUENCE: 295

Asp Thr Leu Met Ile Ser Arg Thr Pro Glu Val Thr Cys Val Val Val
1               5                   10                  15

<210> SEQ ID NO 296
<211> LENGTH: 12
<212> TYPE: PRT
<213> ORGANISM: Homo sapiens

<400> SEQUENCE: 296

Asp Gly Ser Phe Phe Leu Tyr Ser Arg Leu Thr Val
1               5                   10

<210> SEQ ID NO 297
<211> LENGTH: 10
<212> TYPE: PRT
<213> ORGANISM: Homo sapiens

<400> SEQUENCE: 297

Asp Pro Glu Val Gln Phe Asn Trp Tyr Val
1               5                   10

<210> SEQ ID NO 298
<211> LENGTH: 9
<212> TYPE: PRT
<213> ORGANISM: Homo sapiens

<400> SEQUENCE: 298

Asp His Lys Pro Ser Asn Thr Lys Val
1               5

<210> SEQ ID NO 299
<211> LENGTH: 23
<212> TYPE: PRT
<213> ORGANISM: Homo sapiens

<400> SEQUENCE: 299

Asp Leu Cys Gly Cys Tyr Ser Val Ser Ser Val Leu Pro Gly Cys Ala
1               5                   10                  15

Glu Pro Trp Asn His Gly Lys
            20

<210> SEQ ID NO 300
<211> LENGTH: 22

```
<212> TYPE: PRT
<213> ORGANISM: Homo sapiens

<400> SEQUENCE: 300

Leu Ala Gly Lys Pro Thr His Val Asn Val Ser Val Met Ala Glu
1               5                   10                  15

Val Asp Gly Thr Cys Tyr
            20

<210> SEQ ID NO 301
<211> LENGTH: 20
<212> TYPE: PRT
<213> ORGANISM: Homo sapiens

<400> SEQUENCE: 301

Gly Asp Thr Phe Ser Cys Met Val Gly His Glu Ala Leu Pro Leu Ala
1               5                   10                  15

Phe Thr Gln Lys
            20

<210> SEQ ID NO 302
<211> LENGTH: 17
<212> TYPE: PRT
<213> ORGANISM: Homo sapiens

<400> SEQUENCE: 302

Gln Glu Pro Ser Gln Gly Thr Thr Thr Phe Ala Val Thr Ser Ile Leu
1               5                   10                  15

Arg

<210> SEQ ID NO 303
<211> LENGTH: 15
<212> TYPE: PRT
<213> ORGANISM: Homo sapiens

<400> SEQUENCE: 303

Asp Ala Ser Gly Val Thr Phe Thr Trp Thr Pro Ser Ser Gly Lys
1               5                   10                  15

<210> SEQ ID NO 304
<211> LENGTH: 12
<212> TYPE: PRT
<213> ORGANISM: Homo sapiens

<400> SEQUENCE: 304

Thr Phe Thr Cys Thr Ala Ala Tyr Pro Glu Ser Lys
1               5                   10

<210> SEQ ID NO 305
<211> LENGTH: 10
<212> TYPE: PRT
<213> ORGANISM: Homo sapiens

<400> SEQUENCE: 305

Trp Leu Gln Gly Ser Gln Glu Leu Pro Arg
1               5                   10

<210> SEQ ID NO 306
<211> LENGTH: 9
<212> TYPE: PRT
<213> ORGANISM: Homo sapiens

<400> SEQUENCE: 306
```

Ser Ala Val Gln Gly Pro Pro Glu Arg
1               5

<210> SEQ ID NO 307
<211> LENGTH: 9
<212> TYPE: PRT
<213> ORGANISM: Homo sapiens

<400> SEQUENCE: 307

Thr Pro Leu Thr Ala Thr Leu Ser Lys
1               5

<210> SEQ ID NO 308
<211> LENGTH: 7
<212> TYPE: PRT
<213> ORGANISM: Homo sapiens

<400> SEQUENCE: 308

Tyr Leu Thr Trp Ala Ser Arg
1               5

<210> SEQ ID NO 309
<211> LENGTH: 7
<212> TYPE: PRT
<213> ORGANISM: Homo sapiens

<400> SEQUENCE: 309

Val Ala Ala Glu Asp Trp Lys
1               5

<210> SEQ ID NO 310
<211> LENGTH: 7
<212> TYPE: PRT
<213> ORGANISM: Homo sapiens

<400> SEQUENCE: 310

Ser Val Thr Cys His Val Lys
1               5

<210> SEQ ID NO 311
<211> LENGTH: 7
<212> TYPE: PRT
<213> ORGANISM: Homo sapiens

<400> SEQUENCE: 311

Ala Ser Pro Thr Ser Pro Lys
1               5

<210> SEQ ID NO 312
<211> LENGTH: 20
<212> TYPE: PRT
<213> ORGANISM: Homo sapiens

<400> SEQUENCE: 312

Gly Asp Thr Phe Ser Cys Met Val Gly His Glu Ala Leu Pro Leu Ala
1               5                   10                  15

Phe Thr Gln Lys
            20

<210> SEQ ID NO 313
<211> LENGTH: 17
<212> TYPE: PRT
<213> ORGANISM: Homo sapiens

<400> SEQUENCE: 313

Asp Val Leu Val Arg Trp Leu Gln Gly Ser Gln Glu Leu Pro Arg Glu
1               5                   10                  15

Lys

<210> SEQ ID NO 314
<211> LENGTH: 18
<212> TYPE: PRT
<213> ORGANISM: Homo sapiens

<400> SEQUENCE: 314

Pro Thr His Val Asn Val Ser Val Val Met Ala Glu Val Asp Gly Thr
1               5                   10                  15

Cys Tyr

<210> SEQ ID NO 315
<211> LENGTH: 12
<212> TYPE: PRT
<213> ORGANISM: Homo sapiens

<400> SEQUENCE: 315

Thr Phe Thr Cys Thr Ala Ala Tyr Pro Glu Ser Lys
1               5                   10

<210> SEQ ID NO 316
<211> LENGTH: 9
<212> TYPE: PRT
<213> ORGANISM: Homo sapiens

<400> SEQUENCE: 316

Thr Pro Leu Thr Ala Thr Leu Ser Lys
1               5

<210> SEQ ID NO 317
<211> LENGTH: 8
<212> TYPE: PRT
<213> ORGANISM: Homo sapiens

<400> SEQUENCE: 317

Thr Ile Asp Arg Leu Ala Gly Lys
1               5

<210> SEQ ID NO 318
<211> LENGTH: 7
<212> TYPE: PRT
<213> ORGANISM: Homo sapiens

<400> SEQUENCE: 318

Ser Val Thr Cys His Val Lys
1               5

<210> SEQ ID NO 319
<211> LENGTH: 24
<212> TYPE: PRT
<213> ORGANISM: Homo sapiens

<400> SEQUENCE: 319

Asp Ala Ser Gly Val Thr Phe Thr Trp Thr Pro Ser Ser Gly Lys Ser
1               5                   10                  15

Ala Val Gln Gly Pro Pro Glu Arg
            20

<210> SEQ ID NO 320

<211> LENGTH: 22
<212> TYPE: PRT
<213> ORGANISM: Homo sapiens

<400> SEQUENCE: 320

Leu Ala Gly Lys Pro Thr His Val Asn Val Ser Val Val Met Ala Glu
1               5                   10                  15

Val Asp Gly Thr Cys Tyr
            20

<210> SEQ ID NO 321
<211> LENGTH: 17
<212> TYPE: PRT
<213> ORGANISM: Homo sapiens

<400> SEQUENCE: 321

Gln Glu Pro Ser Gln Gly Thr Thr Thr Phe Ala Val Thr Ser Ile Leu
1               5                   10                  15

Arg

<210> SEQ ID NO 322
<211> LENGTH: 10
<212> TYPE: PRT
<213> ORGANISM: Homo sapiens

<400> SEQUENCE: 322

Trp Leu Gln Gly Ser Gln Glu Leu Pro Arg
1               5                   10

<210> SEQ ID NO 323
<211> LENGTH: 9
<212> TYPE: PRT
<213> ORGANISM: Homo sapiens

<400> SEQUENCE: 323

Glu Lys Tyr Leu Thr Trp Ala Ser Arg
1               5

<210> SEQ ID NO 324
<211> LENGTH: 10
<212> TYPE: PRT
<213> ORGANISM: Homo sapiens

<400> SEQUENCE: 324

Gly Phe Ser Pro Lys Asp Val Leu Val Arg
1               5                   10

<210> SEQ ID NO 325
<211> LENGTH: 22
<212> TYPE: PRT
<213> ORGANISM: Homo sapiens

<400> SEQUENCE: 325

Ser Glu Ser Gly Gln Gly Val Thr Ala Arg Asn Phe Pro Pro Ser Gln
1               5                   10                  15

Asp Ala Ser Gly Asp Leu
            20

<210> SEQ ID NO 326
<211> LENGTH: 17
<212> TYPE: PRT
<213> ORGANISM: Homo sapiens

<400> SEQUENCE: 326

```
Thr Pro Ser Ser Gly Lys Ser Ala Val Gln Gly Pro Pro Glu Arg Asp
1               5                   10                  15
Leu

<210> SEQ ID NO 327
<211> LENGTH: 14
<212> TYPE: PRT
<213> ORGANISM: Homo sapiens

<400> SEQUENCE: 327

Cys Ser Thr Gln Pro Asp Gly Asn Val Val Ile Ala Cys Leu
1               5                   10

<210> SEQ ID NO 328
<211> LENGTH: 13
<212> TYPE: PRT
<213> ORGANISM: Homo sapiens

<400> SEQUENCE: 328

Ala Ser Arg Gln Glu Pro Ser Gln Gly Thr Thr Thr Phe
1               5                   10

<210> SEQ ID NO 329
<211> LENGTH: 13
<212> TYPE: PRT
<213> ORGANISM: Homo sapiens

<400> SEQUENCE: 329

Thr Cys Thr Ala Ala Tyr Pro Glu Ser Lys Thr Pro Leu
1               5                   10

<210> SEQ ID NO 330
<211> LENGTH: 13
<212> TYPE: PRT
<213> ORGANISM: Homo sapiens

<400> SEQUENCE: 330

Ala Gly Lys Pro Thr His Val Asn Val Ser Val Val Met
1               5                   10

<210> SEQ ID NO 331
<211> LENGTH: 11
<212> TYPE: PRT
<213> ORGANISM: Homo sapiens

<400> SEQUENCE: 331

Gln Gly Ser Gln Glu Leu Pro Arg Glu Lys Tyr
1               5                   10

<210> SEQ ID NO 332
<211> LENGTH: 13
<212> TYPE: PRT
<213> ORGANISM: Homo sapiens

<400> SEQUENCE: 332

Ser Val Ser Ser Val Leu Pro Gly Cys Ala Glu Pro Trp
1               5                   10

<210> SEQ ID NO 333
<211> LENGTH: 12
<212> TYPE: PRT
<213> ORGANISM: Homo sapiens

<400> SEQUENCE: 333
```

Ala Gly Lys Ser Val Thr Cys His Val Lys His Tyr
1               5                   10

<210> SEQ ID NO 334
<211> LENGTH: 11
<212> TYPE: PRT
<213> ORGANISM: Homo sapiens

<400> SEQUENCE: 334

Ala Ser Pro Thr Ser Pro Lys Val Phe Pro Leu
1               5                   10

<210> SEQ ID NO 335
<211> LENGTH: 8
<212> TYPE: PRT
<213> ORGANISM: Homo sapiens

<400> SEQUENCE: 335

Thr Gln Lys Thr Ile Asp Arg Leu
1               5

<210> SEQ ID NO 336
<211> LENGTH: 8
<212> TYPE: PRT
<213> ORGANISM: Homo sapiens

<400> SEQUENCE: 336

Leu Pro Pro Pro Ser Glu Glu Leu
1               5

<210> SEQ ID NO 337
<211> LENGTH: 8
<212> TYPE: PRT
<213> ORGANISM: Homo sapiens

<400> SEQUENCE: 337

Ala Glu Val Asp Gly Thr Cys Tyr
1               5

<210> SEQ ID NO 338
<211> LENGTH: 8
<212> TYPE: PRT
<213> ORGANISM: Homo sapiens

<400> SEQUENCE: 338

Arg Asp Ala Ser Gly Val Thr Phe
1               5

<210> SEQ ID NO 339
<211> LENGTH: 8
<212> TYPE: PRT
<213> ORGANISM: Homo sapiens

<400> SEQUENCE: 339

Thr Leu Pro Ala Thr Gln Cys Leu
1               5

<210> SEQ ID NO 340
<211> LENGTH: 7
<212> TYPE: PRT
<213> ORGANISM: Homo sapiens

<400> SEQUENCE: 340

Arg Val Ala Ala Glu Asp Trp

```
<210> SEQ ID NO 341
<211> LENGTH: 8
<212> TYPE: PRT
<213> ORGANISM: Homo sapiens

<400> SEQUENCE: 341

Val Gly His Glu Ala Leu Pro Leu
1               5

<210> SEQ ID NO 342
<211> LENGTH: 6
<212> TYPE: PRT
<213> ORGANISM: Homo sapiens

<400> SEQUENCE: 342

Arg Pro Glu Val His Leu
1               5

<210> SEQ ID NO 343
<211> LENGTH: 7
<212> TYPE: PRT
<213> ORGANISM: Homo sapiens

<400> SEQUENCE: 343

Ser Lys Ser Gly Asn Thr Phe
1               5

<210> SEQ ID NO 344
<211> LENGTH: 6
<212> TYPE: PRT
<213> ORGANISM: Homo sapiens

<400> SEQUENCE: 344

Phe Pro Gln Glu Pro Leu
1               5

<210> SEQ ID NO 345
<211> LENGTH: 24
<212> TYPE: PRT
<213> ORGANISM: Homo sapiens

<400> SEQUENCE: 345

Gly Asn Val Val Ile Ala Cys Leu Val Gln Gly Phe Phe Pro Gln Glu
1               5                   10                  15

Pro Leu Ser Val Thr Trp Ser Glu
            20

<210> SEQ ID NO 346
<211> LENGTH: 22
<212> TYPE: PRT
<213> ORGANISM: Homo sapiens

<400> SEQUENCE: 346

Ala Ser Gly Val Thr Phe Thr Trp Thr Pro Ser Ser Gly Lys Ser Ala
1               5                   10                  15

Val Gln Gly Pro Pro Glu
            20

<210> SEQ ID NO 347
<211> LENGTH: 19
<212> TYPE: PRT
<213> ORGANISM: Homo sapiens
```

<400> SEQUENCE: 347

Ser Lys Thr Pro Leu Thr Ala Thr Leu Ser Lys Ser Gly Asn Thr Phe
1               5                   10                  15

Arg Pro Glu

<210> SEQ ID NO 348
<211> LENGTH: 19
<212> TYPE: PRT
<213> ORGANISM: Homo sapiens

<400> SEQUENCE: 348

Ala Ser Pro Thr Ser Pro Lys Val Phe Pro Leu Ser Leu Cys Ser Thr
1               5                   10                  15

Gln Pro Asp

<210> SEQ ID NO 349
<211> LENGTH: 17
<212> TYPE: PRT
<213> ORGANISM: Homo sapiens

<400> SEQUENCE: 349

Arg Leu Ala Gly Lys Pro Thr His Val Asn Val Ser Val Val Met Ala
1               5                   10                  15

Glu

<210> SEQ ID NO 350
<211> LENGTH: 15
<212> TYPE: PRT
<213> ORGANISM: Homo sapiens

<400> SEQUENCE: 350

Leu Val Thr Leu Thr Cys Leu Ala Arg Gly Phe Ser Pro Lys Asp
1               5                   10                  15

<210> SEQ ID NO 351
<211> LENGTH: 15
<212> TYPE: PRT
<213> ORGANISM: Homo sapiens

<400> SEQUENCE: 351

Ser Gly Gln Gly Val Thr Ala Arg Asn Phe Pro Pro Ser Gln Asp
1               5                   10                  15

<210> SEQ ID NO 352
<211> LENGTH: 12
<212> TYPE: PRT
<213> ORGANISM: Homo sapiens

<400> SEQUENCE: 352

Ala Leu Pro Leu Ala Phe Thr Gln Lys Thr Ile Asp
1               5                   10

<210> SEQ ID NO 353
<211> LENGTH: 11
<212> TYPE: PRT
<213> ORGANISM: Homo sapiens

<400> SEQUENCE: 353

Val Leu Val Arg Trp Leu Gln Gly Ser Gln Glu
1               5                   10

```
<210> SEQ ID NO 354
<211> LENGTH: 10
<212> TYPE: PRT
<213> ORGANISM: Homo sapiens

<400> SEQUENCE: 354

Val His Leu Leu Pro Pro Pro Ser Glu Glu
1               5                   10

<210> SEQ ID NO 355
<211> LENGTH: 19
<212> TYPE: PRT
<213> ORGANISM: Homo sapiens

<400> SEQUENCE: 355

Ser Lys Thr Pro Leu Thr Ala Thr Leu Ser Lys Ser Gly Asn Thr Phe
1               5                   10                  15

Arg Pro Glu

<210> SEQ ID NO 356
<211> LENGTH: 15
<212> TYPE: PRT
<213> ORGANISM: Homo sapiens

<400> SEQUENCE: 356

Asp Trp Lys Lys Gly Asp Thr Phe Ser Cys Met Val Gly His Glu
1               5                   10                  15

<210> SEQ ID NO 357
<211> LENGTH: 10
<212> TYPE: PRT
<213> ORGANISM: Homo sapiens

<400> SEQUENCE: 357

Val His Leu Leu Pro Pro Pro Ser Glu Glu
1               5                   10

<210> SEQ ID NO 358
<211> LENGTH: 7
<212> TYPE: PRT
<213> ORGANISM: Homo sapiens

<400> SEQUENCE: 358

Asp Leu Leu Leu Gly Ser Glu
1               5

<210> SEQ ID NO 359
<211> LENGTH: 24
<212> TYPE: PRT
<213> ORGANISM: Homo sapiens

<400> SEQUENCE: 359

Asp Ala Ser Gly Val Thr Phe Thr Trp Thr Pro Ser Ser Gly Lys Ser
1               5                   10                  15

Ala Val Gln Gly Pro Pro Glu Arg
            20

<210> SEQ ID NO 360
<211> LENGTH: 21
<212> TYPE: PRT
<213> ORGANISM: Homo sapiens

<400> SEQUENCE: 360

Asp Thr Phe Ser Cys Met Val Gly His Glu Ala Leu Pro Leu Ala Phe
```

```
1               5                   10                  15
Thr Gln Lys Thr Ile
            20

<210> SEQ ID NO 361
<211> LENGTH: 19
<212> TYPE: PRT
<213> ORGANISM: Homo sapiens

<400> SEQUENCE: 361

Asp Arg Leu Ala Gly Lys Pro Thr His Val Asn Val Ser Val Val Met
1               5                   10                  15

Ala Glu Val

<210> SEQ ID NO 362
<211> LENGTH: 18
<212> TYPE: PRT
<213> ORGANISM: Homo sapiens

<400> SEQUENCE: 362

Asp Leu Leu Leu Gly Ser Glu Ala Asn Leu Thr Cys Thr Leu Thr Gly
1               5                   10                  15

Leu Arg

<210> SEQ ID NO 363
<211> LENGTH: 18
<212> TYPE: PRT
<213> ORGANISM: Homo sapiens

<400> SEQUENCE: 363

Ala Ser Pro Thr Ser Pro Lys Val Phe Pro Leu Ser Leu Cys Ser Thr
1               5                   10                  15

Gln Pro

<210> SEQ ID NO 364
<211> LENGTH: 22
<212> TYPE: PRT
<213> ORGANISM: Homo sapiens

<400> SEQUENCE: 364

Met Ala Gly Lys Pro Thr His Val Asn Val Ser Val Val Met Ala Glu
1               5                   10                  15

Val Asp Gly Thr Cys Tyr
            20

<210> SEQ ID NO 365
<211> LENGTH: 20
<212> TYPE: PRT
<213> ORGANISM: Homo sapiens

<400> SEQUENCE: 365

Gly Asp Thr Phe Ser Cys Met Val Gly His Glu Ala Leu Pro Leu Ala
1               5                   10                  15

Phe Thr Gln Lys
            20

<210> SEQ ID NO 366
<211> LENGTH: 17
<212> TYPE: PRT
<213> ORGANISM: Homo sapiens

<400> SEQUENCE: 366
```

```
Gln Glu Pro Ser Gln Gly Thr Thr Thr Phe Ala Val Thr Ser Ile Leu
1               5                   10                  15
Arg

<210> SEQ ID NO 367
<211> LENGTH: 10
<212> TYPE: PRT
<213> ORGANISM: Homo sapiens

<400> SEQUENCE: 367

Trp Leu Gln Gly Ser Gln Glu Leu Pro Arg
1               5                   10

<210> SEQ ID NO 368
<211> LENGTH: 9
<212> TYPE: PRT
<213> ORGANISM: Homo sapiens

<400> SEQUENCE: 368

Thr Pro Leu Thr Ala Asn Ile Thr Lys
1               5

<210> SEQ ID NO 369
<211> LENGTH: 9
<212> TYPE: PRT
<213> ORGANISM: Homo sapiens

<400> SEQUENCE: 369

Ser Ala Val Gln Gly Pro Pro Glu Arg
1               5

<210> SEQ ID NO 370
<211> LENGTH: 7
<212> TYPE: PRT
<213> ORGANISM: Homo sapiens

<400> SEQUENCE: 370

Tyr Leu Thr Trp Ala Ser Arg
1               5

<210> SEQ ID NO 371
<211> LENGTH: 7
<212> TYPE: PRT
<213> ORGANISM: Homo sapiens

<400> SEQUENCE: 371

Val Ala Ala Glu Asp Trp Lys
1               5

<210> SEQ ID NO 372
<211> LENGTH: 7
<212> TYPE: PRT
<213> ORGANISM: Homo sapiens

<400> SEQUENCE: 372

Ser Val Thr Cys His Val Lys
1               5

<210> SEQ ID NO 373
<211> LENGTH: 20
<212> TYPE: PRT
<213> ORGANISM: Homo sapiens

<400> SEQUENCE: 373
```

```
Gly Asp Thr Phe Ser Cys Met Val Gly His Glu Ala Leu Pro Leu Ala
1               5                   10                  15

Phe Thr Gln Lys
            20

<210> SEQ ID NO 374
<211> LENGTH: 17
<212> TYPE: PRT
<213> ORGANISM: Homo sapiens

<400> SEQUENCE: 374

Asp Val Leu Val Arg Trp Leu Gln Gly Ser Gln Glu Leu Pro Arg Glu
1               5                   10                  15

Lys

<210> SEQ ID NO 375
<211> LENGTH: 18
<212> TYPE: PRT
<213> ORGANISM: Homo sapiens

<400> SEQUENCE: 375

Pro Thr His Val Asn Val Ser Val Val Met Ala Glu Val Asp Gly Thr
1               5                   10                  15

Cys Tyr

<210> SEQ ID NO 376
<211> LENGTH: 9
<212> TYPE: PRT
<213> ORGANISM: Homo sapiens

<400> SEQUENCE: 376

Thr Pro Leu Thr Ala Asn Ile Thr Lys
1               5

<210> SEQ ID NO 377
<211> LENGTH: 8
<212> TYPE: PRT
<213> ORGANISM: Homo sapiens

<400> SEQUENCE: 377

Thr Ile Asp Arg Met Ala Gly Lys
1               5

<210> SEQ ID NO 378
<211> LENGTH: 7
<212> TYPE: PRT
<213> ORGANISM: Homo sapiens

<400> SEQUENCE: 378

Ser Val Thr Cys His Val Lys
1               5

<210> SEQ ID NO 379
<211> LENGTH: 24
<212> TYPE: PRT
<213> ORGANISM: Homo sapiens

<400> SEQUENCE: 379

Asp Ala Ser Gly Ala Thr Phe Thr Trp Thr Pro Ser Ser Gly Lys Ser
1               5                   10                  15

Ala Val Gln Gly Pro Pro Glu Arg
            20
```

<210> SEQ ID NO 380
<211> LENGTH: 22
<212> TYPE: PRT
<213> ORGANISM: Homo sapiens

<400> SEQUENCE: 380

Met Ala Gly Lys Pro Thr His Val Asn Val Ser Val Val Met Ala Glu
1               5                   10                  15

Val Asp Gly Thr Cys Tyr
            20

<210> SEQ ID NO 381
<211> LENGTH: 17
<212> TYPE: PRT
<213> ORGANISM: Homo sapiens

<400> SEQUENCE: 381

Gln Glu Pro Ser Gln Gly Thr Thr Thr Phe Ala Val Thr Ser Ile Leu
1               5                   10                  15

Arg

<210> SEQ ID NO 382
<211> LENGTH: 10
<212> TYPE: PRT
<213> ORGANISM: Homo sapiens

<400> SEQUENCE: 382

Trp Leu Gln Gly Ser Gln Glu Leu Pro Arg
1               5                   10

<210> SEQ ID NO 383
<211> LENGTH: 9
<212> TYPE: PRT
<213> ORGANISM: Homo sapiens

<400> SEQUENCE: 383

Glu Lys Tyr Leu Thr Trp Ala Ser Arg
1               5

<210> SEQ ID NO 384
<211> LENGTH: 10
<212> TYPE: PRT
<213> ORGANISM: Homo sapiens

<400> SEQUENCE: 384

Gly Phe Ser Pro Lys Asp Val Leu Val Arg
1               5                   10

<210> SEQ ID NO 385
<211> LENGTH: 24
<212> TYPE: PRT
<213> ORGANISM: Homo sapiens

<400> SEQUENCE: 385

Thr Asn Pro Ser Gln Asp Val Thr Val Pro Cys Pro Val Pro Pro Pro
1               5                   10                  15

Pro Pro Cys Cys His Pro Arg Leu
            20

<210> SEQ ID NO 386
<211> LENGTH: 21
<212> TYPE: PRT

```
<213> ORGANISM: Homo sapiens

<400> SEQUENCE: 386

Glu Ser Gly Gln Asn Val Thr Ala Arg Asn Phe Pro Pro Ser Gln Asp
1               5                   10                  15

Ala Ser Gly Asp Leu
            20

<210> SEQ ID NO 387
<211> LENGTH: 20
<212> TYPE: PRT
<213> ORGANISM: Homo sapiens

<400> SEQUENCE: 387

Thr Leu Pro Ala Thr Gln Cys Pro Asp Gly Lys Ser Val Thr Cys His
1               5                   10                  15

Val Lys His Tyr
            20

<210> SEQ ID NO 388
<211> LENGTH: 17
<212> TYPE: PRT
<213> ORGANISM: Homo sapiens

<400> SEQUENCE: 388

Thr Pro Ser Ser Gly Lys Ser Ala Val Gln Gly Pro Pro Glu Arg Asp
1               5                   10                  15

Leu

<210> SEQ ID NO 389
<211> LENGTH: 14
<212> TYPE: PRT
<213> ORGANISM: Homo sapiens

<400> SEQUENCE: 389

Asp Ser Thr Pro Gln Asp Gly Asn Val Val Ala Cys Leu
1               5                   10

<210> SEQ ID NO 390
<211> LENGTH: 13
<212> TYPE: PRT
<213> ORGANISM: Homo sapiens

<400> SEQUENCE: 390

Ala Ser Arg Gln Glu Pro Ser Gln Gly Thr Thr Thr Phe
1               5                   10

<210> SEQ ID NO 391
<211> LENGTH: 13
<212> TYPE: PRT
<213> ORGANISM: Homo sapiens

<400> SEQUENCE: 391

Ala Gly Lys Pro Thr His Val Asn Val Ser Val Val Met
1               5                   10

<210> SEQ ID NO 392
<211> LENGTH: 11
<212> TYPE: PRT
<213> ORGANISM: Homo sapiens

<400> SEQUENCE: 392

Gln Gly Ser Gln Glu Leu Pro Arg Glu Lys Tyr
```

```
<210> SEQ ID NO 393
<211> LENGTH: 13
<212> TYPE: PRT
<213> ORGANISM: Homo sapiens

<400> SEQUENCE: 393

Ser Val Ser Ser Val Leu Pro Gly Cys Ala Gln Pro Trp
1               5                   10

<210> SEQ ID NO 394
<211> LENGTH: 11
<212> TYPE: PRT
<213> ORGANISM: Homo sapiens

<400> SEQUENCE: 394

Thr Ala Asn Ile Thr Lys Ser Gly Asn Thr Phe
1               5                   10

<210> SEQ ID NO 395
<211> LENGTH: 8
<212> TYPE: PRT
<213> ORGANISM: Homo sapiens

<400> SEQUENCE: 395

Thr Gln Lys Thr Ile Asp Arg Met
1               5

<210> SEQ ID NO 396
<211> LENGTH: 9
<212> TYPE: PRT
<213> ORGANISM: Homo sapiens

<400> SEQUENCE: 396

Thr Cys Thr Ala Ala His Pro Glu Leu
1               5

<210> SEQ ID NO 397
<211> LENGTH: 8
<212> TYPE: PRT
<213> ORGANISM: Homo sapiens

<400> SEQUENCE: 397

Leu Pro Pro Pro Ser Glu Glu Leu
1               5

<210> SEQ ID NO 398
<211> LENGTH: 8
<212> TYPE: PRT
<213> ORGANISM: Homo sapiens

<400> SEQUENCE: 398

Ala Glu Val Asp Gly Thr Cys Tyr
1               5

<210> SEQ ID NO 399
<211> LENGTH: 7
<212> TYPE: PRT
<213> ORGANISM: Homo sapiens

<400> SEQUENCE: 399

Arg Val Ala Ala Glu Asp Trp
1               5
```

<210> SEQ ID NO 400
<211> LENGTH: 8
<212> TYPE: PRT
<213> ORGANISM: Homo sapiens

<400> SEQUENCE: 400

Val Gly His Glu Ala Leu Pro Leu
1               5

<210> SEQ ID NO 401
<211> LENGTH: 8
<212> TYPE: PRT
<213> ORGANISM: Homo sapiens

<400> SEQUENCE: 401

Arg Asp Ala Ser Gly Ala Thr Phe
1               5

<210> SEQ ID NO 402
<211> LENGTH: 6
<212> TYPE: PRT
<213> ORGANISM: Homo sapiens

<400> SEQUENCE: 402

Arg Pro Glu Val His Leu
1               5

<210> SEQ ID NO 403
<211> LENGTH: 6
<212> TYPE: PRT
<213> ORGANISM: Homo sapiens

<400> SEQUENCE: 403

Phe Pro Gln Glu Pro Leu
1               5

<210> SEQ ID NO 404
<211> LENGTH: 22
<212> TYPE: PRT
<213> ORGANISM: Homo sapiens

<400> SEQUENCE: 404

Leu Cys Gly Cys Tyr Ser Val Ser Val Leu Pro Gly Cys Ala Gln
1               5                   10                  15

Pro Trp Asn His Gly Glu
            20

<210> SEQ ID NO 405
<211> LENGTH: 22
<212> TYPE: PRT
<213> ORGANISM: Homo sapiens

<400> SEQUENCE: 405

Ala Ser Gly Ala Thr Phe Thr Trp Thr Pro Ser Ser Gly Lys Ser Ala
1               5                   10                  15

Val Gln Gly Pro Pro Glu
            20

<210> SEQ ID NO 406
<211> LENGTH: 19
<212> TYPE: PRT
<213> ORGANISM: Homo sapiens

<400> SEQUENCE: 406

Leu Lys Thr Pro Leu Thr Ala Asn Ile Thr Lys Ser Gly Asn Thr Phe
1               5                   10                  15

Arg Pro Glu

<210> SEQ ID NO 407
<211> LENGTH: 17
<212> TYPE: PRT
<213> ORGANISM: Homo sapiens

<400> SEQUENCE: 407

Gly Lys Ser Val Thr Cys His Val Lys His Tyr Thr Asn Pro Ser Gln
1               5                   10                  15

Asp

<210> SEQ ID NO 408
<211> LENGTH: 17
<212> TYPE: PRT
<213> ORGANISM: Homo sapiens

<400> SEQUENCE: 408

Leu Tyr Thr Thr Ser Ser Gln Leu Thr Leu Pro Ala Thr Gln Cys Pro
1               5                   10                  15

Asp

<210> SEQ ID NO 409
<211> LENGTH: 17
<212> TYPE: PRT
<213> ORGANISM: Homo sapiens

<400> SEQUENCE: 409

Arg Met Ala Gly Lys Pro Thr His Val Asn Val Ser Val Val Met Ala
1               5                   10                  15

Glu

<210> SEQ ID NO 410
<211> LENGTH: 15
<212> TYPE: PRT
<213> ORGANISM: Homo sapiens

<400> SEQUENCE: 410

Leu Val Thr Leu Thr Cys Leu Ala Arg Gly Phe Ser Pro Lys Asp
1               5                   10                  15

<210> SEQ ID NO 411
<211> LENGTH: 15
<212> TYPE: PRT
<213> ORGANISM: Homo sapiens

<400> SEQUENCE: 411

Ser Gly Gln Asn Val Thr Ala Arg Asn Phe Pro Pro Ser Gln Asp
1               5                   10                  15

<210> SEQ ID NO 412
<211> LENGTH: 12
<212> TYPE: PRT
<213> ORGANISM: Homo sapiens

<400> SEQUENCE: 412

Ala Leu Pro Leu Ala Phe Thr Gln Lys Thr Ile Asp
1               5                   10

```
<210> SEQ ID NO 413
<211> LENGTH: 11
<212> TYPE: PRT
<213> ORGANISM: Homo sapiens

<400> SEQUENCE: 413

Val Leu Val Arg Trp Leu Gln Gly Ser Gln Glu
1               5                   10

<210> SEQ ID NO 414
<211> LENGTH: 12
<212> TYPE: PRT
<213> ORGANISM: Homo sapiens

<400> SEQUENCE: 414

Ala Asn Leu Thr Cys Thr Leu Thr Gly Leu Arg Asp
1               5                   10

<210> SEQ ID NO 415
<211> LENGTH: 10
<212> TYPE: PRT
<213> ORGANISM: Homo sapiens

<400> SEQUENCE: 415

Val His Leu Leu Pro Pro Pro Ser Glu Glu
1               5                   10

<210> SEQ ID NO 416
<211> LENGTH: 10
<212> TYPE: PRT
<213> ORGANISM: Homo sapiens

<400> SEQUENCE: 416

Thr Phe Thr Cys Thr Ala Ala His Pro Glu
1               5                   10

<210> SEQ ID NO 417
<211> LENGTH: 9
<212> TYPE: PRT
<213> ORGANISM: Homo sapiens

<400> SEQUENCE: 417

Thr Phe Ser Cys Met Val Gly His Glu
1               5

<210> SEQ ID NO 418
<211> LENGTH: 24
<212> TYPE: PRT
<213> ORGANISM: Homo sapiens

<400> SEQUENCE: 418

Arg Asp Leu Cys Gly Cys Tyr Ser Val Ser Ser Val Leu Pro Gly Cys
1               5                   10                  15

Ala Gln Pro Trp Asn His Gly Glu
            20

<210> SEQ ID NO 419
<211> LENGTH: 19
<212> TYPE: PRT
<213> ORGANISM: Homo sapiens

<400> SEQUENCE: 419

Leu Lys Thr Pro Leu Thr Ala Asn Ile Thr Lys Ser Gly Asn Thr Phe
1               5                   10                  15
```

Arg Pro Glu

<210> SEQ ID NO 420
<211> LENGTH: 15
<212> TYPE: PRT
<213> ORGANISM: Homo sapiens

<400> SEQUENCE: 420

Asp Trp Lys Lys Gly Asp Thr Phe Ser Cys Met Val Gly His Glu
1               5                   10                  15

<210> SEQ ID NO 421
<211> LENGTH: 10
<212> TYPE: PRT
<213> ORGANISM: Homo sapiens

<400> SEQUENCE: 421

Val His Leu Leu Pro Pro Pro Ser Glu Glu
1               5                   10

<210> SEQ ID NO 422
<211> LENGTH: 10
<212> TYPE: PRT
<213> ORGANISM: Homo sapiens

<400> SEQUENCE: 422

Thr Phe Thr Cys Thr Ala Ala His Pro Glu
1               5                   10

<210> SEQ ID NO 423
<211> LENGTH: 7
<212> TYPE: PRT
<213> ORGANISM: Homo sapiens

<400> SEQUENCE: 423

Asp Leu Leu Leu Gly Ser Glu
1               5

<210> SEQ ID NO 424
<211> LENGTH: 24
<212> TYPE: PRT
<213> ORGANISM: Homo sapiens

<400> SEQUENCE: 424

Asp Ala Ser Gly Ala Thr Phe Thr Trp Thr Pro Ser Ser Gly Lys Ser
1               5                   10                  15

Ala Val Gln Gly Pro Pro Glu Arg
            20

<210> SEQ ID NO 425
<211> LENGTH: 21
<212> TYPE: PRT
<213> ORGANISM: Homo sapiens

<400> SEQUENCE: 425

Asp Thr Phe Ser Cys Met Val Gly His Glu Ala Leu Pro Leu Ala Phe
1               5                   10                  15

Thr Gln Lys Thr Ile
            20

<210> SEQ ID NO 426
<211> LENGTH: 19
<212> TYPE: PRT
<213> ORGANISM: Homo sapiens

<400> SEQUENCE: 426

Asp Arg Met Ala Gly Lys Pro Thr His Val Asn Val Ser Val Val Met
1               5                   10                  15

Ala Glu Val

<210> SEQ ID NO 427
<211> LENGTH: 17
<212> TYPE: PRT
<213> ORGANISM: Homo sapiens

<400> SEQUENCE: 427

Asp Gly Lys Ser Val Thr Cys His Val Lys His Tyr Thr Asn Pro Ser
1               5                   10                  15

Gln

<210> SEQ ID NO 428
<211> LENGTH: 18
<212> TYPE: PRT
<213> ORGANISM: Homo sapiens

<400> SEQUENCE: 428

Asp Leu Leu Leu Gly Ser Glu Ala Asn Leu Thr Cys Thr Leu Thr Gly
1               5                   10                  15

Leu Arg

<210> SEQ ID NO 429
<211> LENGTH: 17
<212> TYPE: PRT
<213> ORGANISM: Homo sapiens

<400> SEQUENCE: 429

Asp Leu Tyr Thr Thr Ser Ser Gln Leu Thr Leu Pro Ala Thr Gln Cys
1               5                   10                  15

Pro

<210> SEQ ID NO 430
<211> LENGTH: 22
<212> TYPE: PRT
<213> ORGANISM: Homo sapiens

<400> SEQUENCE: 430

Ser Thr Gly Lys Pro Thr Leu Tyr Asn Val Ser Leu Val Met Ser Asp
1               5                   10                  15

Thr Ala Gly Thr Cys Tyr
            20

<210> SEQ ID NO 431
<211> LENGTH: 20
<212> TYPE: PRT
<213> ORGANISM: Homo sapiens

<400> SEQUENCE: 431

Leu Thr Cys Leu Val Thr Asp Leu Thr Thr Tyr Asp Ser Val Thr Ile
1               5                   10                  15

Ser Trp Thr Arg
            20

<210> SEQ ID NO 432
<211> LENGTH: 21
<212> TYPE: PRT

<210> SEQ ID NO 432
<211> LENGTH: 21
<212> TYPE: PRT
<213> ORGANISM: Homo sapiens

<400> SEQUENCE: 432

Gly Leu Thr Phe Gln Gln Asn Ala Ser Ser Met Cys Val Pro Asp Gln
1               5                   10                  15
Asp Thr Ala Ile Arg
            20

<210> SEQ ID NO 433
<211> LENGTH: 16
<212> TYPE: PRT
<213> ORGANISM: Homo sapiens

<400> SEQUENCE: 433

Gly Val Ala Leu His Arg Pro Asp Val Tyr Leu Leu Pro Pro Ala Arg
1               5                   10                  15

<210> SEQ ID NO 434
<211> LENGTH: 15
<212> TYPE: PRT
<213> ORGANISM: Homo sapiens

<400> SEQUENCE: 434

Phe Thr Cys Thr Val Thr His Thr Asp Leu Pro Ser Pro Leu Lys
1               5                   10                  15

<210> SEQ ID NO 435
<211> LENGTH: 15
<212> TYPE: PRT
<213> ORGANISM: Homo sapiens

<400> SEQUENCE: 435

Val Phe Ala Ile Pro Pro Ser Phe Ala Ser Ile Phe Leu Thr Lys
1               5                   10                  15

<210> SEQ ID NO 436
<211> LENGTH: 16
<212> TYPE: PRT
<213> ORGANISM: Homo sapiens

<400> SEQUENCE: 436

Gln Val Gly Ser Gly Val Thr Thr Asp Gln Val Gln Ala Glu Ala Lys
1               5                   10                  15

<210> SEQ ID NO 437
<211> LENGTH: 15
<212> TYPE: PRT
<213> ORGANISM: Homo sapiens

<400> SEQUENCE: 437

Tyr Val Thr Ser Ala Pro Met Pro Glu Pro Gln Ala Pro Gly Arg
1               5                   10                  15

<210> SEQ ID NO 438
<211> LENGTH: 13
<212> TYPE: PRT
<213> ORGANISM: Homo sapiens

<400> SEQUENCE: 438

Glu Ser Asp Trp Leu Gly Gln Ser Met Phe Thr Cys Arg
1               5                   10

<210> SEQ ID NO 439
<211> LENGTH: 13

```
<212> TYPE: PRT
<213> ORGANISM: Homo sapiens

<400> SEQUENCE: 439

Asp Val Met Gln Gly Thr Asp Glu His Val Val Cys Lys
1               5                   10

<210> SEQ ID NO 440
<211> LENGTH: 13
<212> TYPE: PRT
<213> ORGANISM: Homo sapiens

<400> SEQUENCE: 440

Asn Val Pro Leu Pro Val Ile Ala Glu Leu Pro Pro Lys
1               5                   10

<210> SEQ ID NO 441
<211> LENGTH: 12
<212> TYPE: PRT
<213> ORGANISM: Homo sapiens

<400> SEQUENCE: 441

Tyr Ala Ala Thr Ser Gln Val Leu Leu Pro Ser Lys
1               5                   10

<210> SEQ ID NO 442
<211> LENGTH: 11
<212> TYPE: PRT
<213> ORGANISM: Homo sapiens

<400> SEQUENCE: 442

Leu Ile Cys Gln Ala Thr Gly Phe Ser Pro Arg
1               5                   10

<210> SEQ ID NO 443
<211> LENGTH: 8
<212> TYPE: PRT
<213> ORGANISM: Homo sapiens

<400> SEQUENCE: 443

Gln Ile Gln Val Ser Trp Leu Arg
1               5

<210> SEQ ID NO 444
<211> LENGTH: 9
<212> TYPE: PRT
<213> ORGANISM: Homo sapiens

<400> SEQUENCE: 444

Asn Asn Ser Asp Ile Ser Ser Thr Arg
1               5

<210> SEQ ID NO 445
<211> LENGTH: 8
<212> TYPE: PRT
<213> ORGANISM: Homo sapiens

<400> SEQUENCE: 445

Val Ser Val Phe Val Pro Pro Arg
1               5

<210> SEQ ID NO 446
<211> LENGTH: 8
<212> TYPE: PRT
<213> ORGANISM: Homo sapiens
```

```
<400> SEQUENCE: 446

Val Gln His Pro Asn Gly Asn Lys
1               5

<210> SEQ ID NO 447
<211> LENGTH: 8
<212> TYPE: PRT
<213> ORGANISM: Homo sapiens

<400> SEQUENCE: 447

Glu Ser Gly Pro Thr Thr Tyr Lys
1               5

<210> SEQ ID NO 448
<211> LENGTH: 8
<212> TYPE: PRT
<213> ORGANISM: Homo sapiens

<400> SEQUENCE: 448

Val Thr Ser Thr Leu Thr Ile Lys
1               5

<210> SEQ ID NO 449
<211> LENGTH: 8
<212> TYPE: PRT
<213> ORGANISM: Homo sapiens

<400> SEQUENCE: 449

Gly Gln Pro Leu Ser Pro Glu Lys
1               5

<210> SEQ ID NO 450
<211> LENGTH: 7
<212> TYPE: PRT
<213> ORGANISM: Homo sapiens

<400> SEQUENCE: 450

Gln Thr Ile Ser Arg Pro Lys
1               5

<210> SEQ ID NO 451
<211> LENGTH: 7
<212> TYPE: PRT
<213> ORGANISM: Homo sapiens

<400> SEQUENCE: 451

Gly Phe Pro Ser Val Leu Arg
1               5

<210> SEQ ID NO 452
<211> LENGTH: 6
<212> TYPE: PRT
<213> ORGANISM: Homo sapiens

<400> SEQUENCE: 452

Glu Gln Leu Asn Leu Arg
1               5

<210> SEQ ID NO 453
<211> LENGTH: 7
<212> TYPE: PRT
<213> ORGANISM: Homo sapiens

<400> SEQUENCE: 453
```

```
Gln Asn Gly Glu Ala Val Lys
1               5

<210> SEQ ID NO 454
<211> LENGTH: 22
<212> TYPE: PRT
<213> ORGANISM: Homo sapiens

<400> SEQUENCE: 454

Leu Ile Cys Gln Ala Thr Gly Phe Ser Pro Arg Gln Ile Gln Val Ser
1               5                   10                  15

Trp Leu Arg Glu Gly Lys
            20

<210> SEQ ID NO 455
<211> LENGTH: 19
<212> TYPE: PRT
<213> ORGANISM: Homo sapiens

<400> SEQUENCE: 455

Asn Asn Ser Asp Ile Ser Ser Thr Arg Gly Phe Pro Ser Val Leu Arg
1               5                   10                  15

Gly Gly Lys

<210> SEQ ID NO 456
<211> LENGTH: 18
<212> TYPE: PRT
<213> ORGANISM: Homo sapiens

<400> SEQUENCE: 456

Pro Thr Leu Tyr Asn Val Ser Leu Val Met Ser Asp Thr Ala Gly Thr
1               5                   10                  15

Cys Tyr

<210> SEQ ID NO 457
<211> LENGTH: 17
<212> TYPE: PRT
<213> ORGANISM: Homo sapiens

<400> SEQUENCE: 457

Val Ser Val Phe Val Pro Pro Arg Asp Gly Phe Phe Gly Asn Pro Arg
1               5                   10                  15

Lys

<210> SEQ ID NO 458
<211> LENGTH: 16
<212> TYPE: PRT
<213> ORGANISM: Homo sapiens

<400> SEQUENCE: 458

Gln Val Gly Ser Gly Val Thr Thr Asp Gln Val Gln Ala Glu Ala Lys
1               5                   10                  15

<210> SEQ ID NO 459
<211> LENGTH: 13
<212> TYPE: PRT
<213> ORGANISM: Homo sapiens

<400> SEQUENCE: 459

Asp Val Met Gln Gly Thr Asp Glu His Val Val Cys Lys
1               5                   10
```

```
<210> SEQ ID NO 460
<211> LENGTH: 13
<212> TYPE: PRT
<213> ORGANISM: Homo sapiens

<400> SEQUENCE: 460

Asn Val Pro Leu Pro Val Ile Ala Glu Leu Pro Pro Lys
1               5                   10

<210> SEQ ID NO 461
<211> LENGTH: 12
<212> TYPE: PRT
<213> ORGANISM: Homo sapiens

<400> SEQUENCE: 461

Tyr Ala Ala Thr Ser Gln Val Leu Leu Pro Ser Lys
1               5                   10

<210> SEQ ID NO 462
<211> LENGTH: 8
<212> TYPE: PRT
<213> ORGANISM: Homo sapiens

<400> SEQUENCE: 462

Val Gln His Pro Asn Gly Asn Lys
1               5

<210> SEQ ID NO 463
<211> LENGTH: 8
<212> TYPE: PRT
<213> ORGANISM: Homo sapiens

<400> SEQUENCE: 463

Glu Ser Gly Pro Thr Thr Tyr Lys
1               5

<210> SEQ ID NO 464
<211> LENGTH: 8
<212> TYPE: PRT
<213> ORGANISM: Homo sapiens

<400> SEQUENCE: 464

Val Thr Ser Thr Leu Thr Ile Lys
1               5

<210> SEQ ID NO 465
<211> LENGTH: 7
<212> TYPE: PRT
<213> ORGANISM: Homo sapiens

<400> SEQUENCE: 465

Gln Thr Ile Ser Arg Pro Lys
1               5

<210> SEQ ID NO 466
<211> LENGTH: 23
<212> TYPE: PRT
<213> ORGANISM: Homo sapiens

<400> SEQUENCE: 466

Gly Gln Pro Leu Ser Pro Glu Lys Tyr Val Thr Ser Ala Pro Met Pro
1               5                   10                  15

Glu Pro Gln Ala Pro Gly Arg
            20
```

```
<210> SEQ ID NO 467
<211> LENGTH: 21
<212> TYPE: PRT
<213> ORGANISM: Homo sapiens

<400> SEQUENCE: 467

Gly Leu Thr Phe Gln Gln Asn Ala Ser Ser Met Cys Val Pro Asp Gln
1               5                   10                  15

Asp Thr Ala Ile Arg
            20

<210> SEQ ID NO 468
<211> LENGTH: 14
<212> TYPE: PRT
<213> ORGANISM: Homo sapiens

<400> SEQUENCE: 468

Lys Ser Lys Leu Ile Cys Gln Ala Thr Gly Phe Ser Pro Arg
1               5                   10

<210> SEQ ID NO 469
<211> LENGTH: 8
<212> TYPE: PRT
<213> ORGANISM: Homo sapiens

<400> SEQUENCE: 469

Gln Ile Gln Val Ser Trp Leu Arg
1               5

<210> SEQ ID NO 470
<211> LENGTH: 8
<212> TYPE: PRT
<213> ORGANISM: Homo sapiens

<400> SEQUENCE: 470

Asp Gly Phe Phe Gly Asn Pro Arg
1               5

<210> SEQ ID NO 471
<211> LENGTH: 7
<212> TYPE: PRT
<213> ORGANISM: Homo sapiens

<400> SEQUENCE: 471

Gly Phe Pro Ser Val Leu Arg
1               5

<210> SEQ ID NO 472
<211> LENGTH: 6
<212> TYPE: PRT
<213> ORGANISM: Homo sapiens

<400> SEQUENCE: 472

Glu Gln Leu Asn Leu Arg
1               5

<210> SEQ ID NO 473
<211> LENGTH: 23
<212> TYPE: PRT
<213> ORGANISM: Homo sapiens

<400> SEQUENCE: 473

Thr Arg Gln Asn Gly Glu Ala Val Lys Thr His Thr Asn Ile Ser Glu
```

```
                1               5                   10                  15

Ser His Pro Asn Ala Thr Phe
                20

<210> SEQ ID NO 474
<211> LENGTH: 18
<212> TYPE: PRT
<213> ORGANISM: Homo sapiens

<400> SEQUENCE: 474

Val Ser Cys Glu Asn Ser Pro Ser Asp Thr Ser Ser Val Ala Val Gly
1               5                   10                  15

Cys Leu

<210> SEQ ID NO 475
<211> LENGTH: 16
<212> TYPE: PRT
<213> ORGANISM: Homo sapiens

<400> SEQUENCE: 475

Lys Asn Asn Ser Asp Ile Ser Ser Thr Arg Gly Phe Pro Ser Val Leu
1               5                   10                  15

<210> SEQ ID NO 476
<211> LENGTH: 15
<212> TYPE: PRT
<213> ORGANISM: Homo sapiens

<400> SEQUENCE: 476

Val Thr Ser Ala Pro Met Pro Glu Pro Gln Ala Pro Gly Arg Tyr
1               5                   10                  15

<210> SEQ ID NO 477
<211> LENGTH: 13
<212> TYPE: PRT
<213> ORGANISM: Homo sapiens

<400> SEQUENCE: 477

Thr Cys Thr Val Thr His Thr Asp Leu Pro Ser Pro Leu
1               5                   10

<210> SEQ ID NO 478
<211> LENGTH: 13
<212> TYPE: PRT
<213> ORGANISM: Homo sapiens

<400> SEQUENCE: 478

Ser Ala Val Gly Glu Ala Ser Ile Cys Glu Asp Asp Trp
1               5                   10

<210> SEQ ID NO 479
<211> LENGTH: 12
<212> TYPE: PRT
<213> ORGANISM: Homo sapiens

<400> SEQUENCE: 479

Cys Val Pro Asp Gln Asp Thr Ala Ile Arg Val Phe
1               5                   10

<210> SEQ ID NO 480
<211> LENGTH: 12
<212> TYPE: PRT
<213> ORGANISM: Homo sapiens
```

<400> SEQUENCE: 480

Lys Gln Thr Ile Ser Arg Pro Lys Gly Val Ala Leu
1               5                   10

<210> SEQ ID NO 481
<211> LENGTH: 9
<212> TYPE: PRT
<213> ORGANISM: Homo sapiens

<400> SEQUENCE: 481

Ser Pro Arg Gln Ile Gln Val Ser Trp
1               5

<210> SEQ ID NO 482
<211> LENGTH: 9
<212> TYPE: PRT
<213> ORGANISM: Homo sapiens

<400> SEQUENCE: 482

Thr Cys Arg Val Asp His Arg Gly Leu
1               5

<210> SEQ ID NO 483
<211> LENGTH: 9
<212> TYPE: PRT
<213> ORGANISM: Homo sapiens

<400> SEQUENCE: 483

Arg Glu Ser Ala Thr Ile Thr Cys Leu
1               5

<210> SEQ ID NO 484
<211> LENGTH: 8
<212> TYPE: PRT
<213> ORGANISM: Homo sapiens

<400> SEQUENCE: 484

Leu Pro Pro Ala Arg Glu Gln Leu
1               5

<210> SEQ ID NO 485
<211> LENGTH: 8
<212> TYPE: PRT
<213> ORGANISM: Homo sapiens

<400> SEQUENCE: 485

Gly Asn Pro Arg Lys Ser Lys Leu
1               5

<210> SEQ ID NO 486
<211> LENGTH: 7
<212> TYPE: PRT
<213> ORGANISM: Homo sapiens

<400> SEQUENCE: 486

Thr Val Ser Glu Glu Glu Trp
1               5

<210> SEQ ID NO 487
<211> LENGTH: 7
<212> TYPE: PRT
<213> ORGANISM: Homo sapiens

<400> SEQUENCE: 487

Thr Ile Lys Glu Ser Asp Trp
1               5

<210> SEQ ID NO 488
<211> LENGTH: 8
<212> TYPE: PRT
<213> ORGANISM: Homo sapiens

<400> SEQUENCE: 488

Ser Asp Thr Ala Gly Thr Cys Tyr
1               5

<210> SEQ ID NO 489
<211> LENGTH: 7
<212> TYPE: PRT
<213> ORGANISM: Homo sapiens

<400> SEQUENCE: 489

Asp Ser Val Thr Ile Ser Trp
1               5

<210> SEQ ID NO 490
<211> LENGTH: 7
<212> TYPE: PRT
<213> ORGANISM: Homo sapiens

<400> SEQUENCE: 490

Leu Pro Ser Lys Asp Val Met
1               5

<210> SEQ ID NO 491
<211> LENGTH: 7
<212> TYPE: PRT
<213> ORGANISM: Homo sapiens

<400> SEQUENCE: 491

Val Pro Pro Arg Asp Gly Phe
1               5

<210> SEQ ID NO 492
<211> LENGTH: 6
<212> TYPE: PRT
<213> ORGANISM: Homo sapiens

<400> SEQUENCE: 492

His Arg Pro Asp Val Tyr
1               5

<210> SEQ ID NO 493
<211> LENGTH: 7
<212> TYPE: PRT
<213> ORGANISM: Homo sapiens

<400> SEQUENCE: 493

Gln Gln Asn Ala Ser Ser Met
1               5

<210> SEQ ID NO 494
<211> LENGTH: 7
<212> TYPE: PRT
<213> ORGANISM: Homo sapiens

<400> SEQUENCE: 494

Leu Pro Asp Ser Ile Thr Leu
1               5

<210> SEQ ID NO 495
<211> LENGTH: 7
<212> TYPE: PRT
<213> ORGANISM: Homo sapiens

<400> SEQUENCE: 495

Ile Cys Gln Ala Thr Gly Phe
1               5

<210> SEQ ID NO 496
<211> LENGTH: 6
<212> TYPE: PRT
<213> ORGANISM: Homo sapiens

<400> SEQUENCE: 496

Asn Ser Gly Glu Arg Phe
1               5

<210> SEQ ID NO 497
<211> LENGTH: 21
<212> TYPE: PRT
<213> ORGANISM: Homo sapiens

<400> SEQUENCE: 497

Leu Pro Ser Pro Leu Lys Gln Thr Ile Ser Arg Pro Lys Gly Val Ala
1               5                   10                  15

Leu His Arg Pro Asp
            20

<210> SEQ ID NO 498
<211> LENGTH: 17
<212> TYPE: PRT
<213> ORGANISM: Homo sapiens

<400> SEQUENCE: 498

His Arg Gly Leu Thr Phe Gln Gln Asn Ala Ser Ser Met Cys Val Pro
1               5                   10                  15

Asp

<210> SEQ ID NO 499
<211> LENGTH: 17
<212> TYPE: PRT
<213> ORGANISM: Homo sapiens

<400> SEQUENCE: 499

Lys Ser Thr Gly Lys Pro Thr Leu Tyr Asn Val Ser Leu Val Met Ser
1               5                   10                  15

Asp

<210> SEQ ID NO 500
<211> LENGTH: 15
<212> TYPE: PRT
<213> ORGANISM: Homo sapiens

<400> SEQUENCE: 500

Val Phe Val Gln Trp Met Gln Arg Gly Gln Pro Leu Ser Pro Glu
1               5                   10                  15

<210> SEQ ID NO 501
<211> LENGTH: 16
<212> TYPE: PRT
<213> ORGANISM: Homo sapiens

<400> SEQUENCE: 501

Ser Gly Pro Thr Thr Tyr Lys Val Thr Ser Thr Leu Thr Ile Lys Glu
1               5                   10                  15

<210> SEQ ID NO 502
<211> LENGTH: 14
<212> TYPE: PRT
<213> ORGANISM: Homo sapiens

<400> SEQUENCE: 502

His Val Val Cys Lys Val Gln His Pro Asn Gly Asn Lys Glu
1               5                   10

<210> SEQ ID NO 503
<211> LENGTH: 13
<212> TYPE: PRT
<213> ORGANISM: Homo sapiens

<400> SEQUENCE: 503

Ser Ile Thr Leu Ser Trp Lys Tyr Lys Asn Asn Ser Asp
1               5                   10

<210> SEQ ID NO 504
<211> LENGTH: 15
<212> TYPE: PRT
<213> ORGANISM: Homo sapiens

<400> SEQUENCE: 504

Ser Ala Thr Ile Thr Cys Leu Val Thr Gly Phe Ser Pro Ala Asp
1               5                   10                  15

<210> SEQ ID NO 505
<211> LENGTH: 13
<212> TYPE: PRT
<213> ORGANISM: Homo sapiens

<400> SEQUENCE: 505

Leu Pro Pro Lys Val Ser Val Phe Val Pro Pro Arg Asp
1               5                   10

<210> SEQ ID NO 506
<211> LENGTH: 12
<212> TYPE: PRT
<213> ORGANISM: Homo sapiens

<400> SEQUENCE: 506

Trp Leu Gly Gln Ser Met Phe Thr Cys Arg Val Asp
1               5                   10

<210> SEQ ID NO 507
<211> LENGTH: 12
<212> TYPE: PRT
<213> ORGANISM: Homo sapiens

<400> SEQUENCE: 507

Ser Val Thr Ile Ser Trp Thr Arg Gln Asn Gly Glu
1               5                   10

<210> SEQ ID NO 508
<211> LENGTH: 12
<212> TYPE: PRT
<213> ORGANISM: Homo sapiens

<400> SEQUENCE: 508

Ser His Pro Asn Ala Thr Phe Ser Ala Val Gly Glu
1               5                   10

<210> SEQ ID NO 509
<211> LENGTH: 10
<212> TYPE: PRT
<213> ORGANISM: Homo sapiens

<400> SEQUENCE: 509

Arg Phe Thr Cys Thr Val Thr His Thr Asp
1               5                   10

<210> SEQ ID NO 510
<211> LENGTH: 12
<212> TYPE: PRT
<213> ORGANISM: Homo sapiens

<400> SEQUENCE: 510

Thr Ser Ser Val Ala Val Gly Cys Leu Ala Gln Asp
1               5                   10

<210> SEQ ID NO 511
<211> LENGTH: 10
<212> TYPE: PRT
<213> ORGANISM: Homo sapiens

<400> SEQUENCE: 511

Ala Val Lys Thr His Thr Asn Ile Ser Glu
1               5                   10

<210> SEQ ID NO 512
<211> LENGTH: 10
<212> TYPE: PRT
<213> ORGANISM: Homo sapiens

<400> SEQUENCE: 512

Lys Asn Val Pro Leu Pro Val Ile Ala Glu
1               5                   10

<210> SEQ ID NO 513
<211> LENGTH: 9
<212> TYPE: PRT
<213> ORGANISM: Homo sapiens

<400> SEQUENCE: 513

Val Tyr Leu Leu Pro Pro Ala Arg Glu
1               5

<210> SEQ ID NO 514
<211> LENGTH: 11
<212> TYPE: PRT
<213> ORGANISM: Homo sapiens

<400> SEQUENCE: 514

Gly Lys Gln Val Gly Ser Gly Val Thr Thr Asp
1               5                   10

<210> SEQ ID NO 515
<211> LENGTH: 8
<212> TYPE: PRT
<213> ORGANISM: Homo sapiens

<400> SEQUENCE: 515

Thr Tyr Thr Cys Val Ala His Glu
1               5

```
1               5
```

<210> SEQ ID NO 516
<211> LENGTH: 8
<212> TYPE: PRT
<213> ORGANISM: Homo sapiens

<400> SEQUENCE: 516

```
Ala Leu Pro Asn Arg Val Thr Glu
1               5
```

<210> SEQ ID NO 517
<211> LENGTH: 7
<212> TYPE: PRT
<213> ORGANISM: Homo sapiens

<400> SEQUENCE: 517

```
Val Met Gln Gly Thr Asp Glu
1               5
```

<210> SEQ ID NO 518
<211> LENGTH: 6
<212> TYPE: PRT
<213> ORGANISM: Homo sapiens

<400> SEQUENCE: 518

```
Gln Leu Asn Leu Arg Glu
1               5
```

<210> SEQ ID NO 519
<211> LENGTH: 16
<212> TYPE: PRT
<213> ORGANISM: Homo sapiens

<400> SEQUENCE: 519

```
Ser Gly Pro Thr Thr Tyr Lys Val Thr Ser Thr Leu Thr Ile Lys Glu
1               5                   10                  15
```

<210> SEQ ID NO 520
<211> LENGTH: 16
<212> TYPE: PRT
<213> ORGANISM: Homo sapiens

<400> SEQUENCE: 520

```
Gly Lys Gln Val Gly Ser Gly Val Thr Thr Asp Gln Val Gln Ala Glu
1               5                   10                  15
```

<210> SEQ ID NO 521
<211> LENGTH: 14
<212> TYPE: PRT
<213> ORGANISM: Homo sapiens

<400> SEQUENCE: 521

```
His Val Val Cys Lys Val Gln His Pro Asn Gly Asn Lys Glu
1               5                   10
```

<210> SEQ ID NO 522
<211> LENGTH: 15
<212> TYPE: PRT
<213> ORGANISM: Homo sapiens

<400> SEQUENCE: 522

```
Gly Ser Ala Ser Ala Pro Thr Leu Phe Pro Leu Val Ser Cys Glu
1               5                   10                  15
```

<210> SEQ ID NO 523
<211> LENGTH: 12
<212> TYPE: PRT
<213> ORGANISM: Homo sapiens

<400> SEQUENCE: 523

Ser His Pro Asn Ala Thr Phe Ser Ala Val Gly Glu
1               5                   10

<210> SEQ ID NO 524
<211> LENGTH: 10
<212> TYPE: PRT
<213> ORGANISM: Homo sapiens

<400> SEQUENCE: 524

Ala Val Lys Thr His Thr Asn Ile Ser Glu
1               5                   10

<210> SEQ ID NO 525
<211> LENGTH: 10
<212> TYPE: PRT
<213> ORGANISM: Homo sapiens

<400> SEQUENCE: 525

Lys Asn Val Pro Leu Pro Val Ile Ala Glu
1               5                   10

<210> SEQ ID NO 526
<211> LENGTH: 8
<212> TYPE: PRT
<213> ORGANISM: Homo sapiens

<400> SEQUENCE: 526

Thr Tyr Thr Cys Val Ala His Glu
1               5

<210> SEQ ID NO 527
<211> LENGTH: 8
<212> TYPE: PRT
<213> ORGANISM: Homo sapiens

<400> SEQUENCE: 527

Ala Leu Pro Asn Arg Val Thr Glu
1               5

<210> SEQ ID NO 528
<211> LENGTH: 7
<212> TYPE: PRT
<213> ORGANISM: Homo sapiens

<400> SEQUENCE: 528

Asp Asp Trp Asn Ser Gly Glu
1               5

<210> SEQ ID NO 529
<211> LENGTH: 6
<212> TYPE: PRT
<213> ORGANISM: Homo sapiens

<400> SEQUENCE: 529

Gln Leu Asn Leu Arg Glu
1               5

<210> SEQ ID NO 530

<211> LENGTH: 21
<212> TYPE: PRT
<213> ORGANISM: Homo sapiens

<400> SEQUENCE: 530

Asp Leu Pro Ser Pro Leu Lys Gln Thr Ile Ser Arg Pro Lys Gly Val
1               5                   10                  15

Ala Leu His Arg Pro
            20

<210> SEQ ID NO 531
<211> LENGTH: 17
<212> TYPE: PRT
<213> ORGANISM: Homo sapiens

<400> SEQUENCE: 531

Asp His Arg Gly Leu Thr Phe Gln Gln Asn Ala Ser Ser Met Cys Val
1               5                   10                  15

Pro

<210> SEQ ID NO 532
<211> LENGTH: 17
<212> TYPE: PRT
<213> ORGANISM: Homo sapiens

<400> SEQUENCE: 532

Asp Lys Ser Thr Gly Lys Pro Thr Leu Tyr Asn Val Ser Leu Val Met
1               5                   10                  15

Ser

<210> SEQ ID NO 533
<211> LENGTH: 15
<212> TYPE: PRT
<213> ORGANISM: Homo sapiens

<400> SEQUENCE: 533

Asp Trp Asn Ser Gly Glu Arg Phe Thr Cys Thr Val Thr His Thr
1               5                   10                  15

<210> SEQ ID NO 534
<211> LENGTH: 13
<212> TYPE: PRT
<213> ORGANISM: Homo sapiens

<400> SEQUENCE: 534

Asp Ser Ile Thr Leu Ser Trp Lys Tyr Lys Asn Asn Ser
1               5                   10

<210> SEQ ID NO 535
<211> LENGTH: 12
<212> TYPE: PRT
<213> ORGANISM: Homo sapiens

<400> SEQUENCE: 535

Asp Trp Leu Gly Gln Ser Met Phe Thr Cys Arg Val
1               5                   10

<210> SEQ ID NO 536
<211> LENGTH: 12
<212> TYPE: PRT
<213> ORGANISM: Homo sapiens

<400> SEQUENCE: 536

-continued

Asp Thr Ser Ser Val Ala Val Gly Cys Leu Ala Gln
1               5                   10

<210> SEQ ID NO 537
<211> LENGTH: 7
<212> TYPE: PRT
<213> ORGANISM: Homo sapiens

<400> SEQUENCE: 537

Asp Thr Ala Gly Thr Cys Tyr
1               5

<210> SEQ ID NO 538
<211> LENGTH: 22
<212> TYPE: PRT
<213> ORGANISM: Homo sapiens

<400> SEQUENCE: 538

Ser Leu Trp Asn Ala Gly Thr Ser Val Thr Cys Thr Leu Asn His Pro
1               5                   10                  15

Ser Leu Pro Pro Gln Arg
            20

<210> SEQ ID NO 539
<211> LENGTH: 22
<212> TYPE: PRT
<213> ORGANISM: Homo sapiens

<400> SEQUENCE: 539

Val Pro Ala Pro Pro Ser Pro Gln Pro Ala Thr Tyr Thr Cys Val Val
1               5                   10                  15

Ser His Glu Asp Ser Arg
            20

<210> SEQ ID NO 540
<211> LENGTH: 18
<212> TYPE: PRT
<213> ORGANISM: Homo sapiens

<400> SEQUENCE: 540

Asp Ser Tyr Tyr Met Thr Ser Gln Leu Ser Thr Pro Leu Gln Gln
1               5                   10                  15

Trp Arg

<210> SEQ ID NO 541
<211> LENGTH: 19
<212> TYPE: PRT
<213> ORGANISM: Homo sapiens

<400> SEQUENCE: 541

Ala Gln Ala Ser Ser Val Pro Thr Ala Gln Pro Gln Ala Glu Gly Ser
1               5                   10                  15

Leu Ala Lys

<210> SEQ ID NO 542
<211> LENGTH: 14
<212> TYPE: PRT
<213> ORGANISM: Homo sapiens

<400> SEQUENCE: 542

Ser Leu Glu Val Ser Tyr Val Thr Asp His Gly Pro Met Lys
1               5                   10

```
<210> SEQ ID NO 543
<211> LENGTH: 13
<212> TYPE: PRT
<213> ORGANISM: Homo sapiens

<400> SEQUENCE: 543

Ala Thr Phe Thr Cys Phe Val Val Gly Ser Asp Leu Lys
1               5                   10

<210> SEQ ID NO 544
<211> LENGTH: 13
<212> TYPE: PRT
<213> ORGANISM: Homo sapiens

<400> SEQUENCE: 544

Val Pro Thr Gly Gly Val Glu Glu Gly Leu Leu Glu Arg
1               5                   10

<210> SEQ ID NO 545
<211> LENGTH: 12
<212> TYPE: PRT
<213> ORGANISM: Homo sapiens

<400> SEQUENCE: 545

Ala Pro Asp Val Phe Pro Ile Ile Ser Gly Cys Arg
1               5                   10

<210> SEQ ID NO 546
<211> LENGTH: 11
<212> TYPE: PRT
<213> ORGANISM: Homo sapiens

<400> SEQUENCE: 546

Asp Ala His Leu Thr Trp Glu Val Ala Gly Lys
1               5                   10

<210> SEQ ID NO 547
<211> LENGTH: 11
<212> TYPE: PRT
<213> ORGANISM: Homo sapiens

<400> SEQUENCE: 547

His Ser Asn Gly Ser Gln Ser Gln His Ser Arg
1               5                   10

<210> SEQ ID NO 548
<211> LENGTH: 9
<212> TYPE: PRT
<213> ORGANISM: Homo sapiens

<400> SEQUENCE: 548

Cys Val Val Gln His Thr Ala Ser Lys
1               5

<210> SEQ ID NO 549
<211> LENGTH: 7
<212> TYPE: PRT
<213> ORGANISM: Homo sapiens

<400> SEQUENCE: 549

Thr Phe Pro Glu Ile Gln Arg
1               5

<210> SEQ ID NO 550
```

<211> LENGTH: 9
<212> TYPE: PRT
<213> ORGANISM: Homo sapiens

<400> SEQUENCE: 550

Ala Thr Thr Ala Pro Ala Thr Thr Arg
1               5

<210> SEQ ID NO 551
<211> LENGTH: 6
<212> TYPE: PRT
<213> ORGANISM: Homo sapiens

<400> SEQUENCE: 551

Glu Glu Gln Glu Glu Arg
1               5

<210> SEQ ID NO 552
<211> LENGTH: 7
<212> TYPE: PRT
<213> ORGANISM: Homo sapiens

<400> SEQUENCE: 552

Thr Leu Leu Asn Ala Ser Arg
1               5

<210> SEQ ID NO 553
<211> LENGTH: 6
<212> TYPE: PRT
<213> ORGANISM: Homo sapiens

<400> SEQUENCE: 553

Trp Pro Glu Ser Pro Lys
1               5

<210> SEQ ID NO 554
<211> LENGTH: 19
<212> TYPE: PRT
<213> ORGANISM: Homo sapiens

<400> SEQUENCE: 554

Ala Gln Ala Ser Ser Val Pro Thr Ala Gln Pro Gln Ala Glu Gly Ser
1               5                   10                  15
Leu Ala Lys

<210> SEQ ID NO 555
<211> LENGTH: 18
<212> TYPE: PRT
<213> ORGANISM: Homo sapiens

<400> SEQUENCE: 555

Ala Thr Thr Ala Pro Ala Thr Thr Arg Asn Thr Gly Arg Gly Gly Glu
1               5                   10                  15
Glu Lys

<210> SEQ ID NO 556
<211> LENGTH: 15
<212> TYPE: PRT
<213> ORGANISM: Homo sapiens

<400> SEQUENCE: 556

Ala Pro Asp Val Phe Pro Ile Ile Ser Gly Cys Arg His Pro Lys
1               5                   10                  15

```
<210> SEQ ID NO 557
<211> LENGTH: 13
<212> TYPE: PRT
<213> ORGANISM: Homo sapiens

<400> SEQUENCE: 557

Ala Thr Phe Thr Cys Phe Val Val Gly Ser Asp Leu Lys
1               5                   10

<210> SEQ ID NO 558
<211> LENGTH: 10
<212> TYPE: PRT
<213> ORGANISM: Homo sapiens

<400> SEQUENCE: 558

Glu Ile Phe Arg Trp Pro Glu Ser Pro Lys
1               5                   10

<210> SEQ ID NO 559
<211> LENGTH: 11
<212> TYPE: PRT
<213> ORGANISM: Homo sapiens

<400> SEQUENCE: 559

Asp Ala His Leu Thr Trp Glu Val Ala Gly Lys
1               5                   10

<210> SEQ ID NO 560
<211> LENGTH: 9
<212> TYPE: PRT
<213> ORGANISM: Homo sapiens

<400> SEQUENCE: 560

Glu Glu Gln Glu Glu Arg Glu Thr Lys
1               5

<210> SEQ ID NO 561
<211> LENGTH: 9
<212> TYPE: PRT
<213> ORGANISM: Homo sapiens

<400> SEQUENCE: 561

Cys Val Val Gln His Thr Ala Ser Lys
1               5

<210> SEQ ID NO 562
<211> LENGTH: 21
<212> TYPE: PRT
<213> ORGANISM: Homo sapiens

<400> SEQUENCE: 562

Gln Gly Glu Tyr Lys Cys Val Val Gln His Thr Ala Ser Lys Ser Lys
1               5                   10                  15

Lys Glu Ile Phe Arg
            20

<210> SEQ ID NO 563
<211> LENGTH: 22
<212> TYPE: PRT
<213> ORGANISM: Homo sapiens

<400> SEQUENCE: 563

Ser Leu Trp Asn Ala Gly Thr Ser Val Thr Cys Thr Leu Asn His Pro
1               5                   10                  15
```

Ser Leu Pro Pro Gln Arg
            20

<210> SEQ ID NO 564
<211> LENGTH: 22
<212> TYPE: PRT
<213> ORGANISM: Homo sapiens

<400> SEQUENCE: 564

Val Pro Ala Pro Pro Ser Pro Gln Pro Ala Thr Tyr Thr Cys Val Val
1               5                   10                  15

Ser His Glu Asp Ser Arg
            20

<210> SEQ ID NO 565
<211> LENGTH: 18
<212> TYPE: PRT
<213> ORGANISM: Homo sapiens

<400> SEQUENCE: 565

Asp Ser Tyr Tyr Met Thr Ser Ser Gln Leu Ser Thr Pro Leu Gln Gln
1               5                   10                  15

Trp Arg

<210> SEQ ID NO 566
<211> LENGTH: 17
<212> TYPE: PRT
<213> ORGANISM: Homo sapiens

<400> SEQUENCE: 566

Gly Gly Glu Glu Lys Lys Lys Glu Lys Glu Lys Glu Glu Gln Glu Glu
1               5                   10                  15

Arg

<210> SEQ ID NO 567
<211> LENGTH: 14
<212> TYPE: PRT
<213> ORGANISM: Homo sapiens

<400> SEQUENCE: 567

Ser Leu Glu Val Ser Tyr Val Thr Asp His Gly Pro Met Lys
1               5                   10

<210> SEQ ID NO 568
<211> LENGTH: 11
<212> TYPE: PRT
<213> ORGANISM: Homo sapiens

<400> SEQUENCE: 568

His Ser Asn Gly Ser Gln Ser Gln His Ser Arg
1               5                   10

<210> SEQ ID NO 569
<211> LENGTH: 7
<212> TYPE: PRT
<213> ORGANISM: Homo sapiens

<400> SEQUENCE: 569

Thr Phe Pro Glu Ile Gln Arg
1               5

<210> SEQ ID NO 570

```
<211> LENGTH: 7
<212> TYPE: PRT
<213> ORGANISM: Homo sapiens

<400> SEQUENCE: 570

Thr Leu Leu Asn Ala Ser Arg
1               5

<210> SEQ ID NO 571
<211> LENGTH: 24
<212> TYPE: PRT
<213> ORGANISM: Homo sapiens

<400> SEQUENCE: 571

Arg Trp Pro Glu Ser Pro Lys Ala Gln Ala Ser Ser Val Pro Thr Ala
1               5                   10                  15

Gln Pro Gln Ala Glu Gly Ser Leu
            20

<210> SEQ ID NO 572
<211> LENGTH: 19
<212> TYPE: PRT
<213> ORGANISM: Homo sapiens

<400> SEQUENCE: 572

Gly Thr Gln Ser Gln Pro Gln Arg Thr Phe Pro Glu Ile Gln Arg Arg
1               5                   10                  15

Asp Ser Tyr

<210> SEQ ID NO 573
<211> LENGTH: 16
<212> TYPE: PRT
<213> ORGANISM: Homo sapiens

<400> SEQUENCE: 573

Lys Cys Val Val Gln His Thr Ala Ser Lys Ser Lys Lys Glu Ile Phe
1               5                   10                  15

<210> SEQ ID NO 574
<211> LENGTH: 14
<212> TYPE: PRT
<213> ORGANISM: Homo sapiens

<400> SEQUENCE: 574

Glu Arg His Ser Asn Gly Ser Gln Ser Gln His Ser Arg Leu
1               5                   10

<210> SEQ ID NO 575
<211> LENGTH: 15
<212> TYPE: PRT
<213> ORGANISM: Homo sapiens

<400> SEQUENCE: 575

Glu Val Ala Gly Lys Val Pro Thr Gly Gly Val Glu Glu Gly Leu
1               5                   10                  15

<210> SEQ ID NO 576
<211> LENGTH: 14
<212> TYPE: PRT
<213> ORGANISM: Homo sapiens

<400> SEQUENCE: 576

Ala Pro Ala Arg Pro Pro Gln Pro Gly Ser Thr Thr Phe
1               5                   10
```

```
<210> SEQ ID NO 577
<211> LENGTH: 13
<212> TYPE: PRT
<213> ORGANISM: Homo sapiens

<400> SEQUENCE: 577

Arg Val Pro Ala Pro Ser Pro Gln Pro Ala Thr Tyr
1               5                   10

<210> SEQ ID NO 578
<211> LENGTH: 12
<212> TYPE: PRT
<213> ORGANISM: Homo sapiens

<400> SEQUENCE: 578

Thr Cys Val Val Ser His Glu Asp Ser Arg Thr Leu
1               5                   10

<210> SEQ ID NO 579
<211> LENGTH: 11
<212> TYPE: PRT
<213> ORGANISM: Homo sapiens

<400> SEQUENCE: 579

Glu Asp Gln Arg Glu Val Asn Thr Ser Gly Phe
1               5                   10

<210> SEQ ID NO 580
<211> LENGTH: 11
<212> TYPE: PRT
<213> ORGANISM: Homo sapiens

<400> SEQUENCE: 580

Arg Glu Pro Ala Ala Gln Ala Pro Val Lys Leu
1               5                   10

<210> SEQ ID NO 581
<211> LENGTH: 10
<212> TYPE: PRT
<213> ORGANISM: Homo sapiens

<400> SEQUENCE: 581

Asn His Pro Ser Leu Pro Pro Gln Arg Leu
1               5                   10

<210> SEQ ID NO 582
<211> LENGTH: 11
<212> TYPE: PRT
<213> ORGANISM: Homo sapiens

<400> SEQUENCE: 582

Ala Ser Ser Asp Pro Pro Glu Ala Ala Ser Trp
1               5                   10

<210> SEQ ID NO 583
<211> LENGTH: 9
<212> TYPE: PRT
<213> ORGANISM: Homo sapiens

<400> SEQUENCE: 583

His Pro Thr Ser Val Thr Val Thr Trp
1               5
```

```
<210> SEQ ID NO 584
<211> LENGTH: 10
<212> TYPE: PRT
<213> ORGANISM: Homo sapiens

<400> SEQUENCE: 584

Asn Ala Gly Thr Ser Val Thr Cys Thr Leu
1               5                   10

<210> SEQ ID NO 585
<211> LENGTH: 7
<212> TYPE: PRT
<213> ORGANISM: Homo sapiens

<400> SEQUENCE: 585

Val Thr Asp His Gly Pro Met
1               5

<210> SEQ ID NO 586
<211> LENGTH: 7
<212> TYPE: PRT
<213> ORGANISM: Homo sapiens

<400> SEQUENCE: 586

Thr Pro Ala Val Gln Asp Leu
1               5

<210> SEQ ID NO 587
<211> LENGTH: 6
<212> TYPE: PRT
<213> ORGANISM: Homo sapiens

<400> SEQUENCE: 587

Arg Asp Lys Ala Thr Phe
1               5

<210> SEQ ID NO 588
<211> LENGTH: 20
<212> TYPE: PRT
<213> ORGANISM: Homo sapiens

<400> SEQUENCE: 588

Ser Tyr Tyr Met Thr Ser Ser Gln Leu Ser Thr Pro Leu Gln Gln Trp
1               5                   10                  15

Arg Gln Gly Glu
            20

<210> SEQ ID NO 589
<211> LENGTH: 22
<212> TYPE: PRT
<213> ORGANISM: Homo sapiens

<400> SEQUENCE: 589

Gly Ser Leu Ala Lys Ala Thr Thr Ala Pro Ala Thr Thr Arg Asn Thr
1               5                   10                  15

Gly Arg Gly Gly Glu Glu
            20

<210> SEQ ID NO 590
<211> LENGTH: 19
<212> TYPE: PRT
<213> ORGANISM: Homo sapiens

<400> SEQUENCE: 590
```

```
Cys Pro Ser His Thr Gln Pro Leu Gly Val Tyr Leu Leu Thr Pro Ala
1               5                   10                  15

Val Gln Asp

<210> SEQ ID NO 591
<211> LENGTH: 15
<212> TYPE: PRT
<213> ORGANISM: Homo sapiens

<400> SEQUENCE: 591

Tyr Lys Cys Val Val Gln His Thr Ala Ser Lys Ser Lys Lys Glu
1               5                   10                  15

<210> SEQ ID NO 592
<211> LENGTH: 15
<212> TYPE: PRT
<213> ORGANISM: Homo sapiens

<400> SEQUENCE: 592

Val Ser Gly Phe Ser Pro Pro Asn Ile Leu Leu Met Trp Leu Glu
1               5                   10                  15

<210> SEQ ID NO 593
<211> LENGTH: 17
<212> TYPE: PRT
<213> ORGANISM: Homo sapiens

<400> SEQUENCE: 593

Ser Pro Lys Ala Gln Ala Ser Ser Val Pro Thr Ala Gln Pro Gln Ala
1               5                   10                  15

Glu

<210> SEQ ID NO 594
<211> LENGTH: 13
<212> TYPE: PRT
<213> ORGANISM: Homo sapiens

<400> SEQUENCE: 594

Val Phe Pro Ile Ile Ser Gly Cys Arg His Pro Lys Asp
1               5                   10

<210> SEQ ID NO 595
<211> LENGTH: 12
<212> TYPE: PRT
<213> ORGANISM: Homo sapiens

<400> SEQUENCE: 595

Ser Arg Thr Leu Leu Asn Ala Ser Arg Ser Leu Glu
1               5                   10

<210> SEQ ID NO 596
<211> LENGTH: 12
<212> TYPE: PRT
<213> ORGANISM: Homo sapiens

<400> SEQUENCE: 596

Lys Ala Thr Phe Thr Cys Phe Val Val Gly Ser Asp
1               5                   10

<210> SEQ ID NO 597
<211> LENGTH: 12
<212> TYPE: PRT
<213> ORGANISM: Homo sapiens
```

```
<400> SEQUENCE: 597

Val Ala Gly Lys Val Pro Thr Gly Gly Val Glu Glu
1               5                   10

<210> SEQ ID NO 598
<211> LENGTH: 8
<212> TYPE: PRT
<213> ORGANISM: Homo sapiens

<400> SEQUENCE: 598

Ala Ala Ser Trp Leu Leu Cys Glu
1               5

<210> SEQ ID NO 599
<211> LENGTH: 6
<212> TYPE: PRT
<213> ORGANISM: Homo sapiens

<400> SEQUENCE: 599

Ile Phe Arg Trp Pro Glu
1               5

<210> SEQ ID NO 600
<211> LENGTH: 6
<212> TYPE: PRT
<213> ORGANISM: Homo sapiens

<400> SEQUENCE: 600

Ala His Leu Thr Trp Glu
1               5

<210> SEQ ID NO 601
<211> LENGTH: 22
<212> TYPE: PRT
<213> ORGANISM: Homo sapiens

<400> SEQUENCE: 601

Gly Ser Leu Ala Lys Ala Thr Thr Ala Pro Ala Thr Thr Arg Asn Thr
1               5                   10                  15

Gly Arg Gly Gly Glu Glu
            20

<210> SEQ ID NO 602
<211> LENGTH: 15
<212> TYPE: PRT
<213> ORGANISM: Homo sapiens

<400> SEQUENCE: 602

Tyr Lys Cys Val Val Gln His Thr Ala Ser Lys Ser Lys Lys Glu
1               5                   10                  15

<210> SEQ ID NO 603
<211> LENGTH: 15
<212> TYPE: PRT
<213> ORGANISM: Homo sapiens

<400> SEQUENCE: 603

Val Ser Gly Phe Ser Pro Pro Asn Ile Leu Leu Met Trp Leu Glu
1               5                   10                  15

<210> SEQ ID NO 604
<211> LENGTH: 17
<212> TYPE: PRT
<213> ORGANISM: Homo sapiens
```

<400> SEQUENCE: 604

Ser Pro Lys Ala Gln Ala Ser Ser Val Pro Thr Ala Gln Pro Gln Ala
1               5                   10                  15

Glu

<210> SEQ ID NO 605
<211> LENGTH: 13
<212> TYPE: PRT
<213> ORGANISM: Homo sapiens

<400> SEQUENCE: 605

Asp Ser Arg Thr Leu Leu Asn Ala Ser Arg Ser Leu Glu
1               5                   10

<210> SEQ ID NO 606
<211> LENGTH: 11
<212> TYPE: PRT
<213> ORGANISM: Homo sapiens

<400> SEQUENCE: 606

Val Ser Tyr Val Thr Asp His Gly Pro Met Lys
1               5                   10

<210> SEQ ID NO 607
<211> LENGTH: 12
<212> TYPE: PRT
<213> ORGANISM: Homo sapiens

<400> SEQUENCE: 607

Val Ala Gly Lys Val Pro Thr Gly Gly Val Glu Glu
1               5                   10

<210> SEQ ID NO 608
<211> LENGTH: 8
<212> TYPE: PRT
<213> ORGANISM: Homo sapiens

<400> SEQUENCE: 608

Ala Ala Ser Trp Leu Leu Cys Glu
1               5

<210> SEQ ID NO 609
<211> LENGTH: 18
<212> TYPE: PRT
<213> ORGANISM: Homo sapiens

<400> SEQUENCE: 609

Asp Ser Arg Thr Leu Leu Asn Ala Ser Arg Ser Leu Glu Val Ser Tyr
1               5                   10                  15

Val Thr

<210> SEQ ID NO 610
<211> LENGTH: 13
<212> TYPE: PRT
<213> ORGANISM: Homo sapiens

<400> SEQUENCE: 610

Asp Val Phe Pro Ile Ile Ser Gly Cys Arg His Pro Lys
1               5                   10

<210> SEQ ID NO 611
<211> LENGTH: 12

```
<212> TYPE: PRT
<213> ORGANISM: Homo sapiens

<400> SEQUENCE: 611

Asp Lys Ala Thr Phe Thr Cys Phe Val Val Gly Ser
1               5                   10

<210> SEQ ID NO 612
<211> LENGTH: 18
<212> TYPE: PRT
<213> ORGANISM: Homo sapiens

<400> SEQUENCE: 612

Thr Tyr Thr Cys Gln Val Thr Tyr Gln Gly His Thr Phe Glu Asp Ser
1               5                   10                  15

Thr Lys

<210> SEQ ID NO 613
<211> LENGTH: 17
<212> TYPE: PRT
<213> ORGANISM: Homo sapiens

<400> SEQUENCE: 613

Gly Val Ser Ala Tyr Leu Ser Arg Pro Ser Pro Phe Asp Leu Phe Ile
1               5                   10                  15

Arg

<210> SEQ ID NO 614
<211> LENGTH: 17
<212> TYPE: PRT
<213> ORGANISM: Homo sapiens

<400> SEQUENCE: 614

Ala Ala Pro Glu Val Tyr Ala Phe Ala Thr Pro Glu Trp Pro Gly Ser
1               5                   10                  15

Arg

<210> SEQ ID NO 615
<211> LENGTH: 14
<212> TYPE: PRT
<213> ORGANISM: Homo sapiens

<400> SEQUENCE: 615

Val Ala His Thr Pro Ser Ser Thr Asp Trp Val Asp Asn Lys
1               5                   10

<210> SEQ ID NO 616
<211> LENGTH: 15
<212> TYPE: PRT
<213> ORGANISM: Homo sapiens

<400> SEQUENCE: 616

Ser Pro Thr Ile Thr Cys Leu Val Val Asp Leu Ala Pro Ser Lys
1               5                   10                  15

<210> SEQ ID NO 617
<211> LENGTH: 15
<212> TYPE: PRT
<213> ORGANISM: Homo sapiens

<400> SEQUENCE: 617

Asn Gly Thr Leu Thr Val Thr Ser Thr Leu Pro Val Gly Thr Arg
1               5                   10                  15
```

<210> SEQ ID NO 618
<211> LENGTH: 14
<212> TYPE: PRT
<213> ORGANISM: Homo sapiens

<400> SEQUENCE: 618

Ala Val His Glu Ala Ala Ser Pro Ser Gln Thr Val Gln Arg
1               5                   10

<210> SEQ ID NO 619
<211> LENGTH: 11
<212> TYPE: PRT
<213> ORGANISM: Homo sapiens

<400> SEQUENCE: 619

Asp Trp Ile Glu Gly Glu Thr Tyr Gln Cys Arg
1               5                   10

<210> SEQ ID NO 620
<211> LENGTH: 11
<212> TYPE: PRT
<213> ORGANISM: Homo sapiens

<400> SEQUENCE: 620

Ala Ser Gly Lys Pro Val Asn His Ser Thr Arg
1               5                   10

<210> SEQ ID NO 621
<211> LENGTH: 9
<212> TYPE: PRT
<213> ORGANISM: Homo sapiens

<400> SEQUENCE: 621

Gly Thr Val Asn Leu Thr Trp Ser Arg
1               5

<210> SEQ ID NO 622
<211> LENGTH: 8
<212> TYPE: PRT
<213> ORGANISM: Homo sapiens

<400> SEQUENCE: 622

Val Thr His Pro His Leu Pro Arg
1               5

<210> SEQ ID NO 623
<211> LENGTH: 8
<212> TYPE: PRT
<213> ORGANISM: Homo sapiens

<400> SEQUENCE: 623

Asp Phe Thr Pro Pro Thr Val Lys
1               5

<210> SEQ ID NO 624
<211> LENGTH: 7
<212> TYPE: PRT
<213> ORGANISM: Homo sapiens

<400> SEQUENCE: 624

His Ser Thr Thr Gln Pro Arg
1               5

```
<210> SEQ ID NO 625
<211> LENGTH: 6
<212> TYPE: PRT
<213> ORGANISM: Homo sapiens

<400> SEQUENCE: 625

His Trp Leu Ser Asp Arg
1               5

<210> SEQ ID NO 626
<211> LENGTH: 7
<212> TYPE: PRT
<213> ORGANISM: Homo sapiens

<400> SEQUENCE: 626

Thr Phe Ser Val Cys Ser Arg
1               5

<210> SEQ ID NO 627
<211> LENGTH: 6
<212> TYPE: PRT
<213> ORGANISM: Homo sapiens

<400> SEQUENCE: 627

Ala Glu Trp Glu Gln Lys
1               5

<210> SEQ ID NO 628
<211> LENGTH: 6
<212> TYPE: PRT
<213> ORGANISM: Homo sapiens

<400> SEQUENCE: 628

Gln Met Phe Thr Cys Arg
1               5

<210> SEQ ID NO 629
<211> LENGTH: 6
<212> TYPE: PRT
<213> ORGANISM: Homo sapiens

<400> SEQUENCE: 629

Asp Glu Phe Ile Cys Arg
1               5

<210> SEQ ID NO 630
<211> LENGTH: 8
<212> TYPE: PRT
<213> ORGANISM: Homo sapiens

<400> SEQUENCE: 630

Ala Val Ser Val Asn Pro Gly Lys
1               5

<210> SEQ ID NO 631
<211> LENGTH: 7
<212> TYPE: PRT
<213> ORGANISM: Homo sapiens

<400> SEQUENCE: 631

Cys Ala Asp Ser Asn Pro Arg
1               5

<210> SEQ ID NO 632
<211> LENGTH: 24
```

<212> TYPE: PRT
<213> ORGANISM: Homo sapiens

<400> SEQUENCE: 632

Thr Ser Gly Pro Arg Ala Ala Pro Glu Val Tyr Ala Phe Ala Thr Pro
1               5                   10                  15

Glu Trp Pro Gly Ser Arg Asp Lys
            20

<210> SEQ ID NO 633
<211> LENGTH: 20
<212> TYPE: PRT
<213> ORGANISM: Homo sapiens

<400> SEQUENCE: 633

Gly Ser Gly Phe Phe Val Phe Ser Arg Leu Glu Val Thr Arg Ala Glu
1               5                   10                  15

Trp Glu Gln Lys
            20

<210> SEQ ID NO 634
<211> LENGTH: 20
<212> TYPE: PRT
<213> ORGANISM: Homo sapiens

<400> SEQUENCE: 634

Gln Met Phe Thr Cys Arg Val Ala His Thr Pro Ser Thr Asp Trp
1               5                   10                  15

Val Asp Asn Lys
            20

<210> SEQ ID NO 635
<211> LENGTH: 15
<212> TYPE: PRT
<213> ORGANISM: Homo sapiens

<400> SEQUENCE: 635

Thr Phe Ser Val Cys Ser Arg Asp Phe Thr Pro Pro Thr Val Lys
1               5                   10                  15

<210> SEQ ID NO 636
<211> LENGTH: 15
<212> TYPE: PRT
<213> ORGANISM: Homo sapiens

<400> SEQUENCE: 636

Ser Pro Thr Ile Thr Cys Leu Val Val Asp Leu Ala Pro Ser Lys
1               5                   10                  15

<210> SEQ ID NO 637
<211> LENGTH: 13
<212> TYPE: PRT
<213> ORGANISM: Homo sapiens

<400> SEQUENCE: 637

Gly Thr Val Asn Leu Thr Trp Ser Arg Ala Ser Gly Lys
1               5                   10

<210> SEQ ID NO 638
<211> LENGTH: 8
<212> TYPE: PRT
<213> ORGANISM: Homo sapiens

<400> SEQUENCE: 638

```
Pro Val Asn His Ser Thr Arg Lys
1               5

<210> SEQ ID NO 639
<211> LENGTH: 21
<212> TYPE: PRT
<213> ORGANISM: Homo sapiens

<400> SEQUENCE: 639

Val Ala His Thr Pro Ser Ser Thr Asp Trp Val Asp Asn Lys Thr Phe
1               5                   10                  15

Ser Val Cys Ser Arg
            20

<210> SEQ ID NO 640
<211> LENGTH: 17
<212> TYPE: PRT
<213> ORGANISM: Homo sapiens

<400> SEQUENCE: 640

Gly Val Ser Ala Tyr Leu Ser Arg Pro Ser Pro Phe Asp Leu Phe Ile
1               5                   10                  15

Arg

<210> SEQ ID NO 641
<211> LENGTH: 17
<212> TYPE: PRT
<213> ORGANISM: Homo sapiens

<400> SEQUENCE: 641

Ala Ala Pro Glu Val Tyr Ala Phe Ala Thr Pro Glu Trp Pro Gly Ser
1               5                   10                  15

Arg

<210> SEQ ID NO 642
<211> LENGTH: 12
<212> TYPE: PRT
<213> ORGANISM: Homo sapiens

<400> SEQUENCE: 642

Ala Glu Trp Glu Gln Lys Asp Glu Phe Ile Cys Arg
1               5                   10

<210> SEQ ID NO 643
<211> LENGTH: 15
<212> TYPE: PRT
<213> ORGANISM: Homo sapiens

<400> SEQUENCE: 643

Asn Gly Thr Leu Thr Val Thr Ser Thr Leu Pro Val Gly Thr Arg
1               5                   10                  15

<210> SEQ ID NO 644
<211> LENGTH: 14
<212> TYPE: PRT
<213> ORGANISM: Homo sapiens

<400> SEQUENCE: 644

Ala Val His Glu Ala Ala Ser Pro Ser Gln Thr Val Gln Arg
1               5                   10

<210> SEQ ID NO 645
```

```
<211> LENGTH: 11
<212> TYPE: PRT
<213> ORGANISM: Homo sapiens

<400> SEQUENCE: 645

Asp Trp Ile Glu Gly Glu Thr Tyr Gln Cys Arg
1               5                   10

<210> SEQ ID NO 646
<211> LENGTH: 12
<212> TYPE: PRT
<213> ORGANISM: Homo sapiens

<400> SEQUENCE: 646

Lys Thr Lys Gly Ser Gly Phe Phe Val Phe Ser Arg
1               5                   10

<210> SEQ ID NO 647
<211> LENGTH: 11
<212> TYPE: PRT
<213> ORGANISM: Homo sapiens

<400> SEQUENCE: 647

Ala Ser Gly Lys Pro Val Asn His Ser Thr Arg
1               5                   10

<210> SEQ ID NO 648
<211> LENGTH: 8
<212> TYPE: PRT
<213> ORGANISM: Homo sapiens

<400> SEQUENCE: 648

Val Thr His Pro His Leu Pro Arg
1               5

<210> SEQ ID NO 649
<211> LENGTH: 9
<212> TYPE: PRT
<213> ORGANISM: Homo sapiens

<400> SEQUENCE: 649

Ser Thr Thr Lys Thr Ser Gly Pro Arg
1               5

<210> SEQ ID NO 650
<211> LENGTH: 7
<212> TYPE: PRT
<213> ORGANISM: Homo sapiens

<400> SEQUENCE: 650

His Ser Thr Thr Gln Pro Arg
1               5

<210> SEQ ID NO 651
<211> LENGTH: 6
<212> TYPE: PRT
<213> ORGANISM: Homo sapiens

<400> SEQUENCE: 651

Lys Glu Glu Lys Gln Arg
1               5

<210> SEQ ID NO 652
<211> LENGTH: 8
<212> TYPE: PRT
```

<213> ORGANISM: Homo sapiens

<400> SEQUENCE: 652

Ala Val Ser Val Asn Pro Gly Lys
1               5

<210> SEQ ID NO 653
<211> LENGTH: 25
<212> TYPE: PRT
<213> ORGANISM: Homo sapiens

<400> SEQUENCE: 653

Ile Cys Arg Ala Val His Glu Ala Ala Ser Pro Ser Gln Thr Val Gln
1               5                   10                  15

Arg Ala Val Ser Val Asn Pro Gly Lys
            20                  25

<210> SEQ ID NO 654
<211> LENGTH: 23
<212> TYPE: PRT
<213> ORGANISM: Homo sapiens

<400> SEQUENCE: 654

Ser Arg Ala Ser Gly Lys Pro Val Asn His Ser Thr Arg Lys Glu Glu
1               5                   10                  15

Lys Gln Arg Asn Gly Thr Leu
            20

<210> SEQ ID NO 655
<211> LENGTH: 18
<212> TYPE: PRT
<213> ORGANISM: Homo sapiens

<400> SEQUENCE: 655

Glu Asp Ser Thr Lys Lys Cys Ala Asp Ser Asn Pro Arg Gly Val Ser
1               5                   10                  15

Ala Tyr

<210> SEQ ID NO 656
<211> LENGTH: 16
<212> TYPE: PRT
<213> ORGANISM: Homo sapiens

<400> SEQUENCE: 656

Arg Ser Thr Thr Lys Thr Ser Gly Pro Arg Ala Ala Pro Glu Val Tyr
1               5                   10                  15

<210> SEQ ID NO 657
<211> LENGTH: 16
<212> TYPE: PRT
<213> ORGANISM: Homo sapiens

<400> SEQUENCE: 657

Thr Arg Cys Cys Lys Asn Ile Pro Ser Asn Ala Thr Ser Val Thr Leu
1               5                   10                  15

<210> SEQ ID NO 658
<211> LENGTH: 16
<212> TYPE: PRT
<213> ORGANISM: Homo sapiens

<400> SEQUENCE: 658

Gln Ser Ser Cys Asp Gly Gly Gly His Phe Pro Pro Thr Ile Gln Leu

```
                1               5                  10                  15

<210> SEQ ID NO 659
<211> LENGTH: 14
<212> TYPE: PRT
<213> ORGANISM: Homo sapiens

<400> SEQUENCE: 659

Ala Thr Pro Glu Trp Pro Gly Ser Arg Asp Lys Arg Thr Leu
1               5                   10

<210> SEQ ID NO 660
<211> LENGTH: 13
<212> TYPE: PRT
<213> ORGANISM: Homo sapiens

<400> SEQUENCE: 660

Gln Cys Arg Val Thr His Pro His Leu Pro Arg Ala Leu
1               5                   10

<210> SEQ ID NO 661
<211> LENGTH: 13
<212> TYPE: PRT
<213> ORGANISM: Homo sapiens

<400> SEQUENCE: 661

Thr Cys Arg Val Ala His Thr Pro Ser Ser Thr Asp Trp
1               5                   10

<210> SEQ ID NO 662
<211> LENGTH: 13
<212> TYPE: PRT
<213> ORGANISM: Homo sapiens

<400> SEQUENCE: 662

Thr Val Thr Ser Thr Leu Pro Val Gly Thr Arg Asp Trp
1               5                   10

<210> SEQ ID NO 663
<211> LENGTH: 10
<212> TYPE: PRT
<213> ORGANISM: Homo sapiens

<400> SEQUENCE: 663

Ile Arg Lys Ser Pro Thr Ile Thr Cys Leu
1               5                   10

<210> SEQ ID NO 664
<211> LENGTH: 11
<212> TYPE: PRT
<213> ORGANISM: Homo sapiens

<400> SEQUENCE: 664

Ser Thr Ala Ser Thr Thr Gln Glu Gly Glu Leu
1               5                   10

<210> SEQ ID NO 665
<211> LENGTH: 9
<212> TYPE: PRT
<213> ORGANISM: Homo sapiens

<400> SEQUENCE: 665

Met Pro Glu Asp Ile Ser Val Gln Trp
1               5
```

```
<210> SEQ ID NO 666
<211> LENGTH: 9
<212> TYPE: PRT
<213> ORGANISM: Homo sapiens

<400> SEQUENCE: 666

Thr Pro Gly Thr Ile Asn Ile Thr Trp
1               5

<210> SEQ ID NO 667
<211> LENGTH: 7
<212> TYPE: PRT
<213> ORGANISM: Homo sapiens

<400> SEQUENCE: 667

Glu Val Thr Arg Ala Glu Trp
1               5

<210> SEQ ID NO 668
<211> LENGTH: 9
<212> TYPE: PRT
<213> ORGANISM: Homo sapiens

<400> SEQUENCE: 668

Ala Pro Ser Lys Gly Thr Val Asn Leu
1               5

<210> SEQ ID NO 669
<211> LENGTH: 8
<212> TYPE: PRT
<213> ORGANISM: Homo sapiens

<400> SEQUENCE: 669

Thr Pro Pro Thr Val Lys Ile Leu
1               5

<210> SEQ ID NO 670
<211> LENGTH: 7
<212> TYPE: PRT
<213> ORGANISM: Homo sapiens

<400> SEQUENCE: 670

Ser Val Cys Ser Arg Asp Phe
1               5

<210> SEQ ID NO 671
<211> LENGTH: 6
<212> TYPE: PRT
<213> ORGANISM: Homo sapiens

<400> SEQUENCE: 671

Glu Gln Lys Asp Glu Phe
1               5

<210> SEQ ID NO 672
<211> LENGTH: 7
<212> TYPE: PRT
<213> ORGANISM: Homo sapiens

<400> SEQUENCE: 672

Ala Ser Thr Gln Ser Glu Leu
1               5

<210> SEQ ID NO 673
```

```
<211> LENGTH: 6
<212> TYPE: PRT
<213> ORGANISM: Homo sapiens

<400> SEQUENCE: 673

Val Asp Asn Lys Thr Phe
1               5

<210> SEQ ID NO 674
<211> LENGTH: 23
<212> TYPE: PRT
<213> ORGANISM: Homo sapiens

<400> SEQUENCE: 674

Ala Arg His Ser Thr Thr Gln Pro Arg Lys Thr Lys Gly Ser Gly Phe
1               5                   10                  15

Phe Val Phe Ser Arg Leu Glu
            20

<210> SEQ ID NO 675
<211> LENGTH: 19
<212> TYPE: PRT
<213> ORGANISM: Homo sapiens

<400> SEQUENCE: 675

Lys Gln Arg Asn Gly Thr Leu Thr Val Thr Ser Thr Leu Pro Val Gly
1               5                   10                  15

Thr Arg Asp

<210> SEQ ID NO 676
<211> LENGTH: 17
<212> TYPE: PRT
<213> ORGANISM: Homo sapiens

<400> SEQUENCE: 676

Ser Asn Pro Arg Gly Val Ser Ala Tyr Leu Ser Arg Pro Ser Pro Phe
1               5                   10                  15

Asp

<210> SEQ ID NO 677
<211> LENGTH: 15
<212> TYPE: PRT
<213> ORGANISM: Homo sapiens

<400> SEQUENCE: 677

Arg Thr Tyr Thr Cys Gln Val Thr Tyr Gln Gly His Thr Phe Glu
1               5                   10                  15

<210> SEQ ID NO 678
<211> LENGTH: 18
<212> TYPE: PRT
<213> ORGANISM: Homo sapiens

<400> SEQUENCE: 678

Ala Ala Ser Pro Ser Gln Thr Val Gln Arg Ala Val Ser Val Asn Pro
1               5                   10                  15

Gly Lys

<210> SEQ ID NO 679
<211> LENGTH: 15
<212> TYPE: PRT
<213> ORGANISM: Homo sapiens
```

<400> SEQUENCE: 679

Leu Phe Ile Arg Lys Ser Pro Thr Ile Thr Cys Leu Val Val Asp
1               5                   10                  15

<210> SEQ ID NO 680
<211> LENGTH: 14
<212> TYPE: PRT
<213> ORGANISM: Homo sapiens

<400> SEQUENCE: 680

Lys Arg Thr Leu Ala Cys Leu Ile Gln Asn Phe Met Pro Glu
1               5                   10

<210> SEQ ID NO 681
<211> LENGTH: 14
<212> TYPE: PRT
<213> ORGANISM: Homo sapiens

<400> SEQUENCE: 681

Phe Thr Pro Pro Thr Val Lys Ile Leu Gln Ser Ser Cys Asp
1               5                   10

<210> SEQ ID NO 682
<211> LENGTH: 11
<212> TYPE: PRT
<213> ORGANISM: Homo sapiens

<400> SEQUENCE: 682

Leu Thr Leu Ser Gln Lys His Trp Leu Ser Asp
1               5                   10

<210> SEQ ID NO 683
<211> LENGTH: 10
<212> TYPE: PRT
<213> ORGANISM: Homo sapiens

<400> SEQUENCE: 683

Asn Lys Thr Phe Ser Val Cys Ser Arg Asp
1               5                   10

<210> SEQ ID NO 684
<211> LENGTH: 9
<212> TYPE: PRT
<213> ORGANISM: Homo sapiens

<400> SEQUENCE: 684

Ile Ser Val Gln Trp Leu His Asn Glu
1               5

<210> SEQ ID NO 685
<211> LENGTH: 8
<212> TYPE: PRT
<213> ORGANISM: Homo sapiens

<400> SEQUENCE: 685

Phe Ile Cys Arg Ala Val His Glu
1               5

<210> SEQ ID NO 686
<211> LENGTH: 9
<212> TYPE: PRT
<213> ORGANISM: Homo sapiens

<400> SEQUENCE: 686

```
Leu Ser Thr Ala Ser Thr Thr Gln Glu
1               5

<210> SEQ ID NO 687
<211> LENGTH: 8
<212> TYPE: PRT
<213> ORGANISM: Homo sapiens

<400> SEQUENCE: 687

Val Tyr Ala Phe Ala Thr Pro Glu
1               5

<210> SEQ ID NO 688
<211> LENGTH: 7
<212> TYPE: PRT
<213> ORGANISM: Homo sapiens

<400> SEQUENCE: 688

Ser Thr Lys Lys Cys Ala Asp
1               5

<210> SEQ ID NO 689
<211> LENGTH: 7
<212> TYPE: PRT
<213> ORGANISM: Homo sapiens

<400> SEQUENCE: 689

Leu Ala Ser Thr Gln Ser Glu
1               5

<210> SEQ ID NO 690
<211> LENGTH: 6
<212> TYPE: PRT
<213> ORGANISM: Homo sapiens

<400> SEQUENCE: 690

Trp Pro Gly Ser Arg Asp
1               5

<210> SEQ ID NO 691
<211> LENGTH: 22
<212> TYPE: PRT
<213> ORGANISM: Homo sapiens

<400> SEQUENCE: 691

Lys Gln Arg Asn Gly Thr Leu Thr Val Thr Ser Thr Leu Pro Val Gly
1               5                   10                  15

Thr Arg Asp Trp Ile Glu
            20

<210> SEQ ID NO 692
<211> LENGTH: 20
<212> TYPE: PRT
<213> ORGANISM: Homo sapiens

<400> SEQUENCE: 692

Trp Pro Gly Ser Arg Asp Lys Arg Thr Leu Ala Cys Leu Ile Gln Asn
1               5                   10                  15

Phe Met Pro Glu
            20

<210> SEQ ID NO 693
<211> LENGTH: 18
<212> TYPE: PRT
```

```
<213> ORGANISM: Homo sapiens

<400> SEQUENCE: 693

Ala Ala Ser Pro Ser Gln Thr Val Gln Arg Ala Val Ser Val Asn Pro
1               5                   10                  15
Gly Lys

<210> SEQ ID NO 694
<211> LENGTH: 17
<212> TYPE: PRT
<213> ORGANISM: Homo sapiens

<400> SEQUENCE: 694

Asp Gly Gln Val Met Asp Val Asp Leu Ser Thr Ala Ser Thr Thr Gln
1               5                   10                  15
Glu

<210> SEQ ID NO 695
<211> LENGTH: 10
<212> TYPE: PRT
<213> ORGANISM: Homo sapiens

<400> SEQUENCE: 695

Asp Ile Ser Val Gln Trp Leu His Asn Glu
1               5                   10

<210> SEQ ID NO 696
<211> LENGTH: 8
<212> TYPE: PRT
<213> ORGANISM: Homo sapiens

<400> SEQUENCE: 696

Phe Ile Cys Arg Ala Val His Glu
1               5

<210> SEQ ID NO 697
<211> LENGTH: 8
<212> TYPE: PRT
<213> ORGANISM: Homo sapiens

<400> SEQUENCE: 697

Val Tyr Ala Phe Ala Thr Pro Glu
1               5

<210> SEQ ID NO 698
<211> LENGTH: 7
<212> TYPE: PRT
<213> ORGANISM: Homo sapiens

<400> SEQUENCE: 698

Leu Ala Ser Thr Gln Ser Glu
1               5

<210> SEQ ID NO 699
<211> LENGTH: 16
<212> TYPE: PRT
<213> ORGANISM: Homo sapiens

<400> SEQUENCE: 699

Asp Arg Thr Tyr Thr Cys Gln Val Thr Tyr Gln Gly His Thr Phe Glu
1               5                   10                  15

<210> SEQ ID NO 700
```

```
<211> LENGTH: 17
<212> TYPE: PRT
<213> ORGANISM: Homo sapiens

<400> SEQUENCE: 700

Asp Ser Asn Pro Arg Gly Val Ser Ala Tyr Leu Ser Arg Pro Ser Pro
1               5                   10                  15

Phe

<210> SEQ ID NO 701
<211> LENGTH: 15
<212> TYPE: PRT
<213> ORGANISM: Homo sapiens

<400> SEQUENCE: 701

Asp Lys Arg Thr Leu Ala Cys Leu Ile Gln Asn Phe Met Pro Glu
1               5                   10                  15

<210> SEQ ID NO 702
<211> LENGTH: 15
<212> TYPE: PRT
<213> ORGANISM: Homo sapiens

<400> SEQUENCE: 702

Asp Leu Phe Ile Arg Lys Ser Pro Thr Ile Thr Cys Leu Val Val
1               5                   10                  15

<210> SEQ ID NO 703
<211> LENGTH: 14
<212> TYPE: PRT
<213> ORGANISM: Homo sapiens

<400> SEQUENCE: 703

Asp Ile Ser Val Gln Trp Leu His Asn Glu Val Gln Leu Pro
1               5                   10

<210> SEQ ID NO 704
<211> LENGTH: 14
<212> TYPE: PRT
<213> ORGANISM: Homo sapiens

<400> SEQUENCE: 704

Asp Phe Thr Pro Pro Thr Val Lys Ile Leu Gln Ser Ser Cys
1               5                   10

<210> SEQ ID NO 705
<211> LENGTH: 10
<212> TYPE: PRT
<213> ORGANISM: Homo sapiens

<400> SEQUENCE: 705

Asp Asn Lys Thr Phe Ser Val Cys Ser Arg
1               5                   10

<210> SEQ ID NO 706
<211> LENGTH: 7
<212> TYPE: PRT
<213> ORGANISM: Homo sapiens

<400> SEQUENCE: 706

Asp Ser Thr Lys Lys Cys Ala
1               5

<210> SEQ ID NO 707
```

-continued

```
<211> LENGTH: 20
<212> TYPE: PRT
<213> ORGANISM: Homo sapiens

<400> SEQUENCE: 707

Val Asp Asn Ala Leu Gln Ser Gly Asn Ser Gln Glu Ser Val Thr Glu
1               5                   10                  15

Gln Asp Ser Lys
            20

<210> SEQ ID NO 708
<211> LENGTH: 17
<212> TYPE: PRT
<213> ORGANISM: Homo sapiens

<400> SEQUENCE: 708

Val Tyr Ala Cys Glu Val Thr His Gln Gly Leu Ser Ser Pro Val Thr
1               5                   10                  15

Lys

<210> SEQ ID NO 709
<211> LENGTH: 16
<212> TYPE: PRT
<213> ORGANISM: Homo sapiens

<400> SEQUENCE: 709

Ser Gly Thr Ala Ser Val Val Cys Leu Leu Asn Asn Phe Tyr Pro Arg
1               5                   10                  15

<210> SEQ ID NO 710
<211> LENGTH: 14
<212> TYPE: PRT
<213> ORGANISM: Homo sapiens

<400> SEQUENCE: 710

Asp Ser Thr Tyr Ser Leu Ser Ser Thr Leu Thr Leu Ser Lys
1               5                   10

<210> SEQ ID NO 711
<211> LENGTH: 20
<212> TYPE: PRT
<213> ORGANISM: Homo sapiens

<400> SEQUENCE: 711

Val Asp Asn Ala Leu Gln Ser Gly Asn Ser Gln Glu Ser Val Thr Glu
1               5                   10                  15

Gln Asp Ser Lys
            20

<210> SEQ ID NO 712
<211> LENGTH: 19
<212> TYPE: PRT
<213> ORGANISM: Homo sapiens

<400> SEQUENCE: 712

Ser Gly Thr Ala Ser Val Val Cys Leu Leu Asn Asn Phe Tyr Pro Arg
1               5                   10                  15

Glu Ala Lys

<210> SEQ ID NO 713
<211> LENGTH: 18
<212> TYPE: PRT
<213> ORGANISM: Homo sapiens
```

<400> SEQUENCE: 713

Thr Val Ala Ala Pro Ser Val Phe Ile Phe Pro Pro Ser Asp Glu Gln
1               5                   10                  15

Leu Lys

<210> SEQ ID NO 714
<211> LENGTH: 17
<212> TYPE: PRT
<213> ORGANISM: Homo sapiens

<400> SEQUENCE: 714

Val Tyr Ala Cys Glu Val Thr His Gln Gly Leu Ser Ser Pro Val Thr
1               5                   10                  15

Lys

<210> SEQ ID NO 715
<211> LENGTH: 14
<212> TYPE: PRT
<213> ORGANISM: Homo sapiens

<400> SEQUENCE: 715

Asp Ser Thr Tyr Ser Leu Ser Ser Thr Leu Thr Leu Ser Lys
1               5                   10

<210> SEQ ID NO 716
<211> LENGTH: 7
<212> TYPE: PRT
<213> ORGANISM: Homo sapiens

<400> SEQUENCE: 716

Ser Phe Asn Arg Gly Glu Cys
1               5

<210> SEQ ID NO 717
<211> LENGTH: 19
<212> TYPE: PRT
<213> ORGANISM: Homo sapiens

<400> SEQUENCE: 717

Gln Ser Gly Asn Ser Gln Glu Ser Val Thr Glu Gln Asp Ser Lys Asp
1               5                   10                  15

Ser Thr Tyr

<210> SEQ ID NO 718
<211> LENGTH: 9
<212> TYPE: PRT
<213> ORGANISM: Homo sapiens

<400> SEQUENCE: 718

Tyr Pro Arg Glu Ala Lys Val Gln Trp
1               5

<210> SEQ ID NO 719
<211> LENGTH: 9
<212> TYPE: PRT
<213> ORGANISM: Homo sapiens

<400> SEQUENCE: 719

Ile Phe Pro Pro Ser Asp Glu Gln Leu
1               5

```
<210> SEQ ID NO 720
<211> LENGTH: 10
<212> TYPE: PRT
<213> ORGANISM: Homo sapiens

<400> SEQUENCE: 720

Lys Ser Gly Thr Ala Ser Val Val Cys Leu
1               5                   10

<210> SEQ ID NO 721
<211> LENGTH: 9
<212> TYPE: PRT
<213> ORGANISM: Homo sapiens

<400> SEQUENCE: 721

Ala Cys Glu Val Thr His Gln Gly Leu
1               5

<210> SEQ ID NO 722
<211> LENGTH: 8
<212> TYPE: PRT
<213> ORGANISM: Homo sapiens

<400> SEQUENCE: 722

Ser Ser Pro Val Thr Lys Ser Phe
1               5

<210> SEQ ID NO 723
<211> LENGTH: 6
<212> TYPE: PRT
<213> ORGANISM: Homo sapiens

<400> SEQUENCE: 723

Glu Lys His Lys Val Tyr
1               5

<210> SEQ ID NO 724
<211> LENGTH: 8
<212> TYPE: PRT
<213> ORGANISM: Homo sapiens

<400> SEQUENCE: 724

Thr Val Ala Ala Pro Ser Val Phe
1               5

<210> SEQ ID NO 725
<211> LENGTH: 20
<212> TYPE: PRT
<213> ORGANISM: Homo sapiens

<400> SEQUENCE: 725

Gln Leu Lys Ser Gly Thr Ala Ser Val Val Cys Leu Leu Asn Asn Phe
1               5                   10                  15

Tyr Pro Arg Glu
            20

<210> SEQ ID NO 726
<211> LENGTH: 18
<212> TYPE: PRT
<213> ORGANISM: Homo sapiens

<400> SEQUENCE: 726

Val Thr His Gln Gly Leu Ser Ser Pro Val Thr Lys Ser Phe Asn Arg
1               5                   10                  15
```

Gly Glu

<210> SEQ ID NO 727
<211> LENGTH: 15
<212> TYPE: PRT
<213> ORGANISM: Homo sapiens

<400> SEQUENCE: 727

Thr Val Ala Ala Pro Ser Val Phe Ile Phe Pro Pro Ser Asp Glu
1               5                   10                  15

<210> SEQ ID NO 728
<211> LENGTH: 15
<212> TYPE: PRT
<213> ORGANISM: Homo sapiens

<400> SEQUENCE: 728

Ser Thr Tyr Ser Leu Ser Ser Thr Leu Thr Leu Ser Lys Ala Asp
1               5                   10                  15

<210> SEQ ID NO 729
<211> LENGTH: 10
<212> TYPE: PRT
<213> ORGANISM: Homo sapiens

<400> SEQUENCE: 729

Asn Ala Leu Gln Ser Gly Asn Ser Gln Glu
1               5                   10

<210> SEQ ID NO 730
<211> LENGTH: 8
<212> TYPE: PRT
<213> ORGANISM: Homo sapiens

<400> SEQUENCE: 730

Lys His Lys Val Tyr Ala Cys Glu
1               5

<210> SEQ ID NO 731
<211> LENGTH: 8
<212> TYPE: PRT
<213> ORGANISM: Homo sapiens

<400> SEQUENCE: 731

Ala Lys Val Gln Trp Lys Val Asp
1               5

<210> SEQ ID NO 732
<211> LENGTH: 22
<212> TYPE: PRT
<213> ORGANISM: Homo sapiens

<400> SEQUENCE: 732

Gln Asp Ser Lys Asp Ser Thr Tyr Ser Leu Ser Ser Thr Leu Thr Leu
1               5                   10                  15

Ser Lys Ala Asp Tyr Glu
            20

<210> SEQ ID NO 733
<211> LENGTH: 20
<212> TYPE: PRT
<213> ORGANISM: Homo sapiens

<400> SEQUENCE: 733

```
Gln Leu Lys Ser Gly Thr Ala Ser Val Val Cys Leu Leu Asn Asn Phe
1               5                   10                  15

Tyr Pro Arg Glu
            20
```

<210> SEQ ID NO 734
<211> LENGTH: 18
<212> TYPE: PRT
<213> ORGANISM: Homo sapiens

<400> SEQUENCE: 734

```
Ala Lys Val Gln Trp Lys Val Asp Asn Ala Leu Gln Ser Gly Asn Ser
1               5                   10                  15

Gln Glu
```

<210> SEQ ID NO 735
<211> LENGTH: 18
<212> TYPE: PRT
<213> ORGANISM: Homo sapiens

<400> SEQUENCE: 735

```
Val Thr His Gln Gly Leu Ser Ser Pro Val Thr Lys Ser Phe Asn Arg
1               5                   10                  15

Gly Glu
```

<210> SEQ ID NO 736
<211> LENGTH: 15
<212> TYPE: PRT
<213> ORGANISM: Homo sapiens

<400> SEQUENCE: 736

```
Thr Val Ala Ala Pro Ser Val Phe Ile Phe Pro Pro Ser Asp Glu
1               5                   10                  15
```

<210> SEQ ID NO 737
<211> LENGTH: 8
<212> TYPE: PRT
<213> ORGANISM: Homo sapiens

<400> SEQUENCE: 737

```
Lys His Lys Val Tyr Ala Cys Glu
1               5
```

<210> SEQ ID NO 738
<211> LENGTH: 16
<212> TYPE: PRT
<213> ORGANISM: Homo sapiens

<400> SEQUENCE: 738

```
Asp Asn Ala Leu Gln Ser Gly Asn Ser Gln Glu Ser Val Thr Glu Gln
1               5                   10                  15
```

<210> SEQ ID NO 739
<211> LENGTH: 15
<212> TYPE: PRT
<213> ORGANISM: Homo sapiens

<400> SEQUENCE: 739

```
Asp Ser Thr Tyr Ser Leu Ser Ser Thr Leu Thr Leu Ser Lys Ala
1               5                   10                  15
```

<210> SEQ ID NO 740
<211> LENGTH: 13

```
<212> TYPE: PRT
<213> ORGANISM: Homo sapiens

<400> SEQUENCE: 740

Thr Val Ala Ala Pro Ser Val Phe Ile Phe Pro Pro Ser
1               5                   10

<210> SEQ ID NO 741
<211> LENGTH: 20
<212> TYPE: PRT
<213> ORGANISM: Homo sapiens

<400> SEQUENCE: 741

Ala Thr Leu Val Cys Leu Ile Ser Asp Phe Tyr Pro Gly Ala Val Thr
1               5                   10                  15

Val Ala Trp Lys
            20

<210> SEQ ID NO 742
<211> LENGTH: 19
<212> TYPE: PRT
<213> ORGANISM: Homo sapiens

<400> SEQUENCE: 742

Ala Asn Pro Thr Val Thr Leu Phe Pro Pro Ser Ser Glu Glu Leu Gln
1               5                   10                  15

Ala Asn Lys

<210> SEQ ID NO 743
<211> LENGTH: 15
<212> TYPE: PRT
<213> ORGANISM: Homo sapiens

<400> SEQUENCE: 743

Tyr Ala Ala Ser Ser Tyr Leu Ser Leu Thr Pro Glu Gln Trp Lys
1               5                   10                  15

<210> SEQ ID NO 744
<211> LENGTH: 15
<212> TYPE: PRT
<213> ORGANISM: Homo sapiens

<400> SEQUENCE: 744

Ser Tyr Ser Cys Gln Val Thr His Glu Gly Ser Thr Val Glu Lys
1               5                   10                  15

<210> SEQ ID NO 745
<211> LENGTH: 10
<212> TYPE: PRT
<213> ORGANISM: Homo sapiens

<400> SEQUENCE: 745

Ala Gly Val Glu Thr Thr Lys Pro Ser Lys
1               5                   10

<210> SEQ ID NO 746
<211> LENGTH: 8
<212> TYPE: PRT
<213> ORGANISM: Homo sapiens

<400> SEQUENCE: 746

Thr Val Ala Pro Thr Glu Cys Ser
1               5
```

<210> SEQ ID NO 747
<211> LENGTH: 20
<212> TYPE: PRT
<213> ORGANISM: Homo sapiens

<400> SEQUENCE: 747

Ala Thr Leu Val Cys Leu Ile Ser Asp Phe Tyr Pro Gly Ala Val Thr
1               5                   10                  15

Val Ala Trp Lys
            20

<210> SEQ ID NO 748
<211> LENGTH: 19
<212> TYPE: PRT
<213> ORGANISM: Homo sapiens

<400> SEQUENCE: 748

Ala Asn Pro Thr Val Thr Leu Phe Pro Pro Ser Ser Glu Glu Leu Gln
1               5                   10                  15

Ala Asn Lys

<210> SEQ ID NO 749
<211> LENGTH: 18
<212> TYPE: PRT
<213> ORGANISM: Homo sapiens

<400> SEQUENCE: 749

Ser His Arg Ser Tyr Ser Cys Gln Val Thr His Glu Gly Ser Thr Val
1               5                   10                  15

Glu Lys

<210> SEQ ID NO 750
<211> LENGTH: 15
<212> TYPE: PRT
<213> ORGANISM: Homo sapiens

<400> SEQUENCE: 750

Tyr Ala Ala Ser Ser Tyr Leu Ser Leu Thr Pro Glu Gln Trp Lys
1               5                   10                  15

<210> SEQ ID NO 751
<211> LENGTH: 8
<212> TYPE: PRT
<213> ORGANISM: Homo sapiens

<400> SEQUENCE: 751

Thr Val Ala Pro Thr Glu Cys Ser
1               5

<210> SEQ ID NO 752
<211> LENGTH: 7
<212> TYPE: PRT
<213> ORGANISM: Homo sapiens

<400> SEQUENCE: 752

Ala Gly Val Glu Thr Thr Lys
1               5

<210> SEQ ID NO 753
<211> LENGTH: 7
<212> TYPE: PRT
<213> ORGANISM: Homo sapiens

```
<400> SEQUENCE: 753

Ala Asp Gly Ser Pro Val Lys
1               5

<210> SEQ ID NO 754
<211> LENGTH: 23
<212> TYPE: PRT
<213> ORGANISM: Homo sapiens

<400> SEQUENCE: 754

Ser Tyr Ser Cys Gln Val Thr His Glu Gly Ser Thr Val Glu Lys Thr
1               5                   10                  15

Val Ala Pro Thr Glu Cys Ser
            20

<210> SEQ ID NO 755
<211> LENGTH: 24
<212> TYPE: PRT
<213> ORGANISM: Homo sapiens

<400> SEQUENCE: 755

Lys Ala Asp Gly Ser Pro Val Lys Ala Gly Val Glu Thr Thr Lys Pro
1               5                   10                  15

Ser Lys Gln Ser Asn Asn Lys Tyr
            20

<210> SEQ ID NO 756
<211> LENGTH: 21
<212> TYPE: PRT
<213> ORGANISM: Homo sapiens

<400> SEQUENCE: 756

Ser Cys Gln Val Thr His Glu Gly Ser Thr Val Glu Lys Thr Val Ala
1               5                   10                  15

Pro Thr Glu Cys Ser
            20

<210> SEQ ID NO 757
<211> LENGTH: 11
<212> TYPE: PRT
<213> ORGANISM: Homo sapiens

<400> SEQUENCE: 757

Gly Gln Pro Lys Ala Asn Pro Thr Val Thr Leu
1               5                   10

<210> SEQ ID NO 758
<211> LENGTH: 9
<212> TYPE: PRT
<213> ORGANISM: Homo sapiens

<400> SEQUENCE: 758

Tyr Pro Gly Ala Val Thr Val Ala Trp
1               5

<210> SEQ ID NO 759
<211> LENGTH: 8
<212> TYPE: PRT
<213> ORGANISM: Homo sapiens

<400> SEQUENCE: 759

Phe Pro Pro Ser Ser Glu Glu Leu
1               5
```

<210> SEQ ID NO 760
<211> LENGTH: 6
<212> TYPE: PRT
<213> ORGANISM: Homo sapiens

<400> SEQUENCE: 760

Lys Ser His Arg Ser Tyr
1               5

<210> SEQ ID NO 761
<211> LENGTH: 7
<212> TYPE: PRT
<213> ORGANISM: Homo sapiens

<400> SEQUENCE: 761

Gln Ala Asn Lys Ala Thr Leu
1               5

<210> SEQ ID NO 762
<211> LENGTH: 23
<212> TYPE: PRT
<213> ORGANISM: Homo sapiens

<400> SEQUENCE: 762

Thr Thr Lys Pro Ser Lys Gln Ser Asn Asn Lys Tyr Ala Ala Ser Ser
1               5                   10                  15

Tyr Leu Ser Leu Thr Pro Glu
            20

<210> SEQ ID NO 763
<211> LENGTH: 18
<212> TYPE: PRT
<213> ORGANISM: Homo sapiens

<400> SEQUENCE: 763

Gly Gln Pro Lys Ala Asn Pro Thr Val Thr Leu Phe Pro Pro Ser Ser
1               5                   10                  15

Glu Glu

<210> SEQ ID NO 764
<211> LENGTH: 15
<212> TYPE: PRT
<213> ORGANISM: Homo sapiens

<400> SEQUENCE: 764

Gln Trp Lys Ser His Arg Ser Tyr Ser Cys Gln Val Thr His Glu
1               5                   10                  15

<210> SEQ ID NO 765
<211> LENGTH: 14
<212> TYPE: PRT
<213> ORGANISM: Homo sapiens

<400> SEQUENCE: 765

Leu Gln Ala Asn Lys Ala Thr Leu Val Cys Leu Ile Ser Asp
1               5                   10

<210> SEQ ID NO 766
<211> LENGTH: 13
<212> TYPE: PRT
<213> ORGANISM: Homo sapiens

<400> SEQUENCE: 766

Phe Tyr Pro Gly Ala Val Thr Val Ala Trp Lys Ala Asp
1               5                   10

<210> SEQ ID NO 767
<211> LENGTH: 7
<212> TYPE: PRT
<213> ORGANISM: Homo sapiens

<400> SEQUENCE: 767

Lys Thr Val Ala Pro Thr Glu
1               5

<210> SEQ ID NO 768
<211> LENGTH: 23
<212> TYPE: PRT
<213> ORGANISM: Homo sapiens

<400> SEQUENCE: 768

Thr Thr Lys Pro Ser Lys Gln Ser Asn Asn Lys Tyr Ala Ala Ser Ser
1               5                   10                  15

Tyr Leu Ser Leu Thr Pro Glu
            20

<210> SEQ ID NO 769
<211> LENGTH: 18
<212> TYPE: PRT
<213> ORGANISM: Homo sapiens

<400> SEQUENCE: 769

Gly Gln Pro Lys Ala Asn Pro Thr Val Thr Leu Phe Pro Pro Ser Ser
1               5                   10                  15

Glu Glu

<210> SEQ ID NO 770
<211> LENGTH: 15
<212> TYPE: PRT
<213> ORGANISM: Homo sapiens

<400> SEQUENCE: 770

Gln Trp Lys Ser His Arg Ser Tyr Ser Cys Gln Val Thr His Glu
1               5                   10                  15

<210> SEQ ID NO 771
<211> LENGTH: 7
<212> TYPE: PRT
<213> ORGANISM: Homo sapiens

<400> SEQUENCE: 771

Lys Thr Val Ala Pro Thr Glu
1               5

<210> SEQ ID NO 772
<211> LENGTH: 13
<212> TYPE: PRT
<213> ORGANISM: Homo sapiens

<400> SEQUENCE: 772

Asp Phe Tyr Pro Gly Ala Val Thr Val Ala Trp Lys Ala
1               5                   10

<210> SEQ ID NO 773
<211> LENGTH: 20
<212> TYPE: PRT

<213> ORGANISM: Homo sapiens

<400> SEQUENCE: 773

Ala Thr Leu Val Cys Leu Ile Ser Asp Phe Tyr Pro Gly Ala Val Thr
1               5                   10                  15

Val Ala Trp Lys
            20

<210> SEQ ID NO 774
<211> LENGTH: 19
<212> TYPE: PRT
<213> ORGANISM: Homo sapiens

<400> SEQUENCE: 774

Ala Ala Pro Ser Val Thr Leu Phe Pro Pro Ser Ser Glu Glu Leu Gln
1               5                   10                  15

Ala Asn Lys

<210> SEQ ID NO 775
<211> LENGTH: 15
<212> TYPE: PRT
<213> ORGANISM: Homo sapiens

<400> SEQUENCE: 775

Tyr Ala Ala Ser Ser Tyr Leu Ser Leu Thr Pro Glu Gln Trp Lys
1               5                   10                  15

<210> SEQ ID NO 776
<211> LENGTH: 15
<212> TYPE: PRT
<213> ORGANISM: Homo sapiens

<400> SEQUENCE: 776

Ser Tyr Ser Cys Gln Val Thr His Glu Gly Ser Thr Val Glu Lys
1               5                   10                  15

<210> SEQ ID NO 777
<211> LENGTH: 8
<212> TYPE: PRT
<213> ORGANISM: Homo sapiens

<400> SEQUENCE: 777

Thr Val Ala Pro Thr Glu Cys Ser
1               5

<210> SEQ ID NO 778
<211> LENGTH: 7
<212> TYPE: PRT
<213> ORGANISM: Homo sapiens

<400> SEQUENCE: 778

Ala Asp Ser Ser Pro Val Lys
1               5

<210> SEQ ID NO 779
<211> LENGTH: 20
<212> TYPE: PRT
<213> ORGANISM: Homo sapiens

<400> SEQUENCE: 779

Ala Thr Leu Val Cys Leu Ile Ser Asp Phe Tyr Pro Gly Ala Val Thr
1               5                   10                  15

Val Ala Trp Lys

<210> SEQ ID NO 780
<211> LENGTH: 18
<212> TYPE: PRT
<213> ORGANISM: Homo sapiens

<400> SEQUENCE: 780

Ser His Arg Ser Tyr Ser Cys Gln Val Thr His Glu Gly Ser Thr Val
1               5                   10                  15

Glu Lys

<210> SEQ ID NO 781
<211> LENGTH: 19
<212> TYPE: PRT
<213> ORGANISM: Homo sapiens

<400> SEQUENCE: 781

Ala Ala Pro Ser Val Thr Leu Phe Pro Pro Ser Ser Glu Glu Leu Gln
1               5                   10                  15

Ala Asn Lys

<210> SEQ ID NO 782
<211> LENGTH: 15
<212> TYPE: PRT
<213> ORGANISM: Homo sapiens

<400> SEQUENCE: 782

Tyr Ala Ala Ser Ser Tyr Leu Ser Leu Thr Pro Glu Gln Trp Lys
1               5                   10                  15

<210> SEQ ID NO 783
<211> LENGTH: 10
<212> TYPE: PRT
<213> ORGANISM: Homo sapiens

<400> SEQUENCE: 783

Ala Gly Val Glu Thr Thr Thr Pro Ser Lys
1               5                   10

<210> SEQ ID NO 784
<211> LENGTH: 8
<212> TYPE: PRT
<213> ORGANISM: Homo sapiens

<400> SEQUENCE: 784

Thr Val Ala Pro Thr Glu Cys Ser
1               5

<210> SEQ ID NO 785
<211> LENGTH: 7
<212> TYPE: PRT
<213> ORGANISM: Homo sapiens

<400> SEQUENCE: 785

Ala Asp Ser Ser Pro Val Lys
1               5

<210> SEQ ID NO 786
<211> LENGTH: 23
<212> TYPE: PRT
<213> ORGANISM: Homo sapiens

<400> SEQUENCE: 786

Ser Tyr Ser Cys Gln Val Thr His Glu Gly Ser Thr Val Glu Lys Thr
1               5                   10                  15

Val Ala Pro Thr Glu Cys Ser
            20

<210> SEQ ID NO 787
<211> LENGTH: 24
<212> TYPE: PRT
<213> ORGANISM: Homo sapiens

<400> SEQUENCE: 787

Lys Ala Asp Ser Ser Pro Val Lys Ala Gly Val Glu Thr Thr Thr Pro
1               5                   10                  15

Ser Lys Gln Ser Asn Asn Lys Tyr
            20

<210> SEQ ID NO 788
<211> LENGTH: 21
<212> TYPE: PRT
<213> ORGANISM: Homo sapiens

<400> SEQUENCE: 788

Ser Cys Gln Val Thr His Glu Gly Ser Thr Val Glu Lys Thr Val Ala
1               5                   10                  15

Pro Thr Glu Cys Ser
            20

<210> SEQ ID NO 789
<211> LENGTH: 11
<212> TYPE: PRT
<213> ORGANISM: Homo sapiens

<400> SEQUENCE: 789

Gly Gln Pro Lys Ala Ala Pro Ser Val Thr Leu
1               5                   10

<210> SEQ ID NO 790
<211> LENGTH: 9
<212> TYPE: PRT
<213> ORGANISM: Homo sapiens

<400> SEQUENCE: 790

Tyr Pro Gly Ala Val Thr Val Ala Trp
1               5

<210> SEQ ID NO 791
<211> LENGTH: 8
<212> TYPE: PRT
<213> ORGANISM: Homo sapiens

<400> SEQUENCE: 791

Phe Pro Pro Ser Ser Glu Glu Leu
1               5

<210> SEQ ID NO 792
<211> LENGTH: 6
<212> TYPE: PRT
<213> ORGANISM: Homo sapiens

<400> SEQUENCE: 792

Lys Ser His Arg Ser Tyr
1               5

<210> SEQ ID NO 793
<211> LENGTH: 7
<212> TYPE: PRT
<213> ORGANISM: Homo sapiens

<400> SEQUENCE: 793

Gln Ala Asn Lys Ala Thr Leu
1               5

<210> SEQ ID NO 794
<211> LENGTH: 23
<212> TYPE: PRT
<213> ORGANISM: Homo sapiens

<400> SEQUENCE: 794

Thr Thr Thr Pro Ser Lys Gln Ser Asn Lys Tyr Ala Ala Ser Ser
1               5                   10                  15

Tyr Leu Ser Leu Thr Pro Glu
            20

<210> SEQ ID NO 795
<211> LENGTH: 15
<212> TYPE: PRT
<213> ORGANISM: Homo sapiens

<400> SEQUENCE: 795

Gln Trp Lys Ser His Arg Ser Tyr Ser Cys Gln Val Thr His Glu
1               5                   10                  15

<210> SEQ ID NO 796
<211> LENGTH: 18
<212> TYPE: PRT
<213> ORGANISM: Homo sapiens

<400> SEQUENCE: 796

Gly Gln Pro Lys Ala Ala Pro Ser Val Thr Leu Phe Pro Pro Ser Ser
1               5                   10                  15

Glu Glu

<210> SEQ ID NO 797
<211> LENGTH: 14
<212> TYPE: PRT
<213> ORGANISM: Homo sapiens

<400> SEQUENCE: 797

Leu Gln Ala Asn Lys Ala Thr Leu Val Cys Leu Ile Ser Asp
1               5                   10

<210> SEQ ID NO 798
<211> LENGTH: 13
<212> TYPE: PRT
<213> ORGANISM: Homo sapiens

<400> SEQUENCE: 798

Phe Tyr Pro Gly Ala Val Thr Val Ala Trp Lys Ala Asp
1               5                   10

<210> SEQ ID NO 799
<211> LENGTH: 9
<212> TYPE: PRT
<213> ORGANISM: Homo sapiens

<400> SEQUENCE: 799

```
Ser Ser Pro Val Lys Ala Gly Val Glu
1               5

<210> SEQ ID NO 800
<211> LENGTH: 7
<212> TYPE: PRT
<213> ORGANISM: Homo sapiens

<400> SEQUENCE: 800

Lys Thr Val Ala Pro Thr Glu
1               5

<210> SEQ ID NO 801
<211> LENGTH: 23
<212> TYPE: PRT
<213> ORGANISM: Homo sapiens

<400> SEQUENCE: 801

Thr Thr Thr Pro Ser Lys Gln Ser Asn Asn Lys Tyr Ala Ala Ser Ser
1               5                   10                  15

Tyr Leu Ser Leu Thr Pro Glu
            20

<210> SEQ ID NO 802
<211> LENGTH: 15
<212> TYPE: PRT
<213> ORGANISM: Homo sapiens

<400> SEQUENCE: 802

Gln Trp Lys Ser His Arg Ser Tyr Ser Cys Gln Val Thr His Glu
1               5                   10                  15

<210> SEQ ID NO 803
<211> LENGTH: 18
<212> TYPE: PRT
<213> ORGANISM: Homo sapiens

<400> SEQUENCE: 803

Gly Gln Pro Lys Ala Ala Pro Ser Val Thr Leu Phe Pro Pro Ser Ser
1               5                   10                  15

Glu Glu

<210> SEQ ID NO 804
<211> LENGTH: 7
<212> TYPE: PRT
<213> ORGANISM: Homo sapiens

<400> SEQUENCE: 804

Lys Thr Val Ala Pro Thr Glu
1               5

<210> SEQ ID NO 805
<211> LENGTH: 13
<212> TYPE: PRT
<213> ORGANISM: Homo sapiens

<400> SEQUENCE: 805

Asp Phe Tyr Pro Gly Ala Val Thr Val Ala Trp Lys Ala
1               5                   10

<210> SEQ ID NO 806
<211> LENGTH: 20
<212> TYPE: PRT
<213> ORGANISM: Homo sapiens
```

<400> SEQUENCE: 806

Ala Thr Leu Val Cys Leu Ile Ser Asp Phe Tyr Pro Gly Ala Val Thr
1               5                   10                  15

Val Ala Trp Lys
            20

<210> SEQ ID NO 807
<211> LENGTH: 19
<212> TYPE: PRT
<213> ORGANISM: Homo sapiens

<400> SEQUENCE: 807

Ala Ala Pro Ser Val Thr Leu Phe Pro Pro Ser Ser Glu Glu Leu Gln
1               5                   10                  15

Ala Asn Lys

<210> SEQ ID NO 808
<211> LENGTH: 15
<212> TYPE: PRT
<213> ORGANISM: Homo sapiens

<400> SEQUENCE: 808

Tyr Ala Ala Ser Ser Tyr Leu Ser Leu Thr Pro Glu Gln Trp Lys
1               5                   10                  15

<210> SEQ ID NO 809
<211> LENGTH: 15
<212> TYPE: PRT
<213> ORGANISM: Homo sapiens

<400> SEQUENCE: 809

Ser Tyr Ser Cys Gln Val Thr His Glu Gly Ser Thr Val Glu Lys
1               5                   10                  15

<210> SEQ ID NO 810
<211> LENGTH: 10
<212> TYPE: PRT
<213> ORGANISM: Homo sapiens

<400> SEQUENCE: 810

Ala Gly Val Glu Thr Thr Thr Pro Ser Lys
1               5                   10

<210> SEQ ID NO 811
<211> LENGTH: 8
<212> TYPE: PRT
<213> ORGANISM: Homo sapiens

<400> SEQUENCE: 811

Thr Val Ala Pro Thr Glu Cys Ser
1               5

<210> SEQ ID NO 812
<211> LENGTH: 20
<212> TYPE: PRT
<213> ORGANISM: Homo sapiens

<400> SEQUENCE: 812

Ala Thr Leu Val Cys Leu Ile Ser Asp Phe Tyr Pro Gly Ala Val Thr
1               5                   10                  15

Val Ala Trp Lys
            20

<210> SEQ ID NO 813
<211> LENGTH: 19
<212> TYPE: PRT
<213> ORGANISM: Homo sapiens

<400> SEQUENCE: 813

Ala Ala Pro Ser Val Thr Leu Phe Pro Pro Ser Ser Glu Glu Leu Gln
1               5                   10                  15

Ala Asn Lys

<210> SEQ ID NO 814
<211> LENGTH: 15
<212> TYPE: PRT
<213> ORGANISM: Homo sapiens

<400> SEQUENCE: 814

Tyr Ala Ala Ser Ser Tyr Leu Ser Leu Thr Pro Glu Gln Trp Lys
1               5                   10                  15

<210> SEQ ID NO 815
<211> LENGTH: 15
<212> TYPE: PRT
<213> ORGANISM: Homo sapiens

<400> SEQUENCE: 815

Ser Tyr Ser Cys Gln Val Thr His Glu Gly Ser Thr Val Glu Lys
1               5                   10                  15

<210> SEQ ID NO 816
<211> LENGTH: 10
<212> TYPE: PRT
<213> ORGANISM: Homo sapiens

<400> SEQUENCE: 816

Ala Gly Val Glu Thr Thr Thr Pro Ser Lys
1               5                   10

<210> SEQ ID NO 817
<211> LENGTH: 8
<212> TYPE: PRT
<213> ORGANISM: Homo sapiens

<400> SEQUENCE: 817

Thr Val Ala Pro Thr Glu Cys Ser
1               5

<210> SEQ ID NO 818
<211> LENGTH: 7
<212> TYPE: PRT
<213> ORGANISM: Homo sapiens

<400> SEQUENCE: 818

Ala Asp Ser Ser Pro Ala Lys
1               5

<210> SEQ ID NO 819
<211> LENGTH: 24
<212> TYPE: PRT
<213> ORGANISM: Homo sapiens

<400> SEQUENCE: 819

Lys Ala Asp Ser Ser Pro Ala Lys Ala Gly Val Glu Thr Thr Thr Pro
1               5                   10                  15

Ser Lys Gln Ser Asn Asn Lys Tyr
            20

<210> SEQ ID NO 820
<211> LENGTH: 21
<212> TYPE: PRT
<213> ORGANISM: Homo sapiens

<400> SEQUENCE: 820

Ser Cys Gln Val Thr His Glu Gly Ser Thr Val Glu Lys Thr Val Ala
1               5                   10                  15

Pro Thr Glu Cys Ser
            20

<210> SEQ ID NO 821
<211> LENGTH: 11
<212> TYPE: PRT
<213> ORGANISM: Homo sapiens

<400> SEQUENCE: 821

Gly Gln Pro Lys Ala Ala Pro Ser Val Thr Leu
1               5                   10

<210> SEQ ID NO 822
<211> LENGTH: 9
<212> TYPE: PRT
<213> ORGANISM: Homo sapiens

<400> SEQUENCE: 822

Tyr Pro Gly Ala Val Thr Val Ala Trp
1               5

<210> SEQ ID NO 823
<211> LENGTH: 8
<212> TYPE: PRT
<213> ORGANISM: Homo sapiens

<400> SEQUENCE: 823

Phe Pro Pro Ser Ser Glu Glu Leu
1               5

<210> SEQ ID NO 824
<211> LENGTH: 6
<212> TYPE: PRT
<213> ORGANISM: Homo sapiens

<400> SEQUENCE: 824

Lys Ser His Lys Ser Tyr
1               5

<210> SEQ ID NO 825
<211> LENGTH: 7
<212> TYPE: PRT
<213> ORGANISM: Homo sapiens

<400> SEQUENCE: 825

Gln Ala Asn Lys Ala Thr Leu
1               5

<210> SEQ ID NO 826
<211> LENGTH: 23
<212> TYPE: PRT
<213> ORGANISM: Homo sapiens

```
<400> SEQUENCE: 826

Thr Thr Thr Pro Ser Lys Gln Ser Asn Asn Lys Tyr Ala Ala Ser Ser
1               5                   10                  15

Tyr Leu Ser Leu Thr Pro Glu
            20

<210> SEQ ID NO 827
<211> LENGTH: 15
<212> TYPE: PRT
<213> ORGANISM: Homo sapiens

<400> SEQUENCE: 827

Gln Trp Lys Ser His Lys Ser Tyr Ser Cys Gln Val Thr His Glu
1               5                   10                  15

<210> SEQ ID NO 828
<211> LENGTH: 18
<212> TYPE: PRT
<213> ORGANISM: Homo sapiens

<400> SEQUENCE: 828

Gly Gln Pro Lys Ala Ala Pro Ser Val Thr Leu Phe Pro Pro Ser Ser
1               5                   10                  15

Glu Glu

<210> SEQ ID NO 829
<211> LENGTH: 14
<212> TYPE: PRT
<213> ORGANISM: Homo sapiens

<400> SEQUENCE: 829

Leu Gln Ala Asn Lys Ala Thr Leu Val Cys Leu Ile Ser Asp
1               5                   10

<210> SEQ ID NO 830
<211> LENGTH: 13
<212> TYPE: PRT
<213> ORGANISM: Homo sapiens

<400> SEQUENCE: 830

Phe Tyr Pro Gly Ala Val Thr Val Ala Trp Lys Ala Asp
1               5                   10

<210> SEQ ID NO 831
<211> LENGTH: 9
<212> TYPE: PRT
<213> ORGANISM: Homo sapiens

<400> SEQUENCE: 831

Ser Ser Pro Ala Lys Ala Gly Val Glu
1               5

<210> SEQ ID NO 832
<211> LENGTH: 7
<212> TYPE: PRT
<213> ORGANISM: Homo sapiens

<400> SEQUENCE: 832

Lys Thr Val Ala Pro Thr Glu
1               5

<210> SEQ ID NO 833
<211> LENGTH: 23
```

```
<212> TYPE: PRT
<213> ORGANISM: Homo sapiens

<400> SEQUENCE: 833

Thr Thr Thr Pro Ser Lys Gln Ser Asn Asn Lys Tyr Ala Ala Ser Ser
1               5                   10                  15

Tyr Leu Ser Leu Thr Pro Glu
            20

<210> SEQ ID NO 834
<211> LENGTH: 15
<212> TYPE: PRT
<213> ORGANISM: Homo sapiens

<400> SEQUENCE: 834

Gln Trp Lys Ser His Lys Ser Tyr Ser Cys Gln Val Thr His Glu
1               5                   10                  15

<210> SEQ ID NO 835
<211> LENGTH: 18
<212> TYPE: PRT
<213> ORGANISM: Homo sapiens

<400> SEQUENCE: 835

Gly Gln Pro Lys Ala Ala Pro Ser Val Thr Leu Phe Pro Pro Ser Ser
1               5                   10                  15

Glu Glu

<210> SEQ ID NO 836
<211> LENGTH: 7
<212> TYPE: PRT
<213> ORGANISM: Homo sapiens

<400> SEQUENCE: 836

Lys Thr Val Ala Pro Thr Glu
1               5

<210> SEQ ID NO 837
<211> LENGTH: 13
<212> TYPE: PRT
<213> ORGANISM: Homo sapiens

<400> SEQUENCE: 837

Asp Phe Tyr Pro Gly Ala Val Thr Val Ala Trp Lys Ala
1               5                   10

<210> SEQ ID NO 838
<211> LENGTH: 19
<212> TYPE: PRT
<213> ORGANISM: Homo sapiens

<400> SEQUENCE: 838

Ala Ala Pro Ser Val Thr Leu Phe Pro Pro Ser Ser Glu Glu Leu Gln
1               5                   10                  15

Ala Asn Lys

<210> SEQ ID NO 839
<211> LENGTH: 15
<212> TYPE: PRT
<213> ORGANISM: Homo sapiens

<400> SEQUENCE: 839

Tyr Ala Ala Ser Ser Tyr Leu Ser Leu Thr Pro Glu Gln Trp Lys
```

```
1               5                   10                  15
```

<210> SEQ ID NO 840
<211> LENGTH: 16
<212> TYPE: PRT
<213> ORGANISM: Homo sapiens

<400> SEQUENCE: 840

```
Ala Thr Leu Val Cys Leu Ile Ser Asp Phe Tyr Pro Gly Ala Val Lys
1               5                   10                  15
```

<210> SEQ ID NO 841
<211> LENGTH: 17
<212> TYPE: PRT
<213> ORGANISM: Homo sapiens

<400> SEQUENCE: 841

```
Ala Asp Gly Ser Pro Val Asn Thr Gly Val Glu Thr Thr Thr Pro Ser
1               5                   10                  15

Lys
```

<210> SEQ ID NO 842
<211> LENGTH: 15
<212> TYPE: PRT
<213> ORGANISM: Homo sapiens

<400> SEQUENCE: 842

```
Ser Tyr Ser Cys Gln Val Thr His Glu Gly Ser Thr Val Glu Lys
1               5                   10                  15
```

<210> SEQ ID NO 843
<211> LENGTH: 8
<212> TYPE: PRT
<213> ORGANISM: Homo sapiens

<400> SEQUENCE: 843

```
Thr Val Ala Pro Ala Glu Cys Ser
1               5
```

<210> SEQ ID NO 844
<211> LENGTH: 18
<212> TYPE: PRT
<213> ORGANISM: Homo sapiens

<400> SEQUENCE: 844

```
Ser His Arg Ser Tyr Ser Cys Gln Val Thr His Glu Gly Ser Thr Val
1               5                   10                  15

Glu Lys
```

<210> SEQ ID NO 845
<211> LENGTH: 19
<212> TYPE: PRT
<213> ORGANISM: Homo sapiens

<400> SEQUENCE: 845

```
Ala Ala Pro Ser Val Thr Leu Phe Pro Pro Ser Ser Glu Glu Leu Gln
1               5                   10                  15

Ala Asn Lys
```

<210> SEQ ID NO 846
<211> LENGTH: 15
<212> TYPE: PRT
<213> ORGANISM: Homo sapiens -continued

<400> SEQUENCE: 846

Tyr Ala Ala Ser Ser Tyr Leu Ser Leu Thr Pro Glu Gln Trp Lys
1               5                   10                  15

<210> SEQ ID NO 847
<211> LENGTH: 16
<212> TYPE: PRT
<213> ORGANISM: Homo sapiens

<400> SEQUENCE: 847

Ala Thr Leu Val Cys Leu Ile Ser Asp Phe Tyr Pro Gly Ala Val Lys
1               5                   10                  15

<210> SEQ ID NO 848
<211> LENGTH: 17
<212> TYPE: PRT
<213> ORGANISM: Homo sapiens

<400> SEQUENCE: 848

Ala Asp Gly Ser Pro Val Asn Thr Gly Val Glu Thr Thr Thr Pro Ser
1               5                   10                  15

Lys

<210> SEQ ID NO 849
<211> LENGTH: 8
<212> TYPE: PRT
<213> ORGANISM: Homo sapiens

<400> SEQUENCE: 849

Thr Val Ala Pro Ala Glu Cys Ser
1               5

<210> SEQ ID NO 850
<211> LENGTH: 23
<212> TYPE: PRT
<213> ORGANISM: Homo sapiens

<400> SEQUENCE: 850

Ser Tyr Ser Cys Gln Val Thr His Glu Gly Ser Thr Val Glu Lys Thr
1               5                   10                  15

Val Ala Pro Ala Glu Cys Ser
            20

<210> SEQ ID NO 851
<211> LENGTH: 24
<212> TYPE: PRT
<213> ORGANISM: Homo sapiens

<400> SEQUENCE: 851

Lys Ala Asp Gly Ser Pro Val Asn Thr Gly Val Glu Thr Thr Thr Pro
1               5                   10                  15

Ser Lys Gln Ser Asn Asn Lys Tyr
            20

<210> SEQ ID NO 852
<211> LENGTH: 21
<212> TYPE: PRT
<213> ORGANISM: Homo sapiens

<400> SEQUENCE: 852

Ser Cys Gln Val Thr His Glu Gly Ser Thr Val Glu Lys Thr Val Ala
1               5                   10                  15

```
Pro Ala Glu Cys Ser
        20

<210> SEQ ID NO 853
<211> LENGTH: 11
<212> TYPE: PRT
<213> ORGANISM: Homo sapiens

<400> SEQUENCE: 853

Gly Gln Pro Lys Ala Ala Pro Ser Val Thr Leu
1               5                  10

<210> SEQ ID NO 854
<211> LENGTH: 9
<212> TYPE: PRT
<213> ORGANISM: Homo sapiens

<400> SEQUENCE: 854

Tyr Pro Gly Ala Val Lys Val Ala Trp
1               5

<210> SEQ ID NO 855
<211> LENGTH: 8
<212> TYPE: PRT
<213> ORGANISM: Homo sapiens

<400> SEQUENCE: 855

Phe Pro Pro Ser Ser Glu Glu Leu
1               5

<210> SEQ ID NO 856
<211> LENGTH: 6
<212> TYPE: PRT
<213> ORGANISM: Homo sapiens

<400> SEQUENCE: 856

Lys Ser His Arg Ser Tyr
1               5

<210> SEQ ID NO 857
<211> LENGTH: 7
<212> TYPE: PRT
<213> ORGANISM: Homo sapiens

<400> SEQUENCE: 857

Gln Ala Asn Lys Ala Thr Leu
1               5

<210> SEQ ID NO 858
<211> LENGTH: 23
<212> TYPE: PRT
<213> ORGANISM: Homo sapiens

<400> SEQUENCE: 858

Thr Thr Thr Pro Ser Lys Gln Ser Asn Asn Lys Tyr Ala Ala Ser Ser
1               5                  10                  15

Tyr Leu Ser Leu Thr Pro Glu
            20

<210> SEQ ID NO 859
<211> LENGTH: 15
<212> TYPE: PRT
<213> ORGANISM: Homo sapiens
```

```
<400> SEQUENCE: 859

Gln Trp Lys Ser His Arg Ser Tyr Ser Cys Gln Val Thr His Glu
1               5                   10                  15

<210> SEQ ID NO 860
<211> LENGTH: 18
<212> TYPE: PRT
<213> ORGANISM: Homo sapiens

<400> SEQUENCE: 860

Gly Gln Pro Lys Ala Ala Pro Ser Val Thr Leu Phe Pro Pro Ser Ser
1               5                   10                  15

Glu Glu

<210> SEQ ID NO 861
<211> LENGTH: 14
<212> TYPE: PRT
<213> ORGANISM: Homo sapiens

<400> SEQUENCE: 861

Leu Gln Ala Asn Lys Ala Thr Leu Val Cys Leu Ile Ser Asp
1               5                   10

<210> SEQ ID NO 862
<211> LENGTH: 13
<212> TYPE: PRT
<213> ORGANISM: Homo sapiens

<400> SEQUENCE: 862

Phe Tyr Pro Gly Ala Val Lys Val Ala Trp Lys Ala Asp
1               5                   10

<210> SEQ ID NO 863
<211> LENGTH: 9
<212> TYPE: PRT
<213> ORGANISM: Homo sapiens

<400> SEQUENCE: 863

Gly Ser Pro Val Asn Thr Gly Val Glu
1               5

<210> SEQ ID NO 864
<211> LENGTH: 7
<212> TYPE: PRT
<213> ORGANISM: Homo sapiens

<400> SEQUENCE: 864

Lys Thr Val Ala Pro Ala Glu
1               5

<210> SEQ ID NO 865
<211> LENGTH: 23
<212> TYPE: PRT
<213> ORGANISM: Homo sapiens

<400> SEQUENCE: 865

Thr Thr Thr Pro Ser Lys Gln Ser Asn Asn Lys Tyr Ala Ala Ser Ser
1               5                   10                  15

Tyr Leu Ser Leu Thr Pro Glu
                20

<210> SEQ ID NO 866
<211> LENGTH: 15
```

<212> TYPE: PRT
<213> ORGANISM: Homo sapiens

<400> SEQUENCE: 866

Gln Trp Lys Ser His Arg Ser Tyr Ser Cys Gln Val Thr His Glu
1               5                   10                  15

<210> SEQ ID NO 867
<211> LENGTH: 18
<212> TYPE: PRT
<213> ORGANISM: Homo sapiens

<400> SEQUENCE: 867

Gly Gln Pro Lys Ala Ala Pro Ser Val Thr Leu Phe Pro Pro Ser Ser
1               5                   10                  15

Glu Glu

<210> SEQ ID NO 868
<211> LENGTH: 7
<212> TYPE: PRT
<213> ORGANISM: Homo sapiens

<400> SEQUENCE: 868

Lys Thr Val Ala Pro Ala Glu
1               5

<210> SEQ ID NO 869
<211> LENGTH: 13
<212> TYPE: PRT
<213> ORGANISM: Homo sapiens

<400> SEQUENCE: 869

Asp Phe Tyr Pro Gly Ala Val Lys Val Ala Trp Lys Ala
1               5                   10

<210> SEQ ID NO 870
<211> LENGTH: 20
<212> TYPE: PRT
<213> ORGANISM: Homo sapiens

<400> SEQUENCE: 870

Ala Thr Leu Val Cys Leu Val Ser Asp Phe Tyr Pro Gly Ala Val Thr
1               5                   10                  15

Val Ala Trp Lys
            20

<210> SEQ ID NO 871
<211> LENGTH: 19
<212> TYPE: PRT
<213> ORGANISM: Homo sapiens

<400> SEQUENCE: 871

Ala Ala Pro Ser Val Thr Leu Phe Pro Pro Ser Ser Glu Glu Leu Gln
1               5                   10                  15

Ala Asn Lys

<210> SEQ ID NO 872
<211> LENGTH: 15
<212> TYPE: PRT
<213> ORGANISM: Homo sapiens

<400> SEQUENCE: 872

Tyr Ala Ala Ser Ser Tyr Leu Ser Leu Thr Pro Glu Gln Trp Lys

-continued

```
1               5                  10                 15
```

<210> SEQ ID NO 873
<211> LENGTH: 10
<212> TYPE: PRT
<213> ORGANISM: Homo sapiens

<400> SEQUENCE: 873

Val Thr His Glu Gly Ser Thr Val Glu Lys
1               5                  10

<210> SEQ ID NO 874
<211> LENGTH: 10
<212> TYPE: PRT
<213> ORGANISM: Homo sapiens

<400> SEQUENCE: 874

Val Gly Val Glu Thr Thr Lys Pro Ser Lys
1               5                  10

<210> SEQ ID NO 875
<211> LENGTH: 8
<212> TYPE: PRT
<213> ORGANISM: Homo sapiens

<400> SEQUENCE: 875

Thr Val Ala Pro Ala Glu Cys Ser
1               5

<210> SEQ ID NO 876
<211> LENGTH: 20
<212> TYPE: PRT
<213> ORGANISM: Homo sapiens

<400> SEQUENCE: 876

Ala Thr Leu Val Cys Leu Val Ser Asp Phe Tyr Pro Gly Ala Val Thr
1               5                  10                 15

Val Ala Trp Lys
            20

<210> SEQ ID NO 877
<211> LENGTH: 18
<212> TYPE: PRT
<213> ORGANISM: Homo sapiens

<400> SEQUENCE: 877

Ser His Arg Ser Tyr Ser Cys Arg Val Thr His Glu Gly Ser Thr Val
1               5                  10                 15

Glu Lys

<210> SEQ ID NO 878
<211> LENGTH: 19
<212> TYPE: PRT
<213> ORGANISM: Homo sapiens

<400> SEQUENCE: 878

Ala Ala Pro Ser Val Thr Leu Phe Pro Pro Ser Ser Glu Glu Leu Gln
1               5                  10                 15

Ala Asn Lys

<210> SEQ ID NO 879
<211> LENGTH: 15
<212> TYPE: PRT

<213> ORGANISM: Homo sapiens

<400> SEQUENCE: 879

Tyr Ala Ala Ser Ser Tyr Leu Ser Leu Thr Pro Glu Gln Trp Lys
1               5                   10                  15

<210> SEQ ID NO 880
<211> LENGTH: 8
<212> TYPE: PRT
<213> ORGANISM: Homo sapiens

<400> SEQUENCE: 880

Thr Val Ala Pro Ala Glu Cys Ser
1               5

<210> SEQ ID NO 881
<211> LENGTH: 7
<212> TYPE: PRT
<213> ORGANISM: Homo sapiens

<400> SEQUENCE: 881

Val Gly Val Glu Thr Thr Lys
1               5

<210> SEQ ID NO 882
<211> LENGTH: 7
<212> TYPE: PRT
<213> ORGANISM: Homo sapiens

<400> SEQUENCE: 882

Ala Asp Gly Ser Pro Val Lys
1               5

<210> SEQ ID NO 883
<211> LENGTH: 18
<212> TYPE: PRT
<213> ORGANISM: Homo sapiens

<400> SEQUENCE: 883

Val Thr His Glu Gly Ser Thr Val Glu Lys Thr Val Ala Pro Ala Glu
1               5                   10                  15

Cys Ser

<210> SEQ ID NO 884
<211> LENGTH: 24
<212> TYPE: PRT
<213> ORGANISM: Homo sapiens

<400> SEQUENCE: 884

Lys Ala Asp Gly Ser Pro Val Lys Val Gly Val Glu Thr Thr Lys Pro
1               5                   10                  15

Ser Lys Gln Ser Asn Asn Lys Tyr
            20

<210> SEQ ID NO 885
<211> LENGTH: 21
<212> TYPE: PRT
<213> ORGANISM: Homo sapiens

<400> SEQUENCE: 885

Ser Cys Arg Val Thr His Glu Gly Ser Thr Val Glu Lys Thr Val Ala
1               5                   10                  15

Pro Ala Glu Cys Ser

20

<210> SEQ ID NO 886
<211> LENGTH: 11
<212> TYPE: PRT
<213> ORGANISM: Homo sapiens

<400> SEQUENCE: 886

Gly Gln Pro Lys Ala Ala Pro Ser Val Thr Leu
1               5                   10

<210> SEQ ID NO 887
<211> LENGTH: 9
<212> TYPE: PRT
<213> ORGANISM: Homo sapiens

<400> SEQUENCE: 887

Tyr Pro Gly Ala Val Thr Val Ala Trp
1               5

<210> SEQ ID NO 888
<211> LENGTH: 8
<212> TYPE: PRT
<213> ORGANISM: Homo sapiens

<400> SEQUENCE: 888

Phe Pro Pro Ser Ser Glu Glu Leu
1               5

<210> SEQ ID NO 889
<211> LENGTH: 6
<212> TYPE: PRT
<213> ORGANISM: Homo sapiens

<400> SEQUENCE: 889

Lys Ser His Arg Ser Tyr
1               5

<210> SEQ ID NO 890
<211> LENGTH: 7
<212> TYPE: PRT
<213> ORGANISM: Homo sapiens

<400> SEQUENCE: 890

Gln Ala Asn Lys Ala Thr Leu
1               5

<210> SEQ ID NO 891
<211> LENGTH: 23
<212> TYPE: PRT
<213> ORGANISM: Homo sapiens

<400> SEQUENCE: 891

Thr Thr Lys Pro Ser Lys Gln Ser Asn Asn Lys Tyr Ala Ala Ser Ser
1               5                   10                  15

Tyr Leu Ser Leu Thr Pro Glu
            20

<210> SEQ ID NO 892
<211> LENGTH: 15
<212> TYPE: PRT
<213> ORGANISM: Homo sapiens

<400> SEQUENCE: 892

```
Gln Trp Lys Ser His Arg Ser Tyr Ser Cys Arg Val Thr His Glu
1               5                   10                  15
```

<210> SEQ ID NO 893
<211> LENGTH: 18
<212> TYPE: PRT
<213> ORGANISM: Homo sapiens

<400> SEQUENCE: 893

```
Gly Gln Pro Lys Ala Ala Pro Ser Val Thr Leu Phe Pro Pro Ser Ser
1               5                   10                  15

Glu Glu
```

<210> SEQ ID NO 894
<211> LENGTH: 14
<212> TYPE: PRT
<213> ORGANISM: Homo sapiens

<400> SEQUENCE: 894

```
Leu Gln Ala Asn Lys Ala Thr Leu Val Cys Leu Val Ser Asp
1               5                   10
```

<210> SEQ ID NO 895
<211> LENGTH: 13
<212> TYPE: PRT
<213> ORGANISM: Homo sapiens

<400> SEQUENCE: 895

```
Phe Tyr Pro Gly Ala Val Thr Val Ala Trp Lys Ala Asp
1               5                   10
```

<210> SEQ ID NO 896
<211> LENGTH: 9
<212> TYPE: PRT
<213> ORGANISM: Homo sapiens

<400> SEQUENCE: 896

```
Gly Ser Pro Val Lys Val Gly Val Glu
1               5
```

<210> SEQ ID NO 897
<211> LENGTH: 7
<212> TYPE: PRT
<213> ORGANISM: Homo sapiens

<400> SEQUENCE: 897

```
Lys Thr Val Ala Pro Ala Glu
1               5
```

<210> SEQ ID NO 898
<211> LENGTH: 23
<212> TYPE: PRT
<213> ORGANISM: Homo sapiens

<400> SEQUENCE: 898

```
Thr Thr Lys Pro Ser Lys Gln Ser Asn Asn Lys Tyr Ala Ala Ser Ser
1               5                   10                  15

Tyr Leu Ser Leu Thr Pro Glu
            20
```

<210> SEQ ID NO 899
<211> LENGTH: 15
<212> TYPE: PRT
<213> ORGANISM: Homo sapiens

```
<400> SEQUENCE: 899

Gln Trp Lys Ser His Arg Ser Tyr Ser Cys Arg Val Thr His Glu
1               5                   10                  15

<210> SEQ ID NO 900
<211> LENGTH: 18
<212> TYPE: PRT
<213> ORGANISM: Homo sapiens

<400> SEQUENCE: 900

Gly Gln Pro Lys Ala Ala Pro Ser Val Thr Leu Phe Pro Pro Ser Ser
1               5                   10                  15

Glu Glu

<210> SEQ ID NO 901
<211> LENGTH: 7
<212> TYPE: PRT
<213> ORGANISM: Homo sapiens

<400> SEQUENCE: 901

Lys Thr Val Ala Pro Ala Glu
1               5

<210> SEQ ID NO 902
<211> LENGTH: 13
<212> TYPE: PRT
<213> ORGANISM: Homo sapiens

<400> SEQUENCE: 902

Asp Phe Tyr Pro Gly Ala Val Thr Val Ala Trp Lys Ala
1               5                   10

<210> SEQ ID NO 903
<211> LENGTH: 9
<212> TYPE: PRT
<213> ORGANISM: Homo sapiens

<400> SEQUENCE: 903

Thr Phe Ser Cys Met Val Gly His Glu
1               5

<210> SEQ ID NO 904
<211> LENGTH: 9
<212> TYPE: PRT
<213> ORGANISM: Homo sapiens

<400> SEQUENCE: 904

Gly Ser Pro Val Lys Ala Gly Val Glu
1               5
```